(12) United States Patent
Ruben et al.

(10) Patent No.: US 7,914,789 B2
(45) Date of Patent: *Mar. 29, 2011

(54) HEMCM42 ANTIBODIES

(75) Inventors: Steven M. Ruben, Brookeville, MD (US); Craig A. Rosen, Laytonsville, MD (US); Gregory A. Endress, Florence, MA (US)

(73) Assignee: Facet Biotech Corporation, Redwood City, CA (US)

( * ) Notice: Subject to any disclaimer, the term of this patent is extended or adjusted under 35 U.S.C. 154(b) by 587 days.

This patent is subject to a terminal disclaimer.

(21) Appl. No.: 11/801,040

(22) Filed: May 7, 2007

(65) Prior Publication Data
US 2008/0004432 A1 Jan. 3, 2008

Related U.S. Application Data

(60) Division of application No. 11/226,657, filed on Sep. 15, 2005, now Pat. No. 7,482,442, which is a division of application No. 10/062,831, filed on Feb. 5, 2002, now Pat. No. 7,001,992, which is a division of application No. 09/690,454, filed on Oct. 18, 2000, now Pat. No. 6,531,447, which is a continuation of application No. 09/189,144, filed on Nov. 10, 1998, now abandoned, which is a continuation-in-part of application No. PCT/US98/10868, filed on May 28, 1998.

(60) Provisional application No. 60/044,039, filed on May 30, 1997, provisional application No. 60/048,093, filed on May 30, 1997, provisional application No. 60/048,190, filed on May 30, 1997, provisional application No. 60/050,935, filed on May 30, 1997, provisional application No. 60/048,101, filed on May 30, 1997, provisional application No. 60/048,356, filed on May 30, 1997, provisional application No. 60/056,250, filed on Aug. 29, 1997, provisional application No. 60/056,296, filed on Aug. 29, 1997, provisional application No. 60/056,293, filed on Aug. 29, 1997.

(51) Int. Cl.
*A61K 39/395* (2006.01)

(52) U.S. Cl. ............... 424/144.1; 424/133.1; 424/139.1; 424/178.1; 530/387.9; 530/388.22

(58) Field of Classification Search ............... None
See application file for complete search history.

(56) References Cited

U.S. PATENT DOCUMENTS

| | | | |
|---|---|---|---|
| 6,207,642 B1 | 3/2001 | Wiley | |
| 6,531,447 B1 | 3/2003 | Ruben et al. | |
| 6,727,225 B2 | 4/2004 | Wiley | |
| 6,824,773 B2 | 11/2004 | Wiley | |
| 7,001,992 B2 * | 2/2006 | Ruben et al. | 530/387.9 |
| 7,169,387 B2 | 1/2007 | Rennert | |
| 7,208,151 B2 | 4/2007 | Browning et al. | |
| 7,368,531 B2 * | 5/2008 | Rosen et al. | 530/350 |
| 2004/0253610 A1 | 12/2004 | Wiley | |
| 2005/0054047 A1 | 3/2005 | Wiley | |
| 2005/0208046 A1 | 9/2005 | Kim et al. | |
| 2006/0025574 A1 | 2/2006 | Ruben et al. | |
| 2006/0084143 A1 | 4/2006 | Wiley | |
| 2006/0147982 A1 | 7/2006 | Ruben et al. | |
| 2007/0248593 A1 | 10/2007 | Ruben et al. | |
| 2008/0004432 A1 | 1/2008 | Ruben et al. | |
| 2008/0008714 A1 | 1/2008 | Browning et al. | |

FOREIGN PATENT DOCUMENTS

| | | |
|---|---|---|
| WO | WO 95/31544 A1 | 11/1995 |
| WO | WO 97/18235 A | 5/1997 |
| WO | WO 98/54206 A1 | 12/1998 |
| WO | WO 98/55508 A | 12/1998 |
| WO | WO 99/61471 | 12/1999 |
| WO | WO 01/45730 | 6/2001 |

OTHER PUBLICATIONS

Stryer, L. Biochemistry, 4th edition, 1995, W. H. Freeman and Company, pp. 100-102.*
Stedman's Medical Dictionary Online definitions of "isotope", "isotype", "radioisotope" and "radioisotype" downloaded Sep. 29, 2009, four pages.*
U.S. Appl. No. 09/189,144, filed Nov. 10, 1998, Rubin et al.
U.S. Appl. No. 60/056,250, filed Aug. 29, 1997, Yu et al.
U.S. Appl. No. 60/056,293, filed Aug. 29, 1997, Yu et al.
U.S. Appl. No. 60/056,296, filed Aug. 29, 1997, Yu et al.
U.S. Appl. No. 60/044,039, filed May 30, 1997, Carter et al.
U.S. Appl. No. 60/048,093, filed May 30, 1997, Carter et al.
U.S. Appl. No. 60/048,101, filed May 30, 1997, Yu et al.
U.S. Appl. No. 60/048,190, filed May 30, 1997, Carter et al.
U.S. Appl. No. 60/048,356, filed May 30, 1997, Yu et al.
U.S. Appl. No. 60/050,935, filed May 30, 1997, Yu et al.
U.S. Appl. No. 12/324,825, filed Nov. 26, 2008, Ruben et al.
EP Examination Report dated Apr. 25, 2008 for EP 98926105.2.
EP Examination Report dated Jun. 12, 2007 for EP 98926105.2.
EP Examination Report dated Jun. 1, 2006 for EP 98926105.2.
EP Examination Report dated May 6, 2005 for EP 98926105.2.
European Search Report dated Apr. 2, 2004 for EP 98926105.2.
International Preliminary Examination Report dated Nov. 8, 1999 for PCT/U598/10868.
International Search Report mailed Oct. 28, 1998 for PCT/US98/10868.
Hillier et al., Genbank Accession No. N20562 (Dec. 18, 1995).
Hillier et al., Genbank Accession No. N23080 (Dec. 28, 1995).
Hillier et al., Genbank Accession No. H18098 (Jun. 29, 1995).
Hillier et al., Genbank Accession No. N46256 (Feb. 14, 1996).
Hillier et al., Genbank Accession No. N28611 (Jan. 4, 1996).
Hillier et al., Genbank Accession No. R70283 (Jun. 1, 1995).
Hillier et al., Genbank Accession No. T98012 (Mar. 29, 1995).

(Continued)

*Primary Examiner* — Michael Szperka
(74) *Attorney, Agent, or Firm* — Townsend and Townsend and Crew LLP

(57) ABSTRACT

The present invention relates to novel human secreted proteins and isolated nucleic acids containing the coding regions of the genes encoding such proteins. Also provided are vectors, host cells, antibodies, and recombinant methods for producing human secreted proteins. The invention further relates to diagnostic and therapeutic methods useful for diagnosing and treating disorders related to these novel human secreted proteins.

9 Claims, No Drawings

OTHER PUBLICATIONS

Hudson, Genbank Accession No. G23170 (May 31, 1996).
Genexpress, Genbank Accession No. Z44692 (Sep. 21, 1995).
Marra et al., Genbank Accession No. W83277 (Sep. 12, 1996).
Ricke et al., "Sequencing of human chromosome 16p13.3", Datebase EMBL Human _Online, Homo sapiens chromosome 16, cosmid clone 363E3, May 5, 1998.
Genbank Accession No. AI768116 (Dec. 20, 1999).
Hillier et al., Genbank Accession No. AA149044 (May 19, 1997).
Genbank Accession No. AW204761 (Dec. 2, 1999).
Genbank Accession No. AI768403 (Dec. 20, 1999).
Chen et al., Genbank Accession No. AA631934 (Oct. 20, 1997).
Genbank Accession No. AI221536 (Nov. 29, 1998).
Genbank Accession No. AW172990 (Nov. 16, 1999).
Genbank Accession No. AW051452 (Sep. 20, 1999).
Genbank Accession No. AW262030 (Dec. 28, 1999).
Genbank Accession No. AI219327 (Nov. 29, 1998).
Genbank Accession No. BF114971 (Oct. 24, 2000).
Genbank Accession No. AI800959 (Dec. 19, 1999).
Genbank Accession No. AI004154 (Aug. 27, 1998).
Hillier et al., Genbank Accession No. AA149043 (May 19, 1997).
Genbank Accession No. AW338518 (Jan. 31, 2000).
Genbank Accession No. AI568941 (May 14, 1999).
Hillier et al., Genbank Accession No. N41733 (Jan. 24, 1996).
Genbank Accession No. AI827127 (Mar. 7, 2000).
Lanfranchi et al., Genbank Accession No. F25336 (May 13, 1999).
Genbank Accession No. AI313436 (Feb. 3, 1999).
Genbank Accession No. AA994944 (Aug. 27, 1998).
Dias et al., Genbank Accession No. AW938942 (May 30, 2000).
Genbank Accession No. AI761510 (Dec. 21, 1999).
Genbank Accession No. BF063028 (Oct. 16, 2000).
Genbank Accession No. AW628237 (Mar. 31, 2000).
Hillier et al., Genbank Accession No. T56712 (Feb. 7, 1995).
Hillier et al., Genbank Accession No. AI718198 (Jun. 10, 1999).
Hillier et al., Genbank Accession No. R48167 (May 18, 1995).
Genbank Accession No. BF108787 (Oct. 20, 2000).
Genbank Accession No. BF197631 (Oct. 3, 2000).
Genbank Accession No. AI767239 (Dec. 21, 1999).
Genbank Accession No. AW001699 (Mar. 8, 2000).
Genbank Accession No. AI796303 (Dec. 20, 1999).
Genbank Accession No. AI358289 (Feb. 15, 1999).
Genbank Accession No. AW149867 (Nov. 3, 1999).
Genbank Accession No. AA576558 (Sep. 9, 1997).
Genbank Accession No. AI911799 (Dec. 17, 1999).
Genbank Accession No. AA610401 (Dec. 9, 1997).
Liew, Genbank Accession No. N83862 (Apr. 1, 1996).
Genbank Accession No. AI470703 (Apr. 13, 1999).
Genbank Accession No. BG236779 (Feb. 12, 2001).
Genbank Accession No. AI470484 (Apr. 13, 1999).
Genbank Accession No. AI492143 (Mar. 30, 1999).
Hillier et al., Genbank Accession No. T74424 (Mar. 2, 1995).
Genbank Accession No. AW166567 (Nov. 12, 1999).
Genbank Accession No. AI864228 (Aug. 30, 1999).
Genbank Accession No. AI813825 (Mar. 7, 2000).
Genbank Accession No. AI086734 (Oct. 1, 1998).
Genbank Accession No. AI270718 (Dec. 2, 1998).
Genbank Accession No. AI401800 (Mar. 30, 1999).
Genbank Accession No. AI799902 (Dec. 17, 1999).
Hillier et al., Genbank Accession No. H95227 (Nov. 25, 1996).
Genbank Accession No. AI264959 (Nov. 13, 1998).
Genbank Accession No. AI611273 (May 14, 1999).
Genbank Accession No. AI867518 (Dec. 17, 1999).
Genbank Accession No. AA873480 (Apr. 29, 1998).
Genbank Accession No. AA970894 (Jul. 7, 1998).
Adams et al., Genbank Accession No. AA386018 (Apr. 21, 1997).
Genbank Accession No. AI910684 (Jul. 28, 1999).
Genbank Accession No. AI858303 (Mar. 7, 2000).
Genbank Accession No. AI701259 (Dec. 17, 1999).
Genbank Accession No. AI189491 (Oct. 28, 1998).
Genbank Accession No. AW988312 (Jun. 2, 2000).
Hillier et al., Genbank Accession No. T74049 (Mar. 2, 1995).
Genbank Accession No. BE042437 (Jun. 8, 2000).
Charnock-Jones et al., "Extension of incomplete cDNAs (ESTs) by biotin/streptavidin-mediated walking using the polymerase chain reaction", J. of Biotechnology, 35:205-215 (1994).
Colman, "Effects of amino acid sequence changes on antibody-antigen interactions," Research in Immunology, 145:33-36 (1994).
Feng et al., "The Fn14 Immediate-Early Response Gene Is Induced During Liver Regeneration and Highly Expressed in Both Human and Murine Hepatocellular Carcinomas", Am.J.of Pathol., 156(4): 1253-1261 (2000).
Janeway et al., Immunobiology, third edition, 1996, pp. 1:6, 2:2, 2:17, 2:18, 3:2-3:5, and 3:9.
Meighan-Mantha et al., "The Mitogen-indicible Fn14 Gene Encodes a Type I Transmembrane Protein that Modulated Fibroblast Adhesion and Migration", J. Of Biol. Chem., 274(46): 33166-33176 (Nov. 12, 1999).
Skolnick et al., "From genes to protein structure and function," Trends in Biotechnology, 18:34-39, (2000).
Whisstock et al., "Prediction of protein function from protein sequence and structure", Quarterly Reviews of Biophysics, 36:307-340 (2003).
U.S. Appl. No. 09/690,454, Office Action mailed Jan. 17, 2002.
U.S. Appl. No. 09/690,454, Office Action mailed Apr. 26, 2002.
U.S. Appl. No. 09/690,454, Interview Summary mailed Jul. 31, 2002.
U.S. Appl. No. 09/690,454, Office Action mailed Sep. 27, 2002.
U.S. Appl. No. 09/690,454, Notice of Allowance mailed Oct. 16, 2002.
U.S. Appl. No. 10/062,831, Office Action mailed Sep. 8, 2004.
U.S. Appl. No. 10/062,831, Office Action mailed Mar. 11, 2005.
U.S. Appl. No. 10/062,831, Notice of Allowance mailed May 26, 2005.
U.S. Appl. No. 11/226,657, Office Action mailed Jan. 10, 2006.
U.S. Appl. No. 11/226,657, Office Action mailed Oct. 25, 2006.
U.S. Appl. No. 11/226,657, Office Action mailed May 24, 2007.
U.S. Appl. No. 11/226,657, Office Action mailed Feb. 1, 2008.
U.S. Appl. No. 11/226,657, Notice of Allowance mailed Aug. 29, 2008.
U.S. Appl. No. 09/189,144, Office Action mailed May 18, 2000.
U.S. Appl. No. 12/324,825, Non-Final Office Action mailed Jan. 29, 2010.

* cited by examiner

HEMCM42 ANTIBODIES

This application is a continuation of U.S. application Ser. No. 11/226,657, filed Sep. 15, 2005, which is a divisional of U.S. application Ser. No. 10/062,831, filed Feb. 5, 2002, (now U.S. Pat. No. 7,001,992, issued Feb. 21, 2006), which is a divisional of U.S. application Ser. No. 09/690,454, filed Oct. 18, 2000 (now U.S. Pat. No. 6,531,447, issued Mar. 11, 2003), which is a continuation of U.S. application Ser. No. 09/189,144, filed Nov. 10, 1998 (now abandoned), which is a continuation-in-part of International Application No. PCT/US98/10868, filed May 28, 1998, which claims benefit under 35 U.S.C. § 119(e) of U.S. Provisional Applications: 60/044,039; 60/048,093; 60/048,190; 60/050,935; 60/048,101; 60/048,356 (each filed May 30, 1997); and, 60/056,250; 60/056,296; 60/056,293 (each filed Aug. 29, 1997), each of which is incorporated by reference herein in its entirety.

FIELD OF THE INVENTION

This application refers to a "Sequence Listing" listed below, which is provided as an electronic document on two identical compact discs (CD-R), labeled "Copy 1" and "Copy 2." These compact disks each contain the file "PZ006G13AP1C1D2_Seq.List.txt" (187,168 bytes, created on Sep. 12, 2005), which is hereby incorporated by reference in its entirety herein.

This invention relates to newly identified polynucleotides and the polypeptides encoded by these polynucleotides, uses of such polynucleotides and polypeptides, and their production.

BACKGROUND OF THE INVENTION

Unlike bacterium, which exist as a single compartment surrounded by a membrane, human cells and other eucaryotes are subdivided by membranes into many functionally distinct compartments. Each membrane-bounded compartment, or organelle, contains different proteins essential for the function of the organelle. The cell uses "sorting signals," which are amino acid motifs located within the protein, to target proteins to particular cellular organelles.

One type of sorting signal, called a signal sequence, a signal peptide, or a leader sequence, directs a class of proteins to an organelle called the endoplasmic reticulum (ER). The ER separates the membrane-bounded proteins from all other types of proteins. Once localized to the ER, both groups of proteins can be further directed to another organelle called the Golgi apparatus. Here, the Golgi distributes the proteins to vesicles, including secretory vesicles, the cell membrane, lysosomes, and the other organelles.

Proteins targeted to the ER by a signal sequence can be released into the extracellular space as a secreted protein. For example, vesicles containing secreted proteins can fuse with the cell membrane and release their contents into the extracellular space—a process called exocytosis. Exocytosis can occur constitutively or after receipt of a triggering signal. In the latter case, the proteins are stored in secretory vesicles (or secretory granules) until exocytosis is triggered. Similarly, proteins residing on the cell membrane can also be secreted into the extracellular space by proteolytic cleavage of a "linker" holding the protein to the membrane.

Despite the great progress made in recent years, only a small number of genes encoding human secreted proteins have been identified. These secreted proteins include the commercially valuable human insulin, interferon, Factor VIII, human growth hormone, tissue plasminogen activator, and erythropoietin. Thus, in light of the pervasive role of secreted proteins in human physiology, a need exists for identifying and characterizing novel human secreted proteins and the genes that encode them. This knowledge will allow one to detect, to treat, and to prevent medical disorders by using secreted proteins or the genes that encode them.

SUMMARY OF THE INVENTION

The present invention relates to novel polynucleotides and the encoded polypeptides. Moreover, the present invention relates to vectors, host cells, antibodies, and recombinant methods for producing the polypeptides and polynucleotides. Also provided are diagnostic methods for detecting disorders related to the polypeptides, and therapeutic methods for treating such disorders. The invention further relates to screening methods for identifying binding partners of the polypeptides.

DETAILED DESCRIPTION

Definitions

The following definitions are provided to facilitate understanding of certain terms used throughout this specification.

In the present invention, "isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide.

In the present invention, a "secreted" protein refers to those proteins capable of being directed to the ER, secretory vesicles, or the extracellular space as a result of a signal sequence, as well as those proteins released into the extracellular space without necessarily containing a signal sequence. If the secreted protein is released into the extracellular space, the secreted protein can undergo extracellular processing to produce a "mature" protein. Release into the extracellular space can occur by many mechanisms, including exocytosis and proteolytic cleavage.

As used herein, a "polynucleotide" refers to a molecule having a nucleic acid sequence contained in SEQ ID NO:X or the cDNA contained within the clone deposited with the ATCC. For example, the polynucleotide can contain the nucleotide sequence of the full length cDNA sequence, including the 5' and 3' untranslated sequences, the coding region, with or without the signal sequence, the secreted protein coding region, as well as fragments, epitopes, domains, and variants of the nucleic acid sequence. Moreover, as used herein, a "polypeptide" refers to a molecule having the translated amino acid sequence generated from the polynucleotide as broadly defined.

In the present invention, the full length sequence identified as SEQ ID NO:X was often generated by overlapping sequences contained in multiple clones (contig analysis). A representative clone containing all or most of the sequence for SEQ ID NO:X was deposited with the American Type Culture Collection ("ATCC"). As shown in Table 1, each clone is identified by a cDNA Clone ID (Identifier) and the ATCC Deposit Number. The ATCC is located at 10801 University Boulevard, Manassas, Va. 20110-2209, USA. The ATCC deposit was made pursuant to the terms of the Budapest Treaty on the international recognition of the deposit of microorganisms for purposes of patent procedure.

A "polynucleotide" of the present invention also includes those polynucleotides capable of hybridizing, under stringent hybridization conditions, to sequences contained in SEQ ID NO:X, the complement thereof, or the cDNA within the clone deposited with the ATCC. "Stringent hybridization conditions" refers to an overnight incubation at 42° C. in a solution comprising 50% formamide, 5×SSC (750 mM NaCl, 75 mM sodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at about 65° C.

Also contemplated are nucleic acid molecules that hybridize to the polynucleotides of the present invention at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37° C. in a solution comprising 6×SSPE (20×SSPE=3M NaCl; 0.2M NaH$_2$PO$_4$; 0.02M EDTA, pH 7.4), 0.5% SDS, 30% formamide, 100 ug/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Of course, a polynucleotide which hybridizes only to polyA+ sequences (such as any 3' terminal polyA+ tract of a cDNA shown in the sequence listing), or to a complementary stretch of T (or U) residues, would not be included in the definition of "polynucleotide," since such a polynucleotide would hybridize to any nucleic acid molecule containing a poly (A) stretch or the complement thereof (e.g., practically any double-stranded cDNA clone).

The polynucleotide of the present invention can be composed of any polyribonucleotide or polydeoxyribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotide can be composed of triple-stranded regions comprising RNA or DNA or both RNA and DNA. A polynucleotide may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

The polypeptide of the present invention can be composed of amino acids joined to each other by peptide bonds or modified peptide bonds, i.e., peptide isosteres, and may contain amino acids other than the 20 gene-encoded amino acids. The polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1-12 (1983); Seifter et al., Meth Enzymol 182:626-646 (1990); Rattan et al., Ann NY Acad Sci 663:48-62 (1992).)

"SEQ ID NO:X" refers to a polynucleotide sequence while "SEQ ID NO:Y" refers to a polypeptide sequence, both sequences identified by an integer specified in Table 1.

"A polypeptide having biological activity" refers to polypeptides exhibiting activity similar, but not necessarily identical to, an activity of a polypeptide of the present invention, including mature forms, as measured in a particular biological assay, with or without dose dependency. In the case where dose dependency does exist, it need not be identical to that of the polypeptide, but rather substantially similar to the dose-dependence in a given activity as compared to the polypeptide of the present invention (i.e., the candidate polypeptide will exhibit greater activity or not more than about 25-fold less and, preferably, not more than about ten-fold less activity, and most preferably, not more than about three-fold less activity relative to the polypeptide of the present invention.)

Polynucleotides and Polypeptides of the Invention

Features of Protein Encoded by Gene No: 1

This gene maps to chromosome 3 and therefore polynucleotides of the present invention can be used in linkage analysis as a marker for chromosome 3.

This gene is expressed in several fetal tissues including brain, liver, and lung, and to a lesser extent, in adult tissues, particularly skin.

Therefore, polynucleotides and polypeptides of the invention are useful as reagents for differential identification of the tissue(s) or cell type(s) present in a biological sample and for diagnosis of diseases and conditions which include, but are not limited to, developmental, neural, hepatic, or pulmonary disorders, particularly cancers of the above system and tissues. Similarly, polypeptides and antibodies directed to these polypeptides are useful in providing immunological probes for differential identification of the tissue(s) or cell type(s). For a number of disorders of the above tissues or cells, particularly of the central nervous system, hepatic system, and hepatic system, expression of this gene at significantly higher or lower levels may be routinely detected in certain tissues or cell types (e.g. brain, cancerous and wounded tissues) or bodily fluids (e.g., lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution indicates that polynucleotides and polypeptides corresponding to this gene are useful for serving as a target for a variety of blocking agents, as it is likely to be involved in the promotion of a variety of cancers. Furthermore, polynucleotides and polypeptides corresponding to this gene are useful for the diagnosis and treatment of cancer and other proliferative disorders. Expression within embryonic tissue and other cellular sources marked by proliferating cells indicates that this protein may play a role in the regulation of cellular division. Additionally, the expression in hematopoietic cells and tissues indicates that this protein may play a role in the proliferation, differentiation, and/or survival of hematopoietic cell lineages. In such an event, this gene may be useful in the treatment of lymphoproliferative disorders, and in the maintenance and differentiation of various hematopoietic lineages from early hematopoietic stem and committed progenitor cells. Similarly, embryonic development also involves decisions involving cell differentiation and/or apoptosis in pattern formation. Thus this protein may also be involved in apoptosis or tissue differentiation and could again be useful in cancer therapy. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:11 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1155 of SEQ ID NO:11, b is an integer of 15 to 1169, where both a and b correspond to the positions of nucleotide residues shown in SEQ ID NO:11, and where b is greater than or equal to a+14.

Features of Protein Encoded by Gene No: 2

In specific embodiments, the polypeptides of the invention comprise the sequence: MSVPAFIDISEEDQAAELRAY-LKSKGAEISEENSEGGLHVDLAQIIEA CDVCLKED-DKDVESVMNSVVSLLLILEPDKQEALI-ESLCEKLVKFREGERPSL RLQLLSNLFHGMDKNTPVRYTVYCS-LIKVAASCGAIQYIPTELDQVRKWISD WNLT-TEKKHTLLRLLYEALVDCKKSDAASKVM-VELLGSYTEDNASQARVD AHRCIVRALKDPNAFLFDHLLTLKPVKF-LEGELIHDLLTIFVSAKLASYVKFY QNNKDFID-SLGLLHEQNMAKMRLLTFMGMAVENKE-ISFDTMQQELQIGADD VEAFVIDAVRTKMVYCKIDQTQRKV-VVSHSTHRTFGKQQWQQLYDTLNAW KQNLNKVKNSLLSLSDT (SEQ ID NO:83), MSVPAFI-DISEED (SEQ ID NO:84), QAAELRAYLKS KGAE (SEQ ID NO:85), ISEENSEGGLHVDLAQI (SEQ ID NO:86), IEACDVCLK EDDKDVESV (SEQ ID NO:87), VARPSS-LFRSAWSCEW (SEQ ID NO:88), LRL QLLSNLFHG (SEQ ID NO:89), KDVESVMNSVVSLLLIL (SEQ ID NO:90), DAAS KVMVELLGSYTEDNASQARVDA (SEQ ID NO:91), KMRLLTFMGMAVENKEIS (SEQ ID NO:93), and/or VEAFVIDAVR (SEQ ID NO:92). Polynucleotides encoding these polypeptides are also encompassed by the invention. The translation product of this gene shares homology with the *Homo sapiens* GA17 protein (gb accession number AF064603). The gene encoding the disclosed cDNA is thought to reside on the X chromosome. Accordingly, polynucleotides related to this invention are useful as a marker in linkage analysis for the X chromosome.

This gene is expressed primarily in bone, and to a lesser extent, in brain, lung, T-cells, muscle, skin, testis, spleen and macrophages.

Therefore, polynucleotides and polypeptides of the invention are useful as reagents for differential identification of the tissue(s) or cell type(s) present in a biological sample and for diagnosis of diseases and conditions which include, but are not limited to, skeletal, neural, or hematopoietic disorders, particularly bone cancer, osteoarthritis, autoimmune diseases. Similarly, polypeptides and antibodies directed to these polypeptides are useful in providing immunological probes for differential identification of the tissue(s) or cell type(s). For a number of disorders of the above tissues or cells, particularly of the immune system and skeletal system, expression of this gene at significantly higher or lower levels may be routinely detected in certain tissues or cell types (e.g. bone, brain, lung, testis, and cancerous and wounded tissues) or bodily fluids (e.g., lymph, pulmonary surfactant or sputum, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:48 as residues: Arg-31 to Ser-37, Met-50 to Val-56, Glu-80 to Trp-87, Thr-94 to His-99, Tyr-129 to Ser-135, Tyr-193 to Phe-199, Ser-274 to Gln-285, Ala-293 to Lys-302.

The tissue distribution in bone and immune cells and tissues indicates that polynucleotides and polypeptides corresponding to this gene are useful for the diagnosis and/or treatment of skeletal and hematopoietic disorders. Elevated levels of expression of this gene product in bone suggest that it may be useful in influencing bone mass in such conditions as osteoporosis, or in the stimulation or growth of bone, cartilage, and/or tendons, for example. More generally, as evidenced by expression in T-cells and spleen, this gene may play a role in the survival, proliferation, and/or differentiation of hematopoietic cells in general, and may be of use in augmentation of the numbers of stem cells and committed progenitors. Expression of this gene product in macrophage also indicates that it may play a role in mediating responses to infection and controlling immunological responses, such as those that occur during immune surveillance. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:12 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1296 of SEQ ID NO:12, b is an integer of 15 to 1310, where both a and b correspond to the positions of nucleotide residues shown in SEQ ID NO:12, and where b is greater than or equal to a+14.

Features of Protein Encoded by Gene No: 3

The translation product of this gene shares sequence homology with various kinases. The closest homolog is the mouse TIF1 which is a conserved nuclear protein. TIF1 enhances RXR and RAR AF-2 in yeast and interacts in a ligand-dependent manner with several nuclear receptors in yeast and mammalian cells, as well as in vitro. Remarkably, these interactions require the amino acids constituting the AF-2 activating domain conserved in all active NRs. Moreover, the estrogen receptor (ER) AF-2 antagonist hydroxytamoxifen cannot promote ER-TIF1 interaction. TIF1, which contains several conserved domains found in transcriptional regulatory proteins, may be a mediator of ligand-dependent AF-2. Interestingly, the TIF1 N-terminal moiety is fused to B-raf in the mouse oncoprotein T18. One embodiment of this gene comprises polypeptides of the following amino acid sequence: MEAVPEGDWFCTVCLAQQVEGEFTQKPG-FPKRGQKRKSGYSLNFSEGDGRR RRVLLRG RESPAAGPRYSEEGLSPSKRRRLSMRN-HHSDLTFCEIILMEMESHD AAWPFLEPVNPRLVSGY-RRIIKNP MDFSTMRERLLRGGYTSSEEFAADALLV FDNCQTFNEDDSEVGKAGHIMRRFFESR-WEEFYQGKQANL (SEQ ID NO:94), MEAVPEGDW-FCTVCLAQQVE (SEQ ID NO:95), GEFTQKPGFP-KRGQKRKSG YS (SEQ ID NO:96), LNFSEGDGRRRRVLLRGRESP (SEQ ID NO:97), AAGPR YSEEGLSPSKRRRLS (SEQ ID NO:98), MRN-HHSDLTFCEIILMEMESH (SEQ ID NO:99), DAAWP-FLEPVNPRLVSGYRR (SEQ ID NO:100), IIKNPMDF-STMR ERLLRGGYT (SEQ ID NO:101), SSEEFAADALLVFDNCQTFNE (SEQ ID NO:102), DDSEVGKAGHIMRRFFE (SEQ ID NO:103), and/or SRWEEFYQGKQA NL (SEQ ID NO:104). An additional embodiment is the polynucleotides encoding these polypeptides.

This gene is expressed primarily in activated T-cells, and to a lesser extent, in testes and brain.

Therefore, polynucleotides and polypeptides of the invention are useful as reagents for differential identification of the tissue(s) or cell type(s) present in a biological sample and for diagnosis of diseases and conditions which include, but are not limited to, immune, reproductive, or neural disorders, particularly autoimmune diseases, AIDS, leukemias, and cancers. Similarly, polypeptides and antibodies directed to these polypeptides are useful in providing immunological probes for differential identification of the tissue(s) or cell type(s). For a number of disorders of the above tissues or cells, particularly of the immune, reproductive, or neural systems, expression of this gene at significantly higher or lower levels may be routinely detected in certain tissues or cell types (e.g. immune, neural, reproductive, and cancerous and wounded tissues) or bodily fluids (e.g., lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:49 as residues: Ala-31 to Glu-36.

The tissue distribution in activated T-cells, combined with the homology to TIF indicates that polynucleotides and polypeptides corresponding to this gene are useful for modulation of nuclear receptor and ligand interaction in various immune disorders. Furthermore, the secreted protein can also be used to determine biological activity, to raise antibodies, as tissue markers, to isolate cognate ligands or receptors, to identify agents that modulate their interactions and as nutritional supplements. It may also have a very wide range of biological activities. Typical of these are cytokine, cell proliferation/differentiation modulating activity or induction of other cytokines; immunostimulating/immunosuppressant activities (e.g. for treating human immunodeficiency virus infection, cancer, autoimmune diseases and allergy); regulation of hematopoiesis (e.g. for treating anaemia or as adjunct to chemotherapy); stimulation or growth of bone, cartilage, tendons, ligaments and/or nerves (e.g. for treating wounds, stimulation of follicle stimulating hormone (for control of fertility); chemotactic and chemokinetic activities (e.g. for treating infections, tumors); hemostatic or thrombolytic activity (e.g. for treating haemophilia, cardiac infarction etc.); anti-inflammatory activity (e.g. for treating septic shock, Crohn's disease); as antimicrobials; for treating psoriasis or other hyperproliferative diseases; for regulation of metabolism, and behaviour. Also contemplated is the use of the corresponding nucleic acid in gene therapy procedures. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:13 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1125 of SEQ ID NO:13, b is an integer of 15 to 1139, where both a and b correspond to the positions of nucleotide residues shown in SEQ ID NO:13, and where b is greater than or equal to a+14.

Features of Protein Encoded by Gene No: 4

This gene maps to chromosome 11. Accordingly, polynucleotides of the invention can be used in linkage analysis as a marker for chromosome [1]. In specific embodiments, the polypeptides of the invention comprise the sequence: MSEIYLRCQDEQQYARWMAGCRLASKGRTMADSSY (SEQ ID NO:105), LVAP RFQRKFKAKQLTPRILEAHQN-VAQLSLAEAQLRFIQAWQSL (SEQ ID NO:106), VGDV-VKTWRFSNMRQWNVNWDIR (SEQ ID NO:107), EEIDCTEEEMMVFA ALQYHINKLSQS (SEQ ID NO:108), and/or EEIDCTEEEMMVFAALQYHINKLS QS (SEQ ID NO:109). Polynucleotides encoding these polypeptides are also encompassed by the invention.

This gene is expressed primarily in white blood cell types including monocytes, T-cells, neutrophils, and to a lesser extent, in umbilical vein and liver.

Therefore, polynucleotides and polypeptides of the invention are useful as reagents for differential identification of the tissue(s) or cell type(s) present in a biological sample and for diagnosis of diseases and conditions which include, but are not limited to, various diseases of the immune system including AIDS, immunodeficiency diseases, and autoimmune disorders, in addition to hepatic and developmental disorders. Similarly, polypeptides and antibodies directed to these polypeptides are useful in providing immunological probes for differential identification of the tissue(s) or cell type(s). For a number of disorders of the above tissues or cells, particularly of the immune or hepatic system, expression of this gene at significantly higher or lower levels may be routinely detected in certain tissues or cell types (e.g. immune, hepatic, developmental, and cancerous and wounded tissues) or bodily fluids (e.g., lymph, bile, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:50 as residues: Ser-3 to Pro-9, Leu-17 to Leu-29, Asp-64 to Pro-69, Ile-105 to Gln-110, Thr-183 to Gln-200, Cys-239 to Arg-247, Ser-256 to Met-261, Gln-280 to Ala-296, Arg-310 to Thr-321, Lys-363 to Asp-368, Ser-395 to Trp-400, Thr-443 to Asp-453.

The tissue distribution in a variety of immune cells and tissues indicates that polynucleotides and polypeptides corresponding to this gene are useful for replacement therapy in a variety of immune system disorders. Furthermore, polynucleotides and polypeptides corresponding to this gene are useful for the diagnosis and/or treatment of hematopoietic disorders. This gene product is primarily expressed in hematopoietic cells and tissues, suggesting that it plays a role in the survival, proliferation, and/or differentiation of hematopoieitic lineages. This is particularly supported by the expression of this gene product in liver, which is a primary site of definitive hematopoiesis during development. Expression of this gene product in T cells and primary dendritic cells also strongly indicates a role for this protein in immune function and immune surveillance. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:14 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 2257 of SEQ ID NO:14, b is an integer of 15 to 2271, where both a and b correspond to the positions of nucleotide residues shown in SEQ ID NO:14, and where b is greater than or equal to a+14.

Features of Protein Encoded by Gene No: 5

The gene encoding the disclosed cDNA is thought to reside on chromosome 15. Accordingly, polynucleotides related to this invention are useful as a marker in linkage analysis for chromosome 15.

This gene is expressed primarily in brain.

Therefore, polynucleotides and polypeptides of the invention are useful as reagents for differential identification of the tissue(s) or cell type(s) present in a biological sample and for diagnosis of diseases and conditions which include, but are not limited to, neural disorders, particularly neurodegenerative and behaviour conditions, such as mood disorders, schizophrenia and related diseases, bipolar disorder and unipolar depression. Similarly, polypeptides and antibodies directed to these polypeptides are useful in providing immunological probes for differential identification of the tissue(s) or cell type(s). For a number of disorders of the above tissues or cells, particularly of the central nervous system, expression of this gene at significantly higher or lower levels may be routinely detected in certain tissues or cell types (e.g. brain, and cancerous and wounded tissues) or bodily fluids (e.g., lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:51 as residues: Met-1 to Gly-8, Pro-10 to Arg-17, Pro-45 to Ser-55, Gly-63 to Tyr-74.

The tissue distribution in brain indicates that polynucleotides and polypeptides corresponding to this gene are useful for the detection/treatment of neurodegenerative disease states and behavioural disorders such as Alzheimers Disease, Parkinsons Disease, Huntingtons Disease, schizophrenia, mania, dementia, paranoia, obsessive compulsive disorder and panic disorder. Also given the brain-specific expression of this gene, the promoter region of this gene may contain a brain-specific element that could be used for targeting expression of vector systems to the brain in gene replacement therapy. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:15 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 612 of SEQ ID NO:15, b is an integer of 15 to 626, where both a and b correspond to the positions of nucleotide residues shown in SEQ ID NO:15, and where b is greater than or equal to a+14.

Features of Protein Encoded by Gene No: 6

This gene maps to chromosome 1 and therefore, polynucleotides of the invention can be used in linkage analysis as a marker for chromosome 1.

This gene is expressed abundantly in rhabdomyosarcoma, and is expressed to a high level in different regions of the brain and pituitary gland.

Therefore, polynucleotides and polypeptides of the invention are useful as reagents for differential identification of the tissue(s) or cell type(s) present in a biological sample and for diagnosis of diseases and conditions which include, but are not limited to, neurological, muscular, or endocrine disorders, particularly soft tissue tumors, such as fibroids. Similarly, polypeptides and antibodies directed to these polypeptides are useful in providing immunological probes for differential identification of the tissue(s) or cell type(s). For a number of disorders of the above tissues or cells, particularly of the brain, expression of this gene at significantly higher or lower levels may be routinely detected in certain tissues or cell types (e.g. brain, muscle, endocrine, and cancerous and wounded tissues) or bodily fluids (e.g., lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution in rhadomyosarcoma tissue indicates a role for the protein product either in the detection and/or treatment of musculo-skeletal disorders including muscle degeneration, muscle wasting, rhabdomyolysis, muscular dystrophy, cardiomyopathy, fibroids, myomas, and rhabdomyosarcomas. Furthermore, expression in the brain indicates a role for the protein product of this gene in the detection/treatment of neurodegenerative disease states and behavioural disorders such as Alzheimers Disease, Parkinsons Disease, Huntingtons Disease, schizophrenia, mania, dementia, paranoia, obsessive compulsive disorder and panic disorder. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:16 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 2104 of SEQ ID NO:16, b is an integer of 15 to 2118, where both a and b correspond to the positions of nucleotide residues shown in SEQ ID NO:16, and where b is greater than or equal to a+14.

Features of Protein Encoded by Gene No: 7

The translation product of this gene shares sequence homology with the TDAG51 gene which is thought to be important in the mediation of apoptosis and cell death by coupling TCR stimulation to Fas expression. In specific embodiments, the polypeptides of the invention comprise the sequence: KELSFARIKAVECVESTGRHIYFTLV (SEQ ID NO:110) and/or GWNAQITLGLV KFKNQQ (SEQ ID NO:111). The gene encoding the disclosed cDNA is thought to reside on chromosome 1. Accordingly, polynucleotides related to this invention are useful as a marker in linkage analysis for chromosome 1.

This gene is expressed in breast cancer tissue, and to a lesser extent, in macrophage.

Therefore, polynucleotides and polypeptides of the invention are useful as reagents for differential identification of the tissue(s) or cell type(s) present in a biological sample and for diagnosis of diseases and conditions which include, but are not limited to, immune or reproductive disorders, particularly breast cancer. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g. breast, immune, and cancerous and wounded tissues) or bodily fluids (e.g., lymph, breast milk, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:54 as residues: Met-1 to Pro-9, Gln-43 to Glu-49, Phe-95 to Arg-102.

The tissue distribution in breast cancer tissue, combined with the homology to the TDAG51 gene indicates that polynucleotides and polypeptides corresponding to this gene are useful for diagnosis and intervention of immune disorders, such as immunodeficiency, allergy, infection, inflammation, and tissue/organ transplantation. Alternatively, the tissue distribution in tumors of breast origins indicates that polynucleotides and polypeptides corresponding to this gene are useful for the diagnosis and intervention of these tumors, particularly during antigen presentation early in the immune response. Protein, as well as, antibodies directed against the protein may show utility as a tissue-specific marker and/or immunotherapy target for the above listed tissues.

Many polynucleotide sequences, such as EST sequences, are publicly available and accessible through sequence databases. Some of these sequences are related to SEQ ID NO:17 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1062 of SEQ ID NO:17, b is an integer of 15 to 1076, where both a and b correspond to the positions of nucleotide residues shown in SEQ ID NO:17, and where b is greater than or equal to a+14.

Features of Protein Encoded by Gene No: 8

The gene encoding the disclosed cDNA is thought to reside on chromosome 1. Accordingly, polynucleotides related to this invention are useful as a marker in linkage analysis for chromosome 1. One embodiment of this gene comprises the polypeptides of the following amino acid sequence: MVTTIVLGRRFIGSIVKEASQRGKVSLFR-SILLFLTRFTVLTATGWSLCRS LIHLFRTYSFLNLL-FLCYPFGMYIPFLQLNXXLRKTSLFNHMASMGPREA-VSG LAKSRDYLLTLRETWKQ HXRQLYGPDAMP-THACCLSPSLIRSEVEFLKMDFN WRMKEVLVSSML-SAYYVAFVPVWFVKNTHYYDKRW SCX-TLPAGVHQHL RDPHAAPAACQLL (SEQ ID NO:112), MVTTIVLGRRFIGSIVKEASQRGKVS (SEQ ID NO:113), LFRSILLFLTRFTVLTATGWSLC (SEQ ID NO:114), RSLIH LFRTYSFLNLLFLCYPFGMYIPFLQ (SEQ ID NO:115), LNXXLRKTSLFNH MASMG-PREAVSGLAKSR (SEQ ID NO:116), DYLLTL-RETWKQHXRQLYGPD AMPTHACCL (SEQ ID NO:117), SPSLIRSEVEFLKMDFNWRMKEV-LVSSMLSA (SEQ ID NO:118), YYVAFVPVW-FVKNTHYYDKRWSCXTLP (SEQ ID NO:119), and/or AGVHQHLRDPHAAPAACQLL (SEQ ID NO:120). An additional embodiment is the polynucleotides encoding these polypeptides.

This gene is expressed in breast tissue, amniotic cells, and to a lesser extent, in smooth muscle, T-cells, and infant brain.

Therefore, polynucleotides and polypeptides of the invention are useful as reagents for differential identification of the tissue(s) or cell type(s) present in a biological sample and for diagnosis of diseases and conditions which include, but are not limited to, reproductive or developmental disorders, particularly fetal distress syndrome and embryonic wasting. Similarly, polypeptides and antibodies directed to these polypeptides are useful in providing immunological probes for differential identification of the tissue(s) or cell type(s). For a number of disorders of the above tissues or cells, particularly of the female reproductive system, expression of this gene at significantly higher or lower levels may be routinely detected in certain tissues or cell types (e.g. breast, fetal, neural, immune, hematopoietic, muscular, and cancerous and wounded tissues) or bodily fluids (e.g., lymph, amniotic fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution in breast tissue indicates that polynucleotides and polypeptides corresponding to this gene are useful for the diagnosis and/or treatment of reproductive disorders. Alternately, this gene product may be produced by the placenta and then transported to the embryo, where it may play a crucial role in the development and/or survival of the developing embryo or fetus. Expression of this gene product in a vascular-rich tissue such as the breast and amnion also indicates that this gene product may be produced more generally in endothelial cells or within the circulation. In such instances, it may play more generalized roles in vascular function, such as in angiogenesis. It may also be produced in the vasculature and have effects on other cells within the circulation, such as hematopoietic cells. It may serve to promote the proliferation, survival, activation, and/or differentiation of hematopoietic cells, as well as other cells throughout the body. Protein, as well as, antibodies directed against the protein may show utility as a tumor marker and/or immunotherapy targets for the above listed tissues.

Features of Protein Encoded by Gene No: 9

In specific embodiments, the polypeptides of the invention comprise the sequence: LVLGLSXLNNSYNFSF (SEQ ID NO:121), HVVIGSQAEEGQYSLNF (SEQ ID NO:122), HNCNNSVPGKEHPFDITVM (SEQ ID NO:123), FIKYVLSD KEKKVFGIV (SEQ ID NO:124), IPMQVLANVAYII (SEQ ID NO:125), IPMQVL ANVAYII (SEQ ID NO:126), DGKVAVNLAKLKLFR (SEQ ID NO:127), and/or IREKNPDGFLSAA (SEQ ID NO:128). Polynucleotides encoding these polypeptides are also encompassed by the invention. The gene encoding the disclosed cDNA is thought to reside on chromosome 19. Accordingly, polynucleotides related to this invention are useful as a marker in linkage analysis for chromosome 19.

This gene is primarily expressed in the fetal liver/spleen and pituitary gland.

Therefore, polynucleotides and polypeptides of the invention are useful as reagents for differential identification of the tissue(s) or cell type(s) present in a biological sample and for diagnosis of diseases and conditions which include, but are not limited to, immune, hematopoietic, or endocrine disorders, particularly cancers and other proliferative conditions. Similarly, polypeptides and antibodies directed to these polypeptides are useful in providing immunological probes for differential identification of the tissue(s) or cell type(s). For a number of disorders of the above tissues or cells, particularly of the hepatic, immune and hematopoietic systems, expression of this gene at significantly higher or lower levels may be routinely detected in certain tissues or cell types (e.g. liver, spleen, pituitary, developmental, and cancerous and wounded tissues) or bodily fluids (e.g., lymph, amniotic fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:55 as residues: Ser-62 to Cys-71, Thr-78 to Leu-86, Ser-104 to Lys-109, Ser-130 to Ala-135, Gln-168 to Asp-174.

The tissue distribution in fetal liver/spleen indicates that polynucleotides and polypeptides corresponding to this gene are useful for the diagnosis and treatment of hepatic disorders, and disorders of the immune and hematopoietic systems, such as hepatic failure, hepatitis, alcoholic liver diseases, portal hypertension, toxic liver injury, liver transplantation, and neoplasm of the liver. The expression in the fetal liver spleen also indicate its function in hematopoiesis, and therefore the gene may be useful in hematopoietic disorders including anemia, leukemia or cancer radiotherapy/chemotherapy. The expression in the pituitary gland may indicate its use in endocrine disorders with systemic or specific manifestations. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:19 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1323 of SEQ ID NO:19, b is an integer of 15 to 1337, where both a and b correspond to the positions of nucleotide residues shown in SEQ ID NO:19, and where b is greater than or equal to a+14.

Features of Protein Encoded by Gene No: 10

The translation product of this gene shares sequence homology with a DNA binding protein from *Gallus gallus* which is thought to be important in transcriptional regulation of gene expression. In specific embodiments, polypeptides of the invention comprise the sequence: MMFGGYETI (SEQ ID NO:129), YRDESSSELSVDSE VEFQLYSQIH (SEQ ID NO:130), YAQDLDDVIREEEHEEKNSGNSESSSSKPNQ KKLIVLSDSEVIQLSDGSEVITLSDED-SIYRCKGKNVRVQAQENAHGLSSSLQS NELVD-KKCKSDIEKPKSEERSGVIREVMI-IEVSSSEEEESTISEGDNVESW (SEQ ID NO:131), MLLGCEVDDKDDDILLNLVGCENS-VTEGEDGINWSIS (SEQ ID NO:132), DKDIEAQIAN-NRTPGRWT (SEQ ID NO:133), QRYYSANKNIICRNC DKRGHLSKNCPLPRKV (SEQ ID NO:134), and/or RRC-FLCSRRGHLLYS CPAPL CEYCPVPKMLDH-SCLFRHSWDKQCDRCHMLGHYTDACTEI-WRQYHLTTKP GPPKKPKTPSRPSALAYCYH-CAQKGHYGHECPEREVYDPSPVSPFICYYXDK YEIQEREKRLKQKIKVXKKNGVIPEP-SKLPYIKAANENPHHDIRKGRASWKSN RWPQ (SEQ ID NO:135). Polynucleotides encoding these polypeptides are also encompassed by the invention.

This gene is expressed in tonsils and bone marrow.

Therefore, polynucleotides and polypeptides of the invention are useful as reagents for differential identification of the tissue(s) or cell type(s) present in a biological sample and for diagnosis of diseases and conditions which include, but are not limited to, disorders of the immune, hematopoietic, and lymphatic systems. Similarly, polypeptides and antibodies directed to these polypeptides are useful in providing immunological probes for differential identification of the tissue(s) or cell type(s). For a number of disorders of the above tissues or cells, particularly of the immune, hematopoietic, and lymph systems, expression of this gene at significantly higher or lower levels may be routinely detected in certain tissues or cell types (e.g. immune, hematopoietic, and cancerous and wounded tissues) or bodily fluids (e.g., lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution in bone marrow and tonsil tissues, combined with the homology to a DNA binding protein indicates that polynucleotides and polypeptides corresponding to this gene are useful for the treatment and diagnosis of disorders in the immune, hematopoietic, and lymph systems. Furthermore, expression of this gene product in tonsils indicates a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g. by boosting immune responses). Since the gene is expressed in cells of lymphoid origin, the gene or protein, as well as, antibodies directed against the protein may show utility as a tumor marker and/or immunotherapy targets for the above listed tissues. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:20 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1376 of SEQ ID NO:20, b is an integer of 15 to 1390, where both a and b correspond to the positions of nucleotide residues shown in SEQ ID NO:20, and where b is greater than or equal to a+14.

Features of Protein Encoded by Gene No: 11

One embodiment of this gene comprises polypeptides of the following amino acid sequence: MSFPPHLNRPPMGI-PALPPGIPPPQFPGFPPPVPPGTPMI-PVPMSIMAPAPTVLV PTVSMVGKHLGARKDH-PGLKAKENDENCGPTTTVFVGNISEKASDMLIRQLL AKCGLVLSWKRVQGASGKLQAFG-FCEYKEPESTLRALRLLHDLQIGEKKLLV KVDAKT-KAQLDEWKAKKKASNGNARPETVTND-DEEALDEETKRRDQMIKG AIEVLIREYSSELNAPSQESDSH-PRKKKKEKKEDIFRRFPVAPLIPYPLITKEDIN AIEMEEDKRDLISREISKFRDTH-KKLEEEKGKKEKERQEIEKERRERERERERE RERRE-RERERERERREKEKERERE-RERDRDRDRTKERDRDRDRERDRDRDR ERSSDRNKDRIRSREKSRDRERERERE-RERERERERERERERERE (SEQ ID NO:136), MSFPPHL-NRPPMGIPALPPGIPPPQFPGFPPPVPPGTPMIPVP (SEQ ID NO:137), MSIMAPAPTVLVPTVSMVGKHL-GARKDHPGLKAKE (SEQ ID NO:138), NDEN CGPTTTVFVGNISEKASDMLIRQL-LAKCGLVLSWKRV (SEQ ID NO:139), QGA SGKLQAF-GFCEYKEPESTLRALRLLHDLQIGEKKLLV (SEQ ID NO:140), KVDA KTKAQLDEWKAKKKASNGNAR-PETVTNDDEEALDE (SEQ ID NO:141), ETKR RDQMIK-GAIEVLIREYSSELNAPSQESDSHPRKKKK (SEQ ID NO:142), EKKEDI FRRFPVAPLIPYPLITKEDINAI-EMEEDKRDLISREIS (SEQ ID NO:143), KFRDTH KKLEEEKGKKEKERQEIEKERRERERERERERR (SEQ ID NO:144), ERERE RERERERREKEKERERE-RERDRDRDRTKERDRDRDRE (SEQ ID NO:145), and/or RDRDRDRERSSDRNKDRIRSREKSR-DRERERERERERERERERERERE (SEQ ID NO:146). Polynucleotides encoding these polypeptides are also encompassed by the invention.

This gene is expressed in fetal liver/spleen, dendritic, and T-cells.

Therefore, polynucleotides and polypeptides of the invention are useful as reagents for differential identification of the tissue(s) or cell type(s) present in a biological sample and for diagnosis of diseases and conditions which include, but are not limited to, immune or hematopoietic disorders. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g. immune, hematopoietic, and cancerous and wounded tissues) or bodily fluids (e.g., lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution in immune cells and tissues indicates that the protein products of this gene are useful for the treatment and diagnosis of immune system disorders, particularly those involving dendritic or T-cells such as inflammation. Furthermore, this gene product is primarily expressed in hematopoietic cells and tissues, suggesting that it plays a role in the survival, proliferation, and/or differentiation of hematopoietic lineages. This is particularly supported by the expression of this gene product in fetal liver, which is a primary site of definitive hematopoiesis. Expression of this gene product in T cells and primary dendritic cells also strongly indicates a role for this protein in immune function and immune surveillance. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:21 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1417 of SEQ ID NO:21, b is an integer of 15 to 1431, where both a and b correspond to the positions of nucleotide residues shown in SEQ ID NO:21, and where b is greater than or equal to a+14.

Features of Protein Encoded by Gene No: 12

Preferred polypeptides encoded by this gene include the following: MGLNPPGLTSALKPQMEGRLVGGGGSF- SSRGRHPAGWVLPQPCLLL SPTLS FPPACGLLVPSPSLLPAVSSYHLPLGRG-LIRPAFKIKVCSKLTVWCSLPSPSRW RCCHGNAVALP ALGPWRXWEQGSAVRSPAFPVRQAWLPCSGSLTSW (SEQ ID NO:150), KPQMEGRLVGGGGSFSSRGRHP (SEQ ID NO:147), LLVPSPSL LPAVSSYHLPLGRGLIR (SEQ ID NO:148), and/or EQGSAVRSPAFPVR QA WLPC-SGS (SEQ ID NO:149). Also provided are polynucleotides encoding such polypeptides.

This gene is expressed in activated neutrophils, endothelial cells, T cells, and to a lesser extent, in brain and liver.

Therefore, polynucleotides and polypeptides of the invention are useful as reagents for differential identification of the tissue(s) or cell type(s) present in a biological sample and for diagnosis of diseases and conditions which include, but are not limited to, immune, hematopoietic, integumentary, or vascular disorders, particularly immunodeficiencies such as AIDS, and susceptibility to infectious disease. Similarly, polypeptides and antibodies directed to these polypeptides are useful in providing immunological probes for differential identification of the tissue(s) or cell type(s). For a number of disorders of the above tissues or cells, particularly of the immune system and skin, expression of this gene at significantly higher or lower levels may be routinely detected in certain tissues or cell types (e.g. brain, immune, integumentary, and cancerous and wounded tissues) or bodily fluids (e.g., lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:58 as residues: Glu-41 to Val-46.

The tissue distribution in immune cells indicates that the gene product is useful for the diagnosis and/or treatment of a variety of disorders, including hematopoietic disorders, neurological disorders, liver disease, and disorders involving angiogenesis. The expression of this gene product in hematopoietic cells and tissues indicates that it plays a role in the survival, proliferation, and/or differentiation of hematopoietic lineages. This is particularly supported by the expression of this gene product in fetal liver, which is a primary site of definitive hematopoiesis. Expression of this gene product in T cells and neutrophils also strongly indicates a role for this protein in immune function and immune surveillance. Additionally, the tissue distribution indicates that polynucleotides and polypeptides corresponding to this gene are useful for the detection/treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, or sexually-linked disorders. Moreover, expression within endothelial cells indicates that the protein is useful in the treatment and/or diagnosis of a variety of vascular disorders, which include, but are not limited to, embolism, aneurysm, microvascular disease, atherosclerosis, and stroke. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:22 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 2525 of SEQ ID NO:22, b is an integer of 15 to 2539, where both a and b correspond to the positions of nucleotide residues shown in SEQ ID NO:22, and where b is greater than or equal to a+14.

Features of Protein Encoded by Gene No: 13

This gene is expressed in keratinocytes, and to a lesser extent, in endothelial cells and placenta.

Therefore, polynucleotides and polypeptides of the invention are useful as reagents for differential identification of the tissue(s) or cell type(s) present in a biological sample and for diagnosis of diseases and conditions which include, but are not limited to, integumentary or vascular disorders, particularly impaired wound healing and autoimmune disorders. Similarly, polypeptides and antibodies directed to these polypeptides are useful in providing immunological probes for differential identification of the tissue(s) or cell type(s). For a number of disorders of the above tissues or cells, particularly of the skin, expression of this gene at significantly higher or lower levels may be routinely detected in certain tissues or cell types (e.g. integumentary, endothelial, and cancerous and wounded tissues) or bodily fluids (e.g., lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:59 as residues: Pro-35 to Trp-42, Ala-53 to Asp-62, Arg-103 to Pro-113.

The tissue distribution in keratinocytes indicates that the protein products of this gene are useful for the treatment of wound healing deficiency and skin disorders, including congenital disorders (i.e. nevi, moles, freckles, Mongolian spots, hemangiomas, port-wine syndrome), integumentary tumors (i.e. keratoses, Bowen's disease, basal cell carcinoma, squamous cell carcinoma, malignant melanoma, Paget's disease, mycosis fungoides, and Kaposi's sarcoma), injuries and inflammation of the skin (i.e. wounds, rashes, prickly heat disorder, psoriasis, dermatitis), atherosclerosis, uticaria, eczema, photosensitivity, autoimmune disorders (i.e. lupus erythematosus, vitiligo, dermatomyositis, morphea, scleroderma, pemphigoid, and pemphigus), keloids, striae, erythema, petechiae, purpura, and xanthelasma. Moreover, such disorders may predispose increased susceptibility to viral and bacterial infections of the skin (i.e. cold sores, warts, chickenpox, molluscum contagiosum, herpes zoster, boils, cellulitis, erysipelas, impetigo, tinea, athletes foot, and ringworm). Moreover, expression within endothelial cells and pancreatic tissues indicates that the protein product of this gene may be useful in the treatment and/or prevention of a variety of vascular disorders, particularly those involving highly vascularized tissues, which include, but are not limited to, embolism, aneurysm, stroke, atherosclerosis, and microvascular disease. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:23 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1027 of SEQ ID NO:23, b is an integer of 15 to 1041, where both a and b correspond to the positions of nucleotide residues shown in SEQ ID NO:23, and where b is greater than or equal to a+14.

Features of Protein Encoded by Gene No: 14

Preferred polypeptides encoded by this gene comprise the following amino acid sequence: NVTKITLESFLAWKKRKRQEKID KLEQDMERRKADFKAGKAL VISGREVFEFRPELVNDDDEEA (SEQ ID NO:151), and/or ERRKADFKAGKALV ISGREVFE (SEQ ID NO:152). Polynucleotides encoding these polypeptides are also encompassed by the invention. The gene encoding the disclosed cDNA is thought to reside on chromosome 2. Accordingly, polynucleotides related to this invention are useful as a marker in linkage analysis for chromosome 2.

This gene is expressed in kidney, and to a lesser extent, in embryonic tissues.

Therefore, polynucleotides and polypeptides of the invention are useful as reagents for differential identification of the tissue(s) or cell type(s) present in a biological sample and for diagnosis of diseases and conditions which include, but are not limited to, renal, urogenital, or developmental disorders, particularly renal failure. Similarly, polypeptides and antibodies directed to these polypeptides are useful in providing immunological probes for differential identification of the tissue(s) or cell type(s). For a number of disorders of the above tissues or cells, particularly of the kidney, expression of this gene at significantly higher or lower levels may be routinely detected in certain tissues or cell types (e.g. kidney, developmental, and cancerous and wounded tissues) or bodily fluids (e.g., lymph, amniotic fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution in kidney indicates that this gene or gene product could be used in the treatment and/or detection of kidney diseases including renal failure, nephritus, renal tubular acidosis, proteinuria, pyuria, edema, pyelonephritis, hydronephritis, nephrotic syndrome, crush syndrome, glomerulonephritis, hematuria, renal colic and kidney stones, in addition to Wilms Tumor Disease, and congenital kidney abnormalities such as horseshoe kidney, polycystic kidney, and Falconi's syndrome. Expression within embryonic tissue indicates that this protein may play a role in the regulation of cellular division, and may show utility in the diagnosis and treatment of cancer and other proliferative disorders. Similarly, developmental tissues rely on decisions involving cell differentiation and/or apoptosis in pattern formation. Thus this protein may also be involved in apoptosis or tissue differentiation and could again be useful in cancer therapy. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:24 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1948 of SEQ ID NO:24, b is an integer of 15 to 1962, where both a and b correspond to the positions of nucleotide residues shown in SEQ ID NO:24, and where b is greater than or equal to a+14.

Features of Protein Encoded by Gene No: 15

The gene encoding the disclosed cDNA is thought to reside on chromosome 22. Accordingly, polynucleotides related to this invention are useful as a marker in linkage analysis for chromosome 22.

This gene is expressed primarily in brain, and to a lesser extent, in liver.

Therefore, polynucleotides and polypeptides of the invention are useful as reagents for differential identification of the tissue(s) or cell type(s) present in a biological sample and for diagnosis of diseases and conditions which include, but are not limited to, neural or hepatic disorders, particularly depression, manic depression and other neurodegenerative diseases. Similarly, polypeptides and antibodies directed to these polypeptides are useful in providing immunological probes for differential identification of the tissue(s) or cell type(s). For a number of disorders of the above tissues or cells, particularly of the central nervous system, expression of this gene at significantly higher or lower levels may be routinely detected in certain tissues or cell types (e.g. brain, liver, cancerous and wounded tissues) or bodily fluids (e.g., lymph, bile, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution in brain indicates that the protein products of this gene are useful for the treatment of central nervous system disorders such as depression and other mental illnesses, and neurodegenerative disorders, such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, or sexually-linked disorders. Moreover, the expression within liver tissue indicates that polynucleotides and polypeptides corresponding to this gene are useful for the detection and treatment of liver disorders and cancers (e.g. hepatoblastoma, jaundice, hepatitis, liver metabolic diseases and conditions that are attributable to the differentiation of hepatocyte progenitor cells). Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:25 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1214 of SEQ ID NO:25, b is an integer of 15 to 1228, where both a and b correspond to the positions of nucleotide residues shown in SEQ ID NO:25, and where b is greater than or equal to a+14.

Features of Protein Encoded by Gene No: 16

The translation product of this gene shares homology with Prefoldin, which is believed to function as a chaperone that delivers unfolded proteins to cytosolic chaperonins (Cell 93, 863-873 (1998)). In specific embodiments, polypeptides of the invention comprise the following amino acid sequence: MCDELPGE GRWEPGQDR KLCLSFPLGTPARPIKS-VCPTLLSLVFLSRGMEQRVREAVAVSTSAPAPSASEP FLSWGMG LAXFSFPFLYL (SEQ ID NO:153), GASLGSSSSCPSH SWWGQRSVCRETASPLPRWM-LYLDGLATSHFLHHPEPHLLPSPGVFTRLCCH LCPGHXSLSGCVMNSQER EDGSQGKIGSSA (SEQ ID NO:154), TSVLSSSSVYCMQARKLS-VSQRYRKGKEKXARPIPQERKGSDAEGAGAEVET ATASLTLCSIPLLKKTRLSRVGQTL-FIGLAGVPSGKLRQSFLSCPGSHLPSPGSS SHIPRGKX-VLGRGGSKAG (SEQ ID NO:155), ALVKGTGREKRRX-QGPSPKKGRALMQREQELRWRRPLmPLSPSVPSLCS-RKP GLAEWDRRFLLVWLACLVESSGRASYLA-LAPIFPLLGVHHTSREGXVSWAEV AAKPGKN-SRAGKQMGLRVMQKM (SEQ ID NO:156), SFPLGT-PARPIKSVCPTLLSLVFLSRGMEQRV (SEQ ID NO:157), TASPLPRWM LYLDGLATSHFLHHPEPHLLPS (SEQ ID NO:158), RKGSDAEGAGAEVETA TASLTLCSIPLLKKT (SEQ ID NO:159), QREQELRWRRPLPLPSPSVPSLCSRK (SEQ ID NO:160), and/or PLLGVHHTSREGXVSWAE-VAAKPGKNSRA (SEQ ID NO:161). Polynucleotides encoding these polypeptides are also encompassed by the invention. The gene encoding the disclosed cDNA is thought to reside on chromosome 5. Accordingly, polynucleotides related to this invention are useful as a marker in linkage analysis for chromosome 5.

This gene is expressed in fetal brain, and to a lesser extent, in placenta, endothelial cells, fetal lung, and T cells.

Therefore, polynucleotides and polypeptides of the invention are useful as reagents for differential identification of the tissue(s) or cell type(s) present in a biological sample and for diagnosis of diseases and conditions which include, but are not limited to, neural or developmental disorders, particularly restinosis, birth defects and immune disorders. Similarly, polypeptides and antibodies directed to these polypeptides are useful in providing immunological probes for differential identification of the tissue(s) or cell type(s). For a number of disorders of the above tissues or cells, particularly of the cardiovascular system, and developmental process, expression of this gene at significantly higher or lower levels may be routinely detected in certain tissues or cell types (e.g. brain, endothelial cells, developmental, immune, pulmonary, and cancerous and wounded tissues) or bodily fluids (e.g., lymph, pulmonary surfactant or sputum, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:62 as residues: Gln-36 to Lys-42, Glu-89 to Arg-104.

The tissue distribution in brain, combined with the homology to prefoldin indicates that the protein products of this gene are useful for the development of agonists and/or antagonists for treatment of nervous system disorders and fetal developmental disorder, and indicates that the translation product of this gene is useful in the detection and/or treatment of diseases associated with the improper delivery of unfolded proteins to cytosolic chaperoning. Furthermore, the tissue distribution indicates that polynucleotides and polypeptides corresponding to this gene are useful for the detection/treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, sexually-linked disorders, or disorders of the cardiovascular system. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:26 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1326 of SEQ ID NO:26, b is an integer of 15 to 1340, where both a and b correspond to the positions of nucleotide residues shown in SEQ ID NO:26, and where b is greater than or equal to a+14.

Features of Protein Encoded by Gene No: 17

In specific embodiments, polypeptides of the invention comprise the following amino acid sequence: MSVLKGER-QQTLALAVLSVAKENA RDVCCLQGWQD TSCRDTSCAALRGGLQTLFPAPVHFRCG-GPAELKGRGS (SEQ ID NO:162), AHSFTTPEEAR-GAGSMGCRFPFKHTHSPHPRRPEVQ-GAWAGCTSAGEKAEPP PSREPGSQAS RFPLPP (SEQ ID NO:163), GWQDTSCRDTSCAALRGGLQTLFPA (SEQ ID NO:164), and/or GCRFPFKHTHSPHPRRPEVQ-GAWA (SEQ ID NO:165). Polynucleotides encoding these polypeptides are also encompassed by the invention.

This gene is expressed in hemangiopericytoma, and to a lesser extent, in fetal tissues.

Therefore, polynucleotides and polypeptides of the invention are useful as reagents for differential identification of the tissue(s) or cell type(s) present in a biological sample and for diagnosis of diseases and conditions which include, but are not limited to, developmental disorders, particularly hemangiopericytomas and other soft-tissue cancers, as well as other proliferative disorders. Similarly, polypeptides and antibodies directed to these polypeptides are useful in providing immunological probes for differential identification of the tissue(s) or cell type(s). For a number of disorders of the above tissues or cells, expression of this gene at significantly higher or lower levels may be routinely detected in certain tissues or cell types (e.g. fetal, kidney, and cancerous and wounded tissues) or bodily fluids (e.g., lymph, amniotic fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:63 as residues: Glu-43 to Pro-51, Gly-71 to Arg-82, Pro-96 to Arg-103, Thr-130 to Gly-140.

The polynucleotides and polypeptides related to this gene are believed to be useful for the treatment and diagnosis of tumors, particularly hemangiopericytomas, and for the treatment of developmental disorders. Furthermore, the tissue distribution indicates that polynucleotides and polypeptides corresponding to this gene are useful for the diagnosis and/or treatment of disorders of the developing embryo, where it may play a crucial role in the development and/or survival of the developing embryo or fetus. Expression of this gene product in a vascular-rich tissue such as the placenta also indicates that this gene product may be produced more generally in endothelial cells or within the circulation. In such instances, it may play more generalized roles in vascular function, such as in angiogenesis. It may also be produced in the vasculature and have effects on other cells within the circulation, such as hematopoietic cells. It may serve to promote the proliferation, survival, activation, and/or differentiation of hematopoietic cells, as well as other cells throughout the body.

Many polynucleotide sequences, such as EST sequences, are publicly available and accessible through sequence databases. Some of these sequences are related to SEQ ID NO:27 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a-b, where a is any integer between 1 to 792 of SEQ ID NO:27, b is an integer of 15 to 806, where both a and b correspond to the positions of nucleotide residues shown in SEQ ID NO:27, and where b is greater than or equal to a+14.

Features of Protein Encoded by Gene No: 18

In specific embodiments, polypeptides of the invention comprise the following amino acid sequence: PHQVEGR-LGTMETWDSSHEGLLHCRIPLKG-SWVQEPSCQYQWRRTRCMGIP PATSGWPCRAPAFL-CARA EFPASPGGSTNF (SEQ ID NO:166), L VTPPSGGET GDHGNMGQLPRRALALQNSTQGILGP-GAELPVSVEKDKVHGDPASNIRMAM PGTRFPLCSC RIPCQPGGIH (SEQ ID NO:167), EGLLHCRIPLKG-SWVQEPS CQYQWRRTRCMGI (SEQ ID NO:168), and/or QNSTQGILGPGAELPVSVEKDK VHGDPAS (SEQ ID NO:169). Polynucleotides encoding these polypeptides are also encompassed by the invention.

This gene is expressed in fetal liver, and to a lesser extent, in brain and T cells.

Therefore, polynucleotides and polypeptides of the invention are useful as reagents for differential identification of the tissue(s) or cell type(s) present in a biological sample and for diagnosis of diseases and conditions which include, but are not limited to, neural, developmental, hepatic, or immune and hematopoietic disorders. Similarly, polypeptides and antibodies directed to these polypeptides are useful in providing immunological probes for differential identification of the tissue(s) or cell type(s). For a number of disorders of the above tissues or cells, particularly of the hepatic system, nervous system and immune system, expression of this gene at significantly higher or lower levels may be routinely detected in certain tissues or cell types (e.g. immune, liver, brain, cancerous and wounded tissues) or bodily fluids (e.g., lymph, amniotic fluid, bile, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution in brain indicates that the protein products of this gene are useful for the identification of agonists and/or antagonists for the treatment of mental illnesses such as schizophrenia and depression. The gene product may also be useful for monitoring fetal development during pregnancy. Furthermore, the expression of this gene product in fetal liver indicates a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g. by boosting immune responses). Since the gene is expressed in cells of lymphoid origin, the gene or protein, as well as, antibodies directed against the protein may show utility as a tumor marker and/or immunotherapy targets for the above listed tissues. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Alternatively, the tissue distribution indicates that polynucleotides and polypeptides corresponding to this gene are useful for the detection and treatment of liver disorders and cancers (e.g. hepatoblastoma, jaundice, hepatitis, liver metabolic diseases and conditions that are attributable to the differentiation of hepatocyte progenitor cells). Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:28 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a-b, where a is any integer between 1 to 682 of SEQ ID NO:28, b is an integer of 15 to 696, where both a and b correspond to the positions of nucleotide residues shown in SEQ ID NO:28, and where b is greater than or equal to a+14.

Features of Protein Encoded by Gene No: 19

In specific embodiments, polypeptides of the invention comprise the following amino acid sequence: FGTRKKYHLCMIPNLDLNLDRDLVLPD-VSYQVESSEEDQSQT (SEQ ID NO:170), FLLSLGSLVMLLQDLVHSELDGTL-HYTVALHKDGIEMSCEQSIDSPDFHLLD WKCTVEIH KEKKQQSLSLRIHSLRLILLTGFHL-ITXIWKHQISIQIEIQIGY HTQ MVFFPRAE (SEQ ID NO:171), VHSELDGTLHYTVALHKDGIEMSCEQ (SEQ ID NO:172), and/or QSLSLRIHSLRLILLTGFHLITXI-WKHQ (SEQ ID NO:173). Polynucleotides encoding these polypeptides are also encompassed by the invention.

This gene is expressed in T cells, fetal liver, and to a lesser extent in brain.

Therefore, polynucleotides and polypeptides of the invention are useful as reagents for differential identification of the tissue(s) or cell type(s) present in a biological sample and for diagnosis of diseases and conditions which include, but are not limited to, central nervous diseases and immune or hematopoietic disorders. Similarly, polypeptides and antibodies directed to these polypeptides are useful in providing immunological probes for differential identification of the tissue(s) or cell type(s). For a number of disorders of the above tissues or cells, particularly of the central nervous system and immune system, expression of this gene at significantly higher or lower levels may be routinely detected in certain tissues or cell types (e.g. liver, immune, brain, cancerous and wounded tissues) or bodily fluids (e.g. lymph, serum, bile, amniotic fluid, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:65 as residues: Lys-69 to Leu-74, Ser-92 to Phe-97, Asp-109 to Leu-117, Leu-142 to Ser-159, Thr-166 to Glu-183, Ala-191 to Glu-205, Pro-213 to Glu-220.

The tissue distribution in T-cells and brain indicates that the protein products of this gene are useful for the development of drugs for the treatment of disorders affecting the central nervous system and immune system. The expression of this gene product primarily in hematopoietic cells and tissues indicates that it plays a role in the survival, proliferation, and/or differentiation of hematopoietic lineages. This is particularly supported by the expression of this gene product in fetal liver, which is a primary site of definitive hematopoiesis. Expression of this gene product in T cells also strongly indicates a role for this protein in immune function and immune surveillance. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:29 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 993 of SEQ ID NO:29, b is an integer of 15 to 1007, where both a and b correspond to the positions of nucleotide residues shown in SEQ ID NO:29, and where b is greater than or equal to a+14.

Features of Protein Encoded by Gene No: 20

The translation product of this gene shares sequence homology with a *C. elegans* ORF that seems to be a transmembrane protein. (See Accession No. 790406.) In specific embodiments, polypeptides of the invention comprise the following amino acid sequence: MAAACGPGAAGTACS-SACICFCDRGPCLGWNDPDRMLLRDVKALTLHYDR YTTSRSWIPS HSPQLKCVGGTAGCDSYTPKVIQC-QNKGWDGYDVQWECKTDLDI AYKFGKTVVSC-EGYES SEDQYVLRGSCGLEYNLDYTEL-GLQKLKESGKQ HGFASFSDYYYKWSSADSCNMSGLITI VVLLGIAFV-VYKLFLSDGQYSP PPYSEYPPFSHRYQRFTNSAGPPP-PGFKSEFTGPQNTG HGATSGFGSAFTG QQGYENSG-PGFWTGLGTGGILGYLFGSNRAATPFSDSWYYPSYP-PSY PGT WNRAYSPLHGGSGSYSVCSNSDTKTR-TASGYGGTRRR (SEQ ID NO:174), ACSSACICFCDRG-PCLGWNDPDRM (SEQ ID NO:175), TAGCDSYTPKV IQCQNKGWDGYDVQW (SEQ ID NO:176), EYNLDYTELGLQKLKESGK QHGFASFSDYYYK (SEQ ID NO:177), YKLFLSDGQYSPPPYSEYPPFSHRYQRF (SEQ ID NO:178), ENSGPGFWTGLGTGGILGYLFG-SNRA (SEQ ID NO:179), and/or NRAYSPLHGGSGSYS-VCSNSDTKTR (SEQ ID NO:180). Polynucleotides encoding these polypeptides are also encompassed by the invention. This gene maps to chromosome 8, and therefore can be used as a marker in linkage analysis for chromosome 8.

This gene is strongly expressed in fetal liver/spleen and pancreas, and to a lesser extent in T-cells, primary dendritic cells, bone marrow cells, and amygdala.

Therefore, polynucleotides and polypeptides of the invention are useful as reagents for differential identification of the tissue(s) or cell type(s) present in a biological sample and for diagnosis of diseases and conditions which include, but are not limited to, reproductive, immune, hematopoietic, neural, or endocrine disorders, particularly cancer. Similarly, polypeptides and antibodies directed to these polypeptides are useful in providing immunological probes for differential identification of the tissue(s) or cell type(s). For a number of disorders of the above tissues or cells, particularly of the immune system and endocrine system, expression of this gene at significantly higher or lower levels may be routinely detected in certain tissues or cell types (e.g. immune, pancreas, brain, cancerous and wounded tissues) or bodily fluids (e.g., lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:66 as residues: Gly-30 to Asp-35, Tyr-49 to Asp-59, Ala-71 to Thr-77, Gln-84 to Asp-92, Gln-94 to Thr-99, Glu-115 to Val-125, Lys-145 to Lys-151, Ser-159 to Asn-172, Asp-196 to Phe-228, Ser-230 to His-240, Gln-253 to Gly-262, Pro-285 to Tyr-291, Pro-293 to Trp-303, Leu-310 to Ser-316, Ser-321 to Arg-339.

The tissue distribution combined with the homology to a *C. elegans* transmembrane-like protein indicates that the protein product of this gene plays a role important in both vertebrates and invertebrates and is useful for the diagnosis or treatment of disorders related to this gene. Furthermore, the tissue distribution indicates that polynucleotides and polypeptides corresponding to this gene are useful for the diagnosis and/or treatment of hematopoietic disorders. This gene product is primarily expressed in hematopoietic cells and tissues, suggesting that it plays a role in the survival, proliferation, and/or differentiation of hematopoietic lineages. This is particularly supported by the expression of this gene product in fetal liver and bone marrow, the two primary sites of definitive hematopoiesis. Expression of this gene product in T cells and primary dendritic cells also strongly indicates a role for this protein in immune function and immune surveillance. Alternatively, the tissue distribution indicates that polynucleotides and polypeptides corresponding to this gene are useful for the detection, treatment, and/or prevention of various endocrine disorders and cancers, particularly Addison's disease, Cushing's Syndrome, and disorders and/or cancers of the pancreas (e.g. diabetes mellitus), adrenal cortex, ovaries, pituitary (e.g., hyper-, hypopituitarism), thyroid (e.g. hyper-,hypothyroidism), parathyroid (e.g. hyper-, hypoparathyroidism), hypothalamus, and testes. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:30 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 2012 of SEQ ID NO:30, b is an integer of 15 to 2026, where both a and b correspond to the positions of nucleotide residues shown in SEQ ID NO:30, and where b is greater than or equal to a+14.

Features of Protein Encoded by Gene No: 21

This gene is expressed primarily in embryonic tissue, testes, and to a lesser extent in ovary, hepatoma, kidney, endothelial, and smooth muscle cells.

Therefore, polynucleotides and polypeptides of the invention are useful as reagents for differential identification of the tissue(s) or cell type(s) present in a biological sample and for diagnosis of diseases and conditions which include, but are not limited to, metabolic disorder, abnormal embryonic development, or reproductive disorders, such as tumors. Similarly, polypeptides and antibodies directed to these polypeptides are useful in providing immunological probes for differential identification of the tissue(s) or cell type(s). For a number of disorders of the above tissues or cells, particularly of the embryonic or vascular tissues, expression of this gene at significantly higher or lower levels may be routinely detected in certain tissues or cell types (e.g., reproductive, developmental, endothelial, hepatic, renal, and cancerous and wounded tissues) or bodily fluids (e.g., lymph, amniotic fluid, bile, seminal fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution in embryonic and liver tissues, combined with the homology to a conserved NADH dehydrogenase indicates that polynucleotides and polypeptides corresponding to this gene are useful for the diagnosis or treatment of metabolic disorders of embryonic and/or vascular tissues. Furthermore, polynucleotides and polypeptides corresponding to this gene are useful for the diagnosis and/or treatment of disorders of the placenta. Specific expression within the testes and ovaries indicates that this gene product may play a role in the proper establishment and maintenance of normal ovarian and testicular function. Alternately, this gene product may be produced by the placenta and then transported to the embryo, where it may play a crucial role in the development and/or survival of the developing embryo or fetus. Expression of this gene product in a vascular-rich tissue such as the placenta also indicates that this gene product may be produced more generally in endothelial cells or within the circulation. In such instances, it may play more generalized roles in vascular function, such as in angiogenesis. It may also be produced in the vasculature and have effects on other cells within the circulation, such as hematopoietic cells. It may serve to promote the proliferation, survival, activation, and/or differentiation of hematopoietic cells, as well as other cells throughout the body. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:31 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 685 of SEQ ID NO:31, b is an integer of 15 to 699, where both a and b correspond to the positions of nucleotide residues shown in SEQ ID NO:31, and where b is greater than or equal to a+14.

Features of Protein Encoded by Gene No: 22

The translation product of this gene shares sequence homology with alpha 1C adrenergic receptor which is thought to be important in neuronal signal transmission. In specific embodiments, polypeptides of the invention comprise the following amino acid sequence: TESQMKCFLGNSHDTAPRHTCSGQGLHGGXXXTAPLRALQQHSQDGKLCTN SLPAARGGPHKHVVVTVVY SVKHWKPTERSSVSIKKEEETDWDMDQLSKQ RTTYEMKSGSSGVQTEELRHPSL (SEQ ID NO:181), NASWEIHMTQRHVIPXL ARASMXVXXXQRPSELCSSIRRMANSAQIVFPLPVGAPTNTLSSLLYT VLN TGNQQKEAV (SEQ ID NO:182), APLRALQQHSQDGKLCTNSLPAARGGPHKH (SEQ ID NO:183), RSSVSIKKEEETDWDMDQLSKQRTTYE (SEQ ID NO:184), and/or LCSSIRRMANSAQIVFPLPVGAPTNTLSS (SEQ ID NO:185). Polynucleotides encoding these polypeptides are also encompassed by the invention.

This gene is expressed primarily in breast lymph node, testicular tumors, and to a lesser extent, in uterine cancer.

Therefore, polynucleotides and polypeptides of the invention are useful as reagents for differential identification of the tissue(s) or cell type(s) present in a biological sample and for diagnosis of diseases and conditions which include, but are not limited to, immune, reproductive, neural, or proliferative disorders, such as cancers. Similarly, polypeptides and antibodies directed to these polypeptides are useful in providing immunological probes for differential identification of the tissue(s) or cell type(s). For a number of disorders of the above tissues or cells, particularly of the neurologic, breast lymph node, uterine cancer, and testicular cancer, expression of this gene at significantly higher or lower levels may be routinely detected in certain tissues or cell types (e.g. breast, testes, cancerous and wounded tissues) or bodily fluids (e.g., lymph, seminal fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution in lymph, testicular, and uterine tissues indicates that the protein product of this gene may be beneficial in the treatment and/or prevention of a variety of reproductive disorders, and may even show utility in ameliorating disorders related to aberrant immune responses to normal or proliferative tissues. The homology to alpha 1C adrenergic receptor indicates that polynucleotides and polypeptides corresponding to this gene are useful for transmitting signals to neurons. Furthermore, the tissue distribution indicates that the protein product of this gene is useful for the treatment and diagnosis of conditions concerning proper testicular function (e.g. endocrine function, sperm maturation), as well as cancer. Therefore, this gene product is useful in the treatment of male infertility and/or impotence. This gene product is also useful in assays designed to identify binding agents as such agents (antagonists) are useful as male contraceptive agents. Similarly, the protein is believed to by useful in the treatment and/or diagnosis of testicular cancer. The testes are also a site of active gene expression of transcripts that may be expressed, particularly at low levels, in other tissues of the body. Therefore, this gene product may be expressed in other specific tissues or organs where it may play related functional roles in other processes, such as hematopoiesis, inflammation, bone formation, and kidney function, to name a few possible target indications. Protein, as well as, antibodies directed against the protein may show utility as a tissue-specific marker and/or immunotherapy target for the above listed tissues.

Many polynucleotide sequences, such as EST sequences, are publicly available and accessible through sequence databases. Some of these sequences are related to SEQ ID NO:32 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1250 of SEQ ID NO:32, b is an integer of 15 to 1264, where both a and b correspond to the positions of nucleotide residues shown in SEQ ID NO:32, and where b is greater than or equal to a+14.

Features of Protein Encoded by Gene No: 23

The translation product of this gene shares sequence homology with G-protein-coupled receptor which is thought to be important in mediating a wide variety of physiological function and belongs to a gene superfamily with members ranging from chemokine receptor to bradykinin receptor. This gene has also recently been gened by another group, calling the gene platelet activating receptor homolog. (See Accession No. 2580588.) Preferred polypeptide fragments comprise the amino acid sequence: LSIIFLAFVSIDRCLQL (SEQ ID NO:186), GSCFATWAFIQKNTNHRCVSIYLINL LTADFLLTLALPVKIVVDLGVAP-WKLKIFHCQVTACLIYIN (SEQ ID NO:187), and/or KNT-NHRCVSIYLINLLTADFLLTLALPVKIV (SEQ ID NO:188). Also preferred are polynucleotide fragments encoding these polypeptide fragments.

Chemokines, are soluble, low molecular weight members of the cytokine family that have chemo-attractant activity. Chemokines selectively induce chemotaxis of the white blood cells, including leukocytes, such as monocytes, macrophages, eosinophils, basophils, mast cells, and lymphocytes, such as T-cells, B-cells, and polymorphonuclear leukocytes (neutrophils). In addition, Chemokines can selectively induce other changes in responsive cells, including changes in cell shape, transient rises in the concentration of intracellular free calcium ([Ca2+]i), granule exocytosis, integrin upregulation, formation of bioactive lipids (e.g. leukotrienes) and respiratory burst, associated with leukocyte activation. Therefore, the chemokines are early activators of the inflammatory response, causing inflammatory mediator release, chemotaxis and extravasation to sites of infection or inflammation.

The chemokines are related in their primary DNA structure. They share four conserved cysteines, which form disulphide bonds. cDNA cloning and biochemical characterization of several chemokines has revealed they have a leader sequence of 20-25 amino acids, that is cleaved upon secretion to yield a protein of approximately 92 to 99 amino acids (8 to 10 Kd). The family is divided into two branches based upon the conserved cysteine motif, designated as the C—C chemokines (b chemokines) and the C—X—C chemokines (a chemokines), in which the first two conserved cysteines are adjacent, or are separated by, an intervening residue, respectively (Baggiolini, M. and C. A. Dahinden, Immunology Today, 15:127-133 (1994)).

The C—X—C chemokines are potent chemoattractants and activators of neutrophils, such as interleukin 8 (IL-8), PF4 and neutrophil-activating peptide 2 (NAP-2). The C—C chemokines include molecules such as human monocyte chemotactic proteins 1-3 (MCP-1, MCP-2, and MCP-3), RANTES (Regulated on Activation, Normal T Expressed and Secreted), and the macrophage inflammatory proteins 1a and 1b (MIP-1a and MIP-1b). The C—C chemokines have been characterized as chemoattractants and activators of monocytes or lymphocytes, but do not appear to be chemoattractants for neutrophils. For example, recombinant RANTES is a chemo-attractant for monocytes, as well as, for memory T-cells in vitro (Schall, T. J. et al., Nature, 347:669-671 (1990)). Furthermore, a chemokine called lymphotactin, with a single cysteine pair in the molecule, has been identified that attracts lymphocytes (Kelner, G. S., et al., Science, 266:1395-1399 (1994)).

The C—C chemokines are of great scientific and pharmaceutical interest because of their potential role in allergic inflammation. For example, MCP-1 induces exocytosis of human basophils, resulting in release of high levels of histamine and leukotriene C4, in addition to other inflammatory mediators. Since these cellular events are triggered in response to chemokine binding, there remains great interest in the receptors for the C—C chemokines. Recently, a receptor for C—C chemokines has been gened and is reported to bind MIP-1a and RANTES. Accordingly, this MIP-1a/RANTES receptor was designated C—C chemokine receptor 1 (CHR-1; Neote, K. et al., Cell, 72:415-425 (1993); Horuk, R. et al., WO 94/11504, published May 26, 1994; Gao, J.-I. et al. J. Exp. Med., 177: 1421-1427 (1993)). An MCP-1 receptor has also been gened (Charo, I. F. et al., Proc. Natl. Acad. Sci. USA, 91:2752 (1994)). This receptor, designated CKR-2, is reported to bind MCP-1 with high affinity and MCP-3 with lower affinity (ChEO, I, F., et al., Proc. Natl. Acad. Sci. USA, 91:2752-2756 (1994)). CKR-2 has been shown to exist in two isoforms: Isoform A and B. This dichotomy results from the use of an alternative splice site in isoform A mRNA producing a distinct cytoplasmic tail. Isoform B, which is not spliced in this region, has been shown to be a functional receptor for MCP-1 and MCP-3 in both binding and signal transduction assays (Charo, I. F. et al., Proc. Natl. Acad. Sci. USA, 91:2752-2756 (1994); Myers, S. J., et al., J. Biol. Chem., 270:5786-5792 (1995)). More recently, a new receptor called CKR-4 has been described; cRNA from this receptor was reported to produce a Ca2+ activated chloride current in response to MCP-1, MIP-1α and RANTES when injected into X. laevis oocytes (Poer, C. A., et al., J. Biol. Chem., 270: 19495-19500 (1995)). Due to the importance of Ca2+ release in activation of signal transduction pathways in immune cells, one experienced in the art would appreciate the role of this receptor as the primary initiation signal for activating subsequent signalling events.

Similarly, based upon their DNA structure, the MCP-1 receptor (CKR-2) and C—C chemokine receptor 1 are predicted to belong to a superfamily of seven transmembrane spanning G-protein coupled receptors (Gerard C., and Gerard N. P., Annu. Rev. Immunol., 12: 775-808 (1994); Gerard C., and Gerard N. P., Curr. Opin. Immunol., 6:140-145 (1994)). This family of G-protein coupled (serpentine) receptors comprises a large group of integral membrane proteins containing seven transmembrane-spanning regions. These regions, or domains, are believed to represent conserved transmembrane a-helices comprising 20 to 30 hydrophobic amino acids connected by at least eight, divergent extracellular or cytoplasmic loops of primarily hydrophilic amino acids. Most G-protein coupled receptors have single conserved cysteine residues on each of the first two extracellular loops which form disulfide loops that are believed to stabilize functional protein structure. The seven transmembrane regions are designated as TM1, TM2, TM3, TM4, TM5, TM6, and TM7. TM3 is also implicated in signal transduction (Probst, W. C., et al., DNA and Cell Biology, 11:1-20).

The ligands of these receptors include a diverse group of molecules, including small biogenic amine molecules, such as epinethrine and norepinephrine, peptides, such as substance P and neurokinins, and larger proteins, such as chemokines. The receptors are coupled to G proteins, which are heterotrimeric regulatory proteins capable of binding GTP and mediating signal transduction from coupled receptors. For example, by the production of intracellular mediators. The ligand binding sites of G-protein coupled receptors are believed to comprise a hydrophilic socket formed by several G-protein receptor transmembrane domains. The hydrophilic side of each G-protein coupled receptor transmembrane helix is postulated to face inward and form the polar ligand binding site. TM3 has been implicated in several G-protein coupled receptors as having a ligand binding site, which includes the involvement of the TM3 aspartate residue. Additionally, TM5 serines, a TM6 asparagine, and TM6 or TM7 phenylalanines or tyrosines are also implicated in ligand binding.

It is well established that many medically significant biological processes are mediated by proteins participating in signal transduction pathways that involve G-proteins and/or second messengers, e.g. cAMP (Lefkowitz, Nature, 351:353-354 (1991)). For example, in one form of signal transduction, the effect of hormone binding is activation of an enzyme, adenylate cyclase, inside the cell. Enzyme activation by hormones is dependent upon the presence of the nucleotide GTP, which itself, has been shown to influence hormone binding. A G-protein physically connects the hormone receptors to adenylate cyclase. Upon activation of the hormone receptor via binding of its receptive ligand, the G-protein was shown to exchange GTP for bound GDP. The GTP-carrying, active form of the G-protein, then binds to an activated adenylate cyclase. Hydrolysis of GTP to GDP, catalyzed by the G-protein itself, returns the G-protein to its basal, inactive form. Thus, the G-protein serves a dual role, as an intermediate that relays the signal from receptor to downstream effector, as well as a clock that controls the duration of the signal.

G-protein coupled receptors can be coupled intracellularly by heterotrimeric G-proteins to various intracellular enzymes, ion channels, and transporters (Johnson, et al., Endoc., Rev., 10:317-331 (1989)). Different G-protein a-subunits preferentially stimulate particular effectors to modulate various biological functions in a cell. Phosphorylation of cytoplasmic residues of G-protein coupled receptors have been identified as an important mechanism for the regulation of G-protein coupling of some G-protein coupled receptors. G-protein coupled receptors are found in numerous sites within a mammalian host, including dopamine receptors which bind to neuroleptic drugs used for treating psychotic and neurological disorders. Other examples of members of this family include calcitonin, adrenergic, endothelin, cAMP, adenosinse, muscarinic, acetylcholine, serotinin, histamine, thrombin, kinin, follicle stimulating hormone, opsins, endothelial differentiation gene-1 receptor, and rhodopsins, odarant, cytomegalovirus receptors, etc.

Sequencing of two recently gened IL-8 receptor cDNAs have revealed that these C—X—C receptor proteins also share sequence similarity with seven transmembrane-spanning G protein-coupled receptor proteins (Murphy P. M. and H. L. Tiffany, Science, 253:1280-1283 (1991); Murphy et al., WO 93/06299; Holmes, W. E. et al., Science, 253:1278-1290 (1991)). Additional receptors for chemotactic proteins such as anaphylatoxin C5a, and bacterial formylated tripeptide fMLP, have been characterized by cloning and found to encode receptor proteins which share sequence similarity to these transmembrane-spanning proteins (Gerard, N. P. and C. Gerard, Nature, 349: 614-617 (1991); Boulay, F. et al., Biochemistry, 29:11123-11133 (1990)). Although a number of other proteins and genes have been identified that share significant similarity in sequence, tissue expression, and leukocyte subpopulation distribution, to known chemokine receptors, the ligands for these receptors remain undefined. Thus, there is a need to identify other chemokine receptor polypeptides, as these polypeptides may modulate the. Disturbances of such regulation may be involved in disorders relating to the immune or hematopoietic system. Therefore, there is a need for identification and characterization of such human polypeptides which can play a role in detecting, preventing, ameliorating or correcting such disorders. In an attempt to express embodiments of invention via gene therapy, the following protocol may be followed. Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks. pMV-7 (Kirschmeier, P. T. et al, DNA, 7:219-25 (1988) flanked by the long terminal repeats of the Moloney murine sarcoma virus, is digested with EcoRI and HindIII and subsequently treated with calf intestinal phosphatase.

The linear vector is fractionated on agarose gel and purified, using glass beads. The cDNA encoding a polypeptide of the present invention is amplified using PCR primers which correspond to the 5' and 3' end sequences respectively. The 5' primer contains an EcoRI site and the 3' primer contains a HindIII site. Equal quantities of the Moloney murine sarcoma virus linear backbone and the EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted. The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product. Numerous modifications and variations of the present invention are possible in light of the above teachings and, therefore, within the scope of the appended claims, the invention may be practiced otherwise than as particularly described.

This gene is expressed primarily in immune cells, particularly lymphocytes.

Therefore, polynucleotides and polypeptides of the invention are useful as reagents for differential identification of the tissue(s) or cell type(s) present in a biological sample and for diagnosis of diseases and conditions which include, but are not limited to, immune or hematopoietic disorders, particularly leukemias. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g. immune, hematopoietic, and cancerous and wounded tissues) or bodily fluids (e.g., lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:69 as residues: Asp-59 to Asn-65, Lys-72 to Trp-79, Tyr-110 to Val-121, Ala-204 to Asn-215.

The tissue distribution in immune cells, combined with the homology to a conserved G-protein coupled receptor indicates that polynucleotides and polypeptides corresponding to this gene are useful as a chemokine receptor on lymphocytes that regulate immune response, or may even be useful in gene therapy to ameliorate the effects of a defective endogenous G-protein, or may show benefit as an antagonist for such receptors. The protein can also be used to determine biological activity, to raise antibodies, as tissue markers, to isolate cognate ligands or receptors, to identify agents that modulate their interactions and as nutritional supplements. It may also have a very wide range of biological activities. Typical of these are cytokine, cell proliferation/differentiation modulating activity or induction of other cytokines; immunostimulating/immunosuppressant activities (e.g. for treating human immunodeficiency virus infection, cancer, autoimmune diseases and allergy); regulation of hematopoiesis (e.g. for treating anaemia or as adjunct to chemotherapy); stimulation or growth of bone, cartilage, tendons, ligaments and/or nerves (e.g. for treating wounds, stimulation of follicle stimulating hormone (for control of fertility); chemotactic and chemokinetic activities (e.g. for treating infections, tumors); hemostatic or thrombolytic activity (e.g. for treating haemophilia, cardiac infarction etc.); anti-inflammatory activity (e.g. for treating septic shock, Crohn's disease); as antimicrobials; for treating psoriasis or other hyperproliferative diseases; for regulation of metabolism, and behaviour. Also contemplated is the use of the corresponding nucleic acid in gene therapy procedures. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:33 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 983 of SEQ ID NO:33, b is an integer of 15 to 997, where both a and b correspond to the positions of nucleotide residues shown in SEQ ID NO:33, and where b is greater than or equal to a+14.

Features of Protein Encoded by Gene No: 24

The translation product of this gene shares sequence homology with protein disulfide isomerase which is thought to be important in protein folding and protein-protein interaction. This gene also contains shares homology to genes having thioredoxin domains. (See Accession No. 1943817.) This gene also maps to chromosome 9, and therefore may be useful in linkage analysis as a marker for chromosome 9.

This gene is expressed primarily in tumor tissues.

Therefore, polynucleotides and polypeptides of the invention are useful as reagents for differential identification of the tissue(s) or cell type(s) present in a biological sample and for diagnosis of diseases and conditions which include, but are not limited to, proliferative disorders, or disorders involving inappropriate protein folding and protein-protein interaction. Similarly, polypeptides and antibodies directed to these polypeptides are useful in providing immunological probes for differential identification of the tissue(s) or cell type(s). For a number of disorders of the above tissues or cells, particularly of the tumorigenic process, expression of this gene at significantly higher or lower levels may be routinely detected in certain tissues or cell types (e.g., cancerous and wounded tissues) or bodily fluids (e.g., lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:70 as residues: Glu-78 to Asn-83, Asp-91 to Gln-100, Glu-122 to Ser-128, Arg-137 to Pro-143, Asp-157 to Asn-162, Glu-168 to Asn-174, Ser-199 to Gly-206, Pro-213 to Ala-218, Glu-251 to Thr-257, Ser-353 to His-361, Gly-363 to Ala-375, Pro-382 to Phe-387, Arg-401 to Leu-406.

The tissue distribution in proliferative tissues, combined with the homology to a conserved protein disulfide isomerase indicates that polynucleotides and polypeptides corresponding to this gene are useful for regulating protein folding and protein-protein interaction in tumor tissues. Similarly, expression within cellular sources marked by proliferating cells indicates that this protein may play a role in the regulation of cellular division, and may show utility in the diagnosis and treatment of cancer and other proliferative disorders. Similarly, developmental tissues rely on decisions involving cell differentiation and/or apoptosis in pattern formation. Thus this protein may also be involved in apoptosis or tissue differentiation and could again be useful in cancer therapy. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:34 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1900 of SEQ ID NO:34, b is an integer of 15 to 1914, where both a and b correspond to the positions of nucleotide residues shown in SEQ ID NO:34, and where b is greater than or equal to a+14.

Features of Protein Encoded by Gene No: 25

In specific embodiments, polypeptides of the invention comprise the following amino acid sequence: KHTVETRSVAFRKQLNR (SEQ ID NO:189). Polynucleotides encoding these polypeptides are also encompassed by the invention.

This gene is expressed primarily in leukocytes involved in immune defense, including T cells, macrophages, neutrophils, and to a lesser extent, in fetal liver/spleen, synovium, adrenal gland tumor, adipose, and placenta.

Therefore, polynucleotides and polypeptides of the invention are useful as reagents for differential identification of the tissue(s) or cell type(s) present in a biological sample and for diagnosis of diseases and conditions which include, but are not limited to, immune or hematopoietic disorders, particularly defects or disorders in leukocytes. Similarly, polypeptides and antibodies directed to these polypeptides are useful in providing immunological probes for differential identification of the tissue(s) or cell type(s). For a number of disorders of the above tissues or cells, particularly of the immune and defense systems, expression of this gene at significantly higher or lower levels may be routinely detected in certain tissues or cell types (e.g. immune, hematopoietic, hepatic, reproductive, endocrine, developmental, and cancerous and wounded tissues) or bodily fluids (e.g., lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution in immune cells and tissues indicates that polynucleotides and polypeptides corresponding to this gene are useful for regulating the function of leukocytes, and is useful for the diagnosis and/or treatment of disorders in the immune and defense systems. This gene product is primarily expressed in hematopoietic cells and tissues, suggesting that it plays a role in the survival, proliferation, and/or differentiation of hematopoietic lineages. This is particularly supported by the expression of this gene product in fetal liver, which is a primary site of definitive hematopoiesis. Expression of this gene product in T cells and macrophage also strongly indicates a role for this protein in immune function and immune surveillance. Moreover, This gene product may be involved in the regulation of cytokine production, antigen presentation, or other processes that may also suggest a usefulness in the treatment of cancer (e.g. by boosting immune responses). Since the gene is expressed in cells of lymphoid origin, the natural gene product may be involved in immune functions. Therefore it may be also used as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, scleroderma and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:35 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1006 of SEQ ID NO:35, b is an integer of 15 to 1020, where both a and b correspond to the positions of nucleotide residues shown in SEQ ID NO:35, and where b is greater than or equal to a+14.

Features of Protein Encoded by Gene No: 26

In specific embodiments, polypeptides of the invention comprise the following amino acid sequence: PQVLHLRWLPKVLGYRSXPLRLADPSTFXM (SEQ ID NO:190), QLLGFEGNDSAGERRWRGANMQIPLLQVALPLSTEEGTGPSG PTQPSPQGEVRFLRSPRMGGQV PHWEWRSHSLPWVLTSTLSGCEGDLPGFPH QVQLPAAESHTLNTGLLRSDTGQFTPCLKLAFERPSG (SEQ ID NO:191), NDS AGERRWRGANMQIPLLQVALP (SEQ ID NO:192), PSPQGEVRFLRSPRMG GQVPHWEWRSHSL (SEQ ID NO:193), and/or HQVQLPAAESHTLNTGLL RSDTGQFTP (SEQ ID NO:194). Polynucleotides encoding these polypeptides are also encompassed by the invention.

This gene is expressed in colon cancer, breast cancer, neutrophils, T cells, spinal cord, fibroblasts, and vascular endothelial cells.

Therefore, polynucleotides and polypeptides of the invention are useful as reagents for differential identification of the tissue(s) or cell type(s) present in a biological sample and for diagnosis of diseases and conditions which include, but are not limited to, gastrointesinal, reproductive, or immune disorders, particularly cancers, and disorder and abnormalities in leukocytes and other tissues. Similarly, polypeptides and antibodies directed to these polypeptides are useful in providing immunological probes for differential identification of the tissue(s) or cell type(s). For a number of disorders of the above tissues or cells, particularly those cells involved in tumorigenesis and immune defense systems, expression of this gene at significantly higher or lower levels may be routinely detected in certain tissues or cell types (e.g. immune, colon, breast, vascular, and cancerous and wounded tissues) or bodily fluids (e.g., lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution in breast and colon cancer tissues indicates that polynucleotides and polypeptides corresponding to this gene are useful for diagnosis and treatment of cancer or immune system disorders. Furthermore, the tissue distribution in tumors of colon and breast origins indicates that polynucleotides and polypeptides corresponding to this gene are useful for diagnosis and intervention of these tumors, in addition to other tumors where expression has been indicated. Furthermore, the protein product of this gene may be beneficial in the treatment and/or prevention of cancers through enhancing the immune response to tumor cell surface antigens, or even as a preventative through the correction of an aberrant cell-cycle regulator protein by gene therapy. Protein, as well as, antibodies directed against the protein may show utility as a tissue-specific marker and/or immunotherapy target for the above listed tissues.

Many polynucleotide sequences, such as EST sequences, are publicly available and accessible through sequence databases. Some of these sequences are related to SEQ ID NO:36 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 767 of SEQ ID NO:36, b is an integer of 15 to 781, where both a and b correspond to the positions of nucleotide residues shown in SEQ ID NO:36, and where b is greater than or equal to a+14.

Features of Protein Encoded by Gene No: 27

The translation product of this gene shares sequence homology with a mouse pancreatic polypeptide (See Accession No. 200464.). Thus, it is likely that this gene has activity similar to the mouse pancreatic polypeptide. Preferred polypeptide fragments comprise the amino acids sequence: APLETMQNKPRAPQKRALPFPELELRD-YASVLTRYSLGLRNKEPSLGHRWGT QKLGRSPC (SEQ ID NO:195), MQNKPRAPQKRALPFPELELRD-YASVLTRYSLGL RNKEPS LGHRWGTQKLGRSPC-SEGSQGHTTDAADVQNHSKEEQRDAG AQRX-CGQGRHTWAYRXGAQDTSRLTGDPR GGERSPPKCQSMKQQ EGAPSGHCWDQWCHGASEV-VWPESRKRAQIFXSPCRQSPRSSALGAGQKLA VCSP DILCCPTDTLLASHPHSLLTGTQFSGQTQALAPSWCA (SEQ ID NO:196), APQKRALPFPELELRDYASVLTRYSL (SEQ ID NO:197), APQKRALPFPELE LRDYASVL-TRYSLG (SEQ ID NO:198), LGRSPCSEG-SQGHTTDAADVQNHS KEEQR (SEQ ID NO:199), and/or TDTLLASHPHSLLTGTQFSGQTQAL (SEQ ID NO:200). Also preferred are polynucleotide fragments encoding this polypeptide fragment.

This gene is expressed primarily in neutrophils, and to a lesser extent, in induced endothelial cells.

Therefore, polynucleotides and polypeptides of the invention are useful as reagents for differential identification of the tissue(s) or cell type(s) present in a biological sample and for diagnosis of diseases and conditions which include, but are not limited to, immune, hematopoietic, or vascular disorders, particularly disorders in immune cell adhesion. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g. immune, vascular, and cancerous and wounded tissues) or bodily fluids (e.g. lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution in neutrophils and endothelial cells indicates that polynucleotides and polypeptides corresponding to this gene are useful for the regulation of neutrophils or leukocyte adhesion to endothelial cells. It may be used to diagnose or treat disorders associated with neutrophils and vascular endothelial cells. Furthermore, this gene product may be produced more generally in endothelial cells or within the circulation. In such instances, it may play more generalized roles in vascular function, such as in angiogenesis. It may also be produced in the vasculature and have effects on other cells within the circulation, such as hematopoietic cells, or be used as a preventative for embolisms, atherosclerosis, aneurysms, microvascular disease, or stroke. It may serve to promote the proliferation, survival, activation, and/or differentiation of hematopoietic cells, as well as other cells throughout the body. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:37 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 952 of SEQ ID NO:37, b is an integer of 15 to 966, where both a and b correspond to the positions of nucleotide residues shown in SEQ ID NO:37, and where b is greater than or equal to a+14.

Features of Protein Encoded by Gene No: 28

In specific embodiments, polypeptides of the invention comprise the following amino acid sequence: IAQVL-KAEMCLVXRPHPXLLDSHRGWAGETL-RGQGRQEXESDTKAGTLQLQ RQAPL PLTQHSLV-LPISPGPSNHTQS (SEQ ID NO:201), RGWAGETLRGQGR QEXESDT (SEQ ID NO:202), and/or APL PLTQHSLVLPISPGPSN (SEQ ID NO:203). Polynucleotides encoding these polypeptides are also encompassed by the invention.

This gene is expressed primarily in prostate BPH.

Therefore, polynucleotides and polypeptides of the invention are useful as reagents for differential identification of the tissue(s) or cell type(s) present in a biological sample and for diagnosis of diseases and conditions which include, but are not limited to, proliferative or reproductive disorders, particularly benign hypertrophy of the prostate. Similarly, polypeptides and antibodies directed to these polypeptides are useful in providing immunological probes for differential identification of the tissue(s) or cell type(s). For a number of disorders of the above tissues or cells, particularly of the male urogenital system, expression of this gene at significantly higher or lower levels may be routinely detected in certain tissues or cell types (e.g. prostate, urogenital, and cancerous and wounded tissues) or bodily fluids (e.g., lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution in prostate tissue indicates that polynucleotides and polypeptides corresponding to this gene are useful for the diagnosis and treatment of benign or metastatic hypertrophy of the prostate or prostate cancer. Expression within cellular sources marked by proliferating cells indicates that this protein may play a role in the regulation of cellular division, and may show utility in the diagnosis and treatment of cancer and other proliferative disorders. Similarly, developmental tissues rely on decisions involving cell differentiation and/or apoptosis in pattern formation. Thus this protein may also be involved in apoptosis or tissue differentiation and could again be useful in cancer therapy. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:38 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 402 of SEQ ID NO:38, b is an integer of 15 to 416, where both a and b correspond to the positions of nucleotide residues shown in SEQ ID NO:38, and where b is greater than or equal to a+14.

Features of Protein Encoded by Gene No: 29

The translation product of this gene shares sequence homology with C16C10.7, a *C. elegans* gene similar to zinc finger protein, a protein involved in DNA binding. Thus, this protein is expected to share certain biological activities with C16I0.7 including DNA binding activities. One embodiment of this gene comprises polypeptides of the following amino acid sequence: NRERGGAGATFECNICLETAREAVVS-VCGHLYCWPCLHQWLETRPERQECP VCKAGIS-REKVVPLYGRGSQKPQDPRLKTP-PRPQGQRPAPESRGGFQPFGDTG GFHFSFGVGAFPFGFFTTVFNAHEPFR-RGTGVDLGQGHPASSWQDSLFLFLAI FFFFWLLSI (SEQ ID NO:204), NRERGGAGATFECNICLETAREAV-VSVCGHLYCWP CLHQWLETRPERQECPVCKAGIS-REKVVPLYGRGSQKPQDPRLKTPPRPQGQ RPAPES-RGGFQPFGDTGGFHFSFGVGAFPFGFFTTVFNAHEPF-RRGTGVDLGQ GHPASSWQD (SEQ ID NO:205), NRERGGAGATFECNICLETAREAVVSVC GHLYCWP-CLHQWL (SEQ ID NO:206), ETRPERQECPVCKAGIS-REKVVPLYG RGSQKPQDPRLK (SEQ ID NO:207), TPPRPQGQRPAPESRGGFQPFGDTGGFH FSFGVG (SEQ ID NO:208), AFPFGFFTTVFNAHEPFRRGT-GVDLGQGHPAS SWQD (SEQ ID NO:209). An additional embodiment is the polynucleotides encoding these polypeptides.

This gene is expressed primarily in activated T-cells, and to a lesser extent, in fetal brain, TNF-induced amniotic cells and epididymus.

Therefore, polynucleotides and polypeptides of the invention are useful as reagents for differential identification of the tissue(s) or cell type(s) present in a biological sample and for diagnosis of diseases and conditions which include, but are not limited to, immune, neurodegenerative, or developmental disorders. Similarly, polypeptides and antibodies directed to these polypeptides are useful in providing immunological probes for differential identification of the tissue(s) or cell type(s). For a number of disorders of the above tissues or cells, particularly of the immune and central nervous systems, expression of this gene at significantly higher or lower levels may be routinely detected in certain tissues or cell types (e.g. immune, neural, developmental, reproductive, and cancerous and wounded tissues) or bodily fluids (e.g., lymph, amniotic fluid, seminal fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution in T-cells and fetal brain indicates that the protein products of this gene are useful for the diagnosis and treatment of immune and/or neurodegenerative disorders, as well as useful for the promotion of, survival, and differentiation of neurons. Furthermore, the tissue distribution indicates that polynucleotides and polypeptides corresponding to this gene are useful for the diagnosis and/or treatment of hematopoietic disorders. Expression of this gene product in T cells also strongly indicates a role for this protein in immune function and immune surveillance. Expression within embryonic tissue and other cellular sources marked by proliferating cells indicates that this protein may play a role in the regulation of cellular division, and may show utility in the diagnosis and treatment of cancer and other proliferative disorders. Similarly, developmental tissues rely on decisions involving cell differentiation and/or apoptosis in pattern formation. Thus this protein may also be involved in apoptosis or tissue differentiation and could again be useful in cancer therapy. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:39 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1100 of SEQ ID NO:39, b is an integer of 15 to 1114, where both a and b correspond to the positions of nucleotide residues shown in SEQ ID NO:39, and where b is greater than or equal to a+14.

Features of Protein Encoded by Gene No: 30

In specific embodiments, polypeptides of the invention comprise the following amino acid sequence: GLSTGPD-MASLDLFV (SEQ ID NO:210), GRPTRPSQAT RHFLLGTLFTNCLCGTFCFPCLGC-QVAADMNECCLCGTSVAMRTLYRTRYGI PGSICDDY MATLCCPHCTLCQIKRDINRRRAMRTF (SEQ ID NO:211), IKNLIF FMPSVVLKHI HHISVAKDG-EELKLKRCLLNFVASVRAFHHQFLESTHGSPSV DISLDLAKSTMRTAKSCHIVITNRSRDA ISGPVESPH-CDACSTQTAFIHISCNLTP KARETKCATETISKQGSE-QEMSCGLGRTRGST (SEQ ID NO:212), FLLGTLFTN CLCGTFCFPCLGCQ (SEQ ID NO:213), SICDDY MATL-CCPHCTLCQIKRDI (SEQ ID NO:214), SVVLKHI HHIS-VAKDGEELKLKRCLLNFVA (SEQ ID NO:215), NFVAS-VRAFHHQFLESTHGSPSVDIS (SEQ ID NO:216), and/or TAFIHISCN LTPKARETKCATETISKQG (SEQ ID NO:217). Polynucleotides encoding these polypeptides are also encompassed by the invention. The gene encoding the disclosed cDNA is thought to reside on chromosome 4. Accordingly, polynucleotides related to this invention are useful as a marker in linkage analysis for chromosome 4.

This gene is expressed primarily in T-cells, fetal tissues, and placenta, and to a lesser extent in bone marrow.

Therefore, polynucleotides and polypeptides of the invention are useful as reagents for differential identification of the tissue(s) or cell type(s) present in a biological sample and for diagnosis of diseases and conditions which include, but are not limited to, immunological, developmental, or reproductive disorders, including autoimmune diseases or congenital defects. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g. immune, developmental, placental, hematopoietic, and cancerous and wounded tissues) or bodily fluids (e.g. lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution in T-cells and bone marrow indicates that the protein products of this gene are useful for diagnosis and treatment of immunologically mediated disorders as they are thought to play a role in the proliferation, survival, differentiation, and/or activation of a variety of hematopoietic cells, including early progenitors or hematopoietic stem cells. Furthermore, the tissue distribution indicates that polynucleotides and polypeptides corresponding to this gene are useful for the diagnosis and treatment of cancer and other proliferative disorders. Expression within embryonic tissue and other cellular sources marked by proliferating cells indicates that this protein may play a role in the regulation of cellular division. Additionally, the expression in hematopoietic cells and tissues indicates that this protein may play a role in the proliferation, differentiation, and/or survival of hematopoietic cell lineages. In such an event, this gene may be useful in the treatment of lymphoproliferative disorders, and in the maintenance and differentiation of various hematopoietic lineages from early hematopoietic stem and committed progenitor cells. Similarly, embryonic development also involves decisions involving cell differentiation and/or apoptosis in pattern formation. Thus, this protein may also be involved in apoptosis or tissue differentiation and could again be useful in cancer therapy. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:40 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 588 of SEQ ID NO:40, b is an integer of 15 to 602, where both a and b correspond to the positions of nucleotide residues shown in SEQ ID NO:40, and where b is greater than or equal to a+14.

Features of Protein Encoded by Gene No: 31

In specific embodiments, polypeptides of the invention comprise the following amino acid sequence: MKGEIE (SEQ ID NO:218). Polynucleotides encoding these polypeptides are also encompassed by the invention.

This gene is expressed primarily in human skin, and to a lesser extent, in fetal heart tissue.

Therefore, polynucleotides and polypeptides of the invention are useful as reagents for differential identification of the tissue(s) or cell type(s) present in a biological sample and for diagnosis of diseases and conditions which include, but are not limited to, integumentary, developmental, or cardiovascular disorders, particularly wound healing conditions and skin cancers. Similarly, polypeptides and antibodies directed to these polypeptides are useful in providing immunological probes for differential identification of the tissue(s) or cell type(s). For a number of disorders of the above tissues or cells, particularly of the integumentary system, expression of this gene at significantly higher or lower levels may be routinely detected in certain tissues or cell types (e.g. skin, developmental, cardiovascular, and cancerous and wounded tissues) or bodily fluids (e.g., lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution in skin indicates that the protein products of this gene are useful for diagnosis and treatment of skin cancers and wound healing. Moreover, polynucleotides and polypeptides corresponding to this gene are useful for the treatment, diagnosis, and/or prevention of various skin disorders including congenital disorders (i.e. nevi, moles, freckles, Mongolian spots, hemangiomas, port-wine syndrome), integumentary tumors (i.e. keratoses, Bowen's disease, basal cell carcinoma, squamous cell carcinoma, malignant melanoma, Paget's disease, mycosis fungoides, and Kaposi's sarcoma), injuries and inflammation of the skin (i.e. wounds, rashes, prickly beat disorder, psoriasis, dermatitis), atherosclerosis, uticaria, eczema, photosensitivity, autoimmune disorders (i.e. lupus erythematosus, vitiligo, dermatomyositis, morphea, scleroderma, pemphigoid, and pemphigus), keloids, striae, erythema, petechiae, purpura, and xanthelasma. In addition, such disorders may predispose increased susceptibility to viral and bacterial infections of the skin (i.e. cold sores, warts, chickenpox, molluscum contagiosum, herpes zoster, boils, cellulitis, erysipelas, impetigo, tinea, athletes foot, and ringworm).

Moreover, the protein product of this gene may also be useful for the treatment or diagnosis of various connective tissue disorders such as arthritis, trauma, tendonitis, chrondomalacia and inflammation, autoimmune disorders such as rheumatoid arthritis, lupus, scleroderma, and dermatomyositis as well as dwarfism, spinal deformation, and specific joint abnormalities as well as chondrodysplasias (i.e. spondyloepiphyseal dysplasia congenita, familial osteoarthritis, Atelosteogenesis type II, metaphyseal chondrodysplasia type Schmid). Additionally, it may play more generalized roles in vascular function, such as in angiogenesis. It may also be produced in the vasculature and have effects on other cells within the circulation, such as hematopoietic cells. It may serve to promote the proliferation, survival, activation, and/or differentiation of hematopoietic cells, as well as other cells throughout the body. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:41 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 956 of SEQ ID NO:41, b is an integer of 15 to 970, where both a and b correspond to the positions of nucleotide residues shown in SEQ ID NO:41, and where b is greater than or equal to a+14.

Features of Protein Encoded by Gene No: 32

The translation product of this gene shares sequence homology with human Tear Prealbumin (GenBank accession no. gi|307518) and rat Oderant-binding protein (GenBank accession no. gi|207551), both of which are thought to be important in molecule binding and transport. The translation product of this gene is a homolog of the lipocalin family, which are thought to be involved in the transport of small hydrophobic molecules. In specific embodiments, polypeptides of the invention comprise the following amino acid sequence: EFGTSRGRQHRALE (SEQ ID NO:219), HQTPGVTGLSAVEMDQITPALWEALAIDTL-RKLRIGTRRPRIRWGQEAHV PAGAAQE GPLHLLLQRPAPWGXAPHGKACG (SEQ ID NO:220), GLGQGGQGLDGGRK LMY LQELPRRDHYIFYCK-DQHHGGXLHMGKLVGRNSDTNREALEEFKK LVQRKGLSEEDIFTPLQTGSCVPEH (SEQ ID NO:221), SGPSRLRTSLSHPVS DVRATSPPGRRGQ-PLLGGGQSWGPGKRAAWALSTCGGW CTGVGGGG XWGWEWGRGSQALYLPGSSVFRXRIFFW-MHRSSLMKVNVASNFPPPRAVTF TGDTFWASCLR KVLSTTMA-FTYQVPVISSSXRVKDRAAAXPSVTPRNRV FISRAL-CCRPRLVPN (SEQ ID NO:222), GLPEGRRDLVHLD-CGQACHTRCLMS GPPAPQEGEASPSLEVGRAGALAKGQPGHSLPVEAG ALGLAVGEGGGGXG GGAHRRCICQAPPSSAXGFSS-GCTDPPS (SEQ ID NO:223), VEMDQITPA LWEALAID-TLRKLRIGTRRPR (SEQ ID NO:224), RKLMY LQEL-PRRDHYIFYCK DQH (SEQ ID NO:225), EALEEFKKLVQRKGLSEEDIFTP (SEQ ID NO:226), RAT SPPGRRGQPLLGGGQSWGPGKRAA (SEQ ID NO:227), FFWMHRSSLMKV NVASNFPPPRAVTFTGD (SEQ ID NO:228), and/or CLMSGPPAPQEGEASP SLEVGRAGALAK (SEQ ID NO:229). Polynucleotides encoding these polypeptides are also encompassed by the invention.

This gene is expressed primarily in endometrial tumor.

Therefore, polynucleotides and polypeptides of the invention are useful as reagents for differential identification of the tissue(s) or cell type(s) present in a biological sample and for diagnosis of diseases and conditions which include, but are not limited to, reproductive disorders, particularly cancers of the endometrium, skin and haemopoietic system. Similarly, polypeptides and antibodies directed to these polypeptides are useful in providing immunological probes for differential identification of the tissue(s) or cell type(s). For a number of disorders of the above tissues or cells, particularly of the haemopoietic system, expression of this gene at significantly higher or lower levels may be routinely detected in certain tissues or cell types (e.g. immune, reproductive, and cancerous and wounded tissues) or bodily fluids (e.g., lymph, serum, amniotic fluid, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution in endometrium tissue, combined with the homology to the molecule binding and transport gene family indicates that the protein products of this gene are useful for the diagnosis and treatment of cancers of the endometrium and haemopoietic system as well as for the treatment of autoimmune disorders such as inflammation. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:42 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 988 of SEQ ID NO:42, b is an integer of 15 to 1002, where both a and b correspond to the positions of nucleotide residues shown in SEQ ID NO:42, and where b is greater than or equal to a+14.

| Gene No. | cDNA Clone ID | ATCC Deposit Nr and Date | Vector | NT SEQ ID NO: X | Total NT Seq. | 5' NT of Clone Seq. | 3' NT of Clone Seq. | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|---|---|---|---|---|---|---|
| 1 | HSVBZ80 | 97978 Mar. 27, 1997 209075 May 22, 1997 | Uni-ZAP XR | 11 | 1169 | 64 | 1060 | 162 | 162 | 47 | 1 | 38 | 39 | 145 |
| 2 | HTAAU21 | 97978 Mar. 27, 1997 209075 May 22, 1997 | Uni-ZAP XR | 12 | 1310 | 1 | 1310 | 283 | 283 | 48 | 1 | 18 | 19 | 311 |
| 3 | HTLEK16 | 97978 Mar. 27, 1997 209075 May 22, 1997 | Uni-ZAP XR | 13 | 1139 | 19 | 1111 | | 251 | 49 | 1 | 21 | 22 | 46 |
| 4 | HUSIR91 | 97978 Mar. 27, 1997 209075 May 22, 1997 | pSport1 | 14 | 2271 | 743 | 2271 | 59 | 59 | 50 | 1 | 23 | 24 | 467 |

-continued

| Gene No. | cDNA Clone ID | ATCC Deposit Nr and Date | Vector | NT SEQ ID NO: X | Total NT Seq. | 5' NT of Clone Seq. | 3' NT of Clone Seq. | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|---|---|---|---|---|---|---|
| 4 | HUSIR91 | 97978 Mar. 27, 1997 209075 May 22, 1997 | pSport1 | 43 | 2581 | 1035 | 2164 | 1148 | 1148 | 79 | 1 | 27 | 28 | 207 |
| 5 | HADMC21 | 97978 Mar. 27, 1997 209075 May 22, 1997 | pBluescript | 15 | 626 | 60 | 479 | 91 | 91 | 51 | 1 | 51 | 52 | 82 |
| 6 | HAGFM45 | 97978 Mar. 27, 1997 209075 May 22, 1997 | Uni-ZAP XR | 16 | 2118 | 1170 | 2058 | 1248 | 1248 | 52 | 1 | 16 | 17 | 62 |
| 7 | HAIBE65 | 97978 Mar. 27, 1997 209075 May 22, 1997 | Uni-ZAP XR | 17 | 1076 | 396 | 993 | 528 | 528 | 53 | 1 | 31 | 32 | 123 |
| 8 | HAQBH57 | 97978 Mar. 27, 1997 209075 May 22, 1997 | Uni-ZAP XR | 18 | 1379 | 420 | 1306 | 618 | 618 | 54 | 1 | 25 | 26 | 179 |
| 9 | HATCX80 | 97978 Mar. 27, 1997 209075 May 22, 1997 | Uni-ZAP XR | 19 | 1337 | 47 | 1337 | 199 | 199 | 55 | 1 | 18 | 19 | 286 |
| 10 | HCFLQ84 | 97978 Mar. 27, 1997 209075 May 22, 1997 | pSport1 | 20 | 1390 | 237 | 1390 | 410 | 410 | 56 | 1 | 20 | 21 | 33 |
| 11 | HCFLS78 | 97978 Mar. 27, 1997 209075 May 22, 1997 | pSport1 | 21 | 1431 | 178 | 981 | 420 | 420 | 57 | 1 | 21 | 22 | 23 |
| 12 | HTADI12 | 97978 Mar. 27, 1997 209075 May 22, 1997 | Uni-ZAP XR | 22 | 2539 | 69 | 2539 | 104 | 104 | 58 | 1 | 27 | 28 | 46 |
| 13 | HEMCM42 | 97978 Mar. 27, 1997 209075 May 22, 1997 | Uni-ZAP XR | 23 | 1041 | 48 | 1007 | 58 | 58 | 59 | 1 | 29 | 30 | 113 |
| 14 | HEONP72 | 97978 Mar. 27, 1997 209075 May 22, 1997 | pSport1 | 24 | 1962 | 1 | 1947 | 181 | 181 | 60 | 1 | 19 | 20 | 31 |
| 15 | HFCDW34 | 97978 Mar. 27, 1997 209075 May 22, 1997 | Uni-ZAP XR | 25 | 1228 | 321 | 1228 | 525 | 525 | 61 | 1 | 24 | 25 | 80 |
| 16 | HTTEU91 | 97978 Mar. 27, 1997 209075 May 22, 1997 | Uni-ZAP XR | 26 | 1340 | 325 | 1340 | 15 | 15 | 62 | 1 | 18 | 19 | 104 |
| 17 | HHGBF89 | 97978 Mar. 27, 1997 209075 May 22, 1997 | Lambda ZAP II | 27 | 806 | 31 | 806 | 77 | 77 | 63 | 1 | 19 | 20 | 145 |
| 17 | HHGBF89 | 97978 Mar. 27, 1997 209075 May 22, 1997 | Lambda ZAP II | 44 | 796 | 31 | 796 | 77 | 77 | 80 | 1 | 25 | 26 | 145 |
| 18 | HKIYQ65 | 97978 Mar. 27, 1997 209075 May 22, 1997 | pBluescript | 28 | 696 | 1 | 684 | 98 | 98 | 64 | 1 | 17 | 18 | 30 |
| 19 | HKMLN27 | 97978 Mar. 27, 1997 209075 May 22, 1997 | pBluescript | 29 | 1007 | 71 | 963 | 129 | 129 | 65 | 1 | 23 | 24 | 259 |
| 20 | HKIAC30 | 209022 May 08, 1997 | Uni-ZAP XR | 30 | 2026 | 131 | 2018 | 166 | 166 | 66 | 1 | 30 | 31 | 339 |
| 20 | HKIAC30 | 209022 May 08, 1997 | Uni-ZAP XR | 45 | 2017 | 126 | 2007 | 161 | 161 | 81 | 1 | | | 22 |
| 21 | HKIXB95 | 209022 May 08, 1997 | pBluescript | 31 | 699 | 196 | 699 | 230 | 230 | 67 | 1 | 22 | 23 | 26 |

-continued

| Gene No. | cDNA Clone ID | ATCC Deposit Nr and Date | Vector | NT SEQ ID NO: X | Total NT Seq. | 5' NT of Clone Seq. | 3' NT of Clone Seq. | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|---|---|---|---|---|---|---|
| 22 | HLMIY86 | 209022 May 08, 1997 | Lambda ZAP II | 32 | 1264 | 1 | 1264 | 560 | 560 | 68 | 1 | 24 | 25 | 76 |
| 23 | HLYAZ61 | 209022 May 08, 1997 | pSport1 | 33 | 997 | 74 | 997 | 205 | 205 | 69 | 1 | 20 | 21 | 215 |
| 24 | HMQDT36 | 209022 May 08, 1997 | Uni-ZAP XR | 34 | 1914 | 37 | 1897 | 192 | 192 | 70 | 1 | 32 | 33 | 406 |
| 25 | HNEDF25 | 209022 May 08, 1997 | Uni-ZAP XR | 35 | 1020 | 1 | 1010 | 210 | 210 | 71 | 1 | 13 | 14 | 45 |
| 26 | HNFET17 | 209022 May 08, 1997 | Uni-ZAP XR | 36 | 781 | 31 | 781 | 100 | 100 | 72 | 1 | | | 33 |
| 27 | HNHCR46 | 209022 May 08, 1997 | Uni-ZAP XR | 37 | 966 | 19 | 460 | 458 | 458 | 73 | 1 | 24 | 25 | 160 |
| 28 | HPWAS91 | 209022 May 08, 1997 | Uni-ZAP XR | 38 | 416 | 1 | 416 | 95 | 95 | 74 | 1 | 24 | 25 | 25 |
| 29 | HWTAW41 | 209022 May 08, 1997 | Uni-ZAP XR | 39 | 1114 | 804 | 1114 | 50 | 50 | 75 | 1 | 43 | 44 | 91 |
| 30 | HBMUT52 | 209022 May 08, 1997 | Uni-ZAP XR | 40 | 602 | 142 | 602 | 204 | 204 | 76 | 1 | 26 | 27 | 32 |
| 31 | HERAG83 | 209022 May 08, 1997 | Uni-ZAP XR | 41 | 970 | 1 | 970 | 110 | 110 | 77 | 1 | 22 | 23 | 22 |
| 32 | HETFI51 | 209022 May 08, 1997 | Uni-ZAP XR | 42 | 1002 | 1 | 1002 | 43 | 43 | 78 | 1 | 21 | 22 | 173 |
| 32 | HETFI51 | 209022 May 08, 1997 | Uni-ZAP XR | 46 | 981 | 1 | 981 | 23 | 23 | 82 | 1 | 17 | 18 | 30 |

Table 1 summarizes the information corresponding to each "Gene No." described above. The nucleotide sequence identified as "NT SEQ ID NO:X" was assembled from partially homologous ("overlapping") sequences obtained from the "cDNA clone ID" identified in Table 1 and, in some cases, from additional related DNA clones. The overlapping sequences were assembled into a single contiguous sequence of high redundancy (usually three to five overlapping sequences at each nucleotide position), resulting in a final sequence identified as SEQ ID NO:X.

The cDNA Clone ID was deposited on the date and given the corresponding deposit number listed in "ATCC Deposit No:Z and Date." Some of the deposits contain multiple different clones corresponding to the same gene. "Vector" refers to the type of vector contained in the cDNA Clone ID.

"Total NT Seq." refers to the total number of nucleotides in the contig identified by "Gene No." The deposited clone may contain all or most of these sequences, reflected by the nucleotide position indicated as "5' NT of Clone Seq." and the "3' NT of Clone Seq." of SEQ ID NO:X. The nucleotide position of SEQ ID NO:X of the putative start codon (methionine) is identified as "5' NT of Start Codon." Similarly, the nucleotide position of SEQ ID NO:X of the predicted signal sequence is identified as "5' NT of First AA of Signal Pep."

The translated amino acid sequence, beginning with the methionine, is identified as "AA SEQ ID NO:Y," although other reading frames can also be easily translated using known molecular biology techniques. The polypeptides produced by these alternative open reading frames are specifically contemplated by the present invention.

The first and last amino acid position of SEQ ID NO:Y of the predicted signal peptide is identified as "First AA of Sig Pep" and "Last AA of Sig Pep." The predicted first amino acid position of SEQ ID NO:Y of the secreted portion is identified as "Predicted First AA of Secreted Portion." Finally, the amino acid position of SEQ ID NO:Y of the last amino acid in the open reading frame is identified as "Last AA of ORF."

SEQ ID NO:X and the translated SEQ ID NO:Y are sufficiently accurate and otherwise suitable for a variety of uses well known in the art and described further below. For instance, SEQ ID NO:X is useful for designing nucleic acid hybridization probes that will detect nucleic acid sequences contained in SEQ ID NO:X or the cDNA contained in the deposited clone. These probes will also hybridize to nucleic acid molecules in biological samples, thereby enabling a variety of forensic and diagnostic methods of the invention. Similarly, polypeptides identified from SEQ ID NO:Y may be used to generate antibodies which bind specifically to the secreted proteins encoded by the cDNA clones identified in Table 1.

Nevertheless, DNA sequences generated by sequencing reactions can contain sequencing errors. The errors exist as misidentified nucleotides, or as insertions or deletions of nucleotides in the generated DNA sequence. The erroneously inserted or deleted nucleotides cause frame shifts in the reading frames of the predicted amino acid sequence. In these cases, the predicted amino acid sequence diverges from the actual amino acid sequence, even though the generated DNA sequence may be greater than 99.9% identical to the actual DNA sequence (for example, one base insertion or deletion in an open reading frame of over 1000 bases).

Accordingly, for those applications requiring precision in the nucleotide sequence or the amino acid sequence, the present invention provides not only the generated nucleotide sequence identified as SEQ ID NO:X and the predicted translated amino acid sequence identified as SEQ ID NO:Y, but also a sample of plasmid DNA containing a human cDNA of the invention deposited with the ATCC, as set forth in Table 1. The nucleotide sequence of each deposited clone can readily be determined by sequencing the deposited clone in accordance with known methods. The predicted amino acid sequence can then be verified from such deposits. Moreover, the amino acid sequence of the protein encoded by a particular clone can also be directly determined by peptide sequencing or by expressing the protein in a suitable host cell containing the deposited human cDNA, collecting the protein, and determining its sequence.

The present invention also relates to the genes corresponding to SEQ ID NO:X, SEQ ID NO:Y, or the deposited clone. The corresponding gene can be isolated in accordance with known methods using the sequence information disclosed herein. Such methods include preparing probes or primers from the disclosed sequence and identifying or amplifying the corresponding gene from appropriate sources of genomic material.

Also provided in the present invention are species homologs. Species homologs may be isolated and identified by making suitable probes or primers from the sequences provided herein and screening a suitable nucleic acid source for the desired homologue.

The polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

The polypeptides may be in the form of the secreted protein, including the mature form, or may be a part of a larger protein, such as a fusion protein (see below). It is often advantageous to include an additional amino acid sequence which contains secretory or leader sequences, pro-sequences, sequences which aid in purification, such as multiple histidine residues, or an additional sequence for stability during recombinant production.

The polypeptides of the present invention are preferably provided in an isolated form, and preferably are substantially purified. A recombinantly produced version of a polypeptide, including the secreted polypeptide, can be substantially purified by the one-step method described in Smith and Johnson, Gene 67:31-40 (1988). Polypeptides of the invention also can be purified from natural or recombinant sources using antibodies of the invention raised against the secreted protein in methods which are well known in the art.

Signal Sequences

Methods for predicting whether a protein has a signal sequence, as well as the cleavage point for that sequence, are available. For instance, the method of McGeoch, Virus Res. 3:271-286 (1985), uses the information from a short N-terminal charged region and a subsequent uncharged region of the complete (uncleaved) protein. The method of von Heinje, Nucleic Acids Res. 14:4683-4690 (1986) uses the information from the residues surrounding the cleavage site, typically residues—13 to +2, where +1 indicates the amino terminus of the secreted protein. The accuracy of predicting the cleavage points of known mammalian secretory proteins for each of these methods is in the range of 75-80%. (von Heinje, supra.) However, the two methods do not always produce the same predicted cleavage point(s) for a given protein.

In the present case, the deduced amino acid sequence of the secreted polypeptide was analyzed by a computer program called SignalP (Henrik Nielsen et al., Protein Engineering 10:1-6 (1997)), which predicts the cellular location of a protein based on the amino acid sequence. As part of this computational prediction of localization, the methods of McGeoch and von Heinje are incorporated. The analysis of the amino acid sequences of the secreted proteins described herein by this program provided the results shown in Table 1.

As one of ordinary skill would appreciate, however, cleavage sites sometimes vary from organism to organism and cannot be predicted with absolute certainty. Accordingly, the present invention provides secreted polypeptides having a sequence shown in SEQ ID NO:Y which have an N-terminus beginning within 5 residues (i.e., + or −5 residues) of the predicted cleavage point. Similarly, it is also recognized that in some cases, cleavage of the signal sequence from a secreted protein is not entirely uniform, resulting in more than one secreted species. These polypeptides, and the polynucleotides encoding such polypeptides, are contemplated by the present invention.

Moreover, the signal sequence identified by the above analysis may not necessarily predict the naturally occurring signal sequence. For example, the naturally occurring signal sequence may be further upstream from the predicted signal sequence. However, it is likely that the predicted signal sequence will be capable of directing the secreted protein to the ER. These polypeptides, and the polynucleotides encoding such polypeptides, are contemplated by the present invention.

Polynucleotide and Polypeptide Variants

"Variant" refers to a polynucleotide or polypeptide differing from the polynucleotide or polypeptide of the present invention, but retaining essential properties thereof. Generally, variants are overall closely similar, and, in many regions, identical to the polynucleotide or polypeptide of the present invention.

By a polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence encoding the polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence shown in Table 1, the ORF (open reading frame), or any fragment specified as described herein.

As a practical matter, whether any particular nucleic acid molecule or polypeptide is at least 90%, 95%, 96%, 97%, 98% or 99% identical to a nucleotide sequence of the presence invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237-245). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequences shown in Table 1 or to the amino acid sequence encoded by deposited DNA clone can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237-245). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to made for the purposes of the present invention.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5-10, 1-5, or 1-2 amino acids are substituted, deleted, or added in any combination are also preferred. Polynucleotide variants can be produced for a variety of reasons, e.g., to optimize codon expression for a particular host (change codons in the human mRNA to those preferred by a bacterial host such as *E. coli*).

Naturally occurring variants are called "allelic variants," and refer to one of several alternate forms of a gene occupying a given locus on a chromosome of an organism. (Genes II, Lewin, B., ed., John Wiley & Sons, New York (1985).) These allelic variants can vary at either the polynucleotide and/or polypeptide level. Alternatively, non-naturally occurring variants may be produced by mutagenesis techniques or by direct synthesis.

Using known methods of protein engineering and recombinant DNA technology, variants may be generated to improve or alter the characteristics of the polypeptides of the present invention. For instance, one or more amino acids can be deleted from the N-terminus or C-terminus of the secreted protein without substantial loss of biological function. The authors of Ron et al., J. Biol. Chem. 268: 2984-2988 (1993), reported variant KGF proteins having heparin binding activity even after deleting 3, 8, or 27 amino-terminal amino acid residues. Similarly, Interferon gamma exhibited up to ten times higher activity after deleting 8-10 amino acid residues from the carboxy terminus of this protein. (Dobeli et al., J. Biotechnology 7:199-216 (1988).)

Moreover, ample evidence demonstrates that variants often retain a biological activity similar to that of the naturally occurring protein. For example, Gayle and coworkers (J. Biol. Chem 268:22105-22111 (1993)) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." (See, Abstract.) In fact, only 23 unique amino acid sequences, out of more than 3,500 nucleotide sequences examined, produced a protein that significantly differed in activity from wild-type.

Furthermore, even if deleting one or more amino acids from the N-terminus or C-terminus of a polypeptide results in modification or loss of one or more biological functions, other biological activities may still be retained. For example, the ability of a deletion variant to induce and/or to bind antibodies which recognize the secreted form will likely be retained when less than the majority of the residues of the secreted form are removed from the N-terminus or C-terminus. Whether a particular polypeptide lacking N- or C-terminal residues of a protein retains such immunogenic activities can readily be determined by routine methods described herein and otherwise known in the art.

Thus, the invention further includes polypeptide variants which show substantial biological activity. Such variants include deletions, insertions, inversions, repeats, and substitutions selected according to general rules known in the art so as have little effect on activity. For example, guidance concerning how to make phenotypically silent amino acid substitutions is provided in Bowie, J. U. et al., Science 247:1306-1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244:1081-1085 (1989).) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

Besides conservative amino acid substitution, variants of the present invention include (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as an IgG Fc fusion region peptide, or leader or secretory sequence, or a sequence facilitating purification. Such variant polypeptides are deemed to be within the scope of those skilled in the art from the teachings herein.

For example, polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331-340 (1967); Robbins et al., Diabetes 36: 838-845 (1987); Cleland et al., Crit. Rev. Therapeutic Drug Carrier Systems 10:307-377 (1993).)

Polynucleotide and Polypeptide Fragments

In the present invention, a "polynucleotide fragment" refers to a short polynucleotide having a nucleic acid sequence contained in the deposited clone or shown in SEQ ID NO:X. The short nucleotide fragments are preferably at least about 15 nt, and more preferably at least about 20 nt, still more preferably at least about 30 nt, and even more preferably, at least about 40 nt in length. A fragment "at least 20 nt in length," for example, is intended to include 20 or more contiguous bases from the cDNA sequence contained in the deposited clone or the nucleotide sequence shown in SEQ ID NO:X. These nucleotide fragments are useful as diagnostic probes and primers as discussed herein. Of course, larger fragments (e.g., 50, 150, 500, 600, 2000 nucleotides) are preferred.

Moreover, representative examples of polynucleotide fragments of the invention, include, for example, fragments having a sequence from about nucleotide number 1-50, 51-100, 101-150, 151-200, 201-250, 251-300, 301-350, 351-400, 401-450, 451-500, 501-550, 551-600, 651-700, 701-750, 751-800, 800-850, 851-900, 901-950, 951-1000, 1001-1050, 1051-1100, 1101-1150, 1151-1200, 1201-1250, 1251-1300, 1301-1350, 1351-1400, 1401-1450, 1451-1500, 1501-1550, 1551-1600, 1601-1650, 1651-1700, 1701-1750, 1751-1800, 1801-1850, 1851-1900, 1901-1950, 1951-2000, or 2001 to the end of SEQ ID NO:X or the cDNA contained in the deposited clone. In this context "about" includes the particularly recited ranges, larger or smaller by several (5, 4, 3, 2, or 1) nucleotides, at either terminus or at both termini. Preferably, these fragments encode a polypeptide which has biological activity. More preferably, these polynucleotides can be used as probes or primers as discussed herein.

In the present invention, a "polypeptide fragment" refers to a short amino acid sequence contained in SEQ ID NO:Y or encoded by the cDNA contained in the deposited clone. Protein fragments may be "free-standing," or comprised within a larger polypeptide of which the fragment forms a part or region, most preferably as a single continuous region. Representative examples of polypeptide fragments of the invention, include, for example, fragments from about amino acid number 1-20, 21-40, 41-60, 61-80, 81-100, 102-120, 121-140, 141-160, or 161 to the end of the coding region. Moreover, polypeptide fragments can be about 20, 30, 40, 50, 60, 70, 80, 90, 100, 110, 120, 130, 140, or 150 amino acids in length. In this context "about" includes the particularly recited ranges, larger or smaller by several (5, 4, 3, 2, or 1) amino acids, at either extreme or at both extremes.

Preferred polypeptide fragments include the secreted protein as well as the mature form. Further preferred polypeptide fragments include the secreted protein or the mature form having a continuous series of deleted residues from the amino or the carboxy terminus, or both. For example, any number of amino acids, ranging from 1-60, can be deleted from the amino terminus of either the secreted polypeptide or the mature form. Similarly, any number of amino acids, ranging from 1-30, can be deleted from the carboxy terminus of the secreted protein or mature form. Furthermore, any combination of the above amino and carboxy terminus deletions are preferred. Similarly, polynucleotide fragments encoding these polypeptide fragments are also preferred.

Also preferred are polypeptide and polynucleotide fragments characterized by structural or functional domains, such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Polypeptide fragments of SEQ ID NO:Y falling within conserved domains are specifically contemplated by the present invention. Moreover, polynucleotide fragments encoding these domains are also contemplated.

Other preferred fragments are biologically active fragments. Biologically active fragments are those exhibiting activity similar, but not necessarily identical, to an activity of the polypeptide of the present invention. The biological activity of the fragments may include an improved desired activity, or a decreased undesirable activity.

Epitopes & Antibodies

In the present invention, "epitopes" refer to polypeptide fragments having antigenic or immunogenic activity in an animal, especially in a human. A preferred embodiment of the present invention relates to a polypeptide fragment comprising an epitope, as well as the polynucleotide encoding this fragment. A region of a protein molecule to which an antibody can bind is defined as an "antigenic epitope." In contrast, an "immunogenic epitope" is defined as a part of a protein that elicits an antibody response. (See, for instance, Geysen et al., Proc. Natl. Acad. Sci. USA 81:3998-4002 (1983).)

Fragments which function as epitopes may be produced by any conventional means. (See, e.g., Houghten, R. A., Proc. Natl. Acad. Sci. USA 82:5131-5135 (1985) further described in U.S. Pat. No. 4,631,211.)

In the present invention, antigenic epitopes preferably contain a sequence of at least seven, more preferably at least nine, and most preferably between about 15 to about 30 amino acids. Antigenic epitopes are useful to raise antibodies, including monoclonal antibodies, that specifically bind the epitope. (See, for instance, Wilson et al., Cell 37:767-778 (1984); Sutcliffe, J. G. et al., Science 219:660-666 (1983).)

Similarly, immunogenic epitopes can be used to induce antibodies according to methods well known in the art. (See, for instance, Sutcliffe et al., supra; Wilson et al., supra; Chow, M. et al., Proc. Natl. Acad. Sci. USA 82:910-914; and Bittle, F. J. et al., J. Gen. Virol. 66:2347-2354 (1985).) A preferred immunogenic epitope includes the secreted protein. The immunogenic epitopes may be presented together with a carrier protein, such as an albumin, to an animal system (such as rabbit or mouse) or, if it is long enough (at least about 25 amino acids), without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting.)

As used herein, the term "antibody" (Ab) or "monoclonal antibody" (Mab) is meant to include intact molecules as well as antibody fragments (such as, for example, Fab and F(ab')2 fragments) which are capable of specifically binding to protein. Fab and F(ab')2 fragments lack the Fc fragment of intact antibody, clear more rapidly from the circulation, and may have less non-specific tissue binding than an intact antibody. (Wahl et al., J. Nucl. Med. 24:316-325 (1983).) Thus, these fragments are preferred, as well as the products of a FAB or other immunoglobulin expression library. Moreover, antibodies of the present invention include chimeric, single chain, and humanized antibodies.

Fusion Proteins

Any polypeptide of the present invention can be used to generate fusion proteins. For example, the polypeptide of the present invention, when fused to a second protein, can be used as an antigenic tag. Antibodies raised against the polypeptide of the present invention can be used to indirectly detect the second protein by binding to the polypeptide. Moreover, because secreted proteins target cellular locations based on trafficking signals, the polypeptides of the present invention can be used as targeting molecules once fused to other proteins.

Examples of domains that can be fused to polypeptides of the present invention include not only heterologous signal sequences, but also other heterologous functional regions. The fusion does not necessarily need to be direct, but may occur through linker sequences.

Moreover, fusion proteins may also be engineered to improve characteristics of the polypeptide of the present invention. For instance, a region of additional amino acids, particularly charged amino acids, may be added to the N-terminus of the polypeptide to improve stability and persistence during purification from the host cell or subsequent handling and storage. Also, peptide moieties may be added to the polypeptide to facilitate purification. Such regions may be removed prior to final preparation of the polypeptide. The addition of peptide moieties to facilitate handling of polypeptides are familiar and routine techniques in the art.

Moreover, polypeptides of the present invention, including fragments, and specifically epitopes, can be combined with parts of the constant domain of immunoglobulins (IgG), resulting in chimeric polypeptides. These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. (EP A 394,827; Traunecker et al., Nature 331:84-86 (1988).) Fusion proteins having disulfide-linked dimeric structures (due to the IgG) can also be more efficient in binding and neutralizing other molecules, than the monomeric secreted protein or protein fragment alone. (Fountoulakis et al., J. Biochem. 270:3958-3964 (1995).)

Similarly, EP-A-O 464 533 (Canadian counterpart 2045869) discloses fusion proteins comprising various portions of constant region of immunoglobulin molecules together with another human protein or part thereof. In many cases, the Fc part in a fusion protein is beneficial in therapy and diagnosis, and thus can result in, for example, improved pharmacokinetic properties. (EP-A 0232 262.) Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., J. Molecular Recognition 8:52-58 (1995); K. Johanson et al., J. Biol. Chem. 270:9459-9471 (1995).)

Moreover, the polypeptides of the present invention can be fused to marker sequences, such as a peptide which facilitates purification of the fused polypeptide. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Another peptide tag useful for purification, the "HA" tag, corresponds to an epitope derived from the influenza hemagglutinin protein. (Wilson et al., Cell 37:767 (1984).)

Thus, any of these above fusions can be engineered using the polynucleotides or the polypeptides of the present invention.

Vectors, Host Cells, and Protein Production

The present invention also relates to vectors containing the polynucleotide of the present invention, host cells, and the production of polypeptides by recombinant techniques. The vector may be, for example, a phage, plasmid, viral, or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The polynucleotide insert should be operatively linked to an appropriate promoter, such as the phage lambda PL promoter, the E. coli lac, trp, phoA and tac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in E. coli and other bacteria. Representative examples of appropriate hosts include, but are not limited to, bacterial cells, such as E. coli, Streptomyces and Salmonella typhimurium cells; fungal cells, such as yeast cells; insect cells such as Drosophila S2 and Spodoptera Sf9 cells; animal cells such as CHO, COS, 293, and Bowes melanoma cells; and plant cells. Appropriate culture mediums and conditions for the above-described host cells are known in the art.

Among vectors preferred for use in bacteria include pQE70, pQE60 and pQE-9, available from QIAGEN, Inc.; pBluescript vectors, Phagescript vectors, pNH8A, pNH16a, pNH18A, pNH46A, available from Stratagene Cloning Systems, Inc.; and ptrc99a, pKK223-3, pKK233-3, pDR540, pRIT5 available from Pharmacia Biotech, Inc. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986). It is specifically contemplated that the polypeptides of the present invention may in fact be expressed by a host cell lacking a recombinant vector.

A polypeptide of this invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention, and preferably the secreted form, can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

Uses of the Polynucleotides

Each of the polynucleotides identified herein can be used in numerous ways as reagents. The following description should be considered exemplary and utilizes known techniques.

The polynucleotides of the present invention are useful for chromosome identification. There exists an ongoing need to identify new chromosome markers, since few chromosome marking reagents, based on actual sequence data (repeat polymorphisms), are presently available. Each polynucleotide of the present invention can be used as a chromosome marker.

Briefly, sequences can be mapped to chromosomes by preparing PCR primers (preferably 15-25 bp) from the sequences shown in SEQ ID NO:X. Primers can be selected using computer analysis so that primers do not span more than one predicted exon in the genomic DNA. These primers are then used for PCR screening of somatic cell hybrids containing individual human chromosomes. Only those hybrids containing the human gene corresponding to the SEQ ID NO:X will yield an amplified fragment.

Similarly, somatic hybrids provide a rapid method of PCR mapping the polynucleotides to particular chromosomes. Three or more clones can be assigned per day using a single thermal cycler. Moreover, sublocalization of the polynucleotides can be achieved with panels of specific chromosome fragments. Other gene mapping strategies that can be used include in situ hybridization, prescreening with labeled flow-sorted chromosomes, and preselection by hybridization to construct chromosome specific-cDNA libraries.

Precise chromosomal location of the polynucleotides can also be achieved using fluorescence in situ hybridization (FISH) of a metaphase chromosomal spread. This technique uses polynucleotides as short as 500 or 600 bases; however, polynucleotides 2,000-4,000 bp are preferred. For a review of this technique, see Verma et al., "Human Chromosomes: a Manual of Basic Techniques," Pergamon Press, New York (1988).

For chromosome mapping, the polynucleotides can be used individually (to mark a single chromosome or a single site on that chromosome) or in panels (for marking multiple sites and/or multiple chromosomes). Preferred polynucleotides correspond to the noncoding regions of the cDNAs because the coding sequences are more likely conserved within gene families, thus increasing the chance of cross hybridization during chromosomal mapping.

Once a polynucleotide has been mapped to a precise chromosomal location, the physical position of the polynucleotide can be used in linkage analysis. Linkage analysis establishes coinheritance between a chromosomal location and presentation of a particular disease. (Disease mapping data are found, for example, in V. McKusick, Mendelian Inheritance in Man (available on line through Johns Hopkins University Welch Medical Library).) Assuming 1 megabase mapping resolution and one gene per 20 kb, a cDNA precisely localized to a chromosomal region associated with the disease could be one of 50-500 potential causative genes.

Thus, once coinheritance is established, differences in the polynucleotide and the corresponding gene between affected and unaffected individuals can be examined. First, visible structural alterations in the chromosomes, such as deletions or translocations, are examined in chromosome spreads or by PCR. If no structural alterations exist, the presence of point mutations are ascertained. Mutations observed in some or all affected individuals, but not in normal individuals, indicates that the mutation may cause the disease. However, complete sequencing of the polypeptide and the corresponding gene from several normal individuals is required to distinguish the mutation from a polymorphism. If a new polymorphism is identified, this polymorphic polypeptide can be used for further linkage analysis.

Furthermore, increased or decreased expression of the gene in affected individuals as compared to unaffected individuals can be assessed using polynucleotides of the present invention. Any of these alterations (altered expression, chromosomal rearrangement, or mutation) can be used as a diagnostic or prognostic marker.

In addition to the foregoing, a polynucleotide can be used to control gene expression through triple helix formation or antisense DNA or RNA. Both methods rely on binding of the polynucleotide to DNA or RNA. For these techniques, preferred polynucleotides are usually 20 to 40 bases in length and complementary to either the region of the gene involved in transcription (triple helix—see Lee et al., Nucl. Acids Res. 6:3073 (1979); Cooney et al., Science 241:456 (1988); and Dervan et al., Science 251:1360 (1991)) or to the mRNA itself (antisense—Okano, J. Neurochem. 56:560 (1991); Oligodeoxy-nucleotides as Antisense Inhibitors of Gene Expression, CRC Press, Boca Raton, Fla. (1988).) Triple helix formation optimally results in a shut-off of RNA transcription from DNA, while antisense RNA hybridization blocks translation of an mRNA molecule into polypeptide. Both techniques are effective in model systems, and the information disclosed herein can be used to design antisense or triple helix polynucleotides in an effort to treat disease.

Polynucleotides of the present invention are also useful in gene therapy. One goal of gene therapy is to insert a normal gene into an organism having a defective gene, in an effort to correct the genetic defect. The polynucleotides disclosed in the present invention offer a means of targeting such genetic defects in a highly accurate manner. Another goal is to insert a new gene that was not present in the host genome, thereby producing a new trait in the host cell.

The polynucleotides are also useful for identifying individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identifying personnel. This method does not suffer from the current limitations of "Dog Tags" which can be lost, switched, or stolen, making positive identification difficult. The polynucleotides of the present invention can be used as additional DNA markers for RFLP.

The polynucleotides of the present invention can also be used as an alternative to RFLP, by determining the actual base-by-base DNA sequence of selected portions of an individual's genome. These sequences can be used to prepare PCR primers for amplifying and isolating such selected DNA, which can then be sequenced. Using this technique, individuals can be identified because each individual will have a unique set of DNA sequences. Once an unique ID database is established for an individual, positive identification of that individual, living or dead, can be made from extremely small tissue samples.

Forensic biology also benefits from using DNA-based identification techniques as disclosed herein. DNA sequences taken from very small biological samples such as tissues, e.g., hair or skin, or body fluids, e.g., blood, saliva, semen, etc., can be amplified using PCR. In one prior art technique, gene sequences amplified from polymorphic loci, such as DQa class II HLA gene, are used in forensic biology to identify individuals. (Erlich, H., PCR Technology, Freeman and Co.

(1992).) Once these specific polymorphic loci are amplified, they are digested with one or more restriction enzymes, yielding an identifying set of bands on a Southern blot probed with DNA corresponding to the DQa class II HLA gene. Similarly, polynucleotides of the present invention can be used as polymorphic markers for forensic purposes.

There is also a need for reagents capable of identifying the source of a particular tissue. Such need arises, for example, in forensics when presented with tissue of unknown origin. Appropriate reagents can comprise, for example, DNA probes or primers specific to particular tissue prepared from the sequences of the present invention. Panels of such reagents can identify tissue by species and/or by organ type. In a similar fashion, these reagents can be used to screen tissue cultures for contamination.

In the very least, the polynucleotides of the present invention can be used as molecular weight markers on Southern gels, as diagnostic probes for the presence of a specific mRNA in a particular cell type, as a probe to "subtract-out" known sequences in the process of discovering novel polynucleotides, for selecting and making oligomers for attachment to a "gene chip" or other support, to raise anti-DNA antibodies using DNA immunization techniques, and as an antigen to elicit an immune response.

Uses of the Polypeptides

Each of the polypeptides identified herein can be used in numerous ways. The following description should be considered exemplary and utilizes known techniques.

A polypeptide of the present invention can be used to assay protein levels in a biological sample using antibody-based techniques. For example, protein expression in tissues can be studied with classical immunohistological methods. (Jalkanen, M., et al., J. Cell. Biol. 101:976-985 (1985); Jalkanen, M., et al., J. Cell. Biol. 105:3087-3096 (1987).) Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine ($125I$, $121I$), carbon ($14C$), sulfur ($35S$), tritium ($3H$), indium ($112In$), and technetium ($99mTc$), and fluorescent labels, such as fluorescein and rhodamine, and biotin.

In addition to assaying secreted protein levels in a biological sample, proteins can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A protein-specific antibody or antibody fragment which has been labeled with an appropriate detectable imaging moiety, such as a radioisotope (for example, $131I$, $112In$, $99mTc$), a radio-opaque substance, or a material detectable by nuclear magnetic resonance, is introduced (for example, parenterally, subcutaneously, or intraperitoneally) into the mammal. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99 mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).)

Thus, the invention provides a diagnostic method of a disorder, which involves (a) assaying the expression of a polypeptide of the present invention in cells or body fluid of an individual; (b) comparing the level of gene expression with a standard gene expression level, whereby an increase or decrease in the assayed polypeptide gene expression level compared to the standard expression level is indicative of a disorder.

Moreover, polypeptides of the present invention can be used to treat disease. For example, patients can be administered a polypeptide of the present invention in an effort to replace absent or decreased levels of the polypeptide (e.g., insulin), to supplement absent or decreased levels of a different polypeptide (e.g., hemoglobin S for hemoglobin B), to inhibit the activity of a polypeptide (e.g., an oncogene), to activate the activity of a polypeptide (e.g., by binding to a receptor), to reduce the activity of a membrane bound receptor by competing with it for free ligand (e.g., soluble TNF receptors used in reducing inflammation), or to bring about a desired response (e.g., blood vessel growth).

Similarly, antibodies directed to a polypeptide of the present invention can also be used to treat disease. For example, administration of an antibody directed to a polypeptide of the present invention can bind and reduce overproduction of the polypeptide. Similarly, administration of an antibody can activate the polypeptide, such as by binding to a polypeptide bound to a membrane (receptor).

At the very least, the polypeptides of the present invention can be used as molecular weight markers on SDS-PAGE gels or on molecular sieve gel filtration columns using methods well known to those of skill in the art. Polypeptides can also be used to raise antibodies, which in turn are used to measure protein expression from a recombinant cell, as a way of assessing transformation of the host cell. Moreover, the polypeptides of the present invention can be used to test the following biological activities.

Biological Activities

The polynucleotides and polypeptides of the present invention can be used in assays to test for one or more biological activities. If these polynucleotides and polypeptides do exhibit activity in a particular assay, it is likely that these molecules may be involved in the diseases associated with the biological activity. Thus, the polynucleotides and polypeptides could be used to treat the associated disease.

Immune Activity

A polypeptide or polynucleotide of the present invention may be useful in treating deficiencies or disorders of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune deficiencies or disorders may be genetic, somatic, such as cancer or some autoimmune disorders, acquired (e.g., by chemotherapy or toxins), or infectious. Moreover, a polynucleotide or polypeptide of the present invention can be used as a marker or detector of a particular immune system disease or disorder.

A polynucleotide or polypeptide of the present invention may be useful in treating or detecting deficiencies or disorders of hematopoietic cells. A polypeptide or polynucleotide of the present invention could be used to increase differentiation and proliferation of hematopoietic cells, including the pluripotent stem cells, in an effort to treat those disorders associated with a decrease in certain (or many) types hematopoietic cells. Examples of immunologic deficiency syndromes include, but are not limited to: blood protein disorders (e.g. agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

Moreover, a polypeptide or polynucleotide of the present invention could also be used to modulate hemostatic (the stopping of bleeding) or thrombolytic activity (clot formation). For example, by increasing hemostatic or thrombolytic activity, a polynucleotide or polypeptide of the present invention could be used to treat blood coagulation disorders (e.g., afibrinogenemia, factor deficiencies), blood platelet disorders (e.g. thrombocytopenia), or wounds resulting from trauma, surgery, or other causes. Alternatively, a polynucleotide or polypeptide of the present invention that can decrease hemostatic or thrombolytic activity could be used to inhibit or dissolve clotting. These molecules could be important in the treatment of heart attacks (infarction), strokes, or scarring.

A polynucleotide or polypeptide of the present invention may also be useful in treating or detecting autoimmune disorders. Many autoimmune disorders result from inappropriate recognition of self as foreign material by immune cells. This inappropriate recognition results in an immune response leading to the destruction of the host tissue. Therefore, the administration of a polypeptide or polynucleotide of the present invention that inhibits an immune response, particularly the proliferation, differentiation, or chemotaxis of T-cells, may be an effective therapy in preventing autoimmune disorders.

Examples of autoimmune disorders that can be treated or detected by the present invention include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitis, and autoimmune inflammatory eye disease.

Similarly, allergic reactions and conditions, such as asthma (particularly allergic asthma) or other respiratory problems, may also be treated by a polypeptide or polynucleotide of the present invention. Moreover, these molecules can be used to treat anaphylaxis, hypersensitivity to an antigenic molecule, or blood group incompatibility.

A polynucleotide or polypeptide of the present invention may also be used to treat and/or prevent organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of a polypeptide or polynucleotide of the present invention that inhibits an immune response, particularly the proliferation, differentiation, or chemotaxis of T-cells, may be an effective therapy in preventing organ rejection or GVHD.

Similarly, a polypeptide or polynucleotide of the present invention may also be used to modulate inflammation. For example, the polypeptide or polynucleotide may inhibit the proliferation and differentiation of cells involved in an inflammatory response. These molecules can be used to treat inflammatory conditions, both chronic and acute conditions, including inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.)

Hyperproliferative Disorders

A polypeptide or polynucleotide can be used to treat or detect hyperproliferative disorders, including neoplasms. A polypeptide or polynucleotide of the present invention may inhibit the proliferation of the disorder through direct or indirect interactions. Alternatively, a polypeptide or polynucleotide of the present invention may proliferate other cells which can inhibit the hyperproliferative disorder.

For example, by increasing an immune response, particularly increasing antigenic qualities of the hyperproliferative disorder or by proliferating, differentiating, or mobilizing T-cells, hyperproliferative disorders can be treated. This immune response may be increased by either enhancing an existing immune response, or by initiating a new immune response. Alternatively, decreasing an immune response may also be a method of treating hyperproliferative disorders, such as a chemotherapeutic agent.

Examples of hyperproliferative disorders that can be treated or detected by a polynucleotide or polypeptide of the present invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative disorders can also be treated or detected by a polynucleotide or polypeptide of the present invention. Examples of such hyperproliferative disorders include, but are not limited to: hypergammaglobulinemia, lymphoproliferative disorders, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

Infectious Disease

A polypeptide or polynucleotide of the present invention can be used to treat or detect infectious agents. For example, by increasing the immune response, particularly increasing the proliferation and differentiation of B and/or T cells, infectious diseases may be treated. The immune response may be increased by either enhancing an existing immune response, or by initiating a new immune response. Alternatively, the polypeptide or polynucleotide of the present invention may also directly inhibit the infectious agent, without necessarily eliciting an immune response.

Viruses are one example of an infectious agent that can cause disease or symptoms that can be treated or detected by a polynucleotide or polypeptide of the present invention. Examples of viruses, include, but are not limited to the following DNA and RNA viral families: Arbovirus, Adenoviridae, Arenaviridae, Arterivirus, Birnaviridae, Bunyaviridae, Caliciviridae, Circoviridae, Coronaviridae, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza), Papovaviridae, Parvoviridae, Picornaviridae, Poxyiridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiolitis, encephalitis, eye infections (e.g., conjunctivitis, keratitis), chronic fatigue syndrome, hepatitis (A, B, C, E, Chronic Active, Delta), meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. A polypeptide or polynucleotide of the present invention can be used to treat or detect any of these symptoms or diseases.

Similarly, bacterial or fungal agents that can cause disease or symptoms and that can be treated or detected by a polynucleotide or polypeptide of the present invention include, but not limited to, the following Gram-Negative and Gram-positive bacterial families and fungi: Actinomycetales (e.g., *Corynebacterium, Mycobacterium, Norcardia*), Aspergillosis, Bacillaceae (e.g., Anthrax, *Clostridium*), Bacteroidaceae, Blastomycosis, *Bordetella, Borrelia*, Brucellosis, Candidiasis, *Campylobacter*, Coccidioidomycosis, Cryptococcosis, Dermatocycoses, Enterobacteriaceae (*Klebsiella, Salmonella, Serratia, Yersinia*), *Erysipelothrix, Helicobacter*, Legionellosis, Leptospirosis, *Listeria*, Mycoplasmatales, Neisseriaceae (e.g., *Acinetobacter*, Gonorrhea, Menigococcal), Pasteurellacea Infections (e.g., *Actinobacillus, Heamophilus, Pasteurella*), *Pseudomonas*, Rickettsiaceae, Chlamydiaceae, Syphilis, and Staphylococcal. These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis, *Chlamydia*, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. A polypeptide or polynucleotide of the present invention can be used to treat or detect any of these symptoms or diseases.

Moreover, parasitic agents causing disease or symptoms that can be treated or detected by a polynucleotide or polypeptide of the present invention include, but not limited to, the following families: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas. These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), Malaria, pregnancy complications, and toxoplasmosis. A polypeptide or polynucleotide of the present invention can be used to treat or detect any of these symptoms or diseases.

Preferably, treatment using a polypeptide or polynucleotide of the present invention could either be by administering an effective amount of a polypeptide to the patient, or by removing cells from the patient, supplying the cells with a polynucleotide of the present invention, and returning the engineered cells to the patient (ex vivo therapy). Moreover, the polypeptide or polynucleotide of the present invention can be used as an antigen in a vaccine to raise an immune response against infectious disease.

Regeneration

A polynucleotide or polypeptide of the present invention can be used to differentiate, proliferate, and attract cells, leading to the regeneration of tissues. (See, Science 276:59-87 (1997).) The regeneration of tissues could be used to repair, replace, or protect tissue damaged by congenital defects, trauma (wounds, burns, incisions, or ulcers), age, disease (e.g. osteoporosis, osteocarthritis, periodontal disease, liver failure), surgery, including cosmetic plastic surgery, fibrosis, reperfusion injury, or systemic cytokine damage.

Tissues that could be regenerated using the present invention include organs (e.g., pancreas, liver, intestine, kidney, skin, endothelium), muscle (smooth, skeletal or cardiac), vascular (including vascular endothelium), nervous, hematopoietic, and skeletal (bone, cartilage, tendon, and ligament) tissue. Preferably, regeneration occurs without or decreased scarring. Regeneration also may include angiogenesis.

Moreover, a polynucleotide or polypeptide of the present invention may increase regeneration of tissues difficult to heal. For example, increased tendon/ligament regeneration would quicken recovery time after damage. A polynucleotide or polypeptide of the present invention could also be used prophylactically in an effort to avoid damage. Specific diseases that could be treated include of tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using a polynucleotide or polypeptide of the present invention to proliferate and differentiate nerve cells. Diseases that could be treated using this method include central and peripheral nervous system diseases, neuropathies, or mechanical and traumatic disorders (e.g., spinal cord disorders, head trauma, cerebrovascular disease, and stoke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated using the polynucleotide or polypeptide of the present invention.

Chemotaxis

A polynucleotide or polypeptide of the present invention may have chemotaxis activity. A chemotaxic molecule attracts or mobilizes cells (e.g., monocytes, fibroblasts, neutrophils, T-cells, mast cells, eosinophils, epithelial and/or endothelial cells) to a particular site in the body, such as inflammation, infection, or site of hyperproliferation. The mobilized cells can then fight off and/or heal the particular trauma or abnormality.

A polynucleotide or polypeptide of the present invention may increase chemotaxic activity of particular cells. These chemotactic molecules can then be used to treat inflammation, infection, hyperproliferative disorders, or any immune system disorder by increasing the number of cells targeted to a particular location in the body. For example, chemotaxic molecules can be used to treat wounds and other trauma to tissues by attracting immune cells to the injured location. Chemotactic molecules of the present invention can also attract fibroblasts, which can be used to treat wounds.

It is also contemplated that a polynucleotide or polypeptide of the present invention may inhibit chemotactic activity. These molecules could also be used to treat disorders. Thus, a polynucleotide or polypeptide of the present invention could be used as an inhibitor of chemotaxis.

Binding Activity

A polypeptide of the present invention may be used to screen for molecules that bind to the polypeptide or for molecules to which the polypeptide binds. The binding of the polypeptide and the molecule may activate (agonist), increase, inhibit (antagonist), or decrease activity of the polypeptide or the molecule bound. Examples of such molecules include antibodies, oligonucleotides, proteins (e.g., receptors), or small molecules.

Preferably, the molecule is closely related to the natural ligand of the polypeptide, e.g., a fragment of the ligand, or a natural substrate, a ligand, a structural or functional mimetic. (See, Coligan et al., Current Protocols in Immunology 1(2): Chapter 5 (1991).) Similarly, the molecule can be closely related to the natural receptor to which the polypeptide binds, or at least, a fragment of the receptor capable of being bound by the polypeptide (e.g., active site). In either case, the molecule can be rationally designed using known techniques.

Preferably, the screening for these molecules involves producing appropriate cells which express the polypeptide, either as a secreted protein or on the cell membrane. Preferred cells include cells from mammals, yeast, *Drosophila*, or *E. coli*. Cells expressing the polypeptide (or cell membrane containing the expressed polypeptide) are then preferably contacted with a test compound potentially containing the molecule to observe binding, stimulation, or inhibition of activity of either the polypeptide or the molecule.

The assay may simply test binding of a candidate compound to the polypeptide, wherein binding is detected by a label, or in an assay involving competition with a labeled competitor. Further, the assay may test whether the candidate compound results in a signal generated by binding to the polypeptide.

Alternatively, the assay can be carried out using cell-free preparations, polypeptide/molecule affixed to a solid support, chemical libraries, or natural product mixtures. The assay may also simply comprise the steps of mixing a candidate compound with a solution containing a polypeptide, measuring polypeptide/molecule activity or binding, and comparing the polypeptide/molecule activity or binding to a standard.

Preferably, an ELISA assay can measure polypeptide level or activity in a sample (e.g., biological sample) using a monoclonal or polyclonal antibody. The antibody can measure polypeptide level or activity by either binding, directly or indirectly, to the polypeptide or by competing with the polypeptide for a substrate.

All of these above assays can be used as diagnostic or prognostic markers. The molecules discovered using these assays can be used to treat disease or to bring about a particular result in a patient (e.g., blood vessel growth) by activating or inhibiting the polypeptide/molecule. Moreover, the assays can discover agents which may inhibit or enhance the production of the polypeptide from suitably manipulated cells or tissues.

Therefore, the invention includes a method of identifying compounds which bind to a polypeptide of the invention comprising the steps of: (a) incubating a candidate binding compound with a polypeptide of the invention; and (b) determining if binding has occurred. Moreover, the invention includes a method of identifying agonists/antagonists comprising the steps of: (a) incubating a candidate compound with a polypeptide of the invention, (b) assaying a biological activity, and (b) determining if a biological activity of the polypeptide has been altered.

Other Activities

A polypeptide or polynucleotide of the present invention may also increase or decrease the differentiation or proliferation of embryonic stem cells, besides, as discussed above, hematopoietic lineage.

A polypeptide or polynucleotide of the present invention may also be used to modulate mammalian characteristics, such as body height, weight, hair color, eye color, skin, percentage of adipose tissue, pigmentation, size, and shape (e.g., cosmetic surgery). Similarly, a polypeptide or polynucleotide of the present invention may be used to modulate mammalian metabolism affecting catabolism, anabolism, processing, utilization, and storage of energy.

A polypeptide or polynucleotide of the present invention may be used to change a mammal's mental state or physical state by influencing biorhythms, caricadic rhythms, depression (including depressive disorders), tendency for violence, tolerance for pain, reproductive capabilities (preferably by Activin or Inhibin-like activity), hormonal or endocrine levels, appetite, libido, memory, stress, or other cognitive qualities.

A polypeptide or polynucleotide of the present invention may also be used as a food additive or preservative, such as to increase or decrease storage capabilities, fat content, lipid, protein, carbohydrate, vitamins, minerals, cofactors or other nutritional components.

Other Preferred Embodiments

Other preferred embodiments of the claimed invention include an isolated nucleic acid molecule comprising a nucleotide sequence which is at least 95% identical to a sequence of at least about 50 contiguous nucleotides in the nucleotide sequence of SEQ ID NO:X wherein X is any integer as defined in Table 1.

Also preferred is a nucleic acid molecule wherein said sequence of contiguous nucleotides is included in the nucleotide sequence of SEQ ID NO:X in the range of positions beginning with the nucleotide at about the position of the 5' Nucleotide of the Clone Sequence and ending with the nucleotide at about the position of the 3' Nucleotide of the Clone Sequence as defined for SEQ ID NO:X in Table 1.

Also preferred is a nucleic acid molecule wherein said sequence of contiguous nucleotides is included in the nucleotide sequence of SEQ ID NO:X in the range of positions beginning with the nucleotide at about the position of the 5' Nucleotide of the Start Codon and ending with the nucleotide at about the position of the 3' Nucleotide of the Clone Sequence as defined for SEQ ID NO:X in Table 1.

Similarly preferred is a nucleic acid molecule wherein said sequence of contiguous nucleotides is included in the nucleotide sequence of SEQ ID NO:X in the range of positions beginning with the nucleotide at about the position of the 5' Nucleotide of the First Amino Acid of the Signal Peptide and ending with the nucleotide at about the position of the 3' Nucleotide of the Clone Sequence as defined for SEQ ID NO:X in Table 1.

Also preferred is an isolated nucleic acid molecule comprising a nucleotide sequence which is at least 95% identical to a sequence of at least about 150 contiguous nucleotides in the nucleotide sequence of SEQ ID NO:X.

Further preferred is an isolated nucleic acid molecule comprising a nucleotide sequence which is at least 95% identical to a sequence of at least about 500 contiguous nucleotides in the nucleotide sequence of SEQ ID NO:X.

A further preferred embodiment is a nucleic acid molecule comprising a nucleotide sequence which is at least 95% identical to the nucleotide sequence of SEQ ID NO:X beginning with the nucleotide at about the position of the 5' Nucleotide of the First Amino Acid of the Signal Peptide and ending with the nucleotide at about the position of the 3' Nucleotide of the Clone Sequence as defined for SEQ ID NO:X in Table 1.

A further preferred embodiment is an isolated nucleic acid molecule comprising a nucleotide sequence which is at least 95% identical to the complete nucleotide sequence of SEQ ID NO:X.

Also preferred is an isolated nucleic acid molecule which hybridizes under stringent hybridization conditions to a nucleic acid molecule, wherein said nucleic acid molecule which hybridizes does not hybridize under stringent hybridization conditions to a nucleic acid molecule having a nucleotide sequence consisting of only A residues or of only T residues.

Also preferred is a composition of matter comprising a DNA molecule which comprises a human cDNA clone identified by a cDNA Clone Identifier in Table 1, which DNA molecule is contained in the material deposited with the American Type Culture Collection and given the ATCC Deposit Number shown in Table 1 for said cDNA Clone Identifier.

Also preferred is an isolated nucleic acid molecule comprising a nucleotide sequence which is at least 95% identical to a sequence of at least 50 contiguous nucleotides in the nucleotide sequence of a human cDNA clone identified by a cDNA Clone Identifier in Table 1, which DNA molecule is contained in the deposit given the ATCC Deposit Number shown in Table 1.

Also preferred is an isolated nucleic acid molecule, wherein said sequence of at least 50 contiguous nucleotides is included in the nucleotide sequence of the complete open reading frame sequence encoded by said human cDNA clone.

Also preferred is an isolated nucleic acid molecule comprising a nucleotide sequence which is at least 95% identical to sequence of at least 150 contiguous nucleotides in the nucleotide sequence encoded by said human cDNA clone.

A further preferred embodiment is an isolated nucleic acid molecule comprising a nucleotide sequence which is at least 95% identical to sequence of at least 500 contiguous nucleotides in the nucleotide sequence encoded by said human cDNA clone.

A further preferred embodiment is an isolated nucleic acid molecule comprising a nucleotide sequence which is at least 95% identical to the complete nucleotide sequence encoded by said human cDNA clone.

A further preferred embodiment is a method for detecting in a biological sample a nucleic acid molecule comprising a nucleotide sequence which is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1; which method comprises a step of comparing a nucleotide sequence of at least one nucleic acid molecule in said sample with a sequence selected from said group and determining whether the sequence of said nucleic acid molecule in said sample is at least 95% identical to said selected sequence.

Also preferred is the above method wherein said step of comparing sequences comprises determining the extent of nucleic acid hybridization between nucleic acid molecules in said sample and a nucleic acid molecule comprising said sequence selected from said group. Similarly, also preferred is the above method wherein said step of comparing sequences is performed by comparing the nucleotide sequence determined from a nucleic acid molecule in said sample with said sequence selected from said group. The nucleic acid molecules can comprise DNA molecules or RNA molecules.

A further preferred embodiment is a method for identifying the species, tissue or cell type of a biological sample which method comprises a step of detecting nucleic acid molecules in said sample, if any, comprising a nucleotide sequence that is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1.

The method for identifying the species, tissue or cell type of a biological sample can comprise a step of detecting nucleic acid molecules comprising a nucleotide sequence in a panel of at least two nucleotide sequences, wherein at least one sequence in said panel is at least 95% identical to a sequence of at least 50 contiguous nucleotides in a sequence selected from said group.

Also preferred is a method for diagnosing in a subject a pathological condition associated with abnormal structure or expression of a gene encoding a secreted protein identified in Table 1, which method comprises a step of detecting in a biological sample obtained from said subject nucleic acid molecules, if any, comprising a nucleotide sequence that is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1.

The method for diagnosing a pathological condition can comprise a step of detecting nucleic acid molecules comprising a nucleotide sequence in a panel of at least two nucleotide sequences, wherein at least one sequence in said panel is at least 95% identical to a sequence of at least 50 contiguous nucleotides in a sequence selected from said group.

Also preferred is a composition of matter comprising isolated nucleic acid molecules wherein the nucleotide sequences of said nucleic acid molecules comprise a panel of at least two nucleotide sequences, wherein at least one sequence in said panel is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1. The nucleic acid molecules can comprise DNA molecules or RNA molecules.

Also preferred is an isolated polypeptide comprising an amino acid sequence at least 90% identical to a sequence of at least about 10 contiguous amino acids in the amino acid sequence of SEQ ID NO:Y wherein Y is any integer as defined in Table 1.

Also preferred is a polypeptide, wherein said sequence of contiguous amino acids is included in the amino acid sequence of SEQ ID NO:Y in the range of positions beginning with the residue at about the position of the First Amino Acid of the Secreted Portion and ending with the residue at about the Last Amino Acid of the Open Reading Frame as set forth for SEQ ID NO:Y in Table 1.

Also preferred is an isolated polypeptide comprising an amino acid sequence at least 95% identical to a sequence of at least about 30 contiguous amino acids in the amino acid sequence of SEQ ID NO:Y.

Further preferred is an isolated polypeptide comprising an amino acid sequence at least 95% identical to a sequence of at least about 100 contiguous amino acids in the amino acid sequence of SEQ ID NO:Y.

Further preferred is an isolated polypeptide comprising an amino acid sequence at least 95% identical to the complete amino acid sequence of SEQ ID NO:Y.

Further preferred is an isolated polypeptide comprising an amino acid sequence at least 90% identical to a sequence of at least about 10 contiguous amino acids in the complete amino acid sequence of a secreted protein encoded by a human cDNA clone identified by a cDNA Clone Identifier in Table 1 and contained in the deposit with the ATCC Deposit Number shown for said cDNA clone in Table 1.

Also preferred is a polypeptide wherein said sequence of contiguous amino acids is included in the amino acid sequence of a secreted portion of the secreted protein encoded by a human cDNA clone identified by a cDNA Clone Identifier in Table 1 and contained in the deposit with the ATCC Deposit Number shown for said cDNA clone in Table 1.

Also preferred is an isolated polypeptide comprising an amino acid sequence at least 95% identical to a sequence of at least about 30 contiguous amino acids in the amino acid sequence of the secreted portion of the protein encoded by a human cDNA clone identified by a cDNA Clone Identifier in Table 1 and contained in the deposit with the ATCC Deposit Number shown for said cDNA clone in Table 1.

Also preferred is an isolated polypeptide comprising an amino acid sequence at least 95% identical to a sequence of at least about 100 contiguous amino acids in the amino acid sequence of the secreted portion of the protein encoded by a human cDNA clone identified by a cDNA Clone Identifier in Table 1 and contained in the deposit with the ATCC Deposit Number shown for said cDNA clone in Table 1.

Also preferred is an isolated polypeptide comprising an amino acid sequence at least 95% identical to the amino acid sequence of the secreted portion of the protein encoded by a human cDNA clone identified by a cDNA Clone Identifier in Table 1 and contained in the deposit with the ATCC Deposit Number shown for said cDNA clone in Table 1.

Further preferred is an isolated antibody which binds specifically to a polypeptide comprising an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC Deposit Number shown for said cDNA clone in Table 1.

Further preferred is a method for detecting in a biological sample a polypeptide comprising an amino acid sequence which is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC Deposit Number shown for said cDNA clone in Table 1; which method comprises a step of comparing an amino acid sequence of at least one polypeptide molecule in said sample with a sequence selected from said group and determining whether the sequence of said polypeptide molecule in said sample is at least 90% identical to said sequence of at least 10 contiguous amino acids.

Also preferred is the above method wherein said step of comparing an amino acid sequence of at least one polypeptide molecule in said sample with a sequence selected from said group comprises determining the extent of specific binding of polypeptides in said sample to an antibody which binds specifically to a polypeptide comprising an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC Deposit Number shown for said cDNA clone in Table 1.

Also preferred is the above method wherein said step of comparing sequences is performed by comparing the amino acid sequence determined from a polypeptide molecule in said sample with said sequence selected from said group.

Also preferred is a method for identifying the species, tissue or cell type of a biological sample which method comprises a step of detecting polypeptide molecules in said sample, if any, comprising an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC Deposit Number shown for said cDNA clone in Table 1.

Also preferred is the above method for identifying the species, tissue or cell type of a biological sample, which method comprises a step of detecting polypeptide molecules comprising an amino acid sequence in a panel of at least two amino acid sequences, wherein at least one sequence in said panel is at least 90% identical to a sequence of at least 10 contiguous amino acids in a sequence selected from the above group.

Also preferred is a method for diagnosing in a subject a pathological condition associated with abnormal structure or expression of a gene encoding a secreted protein identified in Table 1, which method comprises a step of detecting in a biological sample obtained from said subject polypeptide molecules comprising an amino acid sequence in a panel of at least two amino acid sequences, wherein at least one sequence in said panel is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC Deposit Number shown for said cDNA clone in Table 1.

In any of these methods, the step of detecting said polypeptide molecules includes using an antibody.

Also preferred is an isolated nucleic acid molecule comprising a nucleotide sequence which is at least 95% identical to a nucleotide sequence encoding a polypeptide wherein said polypeptide comprises an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC Deposit Number shown for said cDNA clone in Table 1.

Also preferred is an isolated nucleic acid molecule, wherein said nucleotide sequence encoding a polypeptide has been optimized for expression of said polypeptide in a prokaryotic host.

Also preferred is an isolated nucleic acid molecule, wherein said polypeptide comprises an amino acid sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC Deposit Number shown for said cDNA clone in Table 1.

Further preferred is a method of making a recombinant vector comprising inserting any of the above isolated nucleic acid molecule into a vector. Also preferred is the recombinant vector produced by this method. Also preferred is a method of making a recombinant host cell comprising introducing the vector into a host cell, as well as the recombinant host cell produced by this method.

Also preferred is a method of making an isolated polypeptide comprising culturing this recombinant host cell under conditions such that said polypeptide is expressed and recovering said polypeptide. Also preferred is this method of making an isolated polypeptide, wherein said recombinant host cell is a eukaryotic cell and said polypeptide is a secreted portion of a human secreted protein comprising an amino acid sequence selected from the group consisting of: an amino acid sequence of SEQ ID NO:Y beginning with the residue at the position of the First Amino Acid of the Secreted Portion of SEQ ID NO:Y wherein Y is an integer set forth in Table 1 and said position of the First Amino Acid of the Secreted Portion of SEQ ID NO:Y is defined in Table 1; and an amino acid sequence of a secreted portion of a protein encoded by a human cDNA clone identified by a cDNA Clone Identifier in Table 1 and contained in the deposit with the ATCC Deposit Number shown for said cDNA clone in Table 1. The isolated polypeptide produced by this method is also preferred.

Also preferred is a method of treatment of an individual in need of an increased level of a secreted protein activity, which method comprises administering to such an individual a pharmaceutical composition comprising an amount of an isolated polypeptide, polynucleotide, or antibody of the claimed invention effective to increase the level of said protein activity in said individual.

Having generally described the invention, the same will be more readily understood by reference to the following examples, which are provided by way of illustration and are not intended as limiting.

EXAMPLES

Example 1

Isolation of a Selected cDNA Clone from the Deposited Sample

Each cDNA clone in a cited ATCC deposit is contained in a plasmid vector. Table 1 identifies the vectors used to construct the cDNA library from which each clone was isolated. In many cases, the vector used to construct the library is a phage vector from which a plasmid has been excised. The table immediately below correlates the related plasmid for each phage vector used in constructing the cDNA library. For example, where a particular clone is identified in Table 1 as being isolated in the vector "Lambda Zap," the corresponding deposited clone is in "pBluescript."

| Vector Used to Construct Library | Corresponding Deposited Plasmid |
|---|---|
| Lambda Zap | pBluescript (pBS) |
| Uni-Zap XR | pBluescript (pBS) |
| Zap Express | pBK |
| lafmid BA | plafmid BA |
| pSport1 | pSport1 |
| pCMVSport 2.0 | pCMVSport 2.0 |
| pCMVSport 3.0 | pCMVSport 3.0 |
| pCR ® 2.1 | pCR ® 2.1 |

Vectors Lambda Zap (U.S. Pat. Nos. 5,128,256 and 5,286,636), Uni-Zap XR (U.S. Pat. Nos. 5,128,256 and 5,286,636), Zap Express (U.S. Pat. Nos. 5,128,256 and 5,286,636), pBluescript (pBS) (Short, J. M. et al., Nucleic Acids Res. 16:7583-7600 (1988); Alting-Mees, M. A. and Short, J. M., Nucleic Acids Res. 17:9494 (1989)) and pBK (Alting-Mees, M. A. et al., Strategies 5:58-61 (1992)) are commercially available from Stratagene Cloning Systems, Inc., 11011 N. Torrey Pines Road, La Jolla, Calif., 92037. pBS contains an ampicillin resistance gene and pBK contains a neomycin resistance gene. Both can be transformed into E. coli strain XL-1 Blue, also available from Stratagene. pBS comes in 4 forms SK+, SK−, KS+ and KS. The S and K refers to the orientation of the polylinker to the T7 and T3 primer sequences which flank the polylinker region ("S" is for SacI and "K" is for KpnI which are the first sites on each respective end of the linker). "+" or "−" refer to the orientation of the f1 origin of replication ("ori"), such that in one orientation, single stranded rescue initiated from the f1 ori generates sense strand DNA and in the other, antisense.

Vectors pSport1, pCMVSport 2.0 and pCMVSport 3.0, were obtained from Life Technologies, Inc., P.O. Box 6009, Gaithersburg, Md. 20897. All Sport vectors contain an ampicillin resistance gene and may be transformed into E. coli strain DH10B, also available from Life Technologies. (See, for instance, Gruber, C. E., et al., Focus 15:59 (1993).) Vector lafmid BA (Bento Soares, Columbia University, NY) contains an ampicillin resistance gene and can be transformed into E. coli strain XL-1 Blue. Vector pCR® 2.1, which is available from Invitrogen, 1600 Faraday Avenue, Carlsbad, Calif. 92008, contains an ampicillin resistance gene and may be transformed into E. coli strain DH10B, available from Life Technologies. (See, for instance, Clark, J. M., Nuc. Acids Res. 16:9677-9686 (1988) and Mead, D. et al., Bio/Technology 9: (1991).) Preferably, a polynucleotide of the present invention does not comprise the phage vector sequences identified for the particular clone in Table 1, as well as the corresponding plasmid vector sequences designated above.

The deposited material in the sample assigned the ATCC Deposit Number cited in Table 1 for any given cDNA clone also may contain one or more additional plasmids, each comprising a cDNA clone different from that given clone. Thus, deposits sharing the same ATCC Deposit Number contain at least a plasmid for each cDNA clone identified in Table 1. Typically, each ATCC deposit sample cited in Table 1 comprises a mixture of approximately equal amounts (by weight)

of about 50 plasmid DNAs, each containing a different cDNA clone; but such a deposit sample may include plasmids for more or less than 50 cDNA clones, up to about 500 cDNA clones.

Two approaches can be used to isolate a particular clone from the deposited sample of plasmid DNAs cited for that clone in Table 1. First, a plasmid is directly isolated by screening the clones using a polynucleotide probe corresponding to SEQ ID NO:X.

Particularly, a specific polynucleotide with 30-40 nucleotides is synthesized using an Applied Biosystems DNA synthesizer according to the sequence reported. The oligonucleotide is labeled, for instance, with $^{32}$P-γ-ATP using T4 polynucleotide kinase and purified according to routine methods. (E.g., Maniatis et al., Molecular Cloning: A Laboratory Manual, Cold Spring Harbor Press, Cold Spring, N.Y. (1982).) The plasmid mixture is transformed into a suitable host, as indicated above (such as XL-1 Blue (Stratagene)) using techniques known to those of skill in the art, such as those provided by the vector supplier or in related publications or patents cited above. The transformants are plated on 1.5% agar plates (containing the appropriate selection agent, e.g., ampicillin) to a density of about 150 transformants (colonies) per plate. These plates are screened using Nylon membranes according to routine methods for bacterial colony screening (e.g., Sambrook et al., Molecular Cloning: A Laboratory Manual, 2nd Edit., (1989), Cold Spring Harbor Laboratory Press, pages 1.93 to 1.104), or other techniques known to those of skill in the art.

Alternatively, two primers of 17-20 nucleotides derived from both ends of the SEQ ID NO:X (i.e., within the region of SEQ ID NO:X bounded by the 5' NT and the 3' NT of the clone defined in Table 1) are synthesized and used to amplify the desired cDNA using the deposited cDNA plasmid as a template. The polymerase chain reaction is carried out under routine conditions, for instance, in 25 µl of reaction mixture with 0.5 ug of the above cDNA template. A convenient reaction mixture is 1.5-5 mM $MgCl_2$, 0.01% (w/v) gelatin, 20 µM each of dATP, dCTP, dGTP, dTTP, 25 µmol of each primer and 0.25 Unit of Taq polymerase. Thirty five cycles of PCR (denaturation at 94° C. for 1 min; annealing at 55° C. for 1 min; elongation at 72° C. for 1 min) are performed with a Perkin-Elmer Cetus automated thermal cycler. The amplified product is analyzed by agarose gel electrophoresis and the DNA band with expected molecular weight is excised and purified. The PCR product is verified to be the selected sequence by subcloning and sequencing the DNA product.

Several methods are available for the identification of the 5' or 3' non-coding portions of a gene which may not be present in the deposited clone. These methods include but are not limited to, filter probing, clone enrichment using specific probes, and protocols similar or identical to 5' and 3' "RACE" protocols which are well known in the art. For instance, a method similar to 5' RACE is available for generating the missing 5' end of a desired full-length transcript. (Fromont-Racine et al., Nucleic Acids Res. 21(7):1683-1684 (1993).)

Briefly, a specific RNA oligonucleotide is ligated to the 5' ends of a population of RNA presumably containing full-length gene RNA transcripts. A primer set containing a primer specific to the ligated RNA oligonucleotide and a primer specific to a known sequence of the gene of interest is used to PCR amplify the 5' portion of the desired full-length gene. This amplified product may then be sequenced and used to generate the full length gene.

This above method starts with total RNA isolated from the desired source, although poly-A+ RNA can be used. The RNA preparation can then be treated with phosphatase if necessary to eliminate 5' phosphate groups on degraded or damaged RNA which may interfere with the later RNA ligase step. The phosphatase should then be inactivated and the RNA treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase.

This modified RNA preparation is used as a template for first strand cDNA synthesis using a gene specific oligonucleotide. The first strand synthesis reaction is used as a template for PCR amplification of the desired 5' end using a primer specific to the ligated RNA oligonucleotide and a primer specific to the known sequence of the gene of interest. The resultant product is then sequenced and analyzed to confirm that the 5' end sequence belongs to the desired gene.

Example 2

Isolation of Genomic Clones Corresponding to a Polynucleotide

A human genomic P1 library (Genomic Systems, Inc.) is screened by PCR using primers selected for the cDNA sequence corresponding to SEQ ID NO:X., according to the method described in Example 1. (See also, Sambrook.)

Example 3

Tissue Distribution of Polypeptide

Tissue distribution of mRNA expression of polynucleotides of the present invention is determined using protocols for Northern blot analysis, described by, among others, Sambrook et al. For example, a cDNA probe produced by the method described in Example 1 is labeled with $P^{32}$ using the rediprime™ DNA labeling system (Amersham Life Science), according to manufacturer's instructions. After labeling, the probe is purified using CHROMA SPIN-100™ column (Clontech Laboratories, Inc.), according to manufacturer's protocol number PT1200-1. The purified labeled probe is then used to examine various human tissues for mRNA expression.

Multiple Tissue Northern (MTN) blots containing various human tissues (H) or human immune system tissues (IM) (Clontech) are examined with the labeled probe using ExpressHyb™ hybridization solution (Clontech) according to manufacturer's protocol number PT 190-1. Following hybridization and washing, the blots are mounted and exposed to film at −70° C. overnight, and the films developed according to standard procedures.

Example 4

Chromosomal Mapping of the Polynucleotides

An oligonucleotide primer set is designed according to the sequence at the 5' end of SEQ ID NO:X. This primer preferably spans about 100 nucleotides. This primer set is then used in a polymerase chain reaction under the following set of conditions: 30 seconds, 95° C.; 1 minute, 56° C.; 1 minute, 70° C. This cycle is repeated 32 times followed by one 5 minute cycle at 70° C. Human, mouse, and hamster DNA is used as template in addition to a somatic cell hybrid panel containing individual chromosomes or chromosome fragments (Bios, Inc). The reactions is analyzed on either 8% polyacrylamide gels or 3.5% agarose gels. Chromosome mapping is determined by the presence of an approximately 100 bp PCR fragment in the particular somatic cell hybrid.

Example 5

Bacterial Expression of a Polypeptide

A polynucleotide encoding a polypeptide of the present invention is amplified using PCR oligonucleotide primers corresponding to the 5' and 3' ends of the DNA sequence, as outlined in Example 1, to synthesize insertion fragments. The primers used to amplify the cDNA insert should preferably contain restriction sites, such as BamHI and XbaI, at the 5' end of the primers in order to clone the amplified product into the expression vector. For example, BamHI and XbaI correspond to the restriction enzyme sites on the bacterial expression vector pQE-9. (Qiagen, Inc., Chatsworth, Calif.). This plasmid vector encodes antibiotic resistance (Amp$^r$), a bacterial origin of replication (ori), an IPTG-regulatable promoter/operator (P/O), a ribosome binding site (RBS), a 6-histidine tag (6-His), and restriction enzyme cloning sites.

The pQE-9 vector is digested with BamHI and XbaI and the amplified fragment is ligated into the pQE-9 vector maintaining the reading frame initiated at the bacterial RBS. The ligation mixture is then used to transform the E. coli strain M15/rep4 (Qiagen, Inc.) which contains multiple copies of the plasmid pREP4, which expresses the lacI repressor and also confers kanamycin resistance (Kan$^r$). Transformants are identified by their ability to grow on LB plates and ampicillin/kanamycin resistant colonies are selected. Plasmid DNA is isolated and confirmed by restriction analysis.

Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.$^{600}$) of between 0.4 and 0.6. IPTG (Isopropyl-B-D-thiogalacto pyranoside) is then added to a final concentration of 1 mM. IPTG induces by inactivating the lacI repressor, clearing the P/O leading to increased gene expression.

Cells are grown for an extra 3 to 4 hours. Cells are then harvested by centrifugation (20 mins at 6000×g). The cell pellet is solubilized in the chaotropic agent 6 Molar Guanidine HCl by stirring for 3-4 hours at 4° C. The cell debris is removed by centrifugation, and the supernatant containing the polypeptide is loaded onto a nickel-nitrilo-tri-acetic acid ("Ni-NTA") affinity resin column (available from QIAGEN, Inc., supra). Proteins with a 6×His tag bind to the Ni-NTA resin with high affinity and can be purified in a simple one-step procedure (for details see: The QIAexpressionist (1995) QIAGEN, Inc., supra).

Briefly, the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the polypeptide is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins are eluted by the addition of 250 mM immidazole. Immidazole is removed by a final dialyzing step against PBS or 50 mM sodium acetate pH 6 buffer plus 200 mM NaCl. The purified protein is stored at 4° C. or frozen at −80° C.

In addition to the above expression vector, the present invention further includes an expression vector comprising phage operator and promoter elements operatively linked to a polynucleotide of the present invention, called pHE4a. (ATCC Accession Number 209645, deposited on Feb. 25, 1998.) This vector contains: 1) a neomycinphosphotransferase gene as a selection marker, 2) an E. coli origin of replication, 3) a T5 phage promoter sequence, 4) two lac operator sequences, 5) a Shine-Delgarno sequence, and 6) the lactose operon repressor gene (lacIq). The origin of replication (oriC) is derived from pUC19 (LTI, Gaithersburg, Md.). The promoter sequence and operator sequences are made synthetically.

DNA can be inserted into the pHEa by restricting the vector with NdeI and XbaI, BamHI, XhoI, or Asp718, running the restricted product on a gel, and isolating the larger fragment (the stuffer fragment should be about 310 base pairs). The DNA insert is generated according to the PCR protocol described in Example 1, using PCR primers having restriction sites for NdeI (5' primer) and XbaI, BamHI, XhoI, or Asp718 (3' primer). The PCR insert is gel purified and restricted with compatible enzymes. The insert and vector are ligated according to standard protocols.

The engineered vector could easily be substituted in the above protocol to express protein in a bacterial system.

Example 6

Purification of a Polypeptide from an Inclusion Body

The following alternative method can be used to purify a polypeptide expressed in E coli when it is present in the form of inclusion bodies. Unless otherwise specified, all of the following steps are conducted at 4-10° C.

Upon completion of the production phase of the E. coli fermentation, the cell culture is cooled to 4-10° C. and the cells harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells are then lysed by passing the solution through a microfluidizer (Microfluidics, Corp. or APV Gaulin, Inc.) twice at 4000-6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2-4 hours. After 7000×g centrifugation for 15 min., the pellet is discarded and the polypeptide containing supernatant is incubated at 4° C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4° C. without mixing for 12 hours prior to further purification steps.

To clarify the refolded polypeptide solution, a previously prepared tangential filtration unit equipped with 0.16 μm membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 nm of the effluent is continuously monitored. Fractions are collected and further analyzed by SDS-PAGE.

Fractions containing the polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the polypeptide (determined, for instance, by 16% SDS-PAGE) are then pooled.

The resultant polypeptide should exhibit greater than 95% purity after the above refolding and purification steps. No major contaminant bands should be observed from Commassie blue stained 16% SDS-PAGE gel when 5 µg of purified protein is loaded. The purified protein can also be tested for endotoxin/LPS contamination, and typically the LPS content is less than 0.1 ng/ml according to LAL assays.

Example 7

Cloning and Expression of a Polypeptide in a Baculovirus Expression System

In this example, the plasmid shuttle vector pA2 is used to insert a polynucleotide into a baculovirus to express a polypeptide. This expression vector contains the strong polyhedrin promoter of the *Autographa californica* nuclear polyhedrosis virus (AcMNPV) followed by convenient restriction sites such as BamHI, Xba I and Asp718. The polyadenylation site of the simian virus 40 ("SV40") is used for efficient polyadenylation. For easy selection of recombinant virus, the plasmid contains the beta-galactosidase gene from *E. coli* under control of a weak *Drosophila* promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned polynucleotide.

Many other baculovirus vectors can be used in place of the vector above, such as pAc373, pVL941, and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., Virology 170:31-39 (1989).

Specifically, the cDNA sequence contained in the deposited clone, including the AUG initiation codon and the naturally associated leader sequence identified in Table 1, is amplified using the PCR protocol described in Example 1. If the naturally occurring signal sequence is used to produce the secreted protein, the pA2 vector does not need a second signal peptide. Alternatively, the vector can be modified (pA2 GP) to include a baculovirus leader sequence, using the standard methods described in Summers et al., "A Manual of Methods for Baculovirus Vectors and Insect Cell Culture Procedures," Texas Agricultural Experimental Station Bulletin No. 1555 (1987).

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The plasmid is digested with the corresponding restriction enzymes and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.).

The fragment and the dephosphorylated plasmid are ligated together with T4 DNA ligase. *E. coli* HB101 or other suitable *E. coli* hosts such as XL-1 Blue (Stratagene Cloning Systems, La Jolla, Calif.) cells are transformed with the ligation mixture and spread on culture plates. Bacteria containing the plasmid are identified by digesting DNA from individual colonies and analyzing the digestion product by gel electrophoresis. The sequence of the cloned fragment is confirmed by DNA sequencing.

Five µg of a plasmid containing the polynucleotide is co-transfected with 1.0 µg of a commercially available linearized baculovirus DNA ("BaculoGold™ baculovirus DNA", Pharmingen, San Diego, Calif.), using the lipofection method described by Felgner et al., Proc. Natl. Acad. Sci. USA 84:7413-7417 (1987). One µg of BaculoGold™ virus DNA and 5 µg of the plasmid are mixed in a sterile well of a microtiter plate containing 50 µl of serum-free Grace's medium (Life Technologies Inc., Gaithersburg, Md.). Afterwards, 10 µl Lipofectin plus 90 µl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27° C. The transfection solution is then removed from the plate and 1 ml of Grace's insect medium supplemented with 10% fetal calf serum is added. Cultivation is then continued at 27° C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9-10.) After appropriate incubation, blue stained plaques are picked with the tip of a micropipettor (e.g., Eppendorf). The agar containing the recombinant viruses is then resuspended in a microcentrifuge tube containing 200 µl of Grace's medium and the suspension containing the recombinant baculovirus is used to infect Sf9 cells seeded in 35 mm dishes. Four days later the supernatants of these culture dishes are harvested and then they are stored at 4° C.

To verify the expression of the polypeptide, Sf9 cells are grown in Grace's medium supplemented with 10% heat-inactivated FBS. The cells are infected with the recombinant baculovirus containing the polynucleotide at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 µCi of $^{35}$S-methionine and 5 µCi $^{35}$S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the produced protein.

Example 8

Expression of a Polypeptide in Mammalian Cells

The polypeptide of the present invention can be expressed in a mammalian cell. A typical mammalian expression vector contains a promoter element, which mediates the initiation of transcription of mRNA, a protein coding sequence, and signals required for the termination of transcription and polyadenylation of the transcript. Additional elements include enhancers, Kozak sequences and intervening sequences flanked by donor and acceptor sites for RNA splicing. Highly efficient transcription is achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter).

Suitable expression vectors for use in practicing the present invention include, for example, vectors such as pSVL and pMSG (Pharmacia, Uppsala, Sweden), pRSVcat (ATCC 37152), pSV2dhfr (ATCC 37146), pBC12MI (ATCC 67109), pCMVSport 2.0, and pCMVSport 3.0. Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells.

Alternatively, the polypeptide can be expressed in stable cell lines containing the polynucleotide integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) marker is useful in developing cell lines that carry several hundred or even several thousand copies of the gene of interest. (See, e.g., Alt, F. W., et al., J. Biol. Chem. 253:1357-1370 (1978); Hamlin, J. L. and Ma, C., Biochem. et Biophys. Acta, 1097:107-143 (1990); Page, M. J. and Sydenham, M. A., Biotechnology 9:64-68 (1991).) Another useful selection marker is the enzyme glutamine synthase (GS) (Murphy et al., Biochem J. 227:277-279 (1991); Bebbington et al., Bio/Technology 10:169-175 (1992). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

Derivatives of the plasmid pSV2-dhfr (ATCC Accession No. 37146), the expression vectors pC4 (ATCC Accession No. 209646) and pC6 (ATCC Accession No. 209647) contain the strong promoter (LTR) of the Rous Sarcoma Virus (Cullen et al., Molecular and Cellular Biology, 438-447 (March, 1985)) plus a fragment of the CMV-enhancer (Boshart et al., Cell 41:521-530 (1985).) Multiple cloning sites, e.g., with the restriction enzyme cleavage sites BamHI, XbaI and Asp718, facilitate the cloning of the gene of interest. The vectors also contain the 3' intron, the polyadenylation and termination signal of the rat preproinsulin gene, and the mouse DHFR gene under control of the SV40 early promoter.

Specifically, the plasmid pC6, for example, is digested with appropriate restriction enzymes and then dephosphorylated using calf intestinal phosphates by procedures known in the art. The vector is then isolated from a 1% agarose gel.

A polynucleotide of the present invention is amplified according to the protocol outlined in Example 1. If the naturally occurring signal sequence is used to produce the secreted protein, the vector does not need a second signal peptide. Alternatively, if the naturally occurring signal sequence is not used, the vector can be modified to include a heterologous signal sequence. (See, e.g., WO 96/34891.)

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The amplified fragment is then digested with the same restriction enzyme and purified on a 1% agarose gel. The isolated fragment and the dephosphorylated vector are then ligated with T4 DNA ligase. E. coli HB101 or XL-1 Blue cells are then transformed and bacteria are identified that contain the fragment inserted into plasmid pC6 using, for instance, restriction enzyme analysis.

Chinese hamster ovary cells lacking an active DHFR gene is used for transfection. Five µg of the expression plasmid pC6 is cotransfected with 0.5 µg of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10-14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 µM, 2 µM, 5 µM, 10 mM, 20 mM). The same procedure is repeated until clones are obtained which grow at a concentration of 100-200 µM. Expression of the desired gene product is analyzed, for instance, by SDS-PAGE and Western blot or by reversed phase HPLC analysis.

Example 9

Protein Fusions

The polypeptides of the present invention are preferably fused to other proteins. These fusion proteins can be used for a variety of applications. For example, fusion of the present polypeptides to His-tag, HA-tag, protein A, IgG domains, and maltose binding protein facilitates purification. (See Example 5; see also EP A 394,827; Traunecker, et al., Nature 331:84-86 (1988).) Similarly, fusion to IgG-1, IgG-3, and albumin increases the halflife time in vivo. Nuclear localization signals fused to the polypeptides of the present invention can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule, or the protocol described in Example 5.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector.

For example, if pC4 (Accession No. 209646) is used, the human Fc portion can be ligated into the BamHI cloning site. Note that the 3' BamHI site should be destroyed. Next, the vector containing the human Fc portion is re-restricted with BamHI, linearizing the vector, and a polynucleotide of the present invention, isolated by the PCR protocol described in Example 1, is ligated into this BamHI site. Note that the polynucleotide is cloned without a stop codon, otherwise a fusion protein will not be produced.

If the naturally occurring signal sequence is used to produce the secreted protein, pC4 does not need a second signal peptide. Alternatively, if the naturally occurring signal sequence is not used, the vector can be modified to include a heterologous signal sequence. (See, e.g., WO 96/34891.)

```
Human IgG Fc region:
                                        (SEQ ID NO: 1)
GGGATCCGGAGCCCAAATCTTCTGACAAAACTCACACATGCCCACCGTGC

CCAGCACCTGAATTCGAGGGTGCACCGTCAGTCTTCCTCTTCCCCCCAAA

ACCCAAGGACACCCTCATGATCTCCCGGACTCCTGAGGTCACATGCGTGG

TGGTGGACGTAAGCCACGAAGACCCTGAGGTCAAGTTCAACTGGTACGTG

GACGGCGTGGAGGTGCATAATGCCAAGACAAAGCCGCGGGAGGAGCAGTA

CAACAGCACGTACCGTGTGGTCAGCGTCCTCACCGTCCTGCACCAGGACT

GGCTGAATGGCAAGGAGTACAAGTGCAAGGTCTCCAACAAAGCCCTCCCA

ACCCCCATCGAGAAAACCATCTCCAAAGCCAAAGGGCAGCCCCGAGAACC

ACAGGTGTACACCCTGCCCCCATCCCGGGATGAGCTGACCAAGAACCAGG

TCAGCCTGACCTGCCTGGTCAAAGGCTTCTATCCAAGCGACATCGCCGTG

GAGTGGGAGAGCAATGGGCAGCCGGAGAACAACTACAAGACCACGCCTCC

CGTGCTGGACTCCGACGGCTCCTTCTTCCTCTACAGCAAGCTCACCGTGG

ACAAGAGCAGGTGGCAGCAGGGGAACGTCTTCTCATGCTCCGTGATGCAT

GAGGCTCTGCACAACCACTACACGCAGAAGAGCCTCTCCCTGTCTCCGGG

TAAATGAGTGCGACGGCCGCGACTCTAGAGGAT
```

Example 10

Production of an Antibody from a Polypeptide

The antibodies of the present invention can be prepared by a variety of methods. (See, Current Protocols, Chapter 2.) For example, cells expressing a polypeptide of the present invention is administered to an animal to induce the production of sera containing polyclonal antibodies. In a preferred method, a preparation of the secreted protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or protein binding fragments thereof). Such monoclonal antibodies can be prepared using hybridoma technology. (Köhler et al., Nature 256:495 (1975); Köhler et al., Eur. J. Immunol. 6:511 (1976); Köhler et al., Eur. J. Immunol. 6:292 (1976); Hammerling et al., in: Monoclonal Antibodies and T-Cell Hybridomas, Elsevier, N.Y., pp. 563-681 (1981).) In general, such procedures involve immunizing an animal (preferably a mouse) with polypeptide or, more preferably, with a secreted polypeptide-expressing cell. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100 µg/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP2O), available from the ATCC. After fusion, the resulting hybridoma cells are selectively maintained in HAT medium, and then cloned by limiting dilution as described by Wands et al. (Gastroenterology 80:225-232 (1981).) The hybridoma cells obtained through such a selection are then assayed to identify clones which secrete antibodies capable of binding the polypeptide.

Alternatively, additional antibodies capable of binding to the polypeptide can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the protein-specific antibody can be blocked by the polypeptide. Such antibodies comprise anti-idiotypic antibodies to the protein-specific antibody and can be used to immunize an animal to induce formation of further protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, secreted protein-binding fragments can be produced through the application of recombinant DNA technology or through synthetic chemistry.

For in vivo use of antibodies in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. (See, for review, Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

Example 11

Production of Secreted Protein for High-Throughput Screening Assays

The following protocol produces a supernatant containing a polypeptide to be tested. This supernatant can then be used in the Screening Assays described in Examples 13-20.

First, dilute Poly-D-Lysine (644 587 Boehringer-Mannheim) stock solution (1 mg/ml in PBS) 1:20 in PBS (w/o calcium or magnesium 17-516F Biowhittaker) for a working solution of 50 ug/ml. Add 200 ul of this solution to each well (24 well plates) and incubate at RT for 20 minutes. Be sure to distribute the solution over each well (note: a 12-channel pipetter may be used with tips on every other channel). Aspirate off the Poly-D-Lysine solution and rinse with 1 ml PBS (Phosphate Buffered Saline). The PBS should remain in the well until just prior to plating the cells and plates may be poly-lysine coated in advance for up to two weeks.

Plate 293T cells (do not carry cells past P+20) at $2 \times 10^5$ cells/well in 0.5 ml DMEM (Dulbecco's Modified Eagle Medium) (with 4.5 G/L glucose and L-glutamine (12-604F Biowhittaker))/10% heat inactivated FBS (14-503F Biowhittaker)/1× Penstrep (17-602E Biowhittaker). Let the cells grow overnight.

The next day, mix together in a sterile solution basin: 300 ul Lipofectamine (18324-012 Gibco/BRL) and 5 ml Optimem I (31985070 Gibco/BRL)/96-well plate. With a small volume multi-channel pipetter, aliquot approximately 2 ug of an expression vector containing a polynucleotide insert, produced by the methods described in Examples 8 or 9, into an appropriately labeled 96-well round bottom plate. With a multi-channel pipetter, add 50 ul of the Lipofectamine/Optimem I mixture to each well. Pipette up and down gently to mix. Incubate at RT 15-45 minutes. After about 20 minutes, use a multi-channel pipetter to add 150 ul Optimem I to each well. As a control, one plate of vector DNA lacking an insert should be transfected with each set of transfections.

Preferably, the transfection should be performed by tag-teaming the following tasks. By tag-teaming, hands on time is cut in half, and the cells do not spend too much time on PBS. First, person A aspirates off the media from four 24-well plates of cells, and then person B rinses each well with 0.5-1 ml PBS. Person A then aspirates off PBS rinse, and person B, using a 12-channel pipetter with tips on every other channel, adds the 200 ul of DNA/Lipofectamine/Optimem I complex to the odd wells first, then to the even wells, to each row on the 24-well plates. Incubate at 37° C. for 6 hours.

While cells are incubating, prepare appropriate media, either 1% BSA in DMEM with 1× penstrep, or CHO-5 media (116.6 mg/L of CaCl2 (anhyd); 0.00130 mg/L $CuSO_4$-$5H_2O$; 0.050 mg/L of $Fe(NO_3)_3$-$9H_2O$; 0.417 mg/L of $FeSO_4$-$7H_2O$; 311.80 mg/L of Kcl; 28.64 mg/L of $MgCl_2$; 48.84 mg/L of $MgSO_4$; 6995.50 mg/L of NaCl; 2400.0 mg/L of $NaHCO_3$; 62.50 mg/L of $NaH_2PO_4$—$H_2O$; 71.02 mg/L of $Na_2HPO4$; 0.4320 mg/L of $ZnSO_4$-$7H_2O$; 0.002 mg/L of Arachidonic Acid; 1.022 mg/L of Cholesterol; 0.070 mg/L of DL-alpha-Tocopherol-Acetate; 0.0520 mg/L of Linoleic Acid; 0.010 mg/L of Linolenic Acid; 0.010 mg/L of Myristic Acid; 0.010 mg/L of Oleic Acid; 0.010 mg/L of Palmitric Acid; 0.010 mg/L of Palmitic Acid; 100 mg/L of Pluronic F-68; 0.010 mg/L of Stearic Acid; 2.20 mg/L of Tween 80; 4551 mg/L of D-Glucose; 130.85 mg/ml of L-Alanine; 147.50 mg/ml of L-Arginine-HCL; 7.50 mg/ml of L-Asparagine-$H_2O$; 6.65 mg/ml of L-Aspartic Acid; 29.56 mg/ml of L-Cystine-2HCL-$H_2O$; 31.29 mg/ml of L-Cystine-2HCL; 7.35 mg/ml of L-Glutamic Acid; 365.0 mg/ml of L-Glutamine; 18.75 mg/ml of Glycine; 52.48 mg/ml of L-Histidine-HCL-$H_2O$; 106.97 mg/ml of L-Isoleucine; 111.45 mg/ml of L-Leucine; 163.75 mg/ml of L-Lysine HCL; 32.34 mg/ml of L-Methionine; 68.48 mg/ml of L-Phenylalainine; 40.0 mg/ml of L-Proline; 26.25 mg/ml of L-Serine; 101.05 mg/ml of L-Threonine; 19.22 mg/ml of L-Tryptophan; 91.79 mg/ml of L-Tryrosine-2Na-$2H_2O$; 99.65 mg/ml of L-Valine; 0.0035 mg/L of Biotin; 3.24 mg/L of D-Ca Pantothenate; 11.78 mg/L of Choline Chloride; 4.65 mg/L of Folic Acid; 15.60 mg/L of i-Inositol; 3.02 mg/L of Niacinamide; 3.00 mg/L of Pyridoxal HCL; 0.031 mg/L of Pyridoxine HCL; 0.319 mg/L of Riboflavin; 3.17 mg/L of Thiamine HCL; 0.365 mg/L of Thymidine; and 0.680 mg/L of Vitamin $B_{12}$; 25 mM of HEPES Buffer; 2.39 mg/L of Na Hypoxanthine; 0.105 mg/L of Lipoic Acid; 0.081 mg/L of Sodium Putrescine-2HCL; 55.0 mg/L of Sodium Pyruvate; 0.0067 mg/L of Sodium Selenite; 20 uM of Ethanolamine; 0.122 mg/L of Ferric Citrate; 41.70 mg/L of Methyl-B-Cyclodextrin complexed with Linoleic Acid; 33.33 mg/L of Methyl-B-Cyclodextrin complexed with Oleic Acid; and 10 mg/L of Methyl-B-Cyclodextrin complexed with Retinal) with 2 mm glutamine and 1× penstrep. (BSA (81-068-3 Bayer) 100 gm dissolved in 1 L DMEM for a 10% BSA stock solution). Filter the media and collect 50 ul for endotoxin assay in 15 ml polystyrene conical.

The transfection reaction is terminated, preferably by tag-teaming, at the end of the incubation period. Person A aspirates off the transfection media, while person B adds 1.5 ml appropriate media to each well. Incubate at 37° C. for 45 or 72 hours depending on the media used: 1% BSA for 45 hours or CHO-5 for 72 hours.

On day four, using a 300 ul multichannel pipetter, aliquot 600 ul in one 1 ml deep well plate and the remaining supernatant into a 2 ml deep well. The supernatants from each well can then be used in the assays described in Examples 13-20.

It is specifically understood that when activity is obtained in any of the assays described below using a supernatant, the activity originates from either the polypeptide directly (e.g., as a secreted protein) or by the polypeptide inducing expression of other proteins, which are then secreted into the supernatant. Thus, the invention further provides a method of identifying the protein in the supernatant characterized by an activity in a particular assay.

Example 12

Construction of GAS Reporter Construct

One signal transduction pathway involved in the differentiation and proliferation of cells is called the Jaks-STATs pathway. Activated proteins in the Jaks-STATs pathway bind to gamma activation site "GAS" elements or interferon-sensitive responsive element ("ISRE"), located in the promoter of many genes. The binding of a protein to these elements alter the expression of the associated gene.

GAS and ISRE elements are recognized by a class of transcription factors called Signal Transducers and Activators of Transcription, or "STATs." There are six members of the STATs family. Stat1 and Stat3 are present in many cell types, as is Stat2 (as response to IFN-alpha is widespread). Stat4 is more restricted and is not in many cell types though it has been found in T helper class I, cells after treatment with IL-12. Stat5 was originally called mammary growth factor, but has been found at higher concentrations in other cells including myeloid cells. It can be activated in tissue culture cells by many cytokines.

The STATs are activated to translocate from the cytoplasm to the nucleus upon tyrosine phosphorylation by a set of kinases known as the Janus Kinase ("Jaks") family. Jaks represent a distinct family of soluble tyrosine kinases and include Tyk2, Jak1, Jak2, and Jak3. These kinases display significant sequence similarity and are generally catalytically inactive in resting cells.

The Jaks are activated by a wide range of receptors summarized in the Table below. (Adapted from review by Schidler and Darnell, Ann. Rev. Biochem. 64:621-51 (1995).) A cytokine receptor family, capable of activating Jaks, is divided into two groups: (a) Class 1 includes receptors for IL-2, IL-3, IL-4, IL-6, IL-7, IL-9, IL-11, IL-12, IL-15, Epo, PRL, GH, G-CSF, GM-CSF, LIF, CNTF, and thrombopoietin; and (b) Class 2 includes IFN-a, IFN-g, and IL-10. The Class 1 receptors share a conserved cysteine motif (a set of four conserved cysteines and one tryptophan) and a WSXWS motif (a membrane proxial region encoding Trp-Ser-Xxx-Trp-Ser (SEQ ID NO:2)).

Thus, on binding of a ligand to a receptor, Jaks are activated, which in turn activate STATs, which then translocate and bind to GAS elements. This entire process is encompassed in the Jaks-STATs signal transduction pathway.

Therefore, activation of the Jaks-STATs pathway, reflected by the binding of the GAS or the ISRE element, can be used to indicate proteins involved in the proliferation and differentiation of cells. For example, growth factors and cytokines are known to activate the Jaks-STATs pathway. (See Table below.) Thus, by using GAS elements linked to reporter molecules, activators of the Jaks-STATs pathway can be identified.

To construct a synthetic GAS containing promoter element, which is used in the Biological Assays described in Examples 13-14, a PCR based strategy is employed to generate a GAS-SV40 promoter sequence. The 5' primer contains four tandem copies of the GAS binding site found in the IRF1 promoter and previously demonstrated to bind STATs upon induction with a range of cytokines (Rothman et al., Immunity 1:457-468 (1994).), although other GAS or ISRE elements can be used instead. The 5' primer also contains 18 bp of sequence complementary to the SV40 early promoter sequence and is flanked with an XhoI site. The sequence of the 5' primer is:

(SEQ ID NO: 3)
5':GCGCCTCGAGATTTCCCCGAAATCTAGATTTCCCCGAAATGATTTCC

CCGAAATGATTTCCCCGAAATATCTGCCATCTCAATTAG:3'

The downstream primer is complementary to the SV40 promoter and is flanked with a Hind III site: 5':GCG-GCAAGCTTTTTGCAAAGCCTAGGC:3' (SEQ ID NO:4)

PCR amplification is performed using the SV40 promoter template present in the B-gal:promoter plasmid obtained from Clontech. The resulting PCR fragment is digested with XhoI/Hind III and subcloned into BLSK2-. (Stratagene.) Sequencing with forward and reverse primers confirms that the insert contains the following sequence:

| Ligand | JAKs | | | | STATS | GAS(elements) or ISRE |
| | tyk2 | Jak1 | Jak2 | Jak3 | | |
| --- | --- | --- | --- | --- | --- | --- |
| IFN family | | | | | | |
| IFN-a/B | + | + | − | − | 1, 2, 3 | ISRE |
| IFN-g | | + | + | − | 1 | GAS (IRF1 > Lys6 > IFP) |
| Il-10 | + | ? | ? | − | 1, 3 | |
| gp130 family | | | | | | |
| IL-6 (Pleiotrohic) | + | + | + | ? | 1, 3 | GAS (IRF1 > Lys6 > IFP) |
| Il-11 (Pleiotrohic) | ? | + | ? | ? | 1, 3 | |
| OnM (Pleiotrohic) | ? | + | + | ? | 1, 3 | |
| LIF (Pleiotrohic) | ? | + | + | ? | 1, 3 | |
| CNTF (Pleiotrohic) | −/+ | + | + | ? | 1, 3 | |
| G-CSF (Pleiotrohic) | ? | + | ? | ? | 1, 3 | |
| IL-12 (Pleiotrohic) | + | − | + | + | 1, 3 | |
| g-C family | | | | | | |
| IL-2 (lymphocytes) | − | + | − | + | 1, 3, 5 | GAS |
| IL-4 (lymph/myeloid) | − | + | − | + | 6 | GAS (IRF1 = IFP >> Ly6)(IgH) |
| IL-7 (lymphocytes) | − | + | − | + | 5 | GAS |
| IL-9 (lymphocytes) | − | + | − | + | 5 | GAS |
| IL-13 (lymphocyte) | − | + | ? | ? | 6 | GAS |
| IL-15 | ? | + | ? | + | 5 | GAS |
| gp140 family | | | | | | |
| IL-3 (myeloid) | − | − | + | − | 5 | GAS (IRF1 > IFP >> Ly6) |
| IL-5 (myeloid) | − | − | + | − | 5 | GAS |
| GM-CSF (myeloid) | − | − | + | − | 5 | GAS |
| Growth hormone family | | | | | | |
| GH | ? | − | + | − | 5 | |
| PRL | ? | +/− | + | − | 1, 3, 5 | |
| EPO | ? | − | + | − | 5 | GAS(B-CAS > IRF1 = IFP >> Ly6) |
| Receptor Tyrosine Kinases | | | | | | |
| EGF | ? | + | + | − | 1, 3 | GAS (IRF1) |
| PDGF | ? | + | + | − | 1, 3 | |
| CSF-1 | ? | + | + | − | 1, 3 | GAS (not IRF1) |

```
                                                          (SEQ ID NO: 5)
5': CTCGAGATTTCCCCGAAATCTAGATTTCCCCGAAATGATTTCCCCGA

AATGATTTCCCCGAAATATCTGCCATCTCAATTAGTCAGCAACCATAGTC

CCGCCCCTAACTCCGCCCATCCCGCCCCTAACTCCGCCCAGTTCCGCCCA

TTCTCCGCCCCATGGCTGACTAATTTTTTTATTTATGCAGAGGCCGAGG

CCGCCTCGGCCTCTGAGCTATTCCAGAAGTAGTGAGGAGGCTTTTTTGGA

GGCCTAGGCTTTTGCAAAAAGCTT:3'
```

With this GAS promoter element linked to the SV40 promoter, a GAS:SEAP2 reporter construct is next engineered. Here, the reporter molecule is a secreted alkaline phosphatase, or "SEAP." Clearly, however, any reporter molecule can be instead of SEAP, in this or in any of the other Examples. Well known reporter molecules that can be used instead of SEAP include chloramphenicol acetyltransferase (CAT), luciferase, alkaline phosphatase, B-galactosidase, green fluorescent protein (GFP), or any protein detectable by an antibody.

The above sequence confirmed synthetic GAS-SV40 promoter element is subcloned into the pSEAP-Promoter vector obtained from Clontech using HindIII and XhoI, effectively replacing the SV40 promoter with the amplified GAS:SV40 promoter element, to create the GAS-SEAP vector. However, this vector does not contain a neomycin resistance gene, and therefore, is not preferred for mammalian expression systems.

Thus, in order to generate mammalian stable cell lines expressing the GAS-SEAP reporter, the GAS-SEAP cassette is removed from the GAS-SEAP vector using SalI and NotI, and inserted into a backbone vector containing the neomycin resistance gene, such as pGFP-1 (Clontech), using these restriction sites in the multiple cloning site, to create the GAS-SEAP/Neo vector. Once this vector is transfected into mammalian cells, this vector can then be used as a reporter molecule for GAS binding as described in Examples 13-14.

Other constructs can be made using the above description and replacing GAS with a different promoter sequence. For example, construction of reporter molecules containing NFK-B and EGR promoter sequences are described in Examples 15 and 16. However, many other promoters can be substituted using the protocols described in these Examples. For instance, SRE, IL-2, NFAT, or Osteocalcin promoters can be substituted, alone or in combination (e.g., GAS/NF-KB/EGR, GAS/NF-KB, Il-2/NFAT, or NF-KB/GAS). Similarly, other cell lines can be used to test reporter construct activity, such as HELA (epithelial), HUVEC (endothelial), Reh (B-cell), Saos-2 (osteoblast), HUVAC (aortic), or Cardiomyocyte.

Example 13

High-Throughput Screening Assay for T-cell Activity

The following protocol is used to assess T-cell activity by identifying factors, such as growth factors and cytokines, that may proliferate or differentiate T-cells. T-cell activity is assessed using the GAS/SEAP/Neo construct produced in Example 12. Thus, factors that increase SEAP activity indicate the ability to activate the Jaks-STATS signal transduction pathway. The T-cell used in this assay is Jurkat T-cells (ATCC Accession No. TIB-152), although Molt-3 cells (ATCC Accession No. CRL-1552) and Molt-4 cells (ATCC Accession No. CRL-1582) cells can also be used.

Jurkat T-cells are lymphoblastic CD4+ Th1 helper cells. In order to generate stable cell lines, approximately 2 million Jurkat cells are transfected with the GAS-SEAP/neo vector using DMRIE-C (Life Technologies) (transfection procedure described below). The transfected cells are seeded to a density of approximately 20,000 cells per well and transfectants resistant to 1 mg/ml genticin selected. Resistant colonies are expanded and then tested for their response to increasing concentrations of interferon gamma. The dose response of a selected clone is demonstrated.

Specifically, the following protocol will yield sufficient cells for 75 wells containing 200 ul of cells. Thus, it is either scaled up, or performed in multiple to generate sufficient cells for multiple 96 well plates. Jurkat cells are maintained in RPMI+10% serum with 1% Pen-Strep. Combine 2.5 mls of OPTI-MEM (Life Technologies) with 10 ug of plasmid DNA in a T25 flask. Add 2.5 ml OPTI-MEM containing 50 ul of DMRIE-C and incubate at room temperature for 15-45 mins.

During the incubation period, count cell concentration, spin down the required number of cells ($10^7$ per transfection), and resuspend in OPTI-MEM to a final concentration of $10^7$ cells/ml. Then add 1 ml of $1 \times 10^7$ cells in OPTI-MEM to T25 flask and incubate at 37° C. for 6 hrs. After the incubation, add 10 ml of RPMI+15% serum.

The Jurkat:GAS-SEAP stable reporter lines are maintained in RPMI+10% serum, 1 mg/ml Genticin, and 1% Pen-Strep. These cells are treated with supernatants containing a polypeptide as produced by the protocol described in Example 11.

On the day of treatment with the supernatant, the cells should be washed and resuspended in fresh RPMI+10% serum to a density of 500,000 cells per ml. The exact number of cells required will depend on the number of supernatants being screened. For one 96 well plate, approximately 10 million cells (for 10 plates, 100 million cells) are required.

Transfer the cells to a triangular reservoir boat, in order to dispense the cells into a 96 well dish, using a 12 channel pipette. Using a 12 channel pipette, transfer 200 ul of cells into each well (therefore adding 100,000 cells per well).

After all the plates have been seeded, 50 ul of the supernatants are transferred directly from the 96 well plate containing the supernatants into each well using a 12 channel pipette. In addition, a dose of exogenous interferon gamma (0.1, 1.0, 10 ng) is added to wells H9, H10, and H11 to serve as additional positive controls for the assay.

The 96 well dishes containing Jurkat cells treated with supernatants are placed in an incubator for 48 hrs (note: this time is variable between 48-72 hrs). 35 ul samples from each well are then transferred to an opaque 96 well plate using a 12 channel pipette. The opaque plates should be covered (using cellophane covers) and stored at −20° C. until SEAP assays are performed according to Example 17. The plates containing the remaining treated cells are placed at 4° C. and serve as a source of material for repeating the assay on a specific well if desired.

As a positive control, 100 Unit/ml interferon gamma can be used which is known to activate Jurkat T cells. Over 30 fold induction is typically observed in the positive control wells.

Example 14

High-Throughput Screening Assay Identifying Myeloid Activity

The following protocol is used to assess myeloid activity by identifying factors, such as growth factors and cytokines, that may proliferate or differentiate myeloid cells. Myeloid cell activity is assessed using the GAS/SEAP/Neo construct produced in Example 12. Thus, factors that increase SEAP activity indicate the ability to activate the Jaks-STATS signal transduction pathway. The myeloid cell used in this assay is U937, a pre-monocyte cell line, although TF-1, HL60, or KG1 can be used.

To transiently transfect U937 cells with the GAS/SEAP/Neo construct produced in Example 12, a DEAE-Dextran method (Kharbanda et. al., 1994, Cell Growth & Differentiation, 5:259-265) is used. First, harvest $2 \times 10e^7$ U937 cells and wash with PBS. The U937 cells are usually grown in RPMI 1640 medium containing 10% heat-inactivated fetal bovine serum (FBS) supplemented with 100 units/ml penicillin and 100 mg/ml streptomycin.

Next, suspend the cells in 1 ml of 20 mM Tris-HCl (pH 7.4) buffer containing 0.5 mg/ml DEAE-Dextran, 8 ug GAS-SEAP2 plasmid DNA, 140 mM NaCl, 5 mM KCl, 375 uM $Na_2HPO_4.7H_2O$, 1 mM $MgCl_2$, and 675 uM $CaCl_2$. Incubate at 37° C. for 45 min.

Wash the cells with RPMI 1640 medium containing 10% FBS and then resuspend in 10 ml complete medium and incubate at 37° C. for 36 hr.

The GAS-SEAP/U937 stable cells are obtained by growing the cells in 400 ug/ml G418. The G418-free medium is used for routine growth but every one to two months, the cells should be re-grown in 400 ug/ml G418 for couple of passages.

These cells are tested by harvesting $1 \times 10^8$ cells (this is enough for ten 96-well plates assay) and wash with PBS. Suspend the cells in 200 ml above described growth medium, with a final density of $5 \times 10^5$ cells/ml. Plate 200 ul cells per well in the 96-well plate (or $1 \times 10^5$ cells/well).

Add 50 ul of the supernatant prepared by the protocol described in Example 11. Incubate at 37° C. for 48 to 72 hr. As a positive control, 100 Unit/ml interferon gamma can be used which is known to activate U937 cells. Over 30 fold induction is typically observed in the positive control wells. SEAP assay the supernatant according to the protocol described in Example 17.

Example 15

High-Throughput Screening Assay Identifying Neuronal Activity

When cells undergo differentiation and proliferation, a group of genes are activated through many different signal transduction pathways. One of these genes, EGR1 (early growth response gene 1), is induced in various tissues and cell types upon activation. The promoter of EGR1 is responsible for such induction. Using the EGR1 promoter linked to reporter molecules, activation of cells can be assessed.

Particularly, the following protocol is used to assess neuronal activity in PC12 cell lines. PC12 cells (rat phenochromocytoma cells) are known to proliferate and/or differentiate by activation with a number of mitogens, such as TPA (tetradecanoyl phorbol acetate), NGF (nerve growth factor), and EGF (epidermal growth factor). The EGR1 gene expression is activated during this treatment. Thus, by stably transfecting PC12 cells with a construct containing an EGR promoter linked to SEAP reporter, activation of PC12 cells can be assessed.

The EGR/SEAP reporter construct can be assembled by the following protocol. The EGR-1 promoter sequence (−633 to +1) (Sakamoto K et al., Oncogene 6:867-871 (1991)) can be PCR amplified from human genomic DNA using the following primers:

(SEQ ID NO: 6)
5' GCGCTCGAGGGATGACAGCGATAGAACCCCGG-3'

(SEQ ID NO: 7)
5' GCGAAGCTTCGCGACTCCCCGGATCCGCCTC-3'

Using the GAS:SEAP/Neo vector produced in Example 12, EGR1 amplified product can then be inserted into this vector. Linearize the GAS:SEAP/Neo vector using restriction enzymes XhoI/HindIII, removing the GAS/SV40 stuffer. Restrict the EGR1 amplified product with these same enzymes. Ligate the vector and the EGR1 promoter.

To prepare 96 well-plates for cell culture, two mls of a coating solution (1:30 dilution of collagen type I (Upstate Biotech Inc. Cat#08-115) in 30% ethanol (filter sterilized)) is added per one 10 cm plate or 50 ml per well of the 96-well plate, and allowed to air dry for 2 hr.

PC12 cells are routinely grown in RPMI-1640 medium (Bio Whittaker) containing 10% horse serum (JRH BIOSCIENCES, Cat. #12449-78P), 5% heat-inactivated fetal bovine serum (FBS) supplemented with 100 units/ml penicillin and 100 ug/ml streptomycin on a precoated 10 cm tissue culture dish. One to four split is done every three to four days. Cells are removed from the plates by scraping and resuspended with pipetting up and down for more than 15 times.

Transfect the EGR/SEAP/Neo construct into PC12 using the Lipofectamine protocol described in Example 11. EGR-SEAP/PC12 stable cells are obtained by growing the cells in 300 ug/ml G418. The G418-free medium is used for routine growth but every one to two months, the cells should be re-grown in 300 ug/ml G418 for couple of passages.

To assay for neuronal activity, a 10 cm plate with cells around 70 to 80% confluent is screened by removing the old medium. Wash the cells once with PBS (Phosphate buffered saline). Then starve the cells in low serum medium (RPMI-1640 containing 1% horse serum and 0.5% FBS with antibiotics) overnight.

The next morning, remove the medium and wash the cells with PBS. Scrape off the cells from the plate, suspend the cells well in 2 ml low serum medium. Count the cell number and add more low serum medium to reach final cell density as $5 \times 10^5$ cells/ml.

Add 200 ul of the cell suspension to each well of 96-well plate (equivalent to $1 \times 10^5$ cells/well). Add 50 ul supernatant produced by Example 11, 37° C. for 48 to 72 hr. As a positive control, a growth factor known to activate PC12 cells through EGR can be used, such as 50 ng/ul of Neuronal Growth Factor (NGF). Over fifty-fold induction of SEAP is typically seen in the positive control wells. SEAP assay the supernatant according to Example 17.

Example 16

High-Throughput Screening Assay for T-cell Activity

NF-κB (Nuclear Factor κB) is a transcription factor activated by a wide variety of agents including the inflammatory cytokines IL-1 and TNF, CD30 and CD40, lymphotoxin-alpha and lymphotoxin-beta, by exposure to LPS or thrombin, and by expression of certain viral gene products. As a transcription factor, NF-κB regulates the expression of genes involved in immune cell activation, control of apoptosis (NF-κB appears to shield cells from apoptosis), B and T-cell development, anti-viral and antimicrobial responses, and multiple stress responses.

In non-stimulated conditions, NF-κB is retained in the cytoplasm with I-κB (Inhibitor κB). However, upon stimulation, I-κB is phosphorylated and degraded, causing NF-κB to shuttle to the nucleus, thereby activating transcription of target genes. Target genes activated by NF-κB include IL-2, IL-6, GM-CSF, ICAM-1 and class 1 MHC.

Due to its central role and ability to respond to a range of stimuli, reporter constructs utilizing the NF-κB promoter element are used to screen the supernatants produced in Example 11. Activators or inhibitors of NF-kB would be useful in treating diseases. For example, inhibitors of NF-κB could be used to treat those diseases related to the acute or chronic activation of NF-κB, such as rheumatoid arthritis.

To construct a vector containing the NF-κB promoter element, a PCR based strategy is employed. The upstream primer contains four tandem copies of the NF-κB binding site (GGGGACTTTCCC) (SEQ ID NO:8), 18 bp of sequence complementary to the 5' end of the SV40 early promoter sequence, and is flanked with an XhoI site:

(SEQ ID NO: 9)
5':GCGGCCTCGAGGGGACTTTCCCGGGGACTTTCCGGGGACTTTCCGGG

ACTTTCCATCCTGCCATCTCAATTAG:3'

The downstream primer is complementary to the 3' end of the SV40 promoter and is flanked with a Hind III site:
5':GCGGCAAGCTTTTTGCAAAGCCTAGGC:3' (SEQ ID NO:4)

PCR amplification is performed using the SV40 promoter template present in the pB-gal:promoter plasmid obtained from Clontech. The resulting PCR fragment is digested with XhoI and Hind III and subcloned into BLSK2-. (Stratagene) Sequencing with the T7 and T3 primers confirms the insert contains the following sequence:

(SEQ ID NO: 10)
5':CTCGAGGGGACTTTCCCGGGGACTTTCCGGGGACTTTCCGGGACTTT

CCATCTGCCATCTCAATTAGTCAGCAACCATAGTCCCGCCCCTAACTCCG

CCCATCCCGCCCCTAACTCCGCCCAGTTCCGCCCATTCTCCGCCCCATGG

CTGACTAATTTTTTTATTTATGCAGAGGCCGAGGCCGCCTCGGCCTCTG

AGCTATTCCAGAAGTAGTGAGGAGGCTTTTTTGGAGGCCTAGGCTTTTGC

AAAAAGCTT:3'

Next, replace the SV40 minimal promoter element present in the pSEAP2-promoter plasmid (Clontech) with this NF-κB/SV40 fragment using XhoI and HindIII. However, this vector does not contain a neomycin resistance gene, and therefore, is not preferred for mammalian expression systems.

In order to generate stable mammalian cell lines, the NF-κB/SV40/SEAP cassette is removed from the above NF-κB/SEAP vector using restriction enzymes SalI and NotI, and inserted into a vector containing neomycin resistance. Particularly, the NF-κB/SV40/SEAP cassette was inserted into pGFP-1 (Clontech), replacing the GFP gene, after restricting pGFP-1 with SalI and NotI.

Once NF-κB/SV40/SEAP/Neo vector is created, stable Jurkat T-cells are created and maintained according to the protocol described in Example 13. Similarly, the method for assaying supernatants with these stable Jurkat T-cells is also described in Example 13. As a positive control, exogenous TNF alpha (0.1, 1, 10 ng) is added to wells H9, H10, and H11, with a 5-10 fold activation typically observed.

Example 17

Assay for SEAP Activity

As a reporter molecule for the assays described in Examples 13-16, SEAP activity is assayed using the Tropix Phospho-light Kit (Cat. BP-400) according to the following general procedure. The Tropix Phospho-light Kit supplies the Dilution, Assay, and Reaction Buffers used below.

Prime a dispenser with the 2.5× Dilution Buffer and dispense 15 μl of 2.5× dilution buffer into Optiplates containing 35 μl of a supernatant. Seal the plates with a plastic sealer and incubate at 65° C. for 30 min. Separate the Optiplates to avoid uneven heating.

Cool the samples to room temperature for 15 minutes. Empty the dispenser and prime with the Assay Buffer. Add 50 μl Assay Buffer and incubate at room temperature 5 min. Empty the dispenser and prime with the Reaction Buffer (see the table below). Add 50 μl Reaction Buffer and incubate at room temperature for 20 minutes. Since the intensity of the chemiluminescent signal is time dependent, and it takes about 10 minutes to read 5 plates on luminometer, one should treat 5 plates at each time and start the second set 10 minutes later.

Read the relative light unit in the luminometer. Set H12 as blank, and print the results. An increase in chemiluminescence indicates reporter activity.

| Reaction Buffer Formulation: | | |
|---|---|---|
| # of plates | Rxn buffer diluent (ml) | CSPD (ml) |
| 10 | 60 | 3 |
| 11 | 65 | 3.25 |
| 12 | 70 | 3.5 |
| 13 | 75 | 3.75 |
| 14 | 80 | 4 |
| 15 | 85 | 4.25 |
| 16 | 90 | 4.5 |
| 17 | 95 | 4.75 |
| 18 | 100 | 5 |
| 19 | 105 | 5.25 |
| 20 | 110 | 5.5 |
| 21 | 115 | 5.75 |
| 22 | 120 | 6 |
| 23 | 125 | 6.25 |
| 24 | 130 | 6.5 |
| 25 | 135 | 6.75 |
| 26 | 140 | 7 |
| 27 | 145 | 7.25 |
| 28 | 150 | 7.5 |
| 29 | 155 | 7.75 |
| 30 | 160 | 8 |
| 31 | 165 | 8.25 |
| 32 | 170 | 8.5 |
| 33 | 175 | 8.75 |
| 34 | 180 | 9 |
| 35 | 185 | 9.25 |
| 36 | 190 | 9.5 |
| 37 | 195 | 9.75 |
| 38 | 200 | 10 |
| 39 | 205 | 10.25 |
| 40 | 210 | 10.5 |
| 41 | 215 | 10.75 |
| 42 | 220 | 11 |
| 43 | 225 | 11.25 |
| 44 | 230 | 11.5 |
| 45 | 235 | 11.75 |
| 46 | 240 | 12 |
| 47 | 245 | 12.25 |
| 48 | 250 | 12.5 |
| 49 | 255 | 12.75 |
| 50 | 260 | 13 |

Example 18

High-Throughput Screening Assay Identifying Changes in Small Molecule Concentration and Membrane Permeability Binding of a ligand to a receptor is known to alter intracellular levels of small molecules, such as calcium, potassium, sodium, and pH, as well as alter membrane potential. These alterations can be measured in an assay to identify supernatants which bind to receptors of a particular cell. Although the following protocol describes an assay for calcium, this protocol can easily be modified to detect changes in potassium, sodium, pH, membrane potential, or any other small molecule which is detectable by a fluorescent probe.

The following assay uses Fluorometric Imaging Plate Reader ("FLIPR") to measure changes in fluorescent molecules (Molecular Probes) that bind small molecules. Clearly, any fluorescent molecule detecting a small molecule can be used instead of the calcium fluorescent molecule, fluo-3, used here.

For adherent cells, seed the cells at 10,000-20,000 cells/well in a Co-star black 96-well plate with clear bottom. The plate is incubated in a $CO_2$ incubator for 20 hours. The adherent cells are washed two times in Biotek washer with 200 ul of HBSS (Hank's Balanced Salt Solution) leaving 100 ul of buffer after the final wash.

A stock solution of 1 mg/ml fluo-3 is made in 10% pluronic acid DMSO. To load the cells with fluo-3, 50 ul of 12 ug/ml fluo-3 is added to each well. The plate is incubated at 37° C. in a $CO_2$ incubator for 60 min. The plate is washed four times in the Biotek washer with HBSS leaving 100 ul of buffer.

For non-adherent cells, the cells are spun down from culture media. Cells are re-suspended to $2-5 \times 10^6$ cells/ml with HBSS in a 50-ml conical tube. 4 ul of 1 mg/ml fluo-3 solution in 10% pluronic acid DMSO is added to each ml of cell suspension. The tube is then placed in a 37° C. water bath for 30-60 min. The cells are washed twice with HBSS, resuspended to $1 \times 10^6$ cells/ml, and dispensed into a microplate, 100 ul/well. The plate is centrifuged at 1000 rpm for 5 min. The plate is then washed once in Denley CellWash with 200 ul, followed by an aspiration step to 100 ul final volume.

For a non-cell based assay, each well contains a fluorescent molecule, such as fluo-3. The supernatant is added to the well, and a change in fluorescence is detected.

To measure the fluorescence of intracellular calcium, the FLIPR is set for the following parameters: (1) System gain is 300-800 mW; (2) Exposure time is 0.4 second; (3) Camera F/stop is F/2; (4) Excitation is 488 nm; (5) Emission is 530 nm; and (6) Sample addition is 50 ul. Increased emission at 530 nm indicates an extracellular signaling event which has resulted in an increase in the intracellular $Ca^{++}$ concentration.

Example 19

High-Throughput Screening Assay Identifying Tyrosine Kinase Activity

The Protein Tyrosine Kinases (PTK) represent a diverse group of transmembrane and cytoplasmic kinases. Within the Receptor Protein Tyrosine Kinase RPTK) group are receptors for a range of mitogenic and metabolic growth factors including the PDGF, FGF, EGF, NGF, HGF and Insulin receptor subfamilies. In addition there are a large family of RPTKs for which the corresponding ligand is unknown. Ligands for RPTKs include mainly secreted small proteins, but also membrane-bound and extracellular matrix proteins.

Activation of RPTK by ligands involves ligand-mediated receptor dimerization, resulting in transphosphorylation of the receptor subunits and activation of the cytoplasmic tyrosine kinases. The cytoplasmic tyrosine kinases include receptor associated tyrosine kinases of the src-family (e.g., src, yes, lck, lyn, fyn) and non-receptor linked and cytosolic protein tyrosine kinases, such as the Jak family, members of which mediate signal transduction triggered by the cytokine superfamily of receptors (e.g., the Interleukins, Interferons, GM-CSF, and Leptin).

Because of the wide range of known factors capable of stimulating tyrosine kinase activity, the identification of novel human secreted proteins capable of activating tyrosine kinase signal transduction pathways are of interest. Therefore, the following protocol is designed to identify those novel human secreted proteins capable of activating the tyrosine kinase signal transduction pathways.

Seed target cells (e.g., primary keratinocytes) at a density of approximately 25,000 cells per well in a 96 well Loprodyne Silent Screen Plates purchased from Nalge Nunc (Naperville, Ill.). The plates are sterilized with two 30 minute rinses with 100% ethanol, rinsed with water and dried overnight. Some plates are coated for 2 hr with 100 ml of cell culture grade type I collagen (50 mg/ml), gelatin (2%) or polylysine (50 mg/ml), all of which can be purchased from Sigma Chemicals (St. Louis, Mo.) or 10% Matrigel purchased from Becton Dickinson (Bedford, Mass.), or calf serum, rinsed with PBS and stored at 4° C. Cell growth on these plates is assayed by seeding 5,000 cells/well in growth medium and indirect quantitation of cell number through use of alamarBlue as described by the manufacturer Alamar Biosciences, Inc. (Sacramento, Calif.) after 48 hr. Falcon plate covers #3071 from Becton Dickinson (Bedford, Mass.) are used to cover the Loprodyne Silent Screen Plates. Falcon Microtest III cell culture plates can also be used in some proliferation experiments.

To prepare extracts, A431 cells are seeded onto the nylon membranes of Loprodyne plates (20,000/200 ml/well) and cultured overnight in complete medium. Cells are quiesced by incubation in serum-free basal medium for 24 hr. After 5-20 minutes treatment with EGF (60 ng/ml) or 50 ul of the supernatant produced in Example 11, the medium was removed and 100 ml of extraction buffer ((20 mM HEPES pH 7.5, 0.15 M NaCl, 1% Triton X-100, 0.1% SDS, 2 mM Na3VO4, 2 mM Na4P2O7 and a cocktail of protease inhibitors (#1836170) obtained from Boeheringer Mannheim (Indianapolis, Ind.) is added to each well and the plate is shaken on a rotating shaker for 5 minutes at 4° C. The plate is then placed in a vacuum transfer manifold and the extract filtered through the 0.45 mm membrane bottoms of each well using house vacuum. Extracts are collected in a 96-well catch/assay plate in the bottom of the vacuum manifold and immediately placed on ice. To obtain extracts clarified by centrifugation, the content of each well, after detergent solubilization for 5 minutes, is removed and centrifuged for 15 minutes at 4° C. at 16,000×g.

Test the filtered extracts for levels of tyrosine kinase activity. Although many methods of detecting tyrosine kinase activity are known, one method is described here.

Generally, the tyrosine kinase activity of a supernatant is evaluated by determining its ability to phosphorylate a tyrosine residue on a specific substrate (a biotinylated peptide). Biotinylated peptides that can be used for this purpose include PSK1 (corresponding to amino acids 6-20 of the cell division kinase cdc2-p34) and PSK2 (corresponding to amino acids 1-17 of gastrin). Both peptides are substrates for a range of tyrosine kinases and are available from Boehringer Mannheim.

The tyrosine kinase reaction is set up by adding the following components in order. First, add 10 ul of 5 uM Biotinylated Peptide, then 10 ul ATP/Mg$_{2+}$ (5 mM ATP/50 mM MgCl$_2$), then 10 ul of 5× Assay Buffer (40 mM imidazole hydrochloride, pH7.3, 40 mM beta-glycerophosphate, 1 mM EGTA, 100 mM MgCl$_2$, 5 mM MnCl$_2$, 0.5 mg/ml BSA), then 5 ul of Sodium Vanadate (1 mM), and then 5 ul of water. Mix the components gently and preincubate the reaction mix at 30° C. for 2 min. Initial the reaction by adding 10 ul of the control enzyme or the filtered supernatant.

The tyrosine kinase assay reaction is then terminated by adding 10 ul of 120 mm EDTA and place the reactions on ice.

Tyrosine kinase activity is determined by transferring 50 ul aliquot of reaction mixture to a microtiter plate (MTP) module and incubating at 37° C. for 20 min. This allows the streptavadin coated 96 well plate to associate with the biotinylated peptide. Wash the MTP module with 300 ul/well of PBS four times. Next add 75 ul of anti-phosphotyrosine antibody conjugated to horse radish peroxidase (anti-P-Tyr-POD (0.5 u/ml)) to each well and incubate at 37° C. for one hour. Wash the well as above.

Next add 100 ul of peroxidase substrate solution (Boehringer Mannheim) and incubate at room temperature for at least 5 mins (up to 30 min). Measure the absorbance of the sample at 405 nm by using ELISA reader. The level of bound peroxidase activity is quantitated using an ELISA reader and reflects the level of tyrosine kinase activity.

Example 20

High-Throughput Screening Assay Identifying Phosphorylation Activity

As a potential alternative and/or compliment to the assay of protein tyrosine kinase activity described in Example 19, an assay which detects activation (phosphorylation) of major intracellular signal transduction intermediates can also be used. For example, as described below one particular assay can detect tyrosine phosphorylation of the Erk-1 and Erk-2 kinases. However, phosphorylation of other molecules, such as Raf, JNK, p38 MAP, Map kinase (MEK), MEK kinase, Src, Muscle specific kinase (MuSK), IRAK, Tec, and Janus, as well as any other phosphoserine, phosphotyrosine, or phosphothreonine molecule, can be detected by substituting these molecules for Erk-1 or Erk-2 in the following assay.

Specifically, assay plates are made by coating the wells of a 96-well ELISA plate with 0.1 ml of protein G (1 ug/ml) for 2 hr at room temp, (RT). The plates are then rinsed with PBS and blocked with 3% BSA/PBS for 1 hr at RT. The protein G plates are then treated with 2 commercial monoclonal antibodies (100 ng/well) against Erk-1 and Erk-2 (1 hr at RT) (Santa Cruz Biotechnology). (To detect other molecules, this step can easily be modified by substituting a monoclonal antibody detecting any of the above described molecules.) After 3-5 rinses with PBS, the plates are stored at 4° C. until use.

A431 cells are seeded at 20,000/well in a 96-well Loprodyne filterplate and cultured overnight in growth medium. The cells are then starved for 48 hr in basal medium (DMEM) and then treated with EGF (6 ng/well) or 50 ul of the supernatants obtained in Example 11 for 5-20 minutes. The cells are then solubilized and extracts filtered directly into the assay plate.

After incubation with the extract for 1 hr at RT, the wells are again rinsed. As a positive control, a commercial preparation of MAP kinase (10 ng/well) is used in place of A431 extract. Plates are then treated with a commercial polyclonal (rabbit) antibody (1 ug/ml) which specifically recognizes the phosphorylated epitope of the Erk-1 and Erk-2 kinases (1 hr at RT). This antibody is biotinylated by standard procedures. The bound polyclonal antibody is then quantitated by successive incubations with Europium-streptavidin and Europium fluorescence enhancing reagent in the Wallac DELFIA instrument (time-resolved fluorescence). An increased fluorescent signal over background indicates a phosphorylation.

Example 21

Method of Determining Alterations in a Gene Corresponding to a Polynucleotide

RNA isolated from entire families or individual patients presenting with a phenotype of interest (such as a disease) is be isolated. cDNA is then generated from these RNA samples using protocols known in the art. (See, Sambrook.) The cDNA is then used as a template for PCR, employing primers surrounding regions of interest in SEQ ID NO:X. Suggested PCR conditions consist of 35 cycles at 95° C. for 30 seconds; 60-120 seconds at 52-58° C.; and 60-120 seconds at 70° C., using buffer solutions described in Sidransky, D., et al., Science 252:706 (1991).

PCR products are then sequenced using primers labeled at their 5' end with T4 polynucleotide kinase, employing SequiTherm Polymerase. (Epicentre Technologies). The intron-exon borders of selected exons is also determined and genomic PCR products analyzed to confirm the results. PCR products harboring suspected mutations is then cloned and sequenced to validate the results of the direct sequencing.

PCR products is cloned into T-tailed vectors as described in Holton, T. A. and Graham, M. W., Nucleic Acids Research, 19:1156 (1991) and sequenced with T7 polymerase (United States Biochemical). Affected individuals are identified by mutations not present in unaffected individuals.

Genomic rearrangements are also observed as a method of determining alterations in a gene corresponding to a polynucleotide. Genomic clones isolated according to Example 2 are nick-translated with digoxigenindeoxy-uridine 5'-triphosphate (Boehringer Manheim), and FISH performed as described in Johnson, Cg. et al., Methods Cell Biol. 35:73-99 (1991). Hybridization with the labeled probe is carried out using a vast excess of human cot-1 DNA for specific hybridization to the corresponding genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson, Cv. et al., Genet. Anal. Tech. Appl., 8:75 (1991).) Image collection, analysis and chromosomal fractional length measurements are performed using the ISee Graphical Program System. (Inovision Corporation, Durham, N.C.) Chromosome alterations of the genomic region hybridized by the probe are identified as insertions, deletions, and translocations. These alterations are used as a diagnostic marker for an associated disease.

Example 22

Method of Detecting Abnormal Levels of a Polypeptide in a Biological Sample

A polypeptide of the present invention can be detected in a biological sample, and if an increased or decreased level of the polypeptide is detected, this polypeptide is a marker for a particular phenotype. Methods of detection are numerous, and thus, it is understood that one skilled in the art can modify the following assay to fit their particular needs.

For example, antibody-sandwich ELISAs are used to detect polypeptides in a sample, preferably a biological sample. Wells of a microtiter plate are coated with specific antibodies, at a final concentration of 0.2 to 10 ug/ml. The antibodies are either monoclonal or polyclonal and are produced by the method described in Example 10. The wells are blocked so that non-specific binding of the polypeptide to the well is reduced.

The coated wells are then incubated for >2 hours at RT with a sample containing the polypeptide. Preferably, serial dilutions of the sample should be used to validate results. The plates are then washed three times with deionized or distilled water to remove unbounded polypeptide.

Next, 50 ul of specific antibody-alkaline phosphatase conjugate, at a concentration of 25-400 ng, is added and incubated for 2 hours at room temperature. The plates are again washed three times with deionized or distilled water to remove unbounded conjugate.

Add 75 ul of 4-methylumbelliferyl phosphate (MUP) or p-nitrophenyl phosphate (NPP) substrate solution to each well and incubate 1 hour at room temperature. Measure the reaction by a microtiter plate reader. Prepare a standard curve, using serial dilutions of a control sample, and plot polypeptide concentration on the X-axis (log scale) and fluorescence or absorbance of the Y-axis (linear scale). Interpolate the concentration of the polypeptide in the sample using the standard curve.

Example 23

Formulating a Polypeptide

The secreted polypeptide composition will be formulated and dosed in a fashion consistent with good medical practice, taking into account the clinical condition of the individual patient (especially the side effects of treatment with the secreted polypeptide alone), the site of delivery, the method of administration, the scheduling of administration, and other factors known to practitioners. The "effective amount" for purposes herein is thus determined by such considerations.

As a general proposition, the total pharmaceutically effective amount of secreted polypeptide administered parenterally per dose will be in the range of about 1 µg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the secreted polypeptide is typically administered at a dose rate of about 1 µg/kg/hour to about 50 µg/kg/hour, either by 1-4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing the secreted protein of the invention are administered orally, rectally, parenterally, intracistemally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The secreted polypeptide is also suitably administered by sustained-release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman, U. et al., Biopolymers 22:547-556 (1983)), poly(2-hydroxyethyl methacrylate) (R. Langer et al., J. Biomed. Mater. Res. 15:167-277 (1981), and R. Langer, Chem. Tech. 12:98-105 (1982)), ethylene vinyl acetate (R. Langer et al.) or poly-D-(-)-3-hydroxybutyric acid (EP 133,988). Sustained-release compositions also include liposomally entrapped polypeptides. Liposomes containing the secreted polypeptide are prepared by methods known per se: DE 3,218,121; Epstein et al., Proc. Natl. Acad. Sci. USA 82:3688-3692 (1985); Hwang et al., Proc. Natl. Acad. Sci. USA 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal secreted polypeptide therapy.

For parenteral administration, in one embodiment, the secreted polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The secreted polypeptide is typically formulated in such vehicles at a concentration of about 0.1 mg/ml to 100 mg/ml, preferably 1-10 mg/ml, at a pH of about 3 to 8. It will be understood that the use of certain of the foregoing excipients, carriers, or stabilizers will result in the formation of polypeptide salts.

Any polypeptide to be used for therapeutic administration can be sterile. Sterility is readily accomplished by filtration through sterile filtration membranes (e.g., 0.2 micron membranes). Therapeutic polypeptide compositions generally are placed into a container having a sterile access port, for example, an intravenous solution bag or vial having a stopper pierceable by a hypodermic injection needle.

Polypeptides ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous polypeptide solution, and the resulting mixture is lyophilized. The infusion solution is prepared by reconstituting the lyophilized polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

Example 24

Method of Treating Decreased Levels of the Polypeptide

It will be appreciated that conditions caused by a decrease in the standard or normal expression level of a secreted protein in an individual can be treated by administering the polypeptide of the present invention, preferably in the secreted form. Thus, the invention also provides a method of treatment of an individual in need of an increased level of the polypeptide comprising administering to such an individual a pharmaceutical composition comprising an amount of the polypeptide to increase the activity level of the polypeptide in such an individual.

For example, a patient with decreased levels of a polypeptide receives a daily dose 0.1-100 ug/kg of the polypeptide for six consecutive days. Preferably, the polypeptide is in the secreted form. The exact details of the dosing scheme, based on administration and formulation, are provided in Example 23.

Example 25

Method of Treating Increased Levels of the Polypeptide

Antisense technology is used to inhibit production of a polypeptide of the present invention. This technology is one example of a method of decreasing levels of a polypeptide, preferably a secreted form, due to a variety of etiologies, such as cancer.

For example, a patient diagnosed with abnormally increased levels of a polypeptide is administered intravenously antisense polynucleotides at 0.5, 1.0, 1.5, 2.0 and 3.0 mg/kg day for 21 days. This treatment is repeated after a 7-day rest period if the treatment was well tolerated. The formulation of the antisense polynucleotide is provided in Example 23.

Example 26

Method of Treatment Using Gene Therapy

One method of gene therapy transplants fibroblasts, which are capable of expressing a polypeptide, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37° C. for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., DNA, 7:219-25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention can be amplified using PCR primers which correspond to the 5' and 3' end sequences respectively as set forth in Example 1. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB101, which are then plated onto agar containing kanamycin for the purpose of confirming that the vector has the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether protein is produced.

The engineered fibroblasts are then transplanted onto the host, either alone or after having been grown to confluence on cytodex 3 microcarrier beads.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference. Further, the hard copy of the sequence listing submitted herewith and the corresponding computer readable form are both incorporated herein by reference in their entireties.

What is claimed is:

1. An isolated antibody or a fragment thereof that specifically binds to a protein expressed from the cDNA included in ATCC Deposit No: 209075, which is hybridizable to the complement of SEQ ID NO:23 under stringent conditions.

2. The fragment of the isolated antibody of claim 1 selected from the group consisting of a single chain antibody, a Fab fragment and a F(ab')2 fragment.

3. The isolated antibody or fragment of claim 1 that is humanized or chimeric.

4. The isolated antibody or fragment of claim 1 that is monoclonal.

5. The isolated antibody or fragment of claim 1 that has an Fc region.

6. The isolated antibody or fragment of claim 1 that is labeled with a radioisotope.

7. An isolated antibody that specifically binds to a polypeptide having a sequence comprising SEQ ID NO:59.

8. The isolated antibody of claim 7 that is a humanized or chimeric antibody.

9. An isolated antibody or a Fab fragment thereof that specifically binds to a protein expressed from the cDNA included in ATCC Deposit No: 209075, which is amplifiable using primers of 17-20 nucleotides derived from the ends of SEQ ID NO:23 and its complement.

* * * * *

UNITED STATES PATENT AND TRADEMARK OFFICE
CERTIFICATE OF CORRECTION

| | | |
|---|---|---|
| PATENT NO. | : 7,914,789 B2 | Page 1 of 1 |
| APPLICATION NO. | : 11/801040 | |
| DATED | : March 29, 2011 | |
| INVENTOR(S) | : Steven M. Ruben et al. | |

It is certified that error appears in the above-identified patent and that said Letters Patent is hereby corrected as shown below:

On the title page of the patent, please correct the Assignee as follows:

(73) Assignee: Delete "Facet Biotech Corporation, Redwood City, CA" and insert --Human Genome Sciences, Inc., Rockville, MD--

At Col. 1, lines 3-4, after the words "This application is a"
Delete "continuation" and insert --divisional--

Signed and Sealed this
Nineteenth Day of July, 2011

David J. Kappos
*Director of the United States Patent and Trademark Office*

SEQUENCE LISTING

<160> NUMBER OF SEQ ID NOS: 229

<210> SEQ ID NO 1
<211> LENGTH: 733
<212> TYPE: DNA
<213> ORGANISM: Homo sapiens

<400> SEQUENCE: 1

```
gggatccgga gcccaaatct tctgacaaaa ctcacacatg cccaccgtgc ccagcacctg      60
aattcgaggg tgcaccgtca gtcttcctct tccccccaaa acccaaggac accctcatga     120
tctcccggac tcctgaggtc acatgcgtgg tggtggacgt aagccacgaa gaccctgagg     180
tcaagttcaa ctggtacgtg gacggcgtgg aggtgcataa tgccaagaca aagccgcggg     240
aggagcagta caacagcacg taccgtgtgg tcagcgtcct caccgtcctg caccaggact     300
ggctgaatgg caaggagtac aagtgcaagg tctccaacaa agccctccca accccatcg     360
agaaaaccat ctccaaagcc aaagggcagc ccgagaacc acaggtgtac accctgcccc     420
catcccggga tgagctgacc aagaaccagg tcagcctgac ctgcctggtc aaaggcttct     480
atccaagcga catcgccgtg gagtgggaga gcaatgggca gccggagaac aactacaaga     540
ccacgcctcc cgtgctggac tccgacggct ccttcttcct ctacagcaag ctcaccgtgg     600
acaagagcag gtggcagcag gggaacgtct tctcatgctc cgtgatgcat gaggctctgc     660
acaaccacta cacgcagaag agcctctccc tgtctccggg taaatgagtg cgacggccgc     720
gactctagag gat                                                        733
```

<210> SEQ ID NO 2
<211> LENGTH: 5
<212> TYPE: PRT
<213> ORGANISM: Homo sapiens
<220> FEATURE:
<221> NAME/KEY: Site
<222> LOCATION: (3)
<223> OTHER INFORMATION: Xaa equals any of the twenty naturally ocurring
      L-amino acids

<400> SEQUENCE: 2

Trp Ser Xaa Trp Ser
 1               5

<210> SEQ ID NO 3
<211> LENGTH: 86
<212> TYPE: DNA
<213> ORGANISM: Homo sapiens

<400> SEQUENCE: 3

```
gcgcctcgag atttccccga aatctagatt tccccgaaat gatttccccg aaatgatttc      60
```

```
cccgaaatat ctgccatctc aattag                                          86
```

<210> SEQ ID NO 4
<211> LENGTH: 27
<212> TYPE: DNA
<213> ORGANISM: Homo sapiens

<400> SEQUENCE: 4

```
gcggcaagct ttttgcaaag cctaggc                                         27
```

<210> SEQ ID NO 5
<211> LENGTH: 271
<212> TYPE: DNA
<213> ORGANISM: Homo sapiens

<400> SEQUENCE: 5

```
ctcgagattt ccccgaaatc tagatttccc cgaaatgatt tccccgaaat gatttccccg     60
aaatatctgc catctcaatt agtcagcaac catagtcccg ccccctaactc cgcccatccc    120 gcccctaact ccgcccagtt ccgcccattc tccgcccat ggctgactaa tttttttat      180 ttatgcagag gccgaggccg cctcggcctc tgagctattc cagaagtagt gaggaggctt    240
ttttggaggc ctaggctttt gcaaaaagct t                                    271
```

<210> SEQ ID NO 6
<211> LENGTH: 32
<212> TYPE: DNA
<213> ORGANISM: Homo sapiens

<400> SEQUENCE: 6

```
gcgctcgagg gatgacagcg atagaacccc gg                                   32
```

<210> SEQ ID NO 7
<211> LENGTH: 31
<212> TYPE: DNA
<213> ORGANISM: Homo sapiens

<400> SEQUENCE: 7

```
gcgaagcttc gcgactcccc ggatccgcct c                                    31
```

<210> SEQ ID NO 8
<211> LENGTH: 12
<212> TYPE: DNA
<213> ORGANISM: Homo sapiens

<400> SEQUENCE: 8

```
ggggactttc cc                                                         12
```

<210> SEQ ID NO 9
<211> LENGTH: 73
<212> TYPE: DNA
<213> ORGANISM: Homo sapiens

<400> SEQUENCE: 9

```
gcggcctcga ggggactttc ccggggactt tccggggact ttccgggact ttccatcctg    60
ccatctcaat tag                                                        73
```

<210> SEQ ID NO 10
<211> LENGTH: 256
<212> TYPE: DNA
<213> ORGANISM: Homo sapiens

<400> SEQUENCE: 10

-continued

| | |
|---|---|
| ctcgagggga ctttcccggg gactttccgg ggactttccg ggactttcca tctgccatct | 60 |
| caattagtca gcaaccatag tcccgcccct aactccgccc atcccgcccc taactccgcc | 120 |
| cagttccgcc cattctccgc cccatggctg actaatttt tttatttatg cagaggccga | 180 |
| ggccgcctcg gcctctgagc tattccagaa gtagtgagga ggcttttttg gaggcctagg | 240 |
| cttttgcaaa aagctt | 256 |

<210> SEQ ID NO 11
<211> LENGTH: 1169
<212> TYPE: DNA
<213> ORGANISM: Homo sapiens
<220> FEATURE:
<221> NAME/KEY: SITE
<222> LOCATION: (1151)
<223> OTHER INFORMATION: n equals a,t,g, or c
<220> FEATURE:
<221> NAME/KEY: SITE
<222> LOCATION: (1160)
<223> OTHER INFORMATION: n equals a,t,g, or c
<220> FEATURE:
<221> NAME/KEY: SITE
<222> LOCATION: (1168)
<223> OTHER INFORMATION: n equals a,t,g, or c

<400> SEQUENCE: 11

| | |
|---|---|
| ggggcgcaaa tagggtcagt gggccgcttg gcgktgttcg ttgcggtacc aggtccgcgt | 60 |
| gaggggttcg ggggttctgg gcaggcacaa tggcgtctcg agcaggcccg cgagcggccg | 120 |
| rcaccgacgc agcgagcttt cagcaccggg agcgcgtcgc catgcactac cagatgagtg | 180 |
| tgaccctcaa gtatgaaatc aagaagctga tctacgtaca tctggtcata tggctgctgc | 240 |
| tggttgctaa gatgagcgtg ggacacctga ggctcttgtc acatgatcag gtggccatgc | 300 |
| cctatcagtg ggaatacccg tatttgctga gcattttgcc ctctctcttg ggccttctct | 360 |
| cctttccccg caacaacatt agctacctgg tgctctccat gatcagcatg ggactctttt | 420 |
| ccatcgctcc actcatttat ggcagcatgg agatgttccc tgctgcacag ccttctaccg | 480 |
| ccatggcaag gcctaccgtt tcctctttgg ttttctgcc gtttccatca tgtacctggt | 540 |
| gttggtgttg gcagtgcaag tgcatgcctg gcagttgtac tacagcaaga agctcctaga | 600 |
| ctcttggttc accagcacac aggagaagaa gcataaatga agcctctttg gggtgaagcc | 660 |
| tggacatccc atcgaatgaa aggacactag tacagcggtt ccaaaatccc ttctggtgat | 720 |
| tttagcagct gtgatgttgg tacctggtgc agacccaggc caaagttctg gaaagctcct | 780 |
| tttgccatct gctgaggtgg caaaactata atttattcct ggttggctag aactgggtga | 840 |
| ccaacagcta tgaaacaaat ttcagctgtt tgaagttgaa cttttgaggtt tttctttaag | 900 |
| aatgagcttc gtccttgcct ctactcggtc attctcccca tttccatcca ttacccctta | 960 |
| gccattgaga ctaaaggaaa tagggaataa atcaaattac ttcatctcta ggtcacgggt | 1020 |
| caggaaacat ttgggcagct gctcccttgg cagctgtggt ctcctctgca aagcatttta | 1080 |
| attaaaaacc tcaataaaga tgccctgccc acaaaaaaaa aaaaaaaaaa aattcggggg | 1140 |
| ggggcccggg naaccaattn gcccctana | 1169 |

<210> SEQ ID NO 12
<211> LENGTH: 1310
<212> TYPE: DNA
<213> ORGANISM: Homo sapiens

<400> SEQUENCE: 12

| | |
|---|---|
| aattcggcac gaggcagcgt cgcgcggccc agttcccttt tccggtcggc gtggtcttgc | 60 |

| | |
|---|---|
| gagtggagtg tccgctgtgc ccgggcctgc accatgagcg tcccggcctt catcgacatc | 120 |
| agtgaagaag atcaggctgc tgagcttcgt gcttatctga aatctaaagg agctgagatt | 180 |
| tcagaagaga actcggaagg tggacttcat gttgatttag ctcaaattat tgaagcctgt | 240 |
| gatgtgtgtc tgaaggagga tgataaagat gttgaaagtg tgatgaacag tgtggtatcc | 300 |
| ctactcttga tcctggaacc agacaagcaa gaagctttga ttgaaagcct atgtgaaaag | 360 |
| ctggtcaaat tcgcgaagg tgaacgcccg tctctgagac tgcagttgtt aagcaacctt | 420 |
| ttccacggga tggataagaa tactcctgta agatacacag tgtattgcag ccttattaaa | 480 |
| gtggcagcat cttgtggggc catccagtac atcccaactg agctggatca agttagaaaa | 540 |
| tggatttctg actggaatct caccactgaa aaaaagcaca ccctttaag actactttat | 600 |
| gaggcacttg tggattgtaa gaagagtgat gctgcttcaa agtcatggt ggaattgctc | 660 |
| ggaagttaca cagaggacaa tgcttcccag gctcgagttg atgcccacag gtgtattgta | 720 |
| cgagcattga aagatccaaa tgcatttctt tttgaccacc ttcttacttt aaaaccagtc | 780 |
| aagttttgg aaggcgagct tattcatgat cttttaacca ttttgtgag tgctaaattg | 840 |
| gcatcatatg tcaagtttta tcagaataat aaagacttca ttgattcact ggcctgtta | 900 |
| catgaacaga atatggcaaa aatgagacta cttacttta tgggaatggc agtagaaaat | 960 |
| aaggaaattt cttttgacac aatgcagcaa gaacttcaga ttggagctga tgatgttgaa | 1020 |
| gcatttgtta ttgacgccgt aagaactaaa atggtctact gcaaaattga tcagacccag | 1080 |
| agaaaagtag ttgtcagtca tagcacacat cggacatttg gaaaacagca gtggcaacaa | 1140 |
| ctgtatgaca cacttaatgc ctggaaacaa aatctgaaca aagtgaaaaa cagcctttg | 1200 |
| agtcttctg atacctgagt ttttatgctt ataattttg ttctttgaaa aaaaagccct | 1260 |
| aaatcatagt aaaacattat aaactaaaaa aaaaaaaaa aaaaaaaaa | 1310 |

<210> SEQ ID NO 13
<211> LENGTH: 1139
<212> TYPE: DNA
<213> ORGANISM: Homo sapiens
<220> FEATURE:
<221> NAME/KEY: SITE
<222> LOCATION: (7)
<223> OTHER INFORMATION: n equals a,t,g, or c
<220> FEATURE:
<221> NAME/KEY: SITE
<222> LOCATION: (133)
<223> OTHER INFORMATION: n equals a,t,g, or c
<220> FEATURE:
<221> NAME/KEY: SITE
<222> LOCATION: (968)
<223> OTHER INFORMATION: n equals a,t,g, or c
<220> FEATURE:
<221> NAME/KEY: SITE
<222> LOCATION: (1139)
<223> OTHER INFORMATION: n equals a,t,g, or c

<400> SEQUENCE: 13

| | |
|---|---|
| agggcanact tacagagata tcatatgaga tcacccctcg cattcgtgtc tggcgccaga | 60 |
| ccctcgagcg gtgccggagc gcasccaggt gtgcttgtgc ctgggccagc tggagaggtc | 120 |
| cattgcctgg gangaagtct gtcaacaaag tgacatgtct agtctgccgg aagggtgaca | 180 |
| atgatgagtt tcttctgctt tgtgatgggt gtraccgtgg ctgccacatt tactgccatc | 240 |
| gtcccaagat ggaggctgtc ccagaaggag attggttctg tactgtctgt ttggctcagc | 300 |
| aggtggaggg agaattcact cagaagcctg gtttcccaaa gcgtggccag aagcggaaaa | 360 |
| gtggttattc gctgaacttc tcagagggtg atggccgccg acgccgggta ctgttgaggg | 420 |

| | |
|---|---|
| gccgagaaag cccagcagca gggcctcggt actcggaaga agggctctcc ccctccaagc | 480 |
| ggcggcgact ctctatgcgg aaccaccaca gtgatctcac attttgcgag attatcctga | 540 |
| tggagatgga gtcccatgat gcagcctggc cttcctaga gcctgtgaac ccacgtttgg | 600 |
| tgagtgggta ccggcgcatc atcaaaaatc ctatggattt ttccaccatg cgggagcggc | 660 |
| tgctcagggg agggtacacc agctcagagg agtttgcggc tgatgccctc ctggtatttg | 720 |
| acaactgcca gactttcaac gaggatgact ctgaagtagg caaggctggg cacatcatgc | 780 |
| gccgcttctt cgagagccgc tgggaggagt tttatcaggg aaaacaggcc aatctgtgag | 840 |
| gcaagggagg tggggagtca ccttgtggca tctccccca ccttccaaac aaaaacctgc | 900 |
| cattttcacc tgctgatgct gccctgggtc cagactcaag tcagatacaa ccctgatttt | 960 |
| tgaccttncc cttggcagtg ccccacatcc tcttattcct acatccctt ctcccttccc | 1020 |
| tcctcttgct cctcaagtaa gaggtgcaga gatgaggtcc ttctggacta aaagccaaaa | 1080 |
| aaagaaagaa aaaawaaaa aaaaaaaaa aaaaaaaaaa aaaaaaaan | 1139 |

<210> SEQ ID NO 14
<211> LENGTH: 2271
<212> TYPE: DNA
<213> ORGANISM: Homo sapiens

<400> SEQUENCE: 14

| | |
|---|---|
| gttccggggg atgccagctc acttctcgga cagcgcccag actgaggcct gctaccacat | 60 |
| gctgagccgg ccccagccgc cacccgaccc cctcctgctc cagcgtctgc cacggcccag | 120 |
| ctccctgtca gacaagaccc agctccacag caggtggctg gactcgtcgc ggtgtctcat | 180 |
| gcagcagggc atcaaggccg gggacgcact ctggctgcgc ttcaagtact acagcttctt | 240 |
| cgatttggat cccaagacag accccgtgcg gctgacacac tgtatgagc aggcccggtg | 300 |
| ggacctgctg ctggaggaga ttgactgcac cgaggaggag atgatggtgt ttgccgccct | 360 |
| gcagtaccac atcaacaagc tgtcccagag cggggaggtg ggggagccgg ctggcacaga | 420 |
| cccagggctg gacgacctgg atgtggccct gagcaacctg gaggtgaagc tggaggggtc | 480 |
| ggcgcccaca gatgtgctgg acagcctcac caccatccca gagctcaagg accatctccg | 540 |
| aatctttcgg ccccggaagc tgaccctgaa gggctaccgc caacactggg tggtgttcaa | 600 |
| ggagaccaca ctgtcctact acaagagcca ggacgaggcc cctggggacc ccattcagca | 660 |
| gctcaacctc aagggctgtg aggtggttcc cgatgttaac gtctccggcc agaagttctg | 720 |
| cattaaactc ctagtgccct cccctgaggg catgagtgag atctacctgc ggtgccagga | 780 |
| tgagcagcag tatgcccgct ggatggctgg ctgccgcctg gcctccaaag gccgcaccat | 840 |
| ggccgacagc agctacacca gcgaggtgca ggccatcctg gccttcctca gcctgcagcg | 900 |
| cacgggcagt gggggccgg gcaaccaccc ccacggccct gatgcctctg ccgagggcct | 960 |
| caaccctac ggcctcgttg ccccccgttt ccagcgaaag ttcaaggcca agcagctcac | 1020 |
| cccacggatc ctggaagccc accagaatgt ggcccagttg tcgctggcag aggcccagct | 1080 |
| gcgcttcatc caggcctggc agtccctgcc cgacttcggc atctcctatg tcatggtcag | 1140 |
| gttcaagggc agcaggaaag acgagatcct gggcatcgcc aacaaccgac tgatccgcat | 1200 |
| cgacttggcc gtgggcgacg tggtcaagac ctggcgtttc agcaacatgc gccagtggaa | 1260 |
| tgtcaactgg gacatccggc aggtggccat cgagtttgat gaacacatca atgtggcctt | 1320 |
| cagctgcgtg tctgccagct gccgaattgt acacgagtat atcggggct acattttcct | 1380 |
| gtcgacgcgg gagcgggccc gtggggagga gctggatgaa gacctcttcc tgcagctcac | 1440 |

```
cgggggccat gaggccttct gagggctgtc tgattgcccc tgcctgctc accaccctgt    1500 cacagccact cccaagccca cacccacagg ggctcactgc cccacacccg ctccaggcag    1560
gcacccagct gggcatttca cctgctgtca ctgactttgt gcaggccaag gacctggcag    1620
ggccagacgc tgtaccatca cccaggccag ggatgggggt gggggtccct gagctcatgt    1680 ggtgcccct ttccttgtct gagtggctga ggctgatacc cctgacctat ctgcagtccc    1740
ccagcacaca aggaagacca gatgtagcta caggatgatg aaacatggtt tcaaacgagt    1800
tctttcttgt tacttttaa aatttctttt ttataaatta atatttattt gttggatcct     1860
cctcctttct ctggagctgt gcttgggct actctgacac tctgtctctt catcaccagc    1920
caaggaaagg ggctttcctg ataaagacaa gagttggtta gagaaaggga cacctaagtc    1980
agtctagggt tggaagctag gagagaggtg agggcagaag gcacagctt tcaggaacaa    2040 ggaatagggg ctggggtkgt kgttctcacg ggtaggcgta cctgcagggc ctccttgaag    2100
tacttgggaa ggaggaagcc atcagtattc cctggagtca gaatcacccc attggcagag    2160
cggaagaagg gtattccatc tgctgacaga gccagagatg tgactcatgc cctccccgaa    2220
ggcaaagtca gctcctgctt tgtccagact cacctgccag agccagtggt c            2271

<210> SEQ ID NO 15
<211> LENGTH: 626
<212> TYPE: DNA
<213> ORGANISM: Homo sapiens
<220> FEATURE:
<221> NAME/KEY: SITE
<222> LOCATION: (22)
<223> OTHER INFORMATION: n equals a,t,g, or c
<220> FEATURE:
<221> NAME/KEY: SITE
<222> LOCATION: (591)
<223> OTHER INFORMATION: n equals a,t,g, or c

<400> SEQUENCE: 15
acaacaaaca tcgaaaatcg antatgtgcc ccgaaaagtc ggaacgcagg caatcagtcc      60
gcacgmgcgc aagttcaaca tgaagatgat atgaggccgg ggcgggggc agggaccccc     120 gggcggccgg gcagggggaag gggcctggcc gccacctgct cactctccag tccttcccac    180
ctcctcccta cccttctaca cacgttctct ttctccctcc cgcctccgtc ccctgctgcc    240
ccccgccagc cctcaccacc tgccctcctt ctaccaggac ctcagaagcc cagacctggg    300 gacccccacct acacaggggc attgacagac tggagttgaa agccgacgaa ccgacacgcg    360
gcagagtcaa taattcaata aaaagttac gaactttctc tgtaacttgg gtttcaataa    420 ttatggatt ttatgaaaac ttgaaataat aaaagagaa aaaactatt tcctatagct     480 agtcggaatg caaacttttg acgtcctgat tgctccaggg ccctcttttcc aactcagttt    540 cttgttttc ctcttcctcc tcctcctctt cttcctcctt tctttctctt nccccatggg    600
ggaggggttc attcagggaa aacagg                                         626

<210> SEQ ID NO 16
<211> LENGTH: 2118
<212> TYPE: DNA
<213> ORGANISM: Homo sapiens

<400> SEQUENCE: 16
ttttccagcc atgtcactaa ttgtgaattc ctaccaacta ttgacagaat acagagttga       60
ttttttaata aaaagttata tataattatc cctttaatta aagggagcaa aggggcgttc     120
cacatggaca gaggcttgga ccgaggcctg gtcacagcag cgagcatcca gggtttgcag    180
```

```
ggacgatgtt acagactctg ttttctgcct ggcgtttcac ttgtgtctgc tcctagcctg    240
tgctctgcca gcagcacaga catctgctcc atcagacctc ttccattttg cacagggagt    300
gcaggaggtg aatgttcact ttctgttctc cagtgtcact gttctgtttc cacgggatgg    360
aaagcgcatg ggcctgtgtc cattgtagat ttccttctag atttctgtgt acacacactt    420
gattgttctg gatgaatgtc ttttttaata ctccgaaaat ttcatcatct aagaaaatga    480
ttccatacaa ataactcagc acacaagtga cccaggacat atgcctgcca aagggatgtg    540
ttagaaggct gccttctcat gcgcattgtc acttggatct tgtggtgagg acggccccat    600
ctttcttgcc acagattgag gccacttttg agcaagggag atcctggagt taagacaggt    660
gttgggggca gcctgtattt taccctaggg gcaggtctgc atggtgaccc cacatygcac    720
tggtaaacca tttgagtccc actcttcatc ctggaagtgg gaactggagt cccacccaca    780
gtgcattcag aaagcatgct gtgtggggc tgcttctcag gaggccaggc ccttctgagc    840
ggaaccgtcc tggagagagc ctgccctcgt ttccaggctg cagccgtaac gcactttctc    900
ccaggctgag ggcgggtgtt ctggggtgtc tgccctctgt cggccctgct tcctgccagg    960
acgtggcctc ttccgatcct ttttctctcag acactggagg tctcttctgc cattgtgctg   1020
gtcccatccc aagaattgta ggacagagac cacactgggt cggcggacac aaagtccatc   1080
caggacccag gccgcagagg gagcaggaag agatgctgat agtttgatct agaaaccagc   1140
agctactggc tcaaattcag gttctggcgt caaatagcga catttccagt ttctcttaaa   1200
aaccgtgttt ggtttcagtt gggataggct tgttttgtct gttgaaaatg tttctagttt   1260 ttttcttc attttttctct cattccattt ctgccttaac tttagtttgt tcacagggag   1320
gcaaagctga catgaacctt ttgtcgtggg acttcaggcc acattggctt gaaggcattc   1380
gtttccttct ggggtgggga caggccctca tggcaggctt gttcccgtgg ctctgagcga   1440
ggcctcttcc tgctgggctc ccagactcct gcatccaggc ccccaccttc tcggcttctg   1500
gttttctttt cttttttggta gaacacaaca tctaccattc agttaaacct tctttatctc   1560
ctcctytggc atccatttt ccaaagaaga gtcgagtcct ctgaggtctg tgcttgaaar   1620
ccgtccgaag gcattcttgt tagctttgct tttctcccca tatcccaagg cgaagcgctg   1680
agattcttcc atctaaaaaa ccctcgaccc gaaaccctca ccagataaac tacagtttgt   1740
ttaggaggcc ctgaccttca tggtgtcttt gaagcccaac cactcggttt ccttcggatt   1800 ttcctcccctt tgttcggggt ttggtttggc tcctctgtgt gtgtccgtat cttgttcggt   1860
gtcctcgagg ttgagcttca ctccactgcg gcagaggcag cgtgcacact cggatttgct   1920
acgtttctat atatcttgaa gctaaatgta tatatgagta gtttgccatg agataacaca   1980
gtgtaaacag tagacaccca gaaatcgtga cttctgtgtt ctctccattt gagtattttg   2040 taatttttt gaaatatttg tggacataaa taaaaccaag ctacactaca aaaaaaaaa   2100 aaaaaaactg gagactag                                                2118
```

<210> SEQ ID NO 17
<211> LENGTH: 1076
<212> TYPE: DNA
<213> ORGANISM: Homo sapiens
<220> FEATURE:
<221> NAME/KEY: SITE
<222> LOCATION: (979)
<223> OTHER INFORMATION: n equals a,t,g, or c
<220> FEATURE:
<221> NAME/KEY: SITE
<222> LOCATION: (1007)
<223> OTHER INFORMATION: n equals a,t,g, or c
<220> FEATURE:

```
<221> NAME/KEY: SITE
<222> LOCATION: (1040)
<223> OTHER INFORMATION: n equals a,t,g, or c
<220> FEATURE:
<221> NAME/KEY: SITE
<222> LOCATION: (1050)
<223> OTHER INFORMATION: n equals a,t,g, or c

<400> SEQUENCE: 17
```

| | | | | | |
|---|---|---|---|---|---|
| gcccaaggag | ctcagcttcg | cccgcatcaa | ggccgttgag | tgcgtggaga | gcaccgggcg | 60 |
| ccacatctac | ttcacgctgg | tgaccgaagg | gwgcggcgag | atcgacttcc | gctgcccct | 120 |
| ggaagatccc | ggctggaacg | cccagatcac | cctaggcctg | gtcaagttca | agaaccagca | 180 |
| ggccatccag | acagtgcggg | cccggcagag | cctcgggacc | gggaccctcg | tgtcctaaac | 240 |
| caccgggcgc | accatctttc | cttcatgcta | cccaccacct | cagtgctgag | gtcaaggcag | 300 |
| cttcgttgtt | ccctctggct | tgtgggggca | cggctgtsyt | ccatgtggca | aggtggaagg | 360 |
| catggacgtg | tggaggaggc | gctggagctg | aaggaatgga | cgagccctgg | gaggagggca | 420 |
| gaaggctacg | cagggctgag | gatgaagatg | cagcccctgg | atggtcccag | actctcagga | 480 |
| catgcccagc | tcaggggctt | cgagccacag | gcctggcctc | atatggcatg | aggggggagct | 540 |
| ggcataggag | cccctccct | gctgtggtcc | tgccctctgt | cctgcagact | gctcttagcc | 600 |
| ccctggcttt | gtgccaggcc | tggaggaggg | cagtccccca | tggggtgccg | agccaacgcc | 660 |
| tcaggaatca | ggaggccagc | ctggtaccaa | aaggagtacc | cagggcctgg | tacccaggcc | 720 |
| cactccagaa | tggcctctgg | actcaccttg | agaaggggga | gctgctgggc | ctaaagccca | 780 |
| ctcctggggg | tctcctgctg | cttaggtcct | tttgggaccc | ccacccatcc | aggccctttc | 840 |
| tttgcacact | tcttccccca | cctctaygca | tcttccccc | actgcggtgt | tcggcctgaa | 900 |
| ggtggtgggg | gtgagggggg | gtttggccat | tagcatttca | tgtctttccc | caaatgaaga | 960 |
| tgccctgcaa | agggcagtna | accacaaaaa | aaaaaaaaa | aaaaacntgg | ggggggggcc | 1020 |
| ccgttaacca | ttttggcctn | ataggggggn | ggttttttaaa | aattaattgg | gcccgg | 1076 |

```
<210> SEQ ID NO 18
<211> LENGTH: 1379
<212> TYPE: DNA
<213> ORGANISM: Homo sapiens
<220> FEATURE:
<221> NAME/KEY: SITE
<222> LOCATION: (639)
<223> OTHER INFORMATION: n equals a,t,g, or c
<220> FEATURE:
<221> NAME/KEY: SITE
<222> LOCATION: (697)
<223> OTHER INFORMATION: n equals a,t,g, or c
<220> FEATURE:
<221> NAME/KEY: SITE
<222> LOCATION: (1347)
<223> OTHER INFORMATION: n equals a,t,g, or c
<220> FEATURE:
<221> NAME/KEY: SITE
<222> LOCATION: (1361)
<223> OTHER INFORMATION: n equals a,t,g, or c

<400> SEQUENCE: 18
```

| | | | | | |
|---|---|---|---|---|---|
| ggcacgagca | ccctcccaca | cctccctgaa | cttccatctg | atcgacttca | acttgctgat | 60 |
| ggtgaccacc | atcgttctgg | gccgccgctt | cattgggtcc | atcgtgaagg | aggcctctca | 120 |
| gaggggggaag | gtctccctct | ttcgctccat | cctgctgttc | ctcactcgct | tcaccgttct | 180 |
| cacggcaaca | ggctggagtc | tgtgccgatc | cctcatccac | ctcttcagga | cctactcctt | 240 |
| cctgaacctc | ctgttcctct | gctatccgtt | tgggatgtac | attccgttcc | tgcarctgaa | 300 |

```
ttkcgamcty cgsaagacaa gcctcttcaa ccacatggcc tccatggggc cccgggaggc    360
ggtcagtggc ctggcaaaga gccgggacta cctcctgaca ctgcgggaga cgtggaagca    420
gcacasaaga cagctgtatg gcccggacgc catgcccacc catgcctgct gcctgtcgcc    480
cagcctcatc cgcagtgagg tggagttcct caagatggac ttcaactggc gcatgaagga    540
agtgctcgts agctccatgc tgagcgccta ctatgtggcc tttgtgcctg tytggttcgt    600
gaagaacaca cattactatg acaagcgctg gtcctgtgna actcttcctg ctggtgtcca    660
tcagcacctc cgtgatcctc atgcagcacc tgctgcntgc cagctactgt gacctgctgc    720
acaaggccgc cgcccatctg ggctgttggc agaaggtgga cccagcgctg tgctccaacg    780
tgctgcagca cccgtggact gaagaatgca tgtggccgca gggcgtgctg gtgaagcaca    840
gcaagaacgt ctacaaagcc gtaggccamw acaamgtggc tatcccctct gacgtctccc    900
acttccgctt ccakttcttt ttcagcaaac ccctgcggat cctcaacatc ctcctgctgc    960
tggagggcgc tgtcattgtc tatcagctgt actccctaat gtcctctgaa agtggcacc   1020 agaccatctc gctggccctc atcctcttca gcaactacta tgccttcttc aagctgctcc   1080
gggaccgctt ggtattgggc aaggcctact catactctgc tagcccccag agagacctgg   1140
accaccgttt ctcctgagcc ctggggtcac ctcagggaca gcgtccaggc ttcagcaagg   1200
gctccctggc aaggggctgt tgggtagaag tggtggtggg ggggacaaaa gacaaaaaaa   1260
tccaccagag ctttgtattt ttgttacgta ctgtttcttt gataattgat gtgataagga   1320
aaaaagtcct attttatac tcccaanmaa aaaaaaaaa naaaaagcgg ccgaaagct   1379
```

<210> SEQ ID NO 19
<211> LENGTH: 1337
<212> TYPE: DNA
<213> ORGANISM: Homo sapiens
<220> FEATURE:
<221> NAME/KEY: SITE
<222> LOCATION: (20)
<223> OTHER INFORMATION: n equals a,t,g, or c

<400> SEQUENCE: 19

```
ctggtgttgg gcctgagccn cctcaacaac tcctacaact tcagtttcca cgtggtgatc     60
ggctctcagg cggaagaagg ccagtacagc ctgaacttcc acaactgcaa caattcagtg    120
ccaggaaagg agcatccatt cgacatcacg gtgatgatcc gggagaagaa ccccgatggc    180
ttcctgtcgg cagcggagat gccccttttc aagctctaca tggtcatgtc cgcctgcttc    240
ctggccgctg gcatcttctg ggtgtccatc ctctgcagga cacgtacag cgtcttcaag    300 atccactggc tcatggcggc cttggccttc accaagagca tctctctcct cttccacagc    360
atcaactact acttcatcaa cagccagggg ccaccccatc gaaggccttg ccgkcatgta    420
ctacatcgca cacctgctga agggcgccct cctcttcatc accatcgccc tgattggctc    480
aggctgggct tcatcaagta cgtcctgtcg gataaggaga gaaggtcttt gggatcgtg    540 atccccatgc aggtcctggc caacgtggcc tacatcatca tcgagtcccg cgaggaaggc    600
gccacgaact acgtgctgtg gaaggagatt ttgttcctgg tggacctcat ctgctgtggt    660
gccatcctgt tccccgtagt ctggtccatc cggcatctcc aggatgcgtc tggcacagac    720
gggaaggtgg cagtgaacct ggccaagctg aagctgttcc ggcattacta tgtcatggtc    780
atctgctacg tctacttcac ccgcatcatc gccatcctgc tgcaggtggc tgtgcccttt    840
cagtggcagt ggctgtacma gctcttggtg garggctcca ccctggcctt cttcgtgctc    900
acgggctaca agttccagcc cacagggaac aacccgtacc tgcagctgcc ccaggaggac    960
```

-continued

```
gaggaggatg ttcagatgga gcaagtaatg acggactctg ggttccggga aggcctctcc    1020 aaaagtcaaca aaacagccag cgggcgggaa ctgttatgat cacctccaca tctcagacca    1080
aagggtcgtc ctcccccagc atttctcact cctgcccttc ttccacagcg tatgtgggga    1140
ggtggagggg tccatgtgga ccaggcgccc agctcccggg acsccggttc ccggacaagc    1200
ccatttggaa gaagagtccc ttcctccccc caaatattgg gcagccctgt ccttaccccg    1260
ggaccacccc tcccttccag ctatgtgtac aataatgacc aatctgtttg gctaaaaaaa    1320
aaaaaaaaaa aactcga                                                    1337
```

<210> SEQ ID NO 20
<211> LENGTH: 1390
<212> TYPE: DNA
<213> ORGANISM: Homo sapiens
<220> FEATURE:
<221> NAME/KEY: SITE
<222> LOCATION: (1267)
<223> OTHER INFORMATION: n equals a,t,g, or c

<400> SEQUENCE: 20

```
gccgttttgg ttcccggttg gtgcttcctg ttcgcagctg cggcacttca aggttactga      60 cttttttatga tgtttggtgg ctatgagact atagawgcrt rsgrrgatga tytttatcga     120
gatgagtcat ctagtgaact gagtgttgat agtgaggtgg aatttcaact ctatagccaa     180
attcattatg cccaagatct tgatgatgtc atcagggagg aagagcatga agaaaagaac     240
tctgggaatt cggaatcttc gagtagtaaa ccaaatcaga agaagctaat cgtcctttca     300
gatagtgagg tcatccagct gtcagatggg tcagaggtca tcactttgtc tgatgaagac     360
agtatttata gatgtaaagg aaagaatgtt agagttcaag cacaagaaaa tgcccatggt     420
cttcttcttc tctcttcaatc taatgagctg gttgataaga aatgcaagag tgatattgag     480
aagcctaaat ctgaagagag atcaggtgta atccgagagg tcatgattat agaggtcagt     540
tcaagtgaag aggaagagag caccatttca gaaggtgata atgtgaaag ctggatgcta     600 ctgggatgtg aagtagatga taaagatgat gatatccttc tcaaccttgt gggatgtgaa     660
aactctgtta ctgaaggaga agatggtata aactggtcca tcagtgacaa agacattgag     720
gcccagatag ctaataaccg aacacctgga agatggaccc agcggtacta ttcagccaac     780
aaaaacatta tctgtagaaa ttgtgacaaa cgtggtcatt tatcaaaaaa ctgccccttta    840 ccacgaaaag ttcgtcgctg cttcctgtgc tccaggagag acatctcct gtattcctgt     900 ccagccccc tttgcgaata ctgtcctgtg cctaagatgt tggaccactc atgtcttttc    960
agacattcct gggataaaca gtgtgaccga tgtcatatgc taggccacta tacagatgct    1020
tgcacagaaa tctggaggca gtatcaccta acgaccaaac ctggaccacc caaaaagccg    1080
aagacccctt caagaccatc agccttagca tattgctatc actgcgcgca aaaaggccat    1140
tatggacacg aatgtccaga aagagaagtg tatgacccgt ctccagtatc tccattcatc    1200
tgctactatg rtgacaaata tgaaattcag gagagagaaa agagactaaa acaaaaaata    1260
aaagtantca agaaaaatgg ggttatccca gagccatcca agctacccta tataaaagca    1320
gcaaatgaga accccacca tgatataagg aagggccgtg cctcatggaa aagcaacagg    1380
tggcctcaag                                                           1390
```

<210> SEQ ID NO 21
<211> LENGTH: 1431
<212> TYPE: DNA
<213> ORGANISM: Homo sapiens

<400> SEQUENCE: 21

```
gcctgcagtc gacactagtg gatccaaaga attcggcctg tgcgagtagg cgcttgggca        60
ctcagtctcc ctggcgagcg acgggcagaa atctcgaacc agtggagcgc actcgtaacc       120
tggatcccag aaggtcgcga aggcagtacc gtttcctcag cggcggactg ctgcagtaag       180
aatgtctttt ccacctcatt tgaatcgccc tcccatggga atcccagcac tcccaccagg       240
gatcccaccc ccgcagtttc caggatttcc tccacctgta cctccaggga ccccaatgat       300
tcctgtacca atgagcatta tggctcctgc tccaactgtc ttagtaccca ctgtgtctat       360
ggttggaaag catttgggcg caagaaagga tcatccaggc ttaaaggcta agaaaatga        420
tgaaaattgt ggtcctacta ccactgtttt tgttggcaac atttccgaga agcttcaga        480
catgcttata agacaactct tagctaaatg tggtttggtt ttgagctgga agagagtaca       540
aggtgcttcc ggaaagcttc aagccttcgg attctgtgag tacaaggagc cagaatctac       600
cctccgtgca ctcagattat tacatgacct gcaaattgga gagaaaaagc tactcgttaa       660
agttgatgca aagacaaagg cacagctgga tgaatggaaa gcaagaagaa agcttctaa        720
tgggaatgca aggccagaaa ctgtcactaa tgacgatgaa gaagccttgg atgaagaaac       780
aaagaggaga gatcagatga ttaaaggggc tattgaagtt ttaattcgtg aatactccag       840
tgagctaaat gccccctcac aggaatctga ttctcacccc aggaagaaga agaaggaaaa       900
gaaggaggac attttccgca gatttccagt ggccccactg atcccttatc cactcatcac       960
taaggaggat ataaatgcta tagaaatgga agaagacaaa agagacctga tatctcgaga      1020
gatcagcaaa ttcagagaca cacataagaa actggaagaa gagaaaggca aaaggaaaa       1080
agaaagacag gaaattgaga agaacggag agaaagagag agggagcgtg aaagggaacg      1140
agaaaggcga gaacgggaac gagaaaggga agagaacgt gaacgagaaa aggagaaga       1200
acggagcgg gaacgagaac gggatagga ccgtgaccgg acaaaagaga gagaccgaga       1260
tcgggatcga gagagagatc gtgaccggga tagaaaagg agctcagatc gtaataagga      1320
tcgcattcga tcaagagaaa aaagcagaga tcgtgaaagg gaacgagagc gggaaagaga      1380
gagagagaga gaacgagagc gagaacgaga acgggagcga gagagagaag c              1431
```

<210> SEQ ID NO 22
<211> LENGTH: 2539
<212> TYPE: DNA
<213> ORGANISM: Homo sapiens
<220> FEATURE:
<221> NAME/KEY: SITE
<222> LOCATION: (1283)
<223> OTHER INFORMATION: n equals a,t,g, or c

<400> SEQUENCE: 22

```
gggtgcagga gtgccacccc cagggccctg tcaacctctc tttctcctc catggctgtc        60
tgcctgcgta tctgtctctg agaatcctcg ggcggtcag gggatgtcag gaggggaagg       120
agccgccctc cctatcttgc tgctcctctt ggcactcagg ggcaccttcc atggagccag       180
accgggtgga ggggcttctg ggatttggtg tctgctgctg ccagagcagg aaccccagt        240
ctaggacttg ggcattttaa cagggagaaa gtagtggctt cccttttctc tctctcctcc       300
tttttccctt taagcccaca gattcaggtc atgccaaaag ctctctggtt gtaacctgga       360
gacatgtgga ggggaatggc gatgggatta taggactctc cccatctcgg gccctgaccc       420
tgacccttgc caccaaccca aagacagctg gtgggtttcc ccttggagam aatcctgcgt       480
ttgcctgggc cggccctggc tgccctcagc tttcgctgat ctgccggcc tggagcctcc       540
```

```
catcaccccg cttcttgttg ggcctcaggc actggttacc agaagggggt ctgggtctgc    600
tcaggaatca tgttttgtag cacctcctgt tggaggggtg gagggatgtt cccctgagcc    660
aggctgagac tagaacccca tcttccctga gccaggctga gactagaacc ccatcttccc    720
caccacgcca cccctgtgst kgctacagga gcacagtagt gaaggcctga gctccaggtt    780
tgaaagaccc aactggagcg tggggcgggc aggcagggt tagtgaaagg acacttccag     840
ggttaggaca gagcatttag ccttctggaa gaacccctgc ctggggtggg actgtgcagg    900
ccagagaagg tggcatgggc ctgaacccac ctggactgac ttctgcactg aagccacaga    960
tggagggtag gctggtgggt gggggtggtt cgttctctag ccggggcaga cacccagctg   1020
gctgggtcct tcctcagcct tgcctcctcc tgtccccaac cctttccttt cctcctgctt   1080
gcggactgct ggtcccctct ccttccctcc ttccagctgt ttctagttac cacctacccc   1140
tgggccgtgg actgatcaga ccagcattca aaataaaagt ttgttccaag ttgacagtgt   1200
ggtgctccct gcccagcccc tccaggtgga ggtgctgcca cgggaacgca gttgctctgc   1260
ctgccctggg cccctggcga cantgggagc agggcagtgc tgtgaggagc ccagctttcc   1320
cagtcaggca ggcatggctt ccgtgttcag gctccctcac cagctggtga cacgggacaa   1380
gcttacaaac cttctctgaa cctcagtttt ctcatttaca agaggcaaag catccatcac   1440
cttgtgtgga ttcaragaat gtraggccct ggggtgtcct acacaaggga aaggcttgct   1500
cagtgagcgg tctgcacacc gttagccacc ctgccacctc tgtgccctgg gcaggctcca   1560
aaggaaagct ctggctggga ctgccrggag tctcacacgc tcctgttgac attcccagca   1620
gcygcccctg aggtcgatgt ttgttctgtt tttcttttc tttttgaga cggagtctcg    1680 ctgtgttgcc aggctggagt gcagtggtgt gatctctgct cactgcaacc tccgcctgcc   1740
agtttcaagt gattctctgc ctcagccttc tgagtagctg ggactacagg tgcacgccac   1800
cacgcccagc taacttttttg tatttwagta gagacagggt ttcgccatgt cggccagggt   1860
ggtcttgatc tcctgacctc atgatccacc cgcctcagcc tcccaaagtg ctgggattac   1920
aggtatgagc caccgcaccg ggcctgttct attttctag ttaagggaac tgaagctcag    1980
araggtgtca ccagcargtg ttcattccca tgccagcctt gcccccggc ttttcccagg    2040 caggctcctg cgtgcccact ggctccagcc tggtcctctg tctcttggct gcttcactcc   2100
tgctctttgt cccgactctg gccctgctta caggggccac tacctgctgg tgcctccata   2160
acaagcgtct ggcgttgaga cccctggcat ggcaggggct ttggggtctg gtttccacaa    2220
ggcttagcca tggcagaacc tcgttttatt ttaactcttt gcccctacaa acaaacagca    2280
gtacttgcca gaaccattct tgggattcag gagctcgggc gactgccttg gcctctggcc   2340
gcacccagga gggtggggtt ggatctgtgt agttgccagg cccacacctg ccagcagggg   2400
gctgactgga tccatgcttt actgtgttta atggggtaa caggggtccc tacagccctc     2460
ccagytaaam atttggaaca aaacaccagc ccttttgtag tggatgcaga ataaaattgt    2520
taatccaatc aaaaaaaaa                                                 2539

<210> SEQ ID NO 23
<211> LENGTH: 1043
<212> TYPE: DNA
<213> ORGANISM: Homo sapiens

<400> SEQUENCE: 23
tcgacccacg cgtccgccca cgcgtccgcc cacgcgtccg ggcgcaggac gtgcactatg      60
gctcggggct cgctgcgccg gttgctgcgg ctcctcgtgc tggggctctg gctggcgttg     120
```

| | |
|---|---|
| ctgcgctccg tggccgggga gcaagcgcca ggcaccgccc cctgctcccg cggcagctcc | 180 |
| tggagcgcgg acctggacaa gtgcatggac tgcgcgtctt gcagggcgcg accgcacagc | 240 |
| gacttctgcc tgggctgcgc tgcagcacct cctgcccect tccggctgct ttggcccatc | 300 |
| cttggggggcg ctctgagcct gaccttcgtg ctggggctgc tttctggctt tttggtctgg | 360 |
| agacgatgcc gcaggagaga gaagttcacc accccccatag aggagaccgg cggagagggc | 420 |
| tgcccagctg tggcgctgat ccagtgacaa tgtgcccect gccagccggg gctcgcccac | 480 |
| tcatcattca ttcatccatt ctagagccag tctctgcctc ccagacgcgg cgggagccaa | 540 |
| gctcctccac cacaagggg gtggggggcg gtgaatcacc tctgaggcct gggcccaggg | 600 |
| ttcagggga ccttccaagg tgtctggttg ccctgcctct ggctccagaa cagaaaggga | 660 |
| gcctcacgct ggctcacaca aaacagctga cactgactaa ggaactgcag catttgcaca | 720 |
| ggggagggg gtgccctcct tcctagaggc cctgggggcc aggctgactt gggggcaga | 780 |
| cttgacacta ggccccactc actcagatgt cctgaaattc caccacgggg gtcaccctgg | 840 |
| ggggttaggg acctattttt aacactaggg ggctggccca ctaggagggc tggccctaag | 900 |
| atacagaccc ccccaactcc ccaaagcggg gaggagatat ttatttgggg gagagtttgg | 960 |
| aggggaggga gaatttatta ataaaagaat ctttaacttt aaaaaaaaaa aaaaaaaagg | 1020 |
| gcggccgctc tagaggatcc ctc | 1043 |

```
<210> SEQ ID NO 24
<211> LENGTH: 1962
<212> TYPE: DNA
<213> ORGANISM: Homo sapiens
<220> FEATURE:
<221> NAME/KEY: SITE
<222> LOCATION: (452)
<223> OTHER INFORMATION: n equals a,t,g, or c
<220> FEATURE:
<221> NAME/KEY: SITE
<222> LOCATION: (480)
<223> OTHER INFORMATION: n equals a,t,g, or c

<400> SEQUENCE: 24
```

| | |
|---|---|
| acccacgcgt ccggtacaaa acacagtttt attctatgaa aattttgaga ttattagaaa | 60 |
| cattagattt agggttgcat attaaaaact atatccattt tgccttatta tttagtgtct | 120 |
| cactcaggat ataacacact ataatagaaa atgtagactt cagaatcagg tatatttgag | 180 |
| atggtttgta tactggttct gacacttgtt agctattcat ctttggtaaa ttccccatta | 240 |
| ccctttgtkc acctatwtgt ggggatcagt gcatagtgtg tgtwaagcat ttaatacctg | 300 |
| gcaagtgttc agcaaatttt ttgttctata tatttattat ttgattattg gccctgagga | 360 |
| gtaggtgttt gtttgtttgt ttgtttgttt agttttattt ctcatctcct caggaacaca | 420 |
| aatgaaactt ggatattgtt atggtgcttt tnataatata tttattattt tcagcaattn | 480 |
| attcttgtta aaacaatttc ttatgacaag ttactcatct tcaatggtga aagaaatct | 540 |
| agctcagaat aatatatttt tagtgtttgt atctctggat actcatttg ctcattgcca | 600 |
| cgtaaagtaa aaaatacat aaattagctt attccaatgt aatatcttca ggatagtcat | 660 |
| gggcaaggaa ttaatcacat taagagataa ctgcaactaa gcactatttg aggtgacttc | 720 |
| tgtgaaaaaa aaattaatyc tttaccattg cagcgttctg ccctaggtcc aaatgttacc | 780 |
| aaaatcactc tagaatcttt tcttgcctgg aagaaaagga aagacaaga aagattgat | 840 |
| aaacttgaac aagatatgga aagaaggaaa gctgacttca aagcagggaa agcactagtg | 900 |
| atcagtggtc gtgaagtgtt tgaatttcgt cctgaactgg tcaatgatga tgatgaggaa | 960 |

| | |
|---|---|
| gcagatgata cccgctacac ccagggaaca ggtggtgatg aggttgatga ttcagtgagt | 1020 |
| gtaaatgaca tagatttaag cctgtacatc ccaagagatg tagatgaaac aggtattact | 1080 |
| gtagccagtc ttgaaagatt cagcacatat acttcagata aagatgaaaa caaattaagt | 1140 |
| gaagcttctg gaggtagggc tgaaaatggt gaaagaagtg acttggaaga ggacaacgag | 1200 |
| agggagggaa cggaaaatgg agccattgat gctgttcctg ttgatgaaaa tcttttcact | 1260 |
| ggagaggatt tggatgaact agaagaagaa ttaaatacac ttgatttaga agaatgacac | 1320 |
| caaacacatc gctgaaaaaa ttaagtcagc tcagcacgag ttgaaattga ctacattaat | 1380 |
| ttcttttccac ctagaatcaa caggatgttt atttcctatg ctgattctgg aggagttaac | 1440 |
| ctcctgcaaa aaaggcatct tgtccctaca tcttctcttc tgactttggc tacatctcat | 1500 |
| agtaagttca gagtagttca tgataaattg aaaatataat ggtcattgca gaaaatgatt | 1560 |
| gatgttgtaa ctgtccaccc aagtaagaag tgtatctgcc tttccatctt ttggttttca | 1620 |
| tttgggcatg tgctattacc agaaacaaca aacttatatt taaaataccc ttcatttgac | 1680 |
| acagttttta atgagtgatt taatttcctc tgtatttgta tgtttagaag actgcctaaa | 1740 |
| acatgagcac tgtacttcat aaaggaaacg cgtatgcaga ttcagtattg tgtatctttg | 1800 |
| gacaattaga tggacattta aaatggaact tcttttatct gacaggatca gctacaatgc | 1860 |
| cctgtgttaa attgtttaaa agtttcccctt ttctttttttg ccaataaagt tgtaaataaa | 1920 |
| gaccatcata cattaaaatc caaaaaaaaa aaaaaaaaaa aa | 1962 |

<210> SEQ ID NO 25
<211> LENGTH: 1228
<212> TYPE: DNA
<213> ORGANISM: Homo sapiens
<220> FEATURE:
<221> NAME/KEY: SITE
<222> LOCATION: (580)
<223> OTHER INFORMATION: n equals a,t,g, or c
<220> FEATURE:
<221> NAME/KEY: SITE
<222> LOCATION: (621)
<223> OTHER INFORMATION: n equals a,t,g, or c
<220> FEATURE:
<221> NAME/KEY: SITE
<222> LOCATION: (1159)
<223> OTHER INFORMATION: n equals a,t,g, or c

<400> SEQUENCE: 25

| | |
|---|---|
| ggctgcccag gccccgcact ggaagagcct ccagcagcaa gatgtgaccg ytgtgccgat | 60 |
| gagccccagc agccactccc cagagggggag gcctccacct ctgctgcctg ggggtccagt | 120 |
| gtgtaaggca gctgcatctg caccgagctc cctcctggac cagccgtgcc tctgccccgc | 180 |
| accctctgtc cgcaccgctg ttgccctgac aacgccggat atcacattgg ttctgccccc | 240 |
| tgacatcatc caacaggaag cgtcaccctg agggaggaga cagaagcctg gccaggtga | 300 |
| acagtggtat agcagccact ccagcctctg ctgcagcagc caccctggat gtggctgttc | 360 |
| ggagaggcct gtcccacgga gcccagaggc tgctgtgcgt ggccctggga cagctggacc | 420 |
| ggcctccaga cctcgcccat gacgggagga gtctgtggct gaacatcagg ggcaaggagg | 480 |
| cggctgccct atccatgttc catgtctcca cgccactgcc agtgatgacc ggtggtttcc | 540 |
| tgagctgcat cttgggcttg gtgctgcccc tggcctatgn ttccagcctg acctggtgct | 600 |
| ggtggcgctg gggcctgcca ntgcctgcag ggccccacg ctgcactcct ggctgcaatg | 660 |
| cttcggggc tggcagggg ccgagtcctg gccctcctgg aggagaactc cacacccag | 720 |
| ctagcaggga tcctggcccg ggtgctgaat ggagaggcac ctcctagcct aggcccttcc | 780 |

-continued

| | |
|---|---|
| tctgtggcct ccccagagga cgtccaggcc ctgatgtacc tgagagggca gctggagcct | 840 |
| cagtggaaga tgttgcagtg ccatcctcac ctggtggctt gaaatcggcc aaggtgggag | 900 |
| catttacacc gcagaaatga caccgcacgc cagcgccccg cggccgcgat ccggacccca | 960 |
| agcccacggc tccctcgact ctggggcacg gaaccccgcc cactcccaat ccccgcgccc | 1020 |
| cgccctctcc cacccgtgct tccccgctc caccccctcac ctcacctcgc cccsgcccca | 1080 |
| cccatcgcgc cccggcccgt cccatcgagg cccatgcaac ccacgctcgg tyccgttccg | 1140 |
| gcccctgcgc tckcgctkns ttcgctcccc gcccttgcgc cgttagtaaa catcgctcaa | 1200 |
| acgaaaaaaa aaaaaaaaaa aaactcga | 1228 |

<210> SEQ ID NO 26
<211> LENGTH: 1340
<212> TYPE: DNA
<213> ORGANISM: Homo sapiens
<220> FEATURE:
<221> NAME/KEY: SITE
<222> LOCATION: (847)
<223> OTHER INFORMATION: n equals a,t,g, or c
<220> FEATURE:
<221> NAME/KEY: SITE
<222> LOCATION: (1303)
<223> OTHER INFORMATION: n equals a,t,g, or c
<220> FEATURE:
<221> NAME/KEY: SITE
<222> LOCATION: (1307)
<223> OTHER INFORMATION: n equals a,t,g, or c
<220> FEATURE:
<221> NAME/KEY: SITE
<222> LOCATION: (1314)
<223> OTHER INFORMATION: n equals a,t,g, or c

<400> SEQUENCE: 26

| | |
|---|---|
| aattcggcag agagatggcc gcccccgtgg atctagagct gaagaaggcc ttcacagagc | 60 |
| ttcaagccaa agttattgac actcaacaga aggtgaagct cgcagacata cagattgaac | 120 |
| agctaaacag aacgaaaaag catgcacatc ttacagatac agagatcatg actttggtag | 180 |
| atgagactaa catgtatgaa ggtgtaggaa gaatgtttat tcttcagtcc aaggaagcaa | 240 |
| ttcacagtca gctgttagag aagcagaaaa tagcagaaga aaaaattaaa gaactagaac | 300 |
| agaaaaagtc ctacctggag cgacgttaaa ggaagctgag gacaacatcc gggagatgct | 360 |
| gatggcacga agggcccagt agggagcctc tctgggaagc tcttcctcct gcccctccca | 420 |
| ttcctggtgg gggcagagga gtgtctgcag ggaaacagct tctcctctgc cccgatggat | 480 |
| gctttatttg gatggcctgg caacatcaca ttttctgcat caccctgagc cccatttgct | 540 |
| tcccagccct ggagttttta cccggctttg ctgccacctc tgcccaggac ackcttccct | 600 |
| ctcgggatgt gtgatgaact cccaggagag ggaagatggg agccagggca agataggaag | 660 |
| ctctgcctga gctttccact aggcacgcca gccagaccaa taaaaagcgt ctgtcccact | 720 |
| ctgctaagcc tggttttctt gagcagaggg atggaacaga gggtgagaga ggcagtggcc | 780 |
| gtctccacct cagctcctgc tccctctgca tcagagccct tcctttcttg ggggatgggc | 840 |
| cttgccntct tctcttttcc cttcctgtac ctttgactaa cgctcagctt ccgggcctgc | 900 |
| atgcagtaga cagaagagga agaaagaaca gatgttcaca gctgaatctc agtgaacaga | 960 |
| atagcagtcc ctggatggca gtctgcctaa agattccttt ccctgccttc tcccatacat | 1020 |
| tccaaaagga agttcaacag taagcagcac ctccaagact gtctcctttty ggccartatc | 1080 |
| ataagatgga cgccataatc ctgaggcctc ctagaggctg agggggcaac ggtgtgatcc | 1140 |
| agctggctca tcccagccag gtgggccaat tattcaattt tcaagaattt tgttgcaagc | 1200 |

```
cagttgtcaa acacagccat tataattatg taaatttgca aattatgtta aaaacaagga    1260
caataaatat tcaaaatgca tccctaawwa aaaaaaaaaa aangggnggc cgcnctaggg    1320
gatccaagct tacgtacgcg                                                1340
```

<210> SEQ ID NO 27
<211> LENGTH: 806
<212> TYPE: DNA
<213> ORGANISM: Homo sapiens

<400> SEQUENCE: 27

```
accttcttcc atgtttagtc ccttgggctc tgctaccctc ctgctggagg tgagagcatc      60
ctgtgtgcaa ccagagatgc cctctggctt tcagacctgc ctgcttttca ccctcagccc     120
tttctcactc agcaaaattg tgggggtccc tagtcagcag ctccctgggc agctctctga     180
gcaaggtggt ctctgtggtc atgaaggaga gccggctagg acagtgccgg aaactcagct     240
gcctctcccc ttcaactcag ctggcccccc gcacctgaag tgcacaggag ccgggaagag     300
agtctggagc ccaccccgga gggcagcaca ggaggtgtct ctgcagctgg tgtcctgcca     360
cccctgcagg cagcacacgt cccgggcatt ctccttagcc acagacagaa cagccagtgc     420
cagagtctgc tgtcgttccc ctttaagcac actcattcac cacacccgag gaggccagag     480
gtgcagggag catgggctgt cgcttcccct ttaagcacac tcattcacca cacccgagga    540
ggccagaagt gcagggagca tgggctgggt gcacctccgc aggagagaag gctgagccac     600
cgccgtcccg ggagcccggc tcccaggcct ctcgttttcc cctacctccc taagactttt     660
ctgtcactct ctggccattg aaaggcttct gttccttaaa gtgctgttac actctccttt     720
cccaggatgc agcaagccaa aacagtacca ctgcacgtca gcctgggtga cagagtgaga     780
ccctatctta aaaaaaaaaa aaaaaa                                         806
```

<210> SEQ ID NO 28
<211> LENGTH: 696
<212> TYPE: DNA
<213> ORGANISM: Homo sapiens
<220> FEATURE:
<221> NAME/KEY: SITE
<222> LOCATION: (9)
<223> OTHER INFORMATION: n equals a,t,g, or c
<220> FEATURE:
<221> NAME/KEY: SITE
<222> LOCATION: (21)
<223> OTHER INFORMATION: n equals a,t,g, or c

<400> SEQUENCE: 28

```
gagttcccna cgcggtggcg nccgttttag aaattagtgg atcccccgg gctggcaggg       60 aattcggcac gagcacagag gaaagcgggt gcccggcatg gccatcctga tgttgctggc    120
gggatcccca tgcaccttgt ccttctccac tgatactggc agctcggctc ctggacccaa    180
gatcccttga gtggaattct gcagtgcaag agcccttcgt gggagctgtc ccatgttttcc   240 atggtcccca gtctcccctc cacttggtgg ggtcaccaac tactcaccag aaggggggctt    300 accaagaaag ccctaaaaag ctgttgactt atctgcgctt gttccaactc ttatgccccc     360
aacctgccct accaccacca cgcgctcagc ctgatgtgtt tacatggtac tgtatgtatg    420
ggagagcaga ctgcaccctc cagcaacaac agatgaaagc cagtgagcct actaaccgtg    480
ccatcttgca aactacactt taaaaaaaac tcattgcttt gtattgtagt aaccaatatg    540
tgcagtatac gttgaatgta tatgaacata ctttcctatt tctgttcttt gaaaatgtca    600
gaaatatttt tttctttctc attttatgtt gaactaaaaa ggattaaaaa aaaaatctcc    660
```

-continued

| agamaaaaaa aaaaaaaaaa aaattactgc ggtccg | 696 |

<210> SEQ ID NO 29
<211> LENGTH: 1007
<212> TYPE: DNA
<213> ORGANISM: Homo sapiens
<220> FEATURE:
<221> NAME/KEY: SITE
<222> LOCATION: (922)
<223> OTHER INFORMATION: n equals a,t,g, or c

<400> SEQUENCE: 29

| aattcggcac gaggaaaaaa taccatttgt gtatgatacc caatttggat ctcaatttgg | 60 |
|---|---|
| atagagattt ggtgcttcca gatgtragtt atcaggtgga atccagtgag gaggatcagt | 120 |
| ctcagactat ggatcctcaa ggacaaactc tgctgctttt tctctttgtg gatttccaca | 180 |
| gtgcatttcc agtccagcaa atggaaatct ggggagtcta tactttgctc acaactcatc | 240 |
| tcaatgccat ccttgtggag agccacagtg tagtgcaagg ttccatccaa ttcactgtgg | 300 |
| acaaggtctt ggagcaacat caccaggctg ccaaggctca gcagaaacta caggcctcac | 360 |
| tctcagtggc tgtgaactcc atcatgagta ttctgactgg aagcactagg agcagcttcc | 420 |
| gaaagatgtg tctccagacc cttcaagcag ctgacacaca agagttcagg accaaactgc | 480 |
| acaaagtatt tcgtgagatc acccaacacc aatttcttca ccactgctca tgtgaggtga | 540 |
| agcagctaac cctagaaaaa aaggactcag cccagggcac tgaggacgca cctgataaca | 600 |
| gcagcctgga gctcctagca gataccagcg ggcaagcaga aaacaagagg ctcaagaggg | 660 |
| gcagcccccg catagaggag atgcgagctc tgcgctctgc cagggccccg agcccgtcag | 720 |
| aggccgcccc gcgccgcccg gaagccaccg cggcccccct cactcctaga ggaagggagc | 780 |
| accgcgaggc tcacggcagg gccctggcgc cgggcaggga gagcctcgga agccgcctgg | 840 |
| aggacgtgct gtggctgcag gaggtctcca acctgtcaga gtggctgagt cccagccctg | 900 |
| ggccctgagc cgggtcccct tncgcaagcg cccaccgatc cggargctgc gggcagccgt | 960 |
| tatcccgtgg tttaataaag tgccgcgcgc tcaccaaaaa aaaaaaa | 1007 |

<210> SEQ ID NO 30
<211> LENGTH: 2026
<212> TYPE: DNA
<213> ORGANISM: Homo sapiens

<400> SEQUENCE: 30

| gaattcggca cgagcacgga tccgttgcgg ctgcagctct gcagtcgggc cgttccttcg | 60 |
|---|---|
| ccgccgccag gggtagcggt gtagctgcgc agcgtcgcgc gcgctaccgc acccaggttc | 120 |
| ggcccgtagg cgtctggcag cccggcgcca tcttcatcga gcgccatggc cgcagcctgc | 180 |
| gggccgggag cggccgggta ctgcttgctc ctcggcttgc atttgtttct gctgaccgcg | 240 |
| ggccctgccc tgggctggaa cgaccctgac agaatgttgc tgcgggatgt aaaagctctt | 300 |
| accctccact atgaccgcta taccacctcc cgcaggctgg atcccatccc acagttgaaa | 360 |
| tgtgttggag gcacagctgg ttgtgattct tatacccca aagtcataca gtgtcagaac | 420 |
| aaaggctggg atgggtatga tgtacagtgg gaatgtaaga cggacttaga tattgcatac | 480 |
| aaatttggaa aaactgtggt gagctgtgaa ggctatgagt cctctgaaga ccagtatgta | 540 |
| ctaagaggtt cttgtggctt ggagtataat ttagattata cagaacttgg cctgcagaaa | 600 |
| ctgaaggagt ctgaaagca gcacggcttt gcctctttct ctgattatta ttataagtgg | 660 |
| tcctcggcgg attcctgtaa catgagtgga ttgattacca tcgtggtact ccttgggatc | 720 |

```
gcctttgtag tctataagct gttcctgagt gacgggcagt attctcctcc accgtactct      780
gagtatcctc cattttccca ccgttaccag agattcacca actcagcagg acctcctccc      840
ccaggcttta agtctgagtt cacaggacca cagaatactg gccatggtgc aacttctggt      900
tttggcagtg cttttacagg acaacaagga tatgaaaatt caggaccagg gttctggaca      960
ggcttgggaa ctggtggaat actaggatat ttgtttggca gcaatagagc ggcaacaccc     1020
ttctcagact cgtggtacta cccgtcctat cctccctcct accctggcac gtggaatagg     1080
gcttactcac cccttcatgg aggctcgggc agctattcgg tatgttcaaa ctcagacacg     1140
aaaaccagaa ctgcatcagg atatggtggt accaggagac gataaagtag aaagttggag     1200
tcaaacactg gatgcagaaa ttttggattt ttcatcactt tctctttaga aaaaagtac      1260 tacctgttaa caattgggaa aaggggatat tcaaaagttc tgtggtgtta tgtccagtgt     1320 agcttttgt attctattat ttgaggctaa aagttgatgt gtgacaaaat acttatgtgt      1380
tgtatgtcag tgtaacatgc agatgtatat tgcagttttt gaaagtgatc attactgtgg     1440
aatgctaaaa atacattaat ttctaaaacc tgtgatgccc taagaagcat taagaatgaa     1500
ggtgttgtac taatagaaac taagtacaga aaatttcagt tttaggtggt tgtagctgat     1560
gagttattac ctcatagaga ctataatatt ctatttggta ttatattatt tgatgtttgc     1620
tgttcttcaa acatttaaat caagctttgg actaattatg ctaatttgtg agttctgatc     1680
acttttgagc tctgaagctt tgaatcattc agtggtggag atggccttct ggtaactgaa     1740
tattaccttc tgtaggaaaa ggtggaaaat aagcatctag aaggttgttg tgaatgactc     1800
tgtgctggca aaaatgcttg aaacctctat atttctttcg ttcataagag gtaaaggtca     1860 aattttcaa caaagtcttt taataacaa aagcatgcag ttctctgtga aatctcaaat      1920
attgttgtaa tagtctgttt caatcttaaa aagaatcaat aaaaacaaac aaggggaaaa     1980 aaaaaaaaa aaaaaaaaa aaaaaaaaa aaaaaaaaa actcga                        2026

<210> SEQ ID NO 31
<211> LENGTH: 699
<212> TYPE: DNA
<213> ORGANISM: Homo sapiens
<220> FEATURE:
<221> NAME/KEY: SITE
<222> LOCATION: (2)
<223> OTHER INFORMATION: n equals a,t,g, or c
<220> FEATURE:
<221> NAME/KEY: SITE
<222> LOCATION: (28)
<223> OTHER INFORMATION: n equals a,t,g, or c
<220> FEATURE:
<221> NAME/KEY: SITE
<222> LOCATION: (44)
<223> OTHER INFORMATION: n equals a,t,g, or c

<400> SEQUENCE: 31
gngttttttc cagccaggaa gtgaccgnta ctgcagcacg aganagattg gttgggttgg       60
ttgraaatga cyctgaacat ttatttccat tgcaatttct gtggctgagg agacttaaac     120
tttacaagta ttatcctttt aagatcattt taattttagt tgagtgcaga gggcttttat     180
aacaaacgtg cagaaatttt ggagggctgt gattttttcca gtattaaaca tgcatgcatt    240
aatcttgcag tttattttct cattgtgtat gtatatatcg cttttctctg cagcacgatt    300
tctcttttga taawkcccctt tagggcacaa ctagttatca gtaactgaat gtatcttaat   360
cattatggct gcttctgttt tttcattaac aaaggttatt catatgttag catatagttt    420
ctttgcaccc actatttatg tctgaatcat ttgtcacaag agagtgtgtg ctgatgagat     480
```

```
tgtaagtttg tgtgtttaaa cttttttttg agcgagggaa gaaaaagctg tatgcatttc    540
attgctgtct acaggtttct ttcagattat gttcatgggt ttgtgtgtat acaatatgaa    600
gaatgatctg aagtaattgt gctgtattta tgtttattca ccagtctttg attaaataaa    660
aaggaaaacc agaaaaaaaa aaaaaaaaaa aaaaaaaa                            699
```

<210> SEQ ID NO 32
<211> LENGTH: 1264
<212> TYPE: DNA
<213> ORGANISM: Homo sapiens
<220> FEATURE:
<221> NAME/KEY: SITE
<222> LOCATION: (1057)
<223> OTHER INFORMATION: n equals a,t,g, or c

<400> SEQUENCE: 32

```
ggcacgaggg cactgtttcc tcagtccatg gctgagtaca tcaccggtgt tttctctctt    60
attcctccca tcaagcctaa aaggaatctc tattggagat actgccatta gtgttccttt    120
tataggtgag gaactgaggc atakagggtt ccccagttga accaactgat aaatagtaga    180
acttggattt taattcagtc ttgatgccag ggataaggct cttactttct acctaggct     240 atttctagga aacgcaggag agtgttgaag gggcagagaa agggatccag ttcctttctg    300
tcccgcatcc tagtccctga gaagcaaaga araatgtgtg gcttcttttg ctttgctttt    360
gttgtcatcc cacacatctc caggggamct gggctcttga tcttggsctc ttcccctta    420 actgttaagt gggagcargt aagggggtac agtagggctg gcctggagtt agaggcttgg    480
atgccttagc tcctctgtct gcactccaga actgcctgac ttcatttcgt atgttgtcct    540
ttgttttgac aattgatcca tgtcccagtc cgtctcttct tccttcttga tacttacact    600
gcttctttct gttggtttcc agtgtttaac actgtataca acagtgacga caacgtgttt    660 gtggggccc ccacgggcag cgggaagact atttgtgcag agtttgccat cctgcgaatg    720
ctgctgcaga gctcggaggg gcgctgtgys twcwtcaccm ccatggaggc cctggccaga    780
rcaggtatga cgtggcgctg tgtcatgtga atttcccaag aagcatttca tctgtgattc    840
cgtatgaagg ctttctaagc cctgaaattt gcagggtcat ttcctcagtt tgtgtattaa    900
agaaaagctg ccccagccaa gcgtggtggc tcacgcctgt aatcccagca ctttgggagg    960
ccgaggcggg cagatctccg gagatcagga gttcgagacc agcctggcca acatggtgra   1020
accctgtctc tactaaaawt acagaaatta gctgggngtg gtggtgtgcg cctgtaatcc   1080
cagctacttg gaaggctgag gcaggagaat cgcttgaacc cggaggcgg aggttgcagt    1140 gagccaagtt cgcaccactg cactccagcc tgggcaacaa gagcgagact tcatctcaaa   1200
aaaaaaaaaa aaaaactcga gggggggccc ggtacccaat tcgccctata gtgatcgtat   1260
taca                                                                1264
```

<210> SEQ ID NO 33
<211> LENGTH: 997
<212> TYPE: DNA
<213> ORGANISM: Homo sapiens
<220> FEATURE:
<221> NAME/KEY: SITE
<222> LOCATION: (855)
<223> OTHER INFORMATION: n equals a,t,g, or c
<220> FEATURE:
<221> NAME/KEY: SITE
<222> LOCATION: (881)
<223> OTHER INFORMATION: n equals a,t,g, or c
<220> FEATURE:
<221> NAME/KEY: SITE
<222> LOCATION: (916)

<223> OTHER INFORMATION: n equals a,t,g, or c
<220> FEATURE:
<221> NAME/KEY: SITE
<222> LOCATION: (957)
<223> OTHER INFORMATION: n equals a,t,g, or c

<400> SEQUENCE: 33

```
attggaagtt gttttgcaac ctgggctttt atacagaaga atacgaatca caggtgtgtg      60
agcatctact taattaattt gcttacagcc gatttcctgc ttactctggc attaccagtg     120
aaaattgttg ttgacttggg tgtggcacct tggaagctga agatattcca ctgccaagta     180
acagcctgcc tcatctatat caatatgtat ttatcaatta tcttcttagc atttgtcagc     240
attgaccgct gtcttcagct gacacacagc tgcaagatct accgaataca agaacccgga     300
tttgccaaaa tgatatcaac cgttgtgtgg ctaatggtcc ttcttataat ggtgccaaat     360
atgatgattc ccatcaaaga catcaaggaa aagtcaaatg tgggttgtat ggagtttaaa     420
aaggaatttg gaagaaattg gcatttgctg acaaatttca tatgtgtagc aatattttta     480
aatttctcag ccatcatttt aatatccaat tgccttgtaa ttcgacagct ctacagaaac     540
aaagataatg aaaattaccc aaatgtgaaa aaggctctca tcaacatact tttagtgacc     600
acgggctaca tcatatgctt tgttccttac cacattgtcc gaatcccgta tacccctcagc    660
cagacagaag tcataactga ttgctcaacc aggatttcac tcttcaaagc caaagaggct     720
acactgctcc tggctgtgtc gaacctgtgc tttgatccta tcctgtacta tcacctctca     780
aaagcattcc gctcaaaggt cactgagact tttgcctcmc ctaaagagac caaggtyaga     840
aagaaaaatt aagangtgga aataatggct aaaagacagg nttttttgtgg taccaattct    900
gggctttatg ggaccntaaa gttattatag cttggaaggt aaaaaaaaaa aaagggnggg     960
cgctctagag gttccccgag gggccagctt agggtgc                             997
```

<210> SEQ ID NO 34
<211> LENGTH: 1914
<212> TYPE: DNA
<213> ORGANISM: Homo sapiens
<220> FEATURE:
<221> NAME/KEY: SITE
<222> LOCATION: (1889)
<223> OTHER INFORMATION: n equals a,t,g, or c

<400> SEQUENCE: 34

```
gtgtgagagg cctctctgga agttgtcccg ggtgttcgcc gctggagccc gggtcgagag      60
gacgaggtgc cgctgcctgg agaatcctcc gctgccgtcg gctcccggag cccagccctt     120
tcctaaccca acccaaccta gcccagtccc agccgccagc gcctgtccct gtcacggacc     180
ccagcgttac catgcatcct gccgtcttcc tatccttacc cgacctcaga tgctcccttc     240
tgctcctggt aacttgggtt tttactcctg taacaactga ataacaagt cttgatacag      300
agaatataga tgaaattta aacaatgctg atgttgcttt agtaaatttt tatgctgact      360
ggtgtcgttt cagtcagatg ttgcatccaa ttttttgagga agcttccgat gtcattaagg    420
aagaatttcc aaatgaaaat caagtagtgt ttgccagagt tgattgtgat cagcactctg     480
acatagccca gagatacagg ataagcaaat acccaaccct caaattgttt cgtaatggga     540
tgatgatgaa gagagaatac aggggtcagc gatcagtgaa agcattggca gattacatca     600
ggcaacaaaa aagtgacccc attcaagaaa ttcgggactt agcagaaatc accactcttg     660
atcgcagcaa aagaaatatc attggatatt ttgagcaaaa ggactcggac aactatagag     720
tttttgaacg agtagcgaat attttgcatg atgactgtgc cttttcttct gcatttgggg     780
```

```
atgtttcaaa accggaaaga tatagtggcg acaacataat ctacaaacca ccagggcatt    840
ctgctccgga tatggtgtac ttgggagcta tgacaaattt tgatgtgact tacaattgga    900
ttcaagataa atgtgttcct cttgtccgag aaataacatt tgaaaatgga gaggaattga    960
cagaagaagg actgcctttt ctcatactct ttcacatgaa agaagataca gaaagtttag   1020
aaatattcca gaatgaagta gctcggcaat taataagtga aaaaggtaca ataaacttt    1080 tacatgccga ttgtgacaaa tttagacatc ctcttctgca catacagaaa actccagcag   1140
attgtcctgt aatcgctatt gacagcttta ggcatatgta tgtgtttgga gacttcaaag   1200
atgtattaat tcctggaaaa ctcaagcaat tcgtatttga cttacattct ggaaaactgc   1260
acagagaatt ccatcatgga cctgacccaa ctgatacagc cccaggagag caagcccaag   1320
atgtagcaag cagtccacct gagagctcct tccagaaact agcacccagt gaatataggt   1380
atactctatt gagggatcga gatgagcttt aaaaacttga aaaacagttt gtaagccttt   1440
caacagcagc atcaacctac gtggtggaaa tagtaaacct atattttcat aattctatgt   1500 gtattttat tttgaataaa cagaaagaaa ttttgggttt ttaattttt tctccccgac     1560 tcaaaatgca ttgtcattta atatagtagc ctcttaaaaa aaaaaaaaac ctgctaggat   1620
ttaaaaataa aaatcagagg cctatctcca ctttaaatct gtcctgtaaa agttttataa   1680
atcaaatgaa aggtgacatt gccagaaact taccattaac ttgcactact agggtaggga   1740
ggacttaggg atgtttcctg tgtcgtatgt gcttttcttt ctttcatatg atcaattctg   1800
ttggtatttt cagtatctca tttctcaaag ctaaagagat atacattctg gatacttggg   1860 agggaataa attaaagttt tcacactgna aaaaaaaaa aaaaaaaaac tcga            1914

<210> SEQ ID NO 35
<211> LENGTH: 1020
<212> TYPE: DNA
<213> ORGANISM: Homo sapiens
<220> FEATURE:
<221> NAME/KEY: SITE
<222> LOCATION: (18)
<223> OTHER INFORMATION: n equals a,t,g, or c
<220> FEATURE:
<221> NAME/KEY: SITE
<222> LOCATION: (26)
<223> OTHER INFORMATION: n equals a,t,g, or c
<220> FEATURE:
<221> NAME/KEY: SITE
<222> LOCATION: (1014)
<223> OTHER INFORMATION: n equals a,t,g, or c
<220> FEATURE:
<221> NAME/KEY: SITE
<222> LOCATION: (1015)
<223> OTHER INFORMATION: n equals a,t,g, or c
<220> FEATURE:
<221> NAME/KEY: SITE
<222> LOCATION: (1018)
<223> OTHER INFORMATION: n equals a,t,g, or c

<400> SEQUENCE: 35
gtataattat aaatttgntc ggttcnaccg gtcctgtgtt gcytaaaaac accttataaa     60
agaggagagt atttgataag caattttcat agtagtaaag ttttttttca tctcttaaac   120
taaattgacc atgcatataa tattctttgt ttaaatgaaa gcatactgtt gaaacccgca   180
gtgttgcatt tagaaaacag ttgaacagaa tgtcaatgtg cattcatgca aaaaaacatt   240
taatctgcat ctgtttttaga aaggggaa atgaagcaac ttgtctaaaa atactgcttt    300
acaaagcatt tcagcctttc cccctcagtt ttgcattgat tttttgacaa gtctgtagag   360
cctaatagtt tccatcaaag gcctagatct cttatttagc attttttttca gctcttctct   420
```

| | |
|---|---|
| cagaagttca gctgttgaaa cgaaaactgt actttgtacc ctcacataca aagggatcaa | 480 |
| atttgacctg gtgttatttt agccccaaat ttatgacatt acacaatatt aaaatgtaaa | 540 |
| tgtttcttta cccaaactac ttctagatat tctagtattt gcttctggtg gaattaaatg | 600 |
| acggtaaaat tggctaatta tttgaatgaa tgaatggatg gatgttttgc atgctcaatt | 660 |
| tctaggtcct ttgtctagaa aggaaatttg cctcagttga attagtgaaa tatttctgtc | 720 |
| gttgatatta aaagtgactt ctgagtacag ttaagttcct cctatttgcc actgggctgt | 780 |
| tggttagaag cataggtaac tgattaagta ggtatgatac tgcatttgaa ataagtggac | 840 |
| acaaactatc ctttctccac catggactca atctgagaac aacagcattc atttccattc | 900 |
| atttccatac tggcttttga ttatatgcag attcctagta gcatgcctta cctacagcac | 960 |
| tatgtgcatt tgctgtcaca ataaagtata ttttgtcttg caaaaaaaaa aaannaaggg | 1020 |

<210> SEQ ID NO 36
<211> LENGTH: 781
<212> TYPE: DNA
<213> ORGANISM: Homo sapiens

<400> SEQUENCE: 36

| | |
|---|---|
| aactcctgac ctcaagtgct ccacctgcgt tggcttccca aagtgctggg atacaggagt | 60 |
| ragccactgc gcctggctga tcccagcact tttmaaatga tgccgctcaa agccgtgact | 120 |
| tggcctactt tgaacagcaa acttgttgct gctgttgtca acctgaaggc ctctcaaatg | 180 |
| ccagcttcaa gcagggtgtg aattggccag tgtcagatct caggagtcct gtgttgagag | 240 |
| tgtggctttc agctgcgggg agctgcactt ggtggggaaa gccaggcagg tcaccctcac | 300 |
| agccagataa tgtggaggtc agaacccaag gaagggagtg agacctccac tcccagtggg | 360 |
| ggacctggcc acccatcctt ggggacctga gaaagcgtac ttcaccttgg ggtgaaggct | 420 |
| gggtggggcc agagggacca gtgccctcct cagtgcttag gggcagagcc acctgcagca | 480 |
| atggtatctg catattagcc cctctccacc ttctttctcc cgctgaatca tttccctcaa | 540 |
| agcccaagag ctgtcactgc ttctttctcc ctgggaagaa tgcgtggact ctgcctggtg | 600 |
| atagactgaa gccagaacag tgccacaccc tcgccttaat tccttgctag gtgttctcag | 660 |
| atttatgaga cttcttagtc aaatatgagg gaggttggat gtggtggctt gtgcctgtaa | 720 |
| tcccagcatt ttgggaagcc gaggtgggag gatcccttga gccaggagt ttgagacaag | 780 |
| c | 781 |

<210> SEQ ID NO 37
<211> LENGTH: 966
<212> TYPE: DNA
<213> ORGANISM: Homo sapiens
<220> FEATURE:
<221> NAME/KEY: SITE
<222> LOCATION: (8)
<223> OTHER INFORMATION: n equals a,t,g, or c
<220> FEATURE:
<221> NAME/KEY: SITE
<222> LOCATION: (586)
<223> OTHER INFORMATION: n equals a,t,g, or c

<400> SEQUENCE: 37

| | |
|---|---|
| ccactatngg caattggtac cggcccccc tcgaggaaga taaggtgcag ttcatgccag | 60 |
| aatccccagc ttcccatgca ggctggggac atagtgggtt ctcccgaaat actgggtcac | 120 |
| ttgaatttga tatgatgtat atatattcac ctctagtcca taggtacata tagtctatat | 180 |
| attaaaaaga cattggattt tgacttaaac tagatgtttc tcaagcacac caagacggtg | 240 |

```
ctagagcctg ggtttggcca gagaattggg tcccggtcag aagtgagtgg ggatggctgg      300
cgagcaaggt gtctgtaggg cagcacagga tgtctggtga gcagacagca agcttctgtc      360
ctgccccgag tgctgaggag cgaggtgact gcctacatgg tgatgsaaag atttgggcac      420
gcttccggct ttcaggccaa acaacctcgc ttgctccatg caccactga tcccagcagt       480 ggcccgaggg agctccttcc tgctgcttca tgtctgaca ctttgggggg ctcctttccc        540
caccacgtgg gtcctgtc agcctcgaag tgtcctgcgc ccctcncctg tacgcccagg        600
tgtgcctccc ctggccgcac ytcctctgtg ctcctgcgtc tctctgttct tctttagagt      660
ggttctgcac gtcagcagca tctgtggtgt ggccctggga cccttcagaa cagggggctcc     720 tgcccagctt ctgggtcccc cacctgtggc ccagggaagg ctctttgttc ctcagcccca     780
agctgtatct ggtgagaaca gatgcgtagt cccggagctc aagttctggg aagggcagtg     840
cccttttctg tggggccctg ggcttgttct gcattgtttc aagaggagct gccactcaaa     900
taggcagccc tgcaatcgga gggctgcgtg ctcccccctga tcagccccca gctgcttcct   960
cgtgcc                                                                 966
```

<210> SEQ ID NO 38
<211> LENGTH: 416
<212> TYPE: DNA
<213> ORGANISM: Homo sapiens
<220> FEATURE:
<221> NAME/KEY: SITE
<222> LOCATION: (395)
<223> OTHER INFORMATION: n equals a,t,g, or c

<400> SEQUENCE: 38

```
gaattcggca cgaggtaata ggagccctcg tacctcttgt gttccttaca aacattctca       60
tcagtagctc tacgcgttga ctgggtggtt tgaratggct ggtatacaca gggctttctt     120
ggtgttctgt ctctggggct tarctttgtg tgtggttgga gggccctggt gagattggaa     180
gtaccagaga gtgctgtgtc aggggcagag gggcctgtcg ctggagctgg agggtgcctg     240
cctttgtgtc tgactcartc tcctgtctgc cttgcccccct cagggtctcg ccagcccagc     300
ctctgtggga atctaaaagg artgatgtg dacgtktgac caagcacatc tcagctttta     360
atacctgggc tatttataga cctttgggg gaatngcttg tggaacaaca agggtt          416
```

<210> SEQ ID NO 39
<211> LENGTH: 1114
<212> TYPE: DNA
<213> ORGANISM: Homo sapiens

<400> SEQUENCE: 39

```
tgtgtatttg gggggactga agggtacgtg gggcgaaaca aaaccggcca tggcagcagc      60
ggaggaggag gacggggggcc ccgaagccaa aatcgcgagc ggggcggggc gggcgcgacc   120
ttcgaatgta atatatgttt ggagactgct cgggaagctg tggtcagtgt gtgtggccac    180
ctgtactgtt ggccatgtct tcatcagtgg ctggagacac ggccagaacg gcaagagtgt    240
ccagtatgta aagctgggat cagcagagag aaggttgtcc cgctttatgg gcagggagc     300 cagaagcccc aggatcccag attaaaaact ccaccccgcc cccagggcca gagaccagct    360
ccggagagca gaggggggatt ccagccattt ggtgataccg ggggcttcca cttctcattt   420
ggtgttggtg cttttcccctt tggctttttc accacgtct tcaatgccca tgagcctttc   480
cgccggggta caggtgtgga tctgggacag ggtcacccag cctccagctg gcaggattcc    540
ctcttcctgt ttctcgccat cttcttcttt ttttggctgc tcagtatttg agctatgtct     600
```

```
gcttcctgcc cacctccagc cagagaagaa tcagtattga gggtccctgc tgacccttcc    660
gtactcctgg accccttga cccctctatt tctgttggct aaggccagcc ctggacattg    720
tccaggaagg cctggggagg aggagtgaag tctgtgcata gatgggagag ccttctgctc    780
agaggctcac tcagtaacgt tgtttaattc tctgccctgg ggaaggagga tggattgaga    840
gaatgtcttt ctcctctcct aagtctttgc tttccctgat ttcttgattt gatcttcaaa    900
ggtgggcaaa gttccctctg actcttcccc cactcccat cttactgatt taatttaatt    960
tttcactccc cagagtctaa tatggattct gactcttaag tgcttccgcc ccctcactac   1020
ctcctttaat acaaattcaa taaaaaaggt gaaatataaa aaaaaaaaaa aaaaacycg   1080 gggggggccc cggtccccat tccctttggg gggt                              1114
```

<210> SEQ ID NO 40
<211> LENGTH: 602
<212> TYPE: DNA
<213> ORGANISM: Homo sapiens
<220> FEATURE:
<221> NAME/KEY: SITE
<222> LOCATION: (597)
<223> OTHER INFORMATION: n equals a,t,g, or c

<400> SEQUENCE: 40

```
gggtcgaccc acgcgtccgt cccaggccac aagacatttc ctgctcggaa ccttgtttac     60
taattgtctc tgtggcacat tttgtttccc gtgccttggg tgtcaagttg cagctgatat    120
gaatgaatgc tgtctgtgtg gaacaagcgt cgcaatgagg actctctaca ggacccgata    180
tggcatccct ggatctattt gtgatgacta tatggcaact ctttgctgtc ctcattgtac    240
tctttgccaa atcaagagag atatcaacag aaggagagcc atgcgtactt tctaaaaact    300
gatggtgaaa agctcttacc gaagcaacaa aattcagcag acacctcttc agcttgagtt    360
cttcaccatc ttttgcaact gaaatatgat ggatatgctt aagtacaact gatggcatga    420
aaaaaatcaa attttttgatt tattataaat gaatgttgtc cctgaactta gctaaatggt    480
gcaacttagt ttctccttgc tttcatatta tcgaatttcc tggcttataa acttttttaaa    540 ttacatttga aatataaacc aaatgaaata ttttactgaa aaaaaaaaaa aaaaancccc    600
ca                                                                    602
```

<210> SEQ ID NO 41
<211> LENGTH: 970
<212> TYPE: DNA
<213> ORGANISM: Homo sapiens
<220> FEATURE:
<221> NAME/KEY: SITE
<222> LOCATION: (37)
<223> OTHER INFORMATION: n equals a,t,g, or c

<400> SEQUENCE: 41

```
ggcagagctt aggagaacag ctcccttttgg atccctntca aaggtgatac cattggctcc     60
cagcttagag taagaagctc tgagaagttg aatgaagggt gagatagaga tgctgaaccc    120
attcttscag cttcttctag tgttgttatt tccagaatgg ccaacacccc tacattgata    180
cataaacaca ttccaaggcc ttgtgtaata caaagttcac cgtcctcctg gaataggagc    240
cctgggttct agttctcact ctgccactgg ggaaaatcc aattaaagtc tggtttagtc    300
agcttgggtc accatagact gggtggctta aacagcagac atttatttct ggtagtttct    360
ggaggctaca aatctaagag caaggtgcca gcatggtcac attctggtga gggcctctt    420 cctggcttgt agacggctgc yttctcaccg tgtgctcaca tagcctttcg tgtgtgtgtg    480
```

| | |
|---|---|
| tgtgtgtgtg tgcgtkcgtg caagcttcck gatgtctctt cttagaagga caccaacccc | 540 |
| atcatgagag ccctactctc atgacttagc ctaaccctaa ttaccctcca aaggccccat | 600 |
| ctccaaatgc catcacattg gagggtagag cttcaacata gggattttgg gggacacaaa | 660 |
| cattcagtcc ataacaaagg ctgtagtcct tartttcctt gtctgtgaaa tgagagtgtt | 720 |
| gagattcttt ctagccttta tcatttataa ttctgtgaga tgtagatttg cattattttc | 780 |
| gagttcgagt tatatgaaat gtttccctct acatttcctt gggcaactga gaactgaata | 840 |
| gggctaggtt taaatagagt taggcagtta ggcttattct tttatttaat aagcatttt | 900 |
| ggagcatcta cggtgttcca ggaactgaac tgttgtaaac attggagctg taacagagaa | 960 |
| caaaagagac | 970 |

<210> SEQ ID NO 42
<211> LENGTH: 1002
<212> TYPE: DNA
<213> ORGANISM: Homo sapiens

<400> SEQUENCE: 42

| | |
|---|---|
| gaattcggca cgagccgagg tcggcagcac agagctctgg agatgaagac cctgttcctg | 60 |
| ggtgtcacgc tcggmctggc cgctgccctg tccttmaccc tggrggagga ggatatcaca | 120 |
| gggacctggt acgtgaaggc catggtggtc gataagactt tccggagaca ggaggcccag | 180 |
| aaggtgtccc cagtgaaggt gacagccctg ggcggtggga agttggaagc cacgttcacc | 240 |
| ttcatgaggg aggatcggtg catccagaag aaaatcctgr tgcggaagac ggaggagcct | 300 |
| ggcaaataca gcgcctgtga gcccctcccc caytcccacc cccaccytcc cccaccgcca | 360 |
| accccagtgc accagcctcc acaggtagag agtgccagg ctgcccttt gccagggccc | 420 |
| cagctctgcc cacctccaag gaggggctgg cctctccttc ctgggggct ggtggccctg | 480 |
| acatcagaca ccgggtgtga caggcttgtc cgcagtcgag atggaccaga tcacgcctgc | 540 |
| cctctgggag gccctagcca ttgacacatt gaggaagctg aggattggga caaggaggcc | 600 |
| aaggattaga tggggcagg aagctcatgt acctgcagga gctgcccagg agggaccayt | 660 |
| acatcttta ctgcaaagac cagcaccatg ggggcstgct ccacatggga aagcttgtgg | 720 |
| gtaggaattc tgataccaac cgggaggccc tggaagaatt taagaaattg gtgcagcgca | 780 |
| agggactctc ggaggaggac attttcacgc ccctgcagac gggaagctgc gttcccgaac | 840 |
| actaggcagc ccccgggtct gcacctccag agcccaccct accaccagac acagagcccg | 900 |
| gaccacctgg acctaccctc cagccatgac ccttccctgc tcccacccac ctgactccaa | 960 |
| ataaagtcct tctcccccaa aaaaaaaaa aaaaaaactc ga | 1002 |

<210> SEQ ID NO 43
<211> LENGTH: 2581
<212> TYPE: DNA
<213> ORGANISM: Homo sapiens
<220> FEATURE:
<221> NAME/KEY: SITE
<222> LOCATION: (1591)
<223> OTHER INFORMATION: n equals a,t,g, or c
<220> FEATURE:
<221> NAME/KEY: SITE
<222> LOCATION: (1703)
<223> OTHER INFORMATION: n equals a,t,g, or c

<400> SEQUENCE: 43

| | |
|---|---|
| tgcaaaacca ctggacactg acaagtacg ggatcctggs cgacgcacgc ctcttctttg | 60 |
| ggccccagca ccggsccgtc atccttcggt tgtccaaccg ccgcgcactg cgcctccgtg | 120 |

```
ccagcttctc ccagcccctc ttccaggctg tggstgccat ctgccgcctc ctcagcatcc    180
ggcaccccga ggagctgtcc ctgctccggg ctcctgagaa gaaggagaag aagaagaaag    240
agaaggagcc agaggaagag ctctatgact tgagcaaggt tgtcttggct ggggcgtgg     300
cacctgcact gttccggggg atgccagctc acttctcgga cagcgcccag actgaggcct    360
gctaccacat gctgagccgg ccccagccgc acccgaccc cctcctgctc cagcgtctgc     420
cacggcccag ctccctgtca gacaagaccc agctccacag caggtggctg gactcgtcgc    480
ggtgtctcat gcagcagggc atcaaggccg ggacgcact ctggctgcgc ttcaagtact     540
acagcttctt cgatttggat cccaagacag accccgtgcg gctgacacag ctgtatgagc    600
aggcccggtg ggacctgctg ctggaggaga ttgactgcac cgaggaggag atgatggtgt    660
ttgccgccct gcagtaccac atcaacaagc tgtcccagag cggggaggtg ggggagccgg    720
ctggcacaga cccagggctg gacgacctgg atgtggccct gagcaacctg gaggtgaagc    780
tggaggggtc ggcgcccaca gatgtgctgg acagcctcac caccatccca gagctcaagg    840
accatctccg aatctttcgg ccccggaagc tgaccctgaa gggctaccgc caacactggg    900
tggtgttcaa ggagaccaca ctgtcctact acaagagcca ggacgaggcc ctggggacc     960
ccattcagca gctcaacctc aagggctgtg aggtggttcc cgatgttaac gtctccggcc   1020
agaagttctg cattaaactc ctagtgccct cccctgaggc atgagtgaga tctacctgcg   1080
gtgccaggat gagcagcagt atgcccgctg gatggctggc tgccgcctgg cctccaaagg   1140
ccgcaccatg gccgacagca gctacaccag cgaggtgcag gccatcctgg cyttcctcag   1200
cctgcagcgc acgggcagtg ggggcccggg caaccacccc cacggccctg atgcctctgc   1260
cgagggcctc aacccctacg gcctcgttgc ccccgtttc cagcgaaagt tcaaggccaa    1320
gcagctcacc ccacggatcc tggaagccca ccagaatgtg gcccagttgt cgctggcaga   1380
ggcccagctg cgcttcatcc aggcctggca gtccctgccc gacttcggca tctcctatgt   1440
catggtcagg ttcaagggca gcaggaaaga cgagatcctg ggcatcgcca acaaccgact   1500
gatccgcatc gacttggccg tgggcgacgt ggtcaagacc tggcgtttca gcaacatgcg   1560
ccagtggaat gtcaactggg acatccggca ngtggccatc gagtttgatg aacacatcaa   1620
tgtggccttc agctgcgtgt ctgccagctg ccgaattgta cacgagtata tcggggcta   1680
cattttcctg tcgacgcggg agngggcccg tggggaggag ctggatgaag acctcttcct   1740
gcagctcacc gggggccatg aggccttctg agggctgtct gattgcccct gccctgctca   1800
ccaccctgtc acagccactc ccaagcccac acccacaggg gctcactgcc ccacacccgc   1860
tccaggcagg cacccagctg ggcatttcac ctgctgtcac tgactttgtg caggccaagg   1920
acctggcagg gccagacgct gtaccatcac ccaggcaggg atgggggtg ggggtccctg    1980
agctcatgtg gtgccccctt tccttgtctg agtggctgag gctgataccc ctgacctatc   2040
tgcagtcccc cagcacacaa ggaagaccag atgtagctac aggatgatga acatggttt    2100
caaacgagtt ctttcttgtt acttttttaaa atttcttttt tataaattaa tatttattg    2160
ttggatcctc ctcctttctc tggagctgtg cttgggcta ctctgacact ctgtctcttc    2220
atcaccagcc aaggaaaggg gctttcctga taaagacaag agttggttag agaaagggac   2280
acctaagtca gtctagggtt ggaagctagg agagaggtga gggcagaagg gcacagcttt   2340
caggaacaag gaatagggc tggggtkgtk gttctcacgg gtaggcggta cctgcagggc   2400
ctccttgaag tacttgggaa ggaggaagcc atcagtattc cctggagtca gaatcacccc   2460
attggcagag cggaagaagg gtattccatc tgctgacaga gccagagatg tgactcatgc   2520
```

| | |
|---|---|
| cctcccgaa ggcaaagtca gctcctgctt tgtccagact cacctgccag agccaggggt | 2580 |
| c | 2581 |

<210> SEQ ID NO 44
<211> LENGTH: 796
<212> TYPE: DNA
<213> ORGANISM: Homo sapiens

<400> SEQUENCE: 44

| | |
|---|---|
| accttcttcc atgtttagtc ccttgggctc tgctaccctc ctgctggagg tgagagcatc | 60 |
| ctgtgtgcaa ccagagatgc cctctggctt tcagacctgc ctgcttttca ccctcagccc | 120 |
| tttctcactc agcaaaattg tgggggtccc tagtcagcag ctccctgggc agctctctga | 180 |
| gcaaggtggt ctctgtggtc atgaaggaga gccggctagg acagtgccgg aaactcagct | 240 |
| gcctctcccc ttcaactcag ctggcccccc gcacctgaag tgcacaggag ccgggaagag | 300 |
| agtctggagc ccaccccgga gggcagcaca ggaggtgtct ytgcagctgg tgtcctgcma | 360 |
| cccytgcagg cagmacacgt cccgggcatt ytcyttagcc acagacagaa cagccagtgc | 420 |
| cagagtctgc tgtcgyttcc cctttaagca cactcattca ccacaccga ggaggccaga | 480 |
| ggtgcaggga gcatgggctg tcgttcccct ttaagcacac tcattcacca cacccgagga | 540 |
| ggccagaagt gcagggagca tgggctgggt gcacctccgc aggagagaag gctgagccac | 600 |
| cgccgtcccg ggagcccggc tcccaggcct ctcgttttcc cctacctccc taagactttt | 660 |
| ctgtcactct ctggccattg aaaggcttct gttccttaaa gtgctgttac actctccttt | 720 |
| cccaggatgc agcaagccaa acagtacca ctgcacgtca gcctgggtga cagagtgaga | 780 |
| ccctatctta aaaaaa | 796 |

<210> SEQ ID NO 45
<211> LENGTH: 2017
<212> TYPE: DNA
<213> ORGANISM: Homo sapiens

<400> SEQUENCE: 45

| | |
|---|---|
| aattcggcac gagcggatcc gttgcggctg cagctctgca gtcgggccgt tccttcgccg | 60 |
| ccgccagggg tagcggtgta gctgcgcacg tcgcgcgcgc taccgcaccc aggttcggcc | 120 |
| cgtagcgtct ggcagcccgg cgccatcttc atcgagcgcc atggccgcag cctgcgggcc | 180 |
| gggagcggcg ggtactgctt gctcctcggc ttgcatttgt ttctgctgac cgcgggccct | 240 |
| gcctgggctg gaacgaccct gacagaatgt tgctgcggga tgtaaaagct cttaccctcc | 300 |
| actatgaccg ctataccacc tcccgcagct ggatcccatc ccacagttga atgtgttgg | 360 |
| aggcacagct ggttgtgatt cttataccc aaaagtcata cagtgtcaga acaaaggctg | 420 |
| ggatgggtat gatgtacagt gggaatgtaa gacggactta gatattgcat acaaatttgg | 480 |
| aaaaactgtg gtgagctgtg aaggctatga gtcctctgaa gaccagtatg tactaagagg | 540 |
| ttcttgtggc ttggagtata atttagatta tacagaactt ggcctgcaga aactgaagga | 600 |
| gtctggaaag cagcacggct ttgcctcttt ctctgattat tattataagt ggtcctcggc | 660 |
| ggattcctgt aacatgagtg gattgattac catcgtggta ctccttggga tcgcctttgt | 720 |
| agtctataag ctgttcctga gtgacgggca gtattctcct ccaccgtact ctgagtatcc | 780 |
| tccatttttcc caccgttacc agagattcac caactcagca ggacctcctc cccaggctt | 840 |
| taagtctgag ttcacaggac cacagaatac tggccatggt gcaacttctg gttttggcag | 900 |
| tgcttttaca ggacaacaag gatatgaaaa ttcaggacca gggttctgga caggcttggg | 960 |

```
aactggtgga atactaggat atttgtttgg cagcaataga gcggcaacac ccttctcaga    1020
ctcgtggtac tacccgtcct atcctccctc ctacccctggc acgtggaata gggcttactc   1080
accccttcat ggaggctcgg gcagctattc ggtatgttca aactcagaca cgaaaaccag    1140
aactgcatca ggatatggtg gtaccaggag acgataaagt agaaagttgg agtcaaacac    1200
tggatgcaga aattttggat ttttcatcac tttctcttta gaaaaaaagt actacctgtt    1260
aacaattggg aaaaggggat attcaaaagt tctgtggtgt tatgtccagt gtagcttttt    1320
gtattctatt atttgaggct aaaagttgat gtgtgacaaa atacttatgt gttgtatgtc    1380
agtgtaacat gcagatgtat attgcagttt ttgaaagtga tcattactgt ggaatgctaa    1440
aaatacatta atttctaaaa cctgtgatgc cctaagaagc attaagaatg aaggtgttgt    1500
actaatagaa actaagtaca gaaaatttca gttttaggtg gttgtagctg atgagttatt    1560
acctcataga gactataata ttctatttgg tattatatta tttgatgttt gctgttcttc    1620
aaacatttaa atcaagcttt ggactaatta tgctaatttg tgagttctga tcactttga    1680 gctctgaagc tttgaatcat tcagtggtgg agatggcctt ctggtaactg aatattacct    1740
tctgtaggaa aaggtggaaa ataagcatct agaaggttgt tgtgaatgac tctgtgctgg    1800
caaaaatgct tgaaacctct atatttcttt cgttcataag aggtaaaggt caaattttc     1860 aacaaaagtc ttttaataac aaaagcatgc agttctctgt gaaatctcaa atattgttgt    1920
aatagtctgt ttcaatctta aaagaatca ataaaaacaa acaagggaaa aaaaaaaaaa     1980
aaaaaaaaaa aaaaaaaaaa aaaaaaaaaa aaaaaa                              2017

<210> SEQ ID NO 46
<211> LENGTH: 981
<212> TYPE: DNA
<213> ORGANISM: Homo sapiens

<400> SEQUENCE: 46
tcggcagcac agagctctgg agatgaagac cctgttcctg ggtgtcacgc tcggcctggc     60
gctgccctgt ccttcaccct ggrggaggag gatatcacag ggacctggta cgtgaaggcc    120
atggtggtcg ataagacttt ccggagacag gaggcccaga aggtgtcccc agtgaaggtg    180
acagccctgg gcggtgggaa gttggaagcc acgttcacct tcatgaggga ggatcggtgc    240
atccagaaga aaatcctgrt gcggaagacg gaggagcctg gcaaatacag cgcctgtgag    300
cccctccccc aytcccaccc ccaccytccc ccaccgccaa ccccagtgca ccagcctcca    360
caggtagaga gtgcccaggc tgcccttttg ccagggcccc agctctgccc acctccaagg    420
aggggctggc ctctccttcc tgggggggctg gtggccctga catcagacac cgggtgtgac   480
aggcttgtcc gcagtcgaga tggaccagat cacgcctgcc ctctgggagg ccctagccat    540
tgacacattg aggaagctga ggattgggac aaggaggcca aggattagat gggggcagga    600
agctcatgta cctgcaggag ctgcccagga gggaccayta catcttttac tgcaaagacc    660
agcaccatgg gggcstgctc cacatgggaa agcttgtggg taggaattct gataccaacc    720
gggaggccct ggaagaattt aagaaattgg tgcagcgcaa gggactctcg gaggaggaca    780
ttttcacgcc cctgcagacg ggaagctgcr ttcccgaaca ctaggcagcc cccgggtctg    840
cacctccaga gccccaccta ccaccagaca cagagcccgg accacctgga cctaccctcc    900
agccatgacc cttccctgct cccacccacc tgactccaaa taaagtcctt ctcccccaaa    960
aaaaaaaaaa aaaaaactcg a                                              981

<210> SEQ ID NO 47
```

```
<211> LENGTH: 146
<212> TYPE: PRT
<213> ORGANISM: Homo sapiens
<220> FEATURE:
<221> NAME/KEY: SITE
<222> LOCATION: (146)
<223> OTHER INFORMATION: Xaa equals stop translation

<400> SEQUENCE: 47

Met His Tyr Gln Met Ser Val Thr Leu Lys Tyr Glu Ile Lys Lys Leu
 1               5                  10                  15

Ile Tyr Val His Leu Val Ile Trp Leu Leu Val Ala Lys Met Ser
                20                  25                  30

Val Gly His Leu Arg Leu Leu Ser His Asp Gln Val Ala Met Pro Tyr
                35                  40                  45

Gln Trp Glu Tyr Pro Tyr Leu Leu Ser Ile Leu Pro Ser Leu Leu Gly
        50                  55                  60

Leu Leu Ser Phe Pro Arg Asn Asn Ile Ser Tyr Leu Val Leu Ser Met
65                  70                  75                  80

Ile Ser Met Gly Leu Phe Ser Ile Ala Pro Leu Ile Tyr Gly Ser Met
                85                  90                  95

Glu Met Phe Pro Ala Ala Gln Pro Ser Thr Ala Met Ala Arg Pro Thr
            100                 105                 110

Val Ser Ser Leu Val Phe Leu Pro Phe Pro Ser Cys Thr Trp Cys Trp
            115                 120                 125

Cys Trp Gln Cys Lys Cys Met Pro Gly Ser Cys Thr Thr Ala Arg Ser
        130                 135                 140

Ser Xaa
145

<210> SEQ ID NO 48
<211> LENGTH: 312
<212> TYPE: PRT
<213> ORGANISM: Homo sapiens
<220> FEATURE:
<221> NAME/KEY: SITE
<222> LOCATION: (312)
<223> OTHER INFORMATION: Xaa equals stop translation

<400> SEQUENCE: 48

Met Asn Ser Val Val Ser Leu Leu Leu Ile Leu Glu Pro Asp Lys Gln
 1               5                  10                  15

Glu Ala Leu Ile Glu Ser Leu Cys Glu Lys Leu Val Lys Phe Arg Glu
                20                  25                  30

Gly Glu Arg Pro Ser Leu Arg Leu Gln Leu Leu Ser Asn Leu Phe His
            35                  40                  45

Gly Met Asp Lys Asn Thr Pro Val Arg Tyr Thr Val Tyr Cys Ser Leu
        50                  55                  60

Ile Lys Val Ala Ala Ser Cys Gly Ala Ile Gln Tyr Ile Pro Thr Glu
65                  70                  75                  80

Leu Asp Gln Val Arg Lys Trp Ile Ser Asp Trp Asn Leu Thr Thr Glu
                85                  90                  95

Lys Lys His Thr Leu Leu Arg Leu Leu Tyr Glu Ala Leu Val Asp Cys
            100                 105                 110

Lys Lys Ser Asp Ala Ala Ser Lys Val Met Val Glu Leu Leu Gly Ser
            115                 120                 125

Tyr Thr Glu Asp Asn Ala Ser Gln Ala Arg Val Asp Ala His Arg Cys
        130                 135                 140

Ile Val Arg Ala Leu Lys Asp Pro Asn Ala Phe Leu Phe Asp His Leu
```

```
                145                 150                 155                 160
Leu Thr Leu Lys Pro Val Lys Phe Leu Glu Gly Glu Leu Ile His Asp
                    165                 170                 175

Leu Leu Thr Ile Phe Val Ser Ala Lys Leu Ala Ser Tyr Val Lys Phe
                180                 185                 190

Tyr Gln Asn Asn Lys Asp Phe Ile Asp Ser Leu Gly Leu Leu His Glu
                195                 200                 205

Gln Asn Met Ala Lys Met Arg Leu Leu Thr Phe Met Gly Met Ala Val
            210                 215                 220

Glu Asn Lys Glu Ile Ser Phe Asp Thr Met Gln Gln Glu Leu Gln Ile
225                 230                 235                 240

Gly Ala Asp Asp Val Glu Ala Phe Val Ile Asp Ala Val Arg Thr Lys
                    245                 250                 255

Met Val Tyr Cys Lys Ile Asp Gln Thr Gln Arg Lys Val Val Val Ser
                260                 265                 270

His Ser Thr His Arg Thr Phe Gly Lys Gln Gln Trp Gln Gln Leu Tyr
            275                 280                 285

Asp Thr Leu Asn Ala Trp Lys Gln Asn Leu Asn Lys Val Lys Asn Ser
        290                 295                 300

Leu Leu Ser Leu Ser Asp Thr Xaa
305                 310

<210> SEQ ID NO 49
<211> LENGTH: 64
<212> TYPE: PRT
<213> ORGANISM: Homo sapiens

<400> SEQUENCE: 49

Met Met Ser Phe Phe Cys Phe Val Met Gly Val Thr Val Ala Ala Thr
1               5                   10                  15

Phe Thr Ala Ile Val Pro Arg Trp Arg Leu Ser Gln Lys Glu Ile Gly
                20                  25                  30

Ser Val Leu Ser Val Trp Leu Ser Arg Trp Arg Glu Asn Ser Leu Arg
            35                  40                  45

Ser Leu Val Ser Gln Ser Val Ala Arg Ser Gly Lys Val Lys Val Ile Arg
        50                  55                  60

<210> SEQ ID NO 50
<211> LENGTH: 467
<212> TYPE: PRT
<213> ORGANISM: Homo sapiens

<400> SEQUENCE: 50

Met Leu Ser Arg Pro Gln Pro Pro Asp Pro Leu Leu Gln Arg
1               5                   10                  15

Leu Pro Arg Pro Ser Ser Leu Ser Asp Lys Thr Gln Leu His Ser Arg
                20                  25                  30

Trp Leu Asp Ser Ser Arg Cys Leu Met Gln Gln Gly Ile Lys Ala Gly
            35                  40                  45

Asp Ala Leu Trp Leu Arg Phe Lys Tyr Tyr Ser Phe Phe Asp Leu Asp
        50                  55                  60

Pro Lys Thr Asp Pro Val Arg Leu Thr Gln Leu Tyr Glu Gln Ala Arg
65                  70                  75                  80

Trp Asp Leu Leu Leu Glu Glu Ile Asp Cys Thr Glu Glu Met Met
                85                  90                  95

Val Phe Ala Ala Leu Gln Tyr His Ile Asn Lys Leu Ser Gln Ser Gly
                100                 105                 110
```

Glu Val Gly Glu Pro Ala Gly Thr Asp Pro Gly Leu Asp Asp Leu Asp
            115                 120                 125

Val Ala Leu Ser Asn Leu Glu Val Lys Leu Glu Gly Ser Ala Pro Thr
    130                 135                 140

Asp Val Leu Asp Ser Leu Thr Thr Ile Pro Glu Leu Lys Asp His Leu
145                 150                 155                 160

Arg Ile Phe Arg Pro Arg Lys Leu Thr Leu Lys Gly Tyr Arg Gln His
                165                 170                 175

Trp Val Val Phe Lys Glu Thr Thr Leu Ser Tyr Tyr Lys Ser Gln Asp
            180                 185                 190

Glu Ala Pro Gly Asp Pro Ile Gln Gln Leu Asn Leu Lys Gly Cys Glu
            195                 200                 205

Val Val Pro Asp Val Asn Val Ser Gly Gln Lys Phe Cys Ile Lys Leu
            210                 215                 220

Leu Val Pro Ser Pro Glu Gly Met Ser Glu Ile Tyr Leu Arg Cys Gln
225                 230                 235                 240

Asp Glu Gln Gln Tyr Ala Arg Trp Met Ala Gly Cys Arg Leu Ala Ser
                245                 250                 255

Lys Gly Arg Thr Met Ala Asp Ser Ser Tyr Thr Ser Glu Val Gln Ala
            260                 265                 270

Ile Leu Ala Phe Leu Ser Leu Gln Arg Thr Gly Ser Gly Gly Pro Gly
            275                 280                 285

Asn His Pro His Gly Pro Asp Ala Ser Ala Glu Gly Leu Asn Pro Tyr
            290                 295                 300

Gly Leu Val Ala Pro Arg Phe Gln Arg Lys Phe Lys Ala Lys Gln Leu
305                 310                 315                 320

Thr Pro Arg Ile Leu Glu Ala His Gln Asn Val Ala Gln Leu Ser Leu
                325                 330                 335

Ala Glu Ala Gln Leu Arg Phe Ile Gln Ala Trp Gln Ser Leu Pro Asp
            340                 345                 350

Phe Gly Ile Ser Tyr Val Met Val Arg Phe Lys Gly Ser Arg Lys Asp
            355                 360                 365

Glu Ile Leu Gly Ile Ala Asn Asn Arg Leu Ile Arg Ile Asp Leu Ala
            370                 375                 380

Val Gly Asp Val Val Lys Thr Trp Arg Phe Ser Asn Met Arg Gln Trp
385                 390                 395                 400

Asn Val Asn Trp Asp Ile Arg Gln Val Ala Ile Glu Phe Asp Glu His
                405                 410                 415

Ile Asn Val Ala Phe Ser Cys Val Ser Ala Ser Cys Arg Ile Val His
            420                 425                 430

Glu Tyr Ile Gly Gly Tyr Ile Phe Leu Ser Thr Arg Glu Arg Ala Arg
            435                 440                 445

Gly Glu Glu Leu Asp Glu Asp Leu Phe Leu Gln Leu Thr Gly Gly His
            450                 455                 460

Glu Ala Phe
465

<210> SEQ ID NO 51
<211> LENGTH: 83
<212> TYPE: PRT
<213> ORGANISM: Homo sapiens
<220> FEATURE:
<221> NAME/KEY: SITE
<222> LOCATION: (83)
<223> OTHER INFORMATION: Xaa equals stop translation -continued

```
<400> SEQUENCE: 51

Met Arg Pro Gly Arg Gly Ala Gly Thr Pro Gly Arg Pro Gly Arg Gly
1               5                   10                  15

Arg Gly Leu Ala Ala Thr Cys Ser Leu Ser Ser Pro Ser His Leu Leu
            20                  25                  30

Pro Thr Leu Leu His Thr Phe Ser Phe Ser Leu Pro Pro Ser Pro
        35                  40                  45

Ala Ala Pro Arg Gln Pro Ser Pro Pro Ala Leu Leu Leu Pro Gly Pro
    50                  55                  60

Gln Lys Pro Arg Pro Gly Asp Pro Thr Tyr Thr Gly Ala Leu Thr Asp
65                  70                  75                  80

Trp Ser Xaa

<210> SEQ ID NO 52
<211> LENGTH: 63
<212> TYPE: PRT
<213> ORGANISM: Homo sapiens
<220> FEATURE:
<221> NAME/KEY: SITE
<222> LOCATION: (63)
<223> OTHER INFORMATION: Xaa equals stop translation

<400> SEQUENCE: 52

Met Phe Leu Val Phe Phe Leu Ser Phe Ser His Ser Ile Ser Ala
1               5                   10                  15

Leu Thr Leu Val Cys Ser Gln Gly Gly Lys Ala Asp Met Asn Leu Leu
            20                  25                  30

Ser Trp Asp Phe Arg Pro His Trp Leu Glu Gly Ile Arg Phe Leu Leu
        35                  40                  45

Gly Trp Gly Gln Ala Leu Met Ala Gly Leu Phe Pro Trp Leu Xaa
    50                  55                  60

<210> SEQ ID NO 53
<211> LENGTH: 124
<212> TYPE: PRT
<213> ORGANISM: Homo sapiens
<220> FEATURE:
<221> NAME/KEY: SITE
<222> LOCATION: (114)
<223> OTHER INFORMATION: Xaa equals any of the naturally occurring
      L-amino acids
<220> FEATURE:
<221> NAME/KEY: SITE
<222> LOCATION: (124)
<223> OTHER INFORMATION: Xaa equals stop translation

<400> SEQUENCE: 53

Met Arg Gly Ser Trp His Arg Ser Pro Leu Pro Ala Val Val Leu Pro
1               5                   10                  15

Ser Val Leu Gln Thr Ala Leu Ser Pro Leu Ala Leu Cys Gln Ala Trp
            20                  25                  30

Arg Arg Ala Val Pro His Gly Val Pro Ser Gln Arg Leu Arg Asn Gln
        35                  40                  45

Glu Ala Ser Leu Val Pro Lys Gly Val Pro Arg Ala Trp Tyr Pro Gly
    50                  55                  60

Pro Leu Gln Asn Gly Leu Trp Thr His Leu Glu Lys Gly Glu Leu Leu
65                  70                  75                  80

Gly Leu Lys Pro Thr Pro Gly Gly Leu Leu Leu Arg Ser Phe Trp
            85                  90                  95

Asp Pro His Pro Ser Arg Pro Phe Leu Cys Thr Leu Leu Pro Pro Pro
        100                 105                 110
```

-continued

Leu Xaa Ile Phe Pro Pro Leu Arg Cys Ser Ala Xaa
        115                 120

<210> SEQ ID NO 54
<211> LENGTH: 180
<212> TYPE: PRT
<213> ORGANISM: Homo sapiens
<220> FEATURE:
<221> NAME/KEY: SITE
<222> LOCATION: (8)
<223> OTHER INFORMATION: Xaa equals any of the naturally occurring
      L-amino acids
<220> FEATURE:
<221> NAME/KEY: SITE
<222> LOCATION: (27)
<223> OTHER INFORMATION: Xaa equals any of the naturally occurring
      L-amino acids
<220> FEATURE:
<221> NAME/KEY: SITE
<222> LOCATION: (84)
<223> OTHER INFORMATION: Xaa equals any of the naturally occurring
      L-amino acids
<220> FEATURE:
<221> NAME/KEY: SITE
<222> LOCATION: (85)
<223> OTHER INFORMATION: Xaa equals any of the naturally occurring
      L-amino acids
<220> FEATURE:
<221> NAME/KEY: SITE
<222> LOCATION: (86)
<223> OTHER INFORMATION: Xaa equals any of the naturally occurring
      L-amino acids
<220> FEATURE:
<221> NAME/KEY: SITE
<222> LOCATION: (99)
<223> OTHER INFORMATION: Xaa equals any of the naturally occurring
      L-amino acids
<220> FEATURE:
<221> NAME/KEY: SITE
<222> LOCATION: (180)
<223> OTHER INFORMATION: Xaa equals stop translation

<400> SEQUENCE: 54

Met Thr Ser Ala Gly Pro Val Xaa Leu Phe Leu Leu Val Ser Ile Ser
 1               5                  10                  15

Thr Ser Val Ile Leu Met Gln His Leu Leu Xaa Ala Ser Tyr Cys Asp
            20                  25                  30

Leu Leu His Lys Ala Ala His Leu Gly Cys Trp Gln Lys Val Asp
        35                  40                  45

Pro Ala Leu Cys Ser Asn Val Leu Gln His Pro Trp Thr Glu Glu Cys
    50                  55                  60

Met Trp Pro Gln Gly Val Leu Val Lys His Ser Lys Asn Val Tyr Lys
65                  70                  75                  80

Ala Val Gly Xaa Xaa Xaa Val Ala Ile Pro Ser Asp Val Ser His Phe
                85                  90                  95

Arg Phe Xaa Phe Phe Phe Ser Lys Pro Leu Arg Ile Leu Asn Ile Leu
            100                 105                 110

Leu Leu Leu Glu Gly Ala Val Ile Val Tyr Gln Leu Tyr Ser Leu Met
        115                 120                 125

Ser Ser Glu Lys Trp His Gln Thr Ile Ser Leu Ala Leu Ile Leu Phe
    130                 135                 140

Ser Asn Tyr Tyr Ala Phe Phe Lys Leu Leu Arg Asp Arg Leu Val Leu
145                 150                 155                 160

Gly Lys Ala Tyr Ser Tyr Ser Ala Ser Pro Gln Arg Asp Leu Asp His
                165                 170                 175

Arg Phe Ser Xaa

-continued

```
<210> SEQ ID NO 55
<211> LENGTH: 287
<212> TYPE: PRT
<213> ORGANISM: Homo sapiens
<220> FEATURE:
<221> NAME/KEY: SITE
<222> LOCATION: (221)
<223> OTHER INFORMATION: Xaa equals any of the naturally occurring
      L-amino acids
<220> FEATURE:
<221> NAME/KEY: SITE
<222> LOCATION: (287)
<223> OTHER INFORMATION: Xaa equals stop translation

<400> SEQUENCE: 55

Met Pro Leu Phe Lys Leu Tyr Met Val Met Ser Ala Cys Phe Leu Ala
  1               5                  10                  15

Ala Gly Ile Phe Trp Val Ser Ile Leu Cys Arg Asn Thr Tyr Ser Val
                 20                  25                  30

Phe Lys Ile His Trp Leu Met Ala Ala Leu Ala Phe Thr Lys Ser Ile
             35                  40                  45

Ser Leu Leu Phe His Ser Ile Asn Tyr Tyr Phe Ile Asn Ser Gln Gly
         50                  55                  60

Pro Pro His Arg Arg Pro Cys Arg His Val Leu His Arg Thr Pro Ala
 65                  70                  75                  80

Glu Gly Arg Pro Pro Leu His His Arg Pro Asp Trp Leu Arg Leu
                 85                  90                  95

Gly Phe Ile Lys Tyr Val Leu Ser Asp Lys Glu Lys Val Phe Gly
                100                 105                 110

Ile Val Ile Pro Met Gln Val Leu Ala Asn Val Ala Tyr Ile Ile
            115                 120                 125

Glu Ser Arg Glu Glu Gly Ala Thr Asn Tyr Val Leu Trp Lys Glu Ile
        130                 135                 140

Leu Phe Leu Val Asp Leu Ile Cys Cys Gly Ala Ile Leu Phe Pro Val
145                 150                 155                 160

Val Trp Ser Ile Arg His Leu Gln Asp Ala Ser Gly Thr Asp Gly Lys
                165                 170                 175

Val Ala Val Asn Leu Ala Lys Leu Lys Leu Phe Arg His Tyr Tyr Val
            180                 185                 190

Met Val Ile Cys Tyr Val Tyr Phe Thr Arg Ile Ile Ala Ile Leu Leu
        195                 200                 205

Gln Val Ala Val Pro Phe Gln Trp Gln Trp Leu Tyr Xaa Leu Leu Val
210                 215                 220

Glu Gly Ser Thr Leu Ala Phe Phe Val Leu Thr Gly Tyr Lys Phe Gln
225                 230                 235                 240

Pro Thr Gly Asn Asn Pro Tyr Leu Gln Leu Pro Gln Glu Asp Glu Glu
                245                 250                 255

Asp Val Gln Met Glu Gln Val Met Thr Asp Ser Gly Phe Arg Glu Gly
            260                 265                 270

Leu Ser Lys Val Asn Lys Thr Ala Ser Gly Arg Glu Leu Leu Xaa
        275                 280                 285

<210> SEQ ID NO 56
<211> LENGTH: 34
<212> TYPE: PRT
<213> ORGANISM: Homo sapiens
<220> FEATURE:
<221> NAME/KEY: SITE
```

```
<222> LOCATION: (34)
<223> OTHER INFORMATION: Xaa equals stop translation

<400> SEQUENCE: 56

Met Pro Met Val Phe Leu Leu Leu Phe Asn Leu Met Ser Trp Leu Ile
 1               5                  10                  15

Arg Asn Ala Arg Val Ile Leu Arg Ser Leu Asn Leu Lys Arg Asp Gln
            20                  25                  30

Val Xaa

<210> SEQ ID NO 57
<211> LENGTH: 24
<212> TYPE: PRT
<213> ORGANISM: Homo sapiens
<220> FEATURE:
<221> NAME/KEY: SITE
<222> LOCATION: (24)
<223> OTHER INFORMATION: Xaa equals stop translation

<400> SEQUENCE: 57

Met Lys Ile Val Val Leu Leu Pro Leu Phe Leu Leu Ala Thr Phe Pro
 1               5                  10                  15

Arg Lys Leu Gln Thr Cys Leu Xaa
            20

<210> SEQ ID NO 58
<211> LENGTH: 47
<212> TYPE: PRT
<213> ORGANISM: Homo sapiens
<220> FEATURE:
<221> NAME/KEY: SITE
<222> LOCATION: (47)
<223> OTHER INFORMATION: Xaa equals stop translation

<400> SEQUENCE: 58

Met Ser Gly Gly Glu Gly Ala Ala Leu Pro Ile Leu Leu Leu Leu Leu
 1               5                  10                  15

Ala Leu Arg Gly Thr Phe His Gly Ala Arg Pro Gly Gly Gly Ala Ser
            20                  25                  30

Gly Ile Trp Cys Leu Leu Leu Pro Glu Gln Glu Pro Pro Val Xaa
            35                  40                  45

<210> SEQ ID NO 59
<211> LENGTH: 129
<212> TYPE: PRT
<213> ORGANISM: Homo sapiens

<400> SEQUENCE: 59

Met Ala Arg Gly Ser Leu Arg Arg Leu Leu Arg Leu Leu Val Leu Gly
 1               5                  10                  15

Leu Trp Leu Ala Leu Leu Arg Ser Val Ala Gly Glu Gln Ala Pro Gly
            20                  25                  30

Thr Ala Pro Cys Ser Arg Gly Ser Ser Trp Ser Ala Asp Leu Asp Lys
            35                  40                  45

Cys Met Asp Cys Ala Ser Cys Arg Ala Arg Pro His Ser Asp Phe Cys
 50                  55                  60

Leu Gly Cys Ala Ala Ala Pro Pro Ala Pro Phe Arg Leu Leu Trp Pro
 65                  70                  75                  80

Ile Leu Gly Gly Ala Leu Ser Leu Thr Phe Val Leu Gly Leu Leu Ser
                85                  90                  95

Gly Phe Leu Val Trp Arg Arg Cys Arg Arg Arg Glu Lys Phe Thr Thr
                100                 105                 110
```

-continued

```
Pro Ile Glu Glu Thr Gly Gly Glu Gly Cys Pro Ala Val Ala Leu Ile
        115                 120                 125
Gln

<210> SEQ ID NO 60
<211> LENGTH: 32
<212> TYPE: PRT
<213> ORGANISM: Homo sapiens
<220> FEATURE:
<221> NAME/KEY: SITE
<222> LOCATION: (26)
<223> OTHER INFORMATION: Xaa equals any of the naturally occurring
      L-amino acids
<220> FEATURE:
<221> NAME/KEY: SITE
<222> LOCATION: (32)
<223> OTHER INFORMATION: Xaa equals stop translation

<400> SEQUENCE: 60

Met Val Cys Ile Leu Val Leu Thr Leu Val Ser Tyr Ser Ser Leu Val
 1               5                  10                  15

Asn Ser Pro Leu Pro Phe Val His Leu Xaa Val Gly Ile Ser Ala Xaa
            20                  25                  30

<210> SEQ ID NO 61
<211> LENGTH: 81
<212> TYPE: PRT
<213> ORGANISM: Homo sapiens
<220> FEATURE:
<221> NAME/KEY: SITE
<222> LOCATION: (19)
<223> OTHER INFORMATION: Xaa equals any of the naturally occurring
      L-amino acids
<220> FEATURE:
<221> NAME/KEY: SITE
<222> LOCATION: (33)
<223> OTHER INFORMATION: Xaa equals any of the naturally occurring
      L-amino acids
<220> FEATURE:
<221> NAME/KEY: SITE
<222> LOCATION: (81)
<223> OTHER INFORMATION: Xaa equals stop translation

<400> SEQUENCE: 61

Met Thr Gly Gly Phe Leu Ser Cys Ile Leu Gly Leu Val Leu Pro Leu
 1               5                  10                  15

Ala Tyr Xaa Ser Ser Leu Thr Trp Cys Trp Arg Trp Gly Leu Pro
            20                  25                  30

Xaa Pro Ala Gly Pro Pro Arg Cys Thr Pro Gly Cys Asn Ala Ser Gly
            35                  40                  45

Ala Gly Arg Gly Pro Ser Pro Gly Pro Pro Gly Gly Glu Leu His Thr
     50                  55                  60

Pro Ala Ser Arg Asp Pro Gly Pro Gly Ala Glu Trp Arg Gly Thr Ser
 65                  70                  75                  80

Xaa

<210> SEQ ID NO 62
<211> LENGTH: 104
<212> TYPE: PRT
<213> ORGANISM: Homo sapiens

<400> SEQUENCE: 62

Met Ala Ala Pro Val Asp Leu Glu Leu Lys Lys Ala Phe Thr Glu Leu
 1               5                  10                  15

Gln Ala Lys Val Ile Asp Thr Gln Gln Lys Val Lys Leu Ala Asp Ile
```

```
                    20                  25                  30

Gln Ile Glu Gln Leu Asn Arg Thr Lys Lys His Ala His Leu Thr Asp
                35                  40                  45

Thr Glu Ile Met Thr Leu Val Asp Glu Thr Asn Met Tyr Glu Gly Val
         50                  55                  60

Gly Arg Met Phe Ile Leu Gln Ser Lys Glu Ala Ile His Ser Gln Leu
 65                  70                  75                  80

Leu Glu Lys Gln Lys Ile Ala Glu Glu Lys Ile Lys Glu Leu Glu Gln
                85                  90                  95

Lys Lys Ser Tyr Leu Glu Arg Arg
                100
```

<210> SEQ ID NO 63
<211> LENGTH: 146
<212> TYPE: PRT
<213> ORGANISM: Homo sapiens
<220> FEATURE:
<221> NAME/KEY: SITE
<222> LOCATION: (146)
<223> OTHER INFORMATION: Xaa equals stop translation

<400> SEQUENCE: 63

```
Met Pro Ser Gly Phe Gln Thr Cys Leu Leu Phe Thr Leu Ser Pro Phe
 1               5                  10                  15

Ser Leu Ser Lys Ile Val Gly Val Pro Ser Gln Gln Leu Pro Gly Gln
                20                  25                  30

Leu Ser Glu Gln Gly Gly Leu Cys Gly His Glu Gly Glu Pro Ala Arg
             35                  40                  45

Thr Val Pro Glu Thr Gln Leu Pro Leu Pro Phe Asn Ser Ala Gly Pro
         50                  55                  60

Pro His Leu Lys Cys Thr Gly Ala Gly Lys Arg Val Trp Ser Pro Pro
 65                  70                  75                  80

Arg Arg Ala Ala Gln Glu Val Ser Leu Gln Leu Val Ser Cys His Pro
                85                  90                  95

Cys Arg Gln His Thr Ser Arg Ala Phe Ser Leu Ala Thr Asp Arg Thr
                100                 105                 110

Ala Ser Ala Arg Val Cys Cys Arg Ser Pro Leu Ser Thr Leu Ile His
             115                 120                 125

His Thr Arg Gly Gly Gln Arg Cys Arg Glu His Gly Leu Ser Leu Pro
         130                 135                 140

Leu Xaa
145
```

<210> SEQ ID NO 64
<211> LENGTH: 31
<212> TYPE: PRT
<213> ORGANISM: Homo sapiens
<220> FEATURE:
<221> NAME/KEY: SITE
<222> LOCATION: (31)
<223> OTHER INFORMATION: Xaa equals stop translation

<400> SEQUENCE: 64

```
Met Ala Ile Leu Met Leu Leu Ala Gly Ser Pro Cys Thr Leu Ser Phe
 1               5                  10                  15

Ser Thr Asp Thr Gly Ser Ser Ala Pro Gly Pro Lys Ile Pro Xaa
                20                  25                  30
```

<210> SEQ ID NO 65
<211> LENGTH: 260

```
<212> TYPE: PRT
<213> ORGANISM: Homo sapiens
<220> FEATURE:
<221> NAME/KEY: SITE
<222> LOCATION: (260)
<223> OTHER INFORMATION: Xaa equals stop translation

<400> SEQUENCE: 65
```

Met Asp Pro Gln Gly Gln Thr Leu Leu Leu Phe Leu Phe Val Asp Phe
1               5                   10                  15

His Ser Ala Phe Pro Val Gln Met Glu Ile Trp Gly Val Tyr Thr
            20                  25                  30

Leu Leu Thr Thr His Leu Asn Ala Ile Leu Val Glu Ser His Ser Val
        35                  40                  45

Val Gln Gly Ser Ile Gln Phe Thr Val Asp Lys Val Leu Glu Gln His
    50                  55                  60

His Gln Ala Ala Lys Ala Gln Gln Lys Leu Gln Ala Ser Leu Ser Val
65                  70                  75                  80

Ala Val Asn Ser Ile Met Ser Ile Leu Thr Gly Ser Thr Arg Ser Ser
                85                  90                  95

Phe Arg Lys Met Cys Leu Gln Thr Leu Gln Ala Asp Thr Gln Glu
            100                 105                 110

Phe Arg Thr Lys Leu His Lys Val Phe Arg Glu Ile Thr Gln His Gln
        115                 120                 125

Phe Leu His His Cys Ser Cys Glu Val Lys Gln Leu Thr Leu Glu Lys
    130                 135                 140

Lys Asp Ser Ala Gln Gly Thr Glu Asp Ala Pro Asp Asn Ser Ser Leu
145                 150                 155                 160

Glu Leu Leu Ala Asp Thr Ser Gly Gln Ala Glu Asn Lys Arg Leu Lys
                165                 170                 175

Arg Gly Ser Pro Arg Ile Glu Glu Met Arg Ala Leu Arg Ser Ala Arg
            180                 185                 190

Ala Pro Ser Pro Ser Glu Ala Ala Pro Arg Arg Pro Glu Ala Thr Ala
        195                 200                 205

Ala Pro Leu Thr Pro Arg Gly Arg Glu His Arg Glu Ala His Gly Arg
    210                 215                 220

Ala Leu Ala Pro Gly Arg Ala Ser Leu Gly Ser Arg Leu Glu Asp Val
225                 230                 235                 240

Leu Trp Leu Gln Glu Val Ser Asn Leu Ser Glu Trp Leu Ser Pro Ser
                245                 250                 255

Pro Gly Pro Xaa
            260

```
<210> SEQ ID NO 66
<211> LENGTH: 339
<212> TYPE: PRT
<213> ORGANISM: Homo sapiens

<400> SEQUENCE: 66
```

Met Ala Ala Ala Cys Gly Pro Gly Ala Ala Gly Tyr Cys Leu Leu Leu
1               5                   10                  15

Gly Leu His Leu Phe Leu Leu Thr Ala Gly Pro Ala Leu Gly Trp Asn
            20                  25                  30

Asp Pro Asp Arg Met Leu Leu Arg Asp Val Lys Ala Leu Thr Leu His
        35                  40                  45

Tyr Asp Arg Tyr Thr Thr Ser Arg Arg Leu Asp Pro Ile Pro Gln Leu
    50                  55                  60

```
Lys Cys Val Gly Gly Thr Ala Gly Cys Asp Ser Tyr Thr Pro Lys Val
 65                  70                  75                  80

Ile Gln Cys Gln Asn Lys Gly Trp Asp Gly Tyr Asp Val Gln Trp Glu
                 85                  90                  95

Cys Lys Thr Asp Leu Asp Ile Ala Tyr Lys Phe Gly Lys Thr Val Val
            100                 105                 110

Ser Cys Glu Gly Tyr Glu Ser Ser Glu Asp Gln Tyr Val Leu Arg Gly
        115                 120                 125

Ser Cys Gly Leu Glu Tyr Asn Leu Asp Tyr Thr Glu Leu Gly Leu Gln
    130                 135                 140

Lys Leu Lys Glu Ser Gly Lys Gln His Gly Phe Ala Ser Phe Ser Asp
145                 150                 155                 160

Tyr Tyr Tyr Lys Trp Ser Ser Ala Asp Ser Cys Asn Met Ser Gly Leu
                165                 170                 175

Ile Thr Ile Val Val Leu Leu Gly Ile Ala Phe Val Val Tyr Lys Leu
            180                 185                 190

Phe Leu Ser Asp Gly Gln Tyr Ser Pro Pro Tyr Ser Glu Tyr Pro
        195                 200                 205

Pro Phe Ser His Arg Tyr Gln Arg Phe Thr Asn Ser Ala Gly Pro Pro
    210                 215                 220

Pro Pro Gly Phe Lys Ser Glu Phe Thr Gly Pro Gln Asn Thr Gly His
225                 230                 235                 240

Gly Ala Thr Ser Gly Phe Gly Ser Ala Phe Thr Gly Gln Gln Gly Tyr
                245                 250                 255

Glu Asn Ser Gly Pro Gly Phe Trp Thr Gly Leu Gly Thr Gly Gly Ile
            260                 265                 270

Leu Gly Tyr Leu Phe Gly Ser Asn Arg Ala Ala Thr Pro Phe Ser Asp
        275                 280                 285

Ser Trp Tyr Tyr Pro Ser Tyr Pro Pro Ser Tyr Pro Gly Thr Trp Asn
290                 295                 300

Arg Ala Tyr Ser Pro Leu His Gly Gly Ser Gly Ser Tyr Ser Val Cys
305                 310                 315                 320

Ser Asn Ser Asp Thr Lys Thr Arg Thr Ala Ser Gly Tyr Gly Gly Thr
                325                 330                 335

Arg Arg Arg

<210> SEQ ID NO 67
<211> LENGTH: 27
<212> TYPE: PRT
<213> ORGANISM: Homo sapiens
<220> FEATURE:
<221> NAME/KEY: SITE
<222> LOCATION: (27)
<223> OTHER INFORMATION: Xaa equals stop translation

<400> SEQUENCE: 67

Met His Ala Leu Ile Leu Gln Phe Ile Phe Ser Leu Cys Met Tyr Ile
 1               5                  10                  15

Ser Leu Phe Ser Ala Ala Arg Phe Leu Phe Xaa
             20                  25

<210> SEQ ID NO 68
<211> LENGTH: 76
<212> TYPE: PRT
<213> ORGANISM: Homo sapiens
<220> FEATURE:
<221> NAME/KEY: SITE
<222> LOCATION: (64)
<223> OTHER INFORMATION: Xaa equals any of the naturally occurring
```

```
        L-amino acids
<220> FEATURE:
<221> NAME/KEY: SITE
<222> LOCATION: (65)
<223> OTHER INFORMATION: Xaa equals any of the naturally occurring
        L-amino acids

<400> SEQUENCE: 68

Met Ser Gln Ser Val Ser Ser Ser Phe Leu Ile Leu Thr Leu Leu Leu
1               5                   10                  15

Ser Val Gly Phe Gln Cys Leu Thr Leu Tyr Thr Thr Val Thr Thr Thr
            20                  25                  30

Cys Leu Trp Gly Pro Pro Arg Ala Ala Gly Arg Leu Phe Val Gln Ser
        35                  40                  45

Leu Pro Ser Cys Glu Cys Cys Cys Arg Ala Arg Arg Gly Ala Val Xaa
    50                  55                  60

Xaa Ser Pro Pro Trp Arg Pro Trp Pro Glu Gln Val
65                  70                  75

<210> SEQ ID NO 69
<211> LENGTH: 216
<212> TYPE: PRT
<213> ORGANISM: Homo sapiens
<220> FEATURE:
<221> NAME/KEY: SITE
<222> LOCATION: (216)
<223> OTHER INFORMATION: Xaa equals stop translation

<400> SEQUENCE: 69

Met Tyr Leu Ser Ile Ile Phe Leu Ala Phe Val Ser Ile Asp Arg Cys
1               5                   10                  15

Leu Gln Leu Thr His Ser Cys Lys Ile Tyr Arg Ile Gln Glu Pro Gly
            20                  25                  30

Phe Ala Lys Met Ile Ser Thr Val Val Trp Leu Met Val Leu Leu Ile
        35                  40                  45

Met Val Pro Asn Met Met Ile Pro Ile Lys Asp Ile Lys Glu Lys Ser
    50                  55                  60

Asn Val Gly Cys Met Glu Phe Lys Glu Phe Gly Arg Asn Trp His
65                  70                  75                  80

Leu Leu Thr Asn Phe Ile Cys Val Ala Ile Phe Leu Asn Phe Ser Ala
                85                  90                  95

Ile Ile Leu Ile Ser Asn Cys Leu Val Ile Arg Gln Leu Tyr Arg Asn
            100                 105                 110

Lys Asp Asn Glu Asn Tyr Pro Asn Val Lys Ala Leu Ile Asn Ile
        115                 120                 125

Leu Leu Val Thr Thr Gly Tyr Ile Ile Cys Phe Val Pro Tyr His Ile
    130                 135                 140

Val Arg Ile Pro Tyr Thr Leu Ser Gln Thr Glu Val Ile Thr Asp Cys
145                 150                 155                 160

Ser Thr Arg Ile Ser Leu Phe Lys Ala Lys Glu Ala Thr Leu Leu Leu
                165                 170                 175

Ala Val Ser Asn Leu Cys Phe Asp Pro Ile Leu Tyr Tyr His Leu Ser
            180                 185                 190

Lys Ala Phe Arg Ser Lys Val Thr Glu Thr Phe Ala Ser Pro Lys Glu
        195                 200                 205

Thr Lys Val Arg Lys Lys Asn Xaa
    210                 215

<210> SEQ ID NO 70
```

-continued

```
<211> LENGTH: 407
<212> TYPE: PRT
<213> ORGANISM: Homo sapiens
<220> FEATURE:
<221> NAME/KEY: SITE
<222> LOCATION: (407)
<223> OTHER INFORMATION: Xaa equals stop translation

<400> SEQUENCE: 70

Met His Pro Ala Val Phe Leu Ser Leu Pro Asp Leu Arg Cys Ser Leu
1               5                   10                  15

Leu Leu Leu Val Thr Trp Val Phe Thr Pro Val Thr Thr Glu Ile Thr
            20                  25                  30

Ser Leu Asp Thr Glu Asn Ile Asp Glu Ile Leu Asn Asn Ala Asp Val
        35                  40                  45

Ala Leu Val Asn Phe Tyr Ala Asp Trp Cys Arg Phe Ser Gln Met Leu
    50                  55                  60

His Pro Ile Phe Glu Glu Ala Ser Asp Val Ile Lys Glu Glu Phe Pro
65                  70                  75                  80

Asn Glu Asn Gln Val Val Phe Ala Arg Val Asp Cys Asp Gln His Ser
                85                  90                  95

Asp Ile Ala Gln Arg Tyr Arg Ile Ser Lys Tyr Pro Thr Leu Lys Leu
            100                 105                 110

Phe Arg Asn Gly Met Met Met Lys Arg Glu Tyr Arg Gly Gln Arg Ser
        115                 120                 125

Val Lys Ala Leu Ala Asp Tyr Ile Arg Gln Gln Lys Ser Asp Pro Ile
    130                 135                 140

Gln Glu Ile Arg Asp Leu Ala Glu Ile Thr Thr Leu Asp Arg Ser Lys
145                 150                 155                 160

Arg Asn Ile Ile Gly Tyr Phe Glu Gln Lys Asp Ser Asp Asn Tyr Arg
                165                 170                 175

Val Phe Glu Arg Val Ala Asn Ile Leu His Asp Asp Cys Ala Phe Leu
            180                 185                 190

Ser Ala Phe Gly Asp Val Ser Lys Pro Glu Arg Tyr Ser Gly Asp Asn
        195                 200                 205

Ile Ile Tyr Lys Pro Pro Gly His Ser Ala Pro Asp Met Val Tyr Leu
    210                 215                 220

Gly Ala Met Thr Asn Phe Asp Val Thr Tyr Asn Trp Ile Gln Asp Lys
225                 230                 235                 240

Cys Val Pro Leu Val Arg Glu Ile Thr Phe Glu Asn Gly Glu Glu Leu
                245                 250                 255

Thr Glu Glu Gly Leu Pro Phe Leu Ile Leu Phe His Met Lys Glu Asp
            260                 265                 270

Thr Glu Ser Leu Glu Ile Phe Gln Asn Glu Val Ala Arg Gln Leu Ile
        275                 280                 285

Ser Glu Lys Gly Thr Ile Asn Phe Leu His Ala Asp Cys Asp Lys Phe
    290                 295                 300

Arg His Pro Leu Leu His Ile Gln Lys Thr Pro Ala Asp Cys Pro Val
305                 310                 315                 320

Ile Ala Ile Asp Ser Phe Arg His Met Tyr Val Phe Gly Asp Phe Lys
                325                 330                 335

Asp Val Leu Ile Pro Gly Lys Leu Lys Gln Phe Val Phe Asp Leu His
            340                 345                 350

Ser Gly Lys Leu His Arg Glu Phe His His Gly Pro Asp Pro Thr Asp
        355                 360                 365

Thr Ala Pro Gly Glu Gln Ala Gln Asp Val Ala Ser Ser Pro Pro Glu
```

```
                    370                 375                 380
Ser Ser Phe Gln Lys Leu Ala Pro Ser Glu Tyr Arg Tyr Thr Leu Leu
385                 390                 395                 400

Arg Asp Arg Asp Glu Leu Xaa
            405

<210> SEQ ID NO 71
<211> LENGTH: 45
<212> TYPE: PRT
<213> ORGANISM: Homo sapiens

<400> SEQUENCE: 71

Met Ser Met Cys Ile His Ala Lys Lys His Leu Ile Cys Ile Cys Phe
1               5                   10                  15

Arg Lys Gly Gly Asn Glu Ala Thr Cys Leu Lys Ile Leu Leu Tyr Lys
            20                  25                  30

Ala Phe Gln Pro Phe Pro Leu Ser Phe Ala Leu Ile Phe
        35                  40                  45

<210> SEQ ID NO 72
<211> LENGTH: 34
<212> TYPE: PRT
<213> ORGANISM: Homo sapiens
<220> FEATURE:
<221> NAME/KEY: SITE
<222> LOCATION: (34)
<223> OTHER INFORMATION: Xaa equals stop translation

<400> SEQUENCE: 72

Met Pro Leu Lys Ala Val Thr Trp Pro Thr Leu Asn Ser Lys Leu Val
1               5                   10                  15

Ala Ala Val Val Asn Leu Lys Ala Ser Gln Met Pro Ala Ser Ser Arg
            20                  25                  30

Val Xaa

<210> SEQ ID NO 73
<211> LENGTH: 160
<212> TYPE: PRT
<213> ORGANISM: Homo sapiens
<220> FEATURE:
<221> NAME/KEY: SITE
<222> LOCATION: (55)
<223> OTHER INFORMATION: Xaa equals any of the naturally occurring
      L-amino acids

<400> SEQUENCE: 73

Met Ala Pro Leu Ile Pro Ala Val Ala Arg Gly Ser Ser Phe Leu Leu
1               5                   10                  15

Leu His Ala Leu Thr Leu Trp Gly Ala Pro Phe Pro Thr Thr Trp Val
            20                  25                  30

Ser Cys Gln Pro Arg Ser Val Leu Arg Pro Ser Pro Val Arg Pro Gly
        35                  40                  45

Val Pro Pro Leu Ala Ala Xaa Pro Leu Cys Ser Cys Val Ser Leu Phe
    50                  55                  60

Phe Phe Arg Val Val Leu His Val Ser Ser Ile Cys Gly Val Ala Leu
65                  70                  75                  80

Gly Pro Phe Arg Thr Gly Ala Pro Ala Gln Leu Leu Gly Pro Pro Pro
            85                  90                  95

Val Ala Gln Gly Arg Leu Phe Val Pro Gln Pro Gln Ala Val Ser Gly
        100                 105                 110

Glu Asn Arg Cys Val Val Pro Glu Leu Lys Phe Trp Glu Gly Gln Cys
```

```
              115                 120                 125
Pro Phe Leu Trp Gly Pro Gly Leu Val Leu His Cys Phe Lys Arg Ser
    130                 135                 140
Cys His Ser Asn Arg Gln Pro Cys Asn Arg Arg Ala Ala Cys Ser Pro
145                 150                 155                 160

<210> SEQ ID NO 74
<211> LENGTH: 26
<212> TYPE: PRT
<213> ORGANISM: Homo sapiens
<220> FEATURE:
<221> NAME/KEY: SITE
<222> LOCATION: (17)
<223> OTHER INFORMATION: Xaa equals any of the naturally occurring
      L-amino acids
<220> FEATURE:
<221> NAME/KEY: SITE
<222> LOCATION: (26)
<223> OTHER INFORMATION: Xaa equals stop translation

<400> SEQUENCE: 74

Met Ala Gly Ile His Arg Ala Phe Leu Val Phe Cys Leu Trp Gly Leu
1               5                   10                  15

Xaa Leu Cys Val Val Gly Gly Pro Trp Xaa
            20                  25

<210> SEQ ID NO 75
<211> LENGTH: 91
<212> TYPE: PRT
<213> ORGANISM: Homo sapiens

<400> SEQUENCE: 75

Met Ala Ala Ala Glu Glu Glu Asp Gly Gly Pro Glu Ala Lys Ile Ala
1               5                   10                  15

Ser Gly Ala Gly Arg Ala Arg Pro Ser Asn Val Ile Tyr Val Trp Arg
            20                  25                  30

Leu Leu Gly Lys Leu Trp Ser Val Cys Val Ala Thr Cys Thr Val Gly
        35                  40                  45

His Val Phe Ile Ser Gly Trp Arg His Gly Gln Asn Gly Lys Ser Val
    50                  55                  60

Gln Tyr Val Lys Leu Gly Ser Ala Glu Arg Arg Leu Ser Arg Phe Met
65                  70                  75                  80

Gly Glu Gly Ala Arg Ser Pro Arg Ile Pro Asp
                85                  90

<210> SEQ ID NO 76
<211> LENGTH: 33
<212> TYPE: PRT
<213> ORGANISM: Homo sapiens
<220> FEATURE:
<221> NAME/KEY: SITE
<222> LOCATION: (33)
<223> OTHER INFORMATION: Xaa equals stop translation

<400> SEQUENCE: 76

Met Thr Ile Trp Gln Leu Phe Ala Val Leu Ile Val Leu Phe Ala Lys
1               5                   10                  15

Ser Arg Glu Ile Ser Thr Glu Gly Glu Pro Cys Val Leu Ser Lys Asn
            20                  25                  30

Xaa

<210> SEQ ID NO 77
<211> LENGTH: 23
```

```
<212> TYPE: PRT
<213> ORGANISM: Homo sapiens
<220> FEATURE:
<221> NAME/KEY: SITE
<222> LOCATION: (6)
<223> OTHER INFORMATION: Xaa equals any of the naturally occurring
      L-amino acids
<220> FEATURE:
<221> NAME/KEY: SITE
<222> LOCATION: (23)
<223> OTHER INFORMATION: Xaa equals stop translation

<400> SEQUENCE: 77

Met Leu Asn Pro Phe Xaa Gln Leu Leu Leu Val Leu Leu Phe Pro Glu
1               5                   10                  15

Trp Pro Thr Pro Leu His Xaa
            20

<210> SEQ ID NO 78
<211> LENGTH: 173
<212> TYPE: PRT
<213> ORGANISM: Homo sapiens
<220> FEATURE:
<221> NAME/KEY: SITE
<222> LOCATION: (18)
<223> OTHER INFORMATION: Xaa equals any of the naturally occurring
      L-amino acids
<220> FEATURE:
<221> NAME/KEY: SITE
<222> LOCATION: (21)
<223> OTHER INFORMATION: Xaa equals any of the naturally occurring
      L-amino acids
<220> FEATURE:
<221> NAME/KEY: SITE
<222> LOCATION: (80)
<223> OTHER INFORMATION: Xaa equals any of the naturally occurring
      L-amino acids
<220> FEATURE:
<221> NAME/KEY: SITE
<222> LOCATION: (102)
<223> OTHER INFORMATION: Xaa equals any of the naturally occurring
      L-amino acids

<400> SEQUENCE: 78

Met Lys Thr Leu Phe Leu Gly Val Thr Leu Gly Leu Ala Ala Ala Leu
1               5                   10                  15

Ser Xaa Thr Leu Xaa Glu Glu Asp Ile Thr Gly Thr Trp Tyr Val Lys
            20                  25                  30

Ala Met Val Val Asp Lys Thr Phe Arg Arg Gln Glu Ala Gln Lys Val
            35                  40                  45

Ser Pro Val Lys Val Thr Ala Leu Gly Gly Gly Lys Leu Glu Ala Thr
50                  55                  60

Phe Thr Phe Met Arg Glu Asp Arg Cys Ile Gln Lys Lys Ile Leu Xaa
65                  70                  75                  80

Arg Lys Thr Glu Glu Pro Gly Lys Tyr Ser Ala Cys Glu Pro Leu Pro
            85                  90                  95

His Ser His Pro His Xaa Pro Pro Pro Thr Pro Val His Gln Pro
            100                 105                 110

Pro Gln Val Glu Ser Ala Gln Ala Ala Leu Leu Pro Gly Pro Gln Leu
            115                 120                 125

Cys Pro Pro Pro Arg Arg Gly Trp Pro Leu Leu Pro Gly Gly Leu Val
            130                 135                 140

Ala Leu Thr Ser Asp Thr Gly Cys Asp Arg Leu Val Arg Ser Arg Asp
145                 150                 155                 160

Gly Pro Asp His Ala Cys Pro Leu Gly Gly Pro Ser His
            165                 170
```

```
<210> SEQ ID NO 79
<211> LENGTH: 208
<212> TYPE: PRT
<213> ORGANISM: Homo sapiens
<220> FEATURE:
<221> NAME/KEY: SITE
<222> LOCATION: (148)
<223> OTHER INFORMATION: Xaa equals any of the naturally occurring
      L-amino acids
<220> FEATURE:
<221> NAME/KEY: SITE
<222> LOCATION: (186)
<223> OTHER INFORMATION: Xaa equals any of the naturally occurring
      L-amino acids
<220> FEATURE:
<221> NAME/KEY: SITE
<222> LOCATION: (208)
<223> OTHER INFORMATION: Xaa equals stop translation

<400> SEQUENCE: 79

Met Ala Asp Ser Ser Tyr Thr Ser Glu Val Gln Ala Ile Leu Ala Phe
1               5                   10                  15

Leu Ser Leu Gln Arg Thr Gly Ser Gly Gly Pro Gly Asn His Pro His
            20                  25                  30

Gly Pro Asp Ala Ser Ala Glu Gly Leu Asn Pro Tyr Gly Leu Val Ala
        35                  40                  45

Pro Arg Phe Gln Arg Lys Phe Lys Ala Lys Gln Leu Thr Pro Arg Ile
    50                  55                  60

Leu Glu Ala His Gln Asn Val Ala Gln Leu Ser Leu Ala Glu Ala Gln
65                  70                  75                  80

Leu Arg Phe Ile Gln Ala Trp Gln Ser Leu Pro Asp Phe Gly Ile Ser
                85                  90                  95

Tyr Val Met Val Arg Phe Lys Gly Ser Arg Lys Asp Glu Ile Leu Gly
            100                 105                 110

Ile Ala Asn Asn Arg Leu Ile Arg Ile Asp Leu Ala Val Gly Asp Val
        115                 120                 125

Val Lys Thr Trp Arg Phe Ser Asn Met Arg Gln Trp Asn Val Asn Trp
    130                 135                 140

Asp Ile Arg Xaa Val Ala Ile Glu Phe Asp Glu His Ile Asn Val Ala
145                 150                 155                 160

Phe Ser Cys Val Ser Ala Ser Cys Arg Ile Val His Glu Tyr Ile Gly
                165                 170                 175

Gly Tyr Ile Phe Leu Ser Thr Arg Glu Xaa Ala Arg Gly Glu Glu Leu
            180                 185                 190

Asp Glu Asp Leu Phe Leu Gln Leu Thr Gly Gly His Glu Ala Phe Xaa
        195                 200                 205

<210> SEQ ID NO 80
<211> LENGTH: 146
<212> TYPE: PRT
<213> ORGANISM: Homo sapiens
<220> FEATURE:
<221> NAME/KEY: SITE
<222> LOCATION: (95)
<223> OTHER INFORMATION: Xaa equals any of the naturally occurring
      L-amino acids
<220> FEATURE:
<221> NAME/KEY: SITE
<222> LOCATION: (100)
<223> OTHER INFORMATION: Xaa equals any of the naturally occurring
      L-amino acids
<220> FEATURE:
<221> NAME/KEY: SITE
<222> LOCATION: (146)
```

<223> OTHER INFORMATION: Xaa equals stop translation

<400> SEQUENCE: 80

Met Pro Ser Gly Phe Gln Thr Cys Leu Leu Phe Thr Leu Ser Pro Phe
1               5                   10                  15

Ser Leu Ser Lys Ile Val Gly Val Pro Ser Gln Gln Leu Pro Gly Gln
            20                  25                  30

Leu Ser Glu Gln Gly Gly Leu Cys Gly His Glu Gly Glu Pro Ala Arg
        35                  40                  45

Thr Val Pro Glu Thr Gln Leu Pro Leu Pro Phe Asn Ser Ala Gly Pro
    50                  55                  60

Pro His Leu Lys Cys Thr Gly Ala Gly Lys Arg Val Trp Ser Pro Pro
65                  70                  75                  80

Arg Arg Ala Ala Gln Glu Val Ser Leu Gln Leu Val Ser Cys Xaa Pro
                85                  90                  95

Cys Arg Gln Xaa Thr Ser Arg Ala Phe Ser Leu Ala Thr Asp Arg Thr
            100                 105                 110

Ala Ser Ala Arg Val Cys Cys Arg Phe Pro Phe Lys His Thr His Ser
        115                 120                 125

Pro His Pro Arg Arg Pro Glu Val Gln Gly Ala Trp Ala Val Val Pro
    130                 135                 140

Leu Xaa
145

<210> SEQ ID NO 81
<211> LENGTH: 23
<212> TYPE: PRT
<213> ORGANISM: Homo sapiens
<220> FEATURE:
<221> NAME/KEY: SITE
<222> LOCATION: (23)
<223> OTHER INFORMATION: Xaa equals stop translation

<400> SEQUENCE: 81

Met Ala Ala Ala Cys Gly Pro Gly Ala Ala Gly Thr Ala Cys Ser Ser
1               5                   10                  15

Ala Cys Ile Cys Phe Cys Xaa
            20

<210> SEQ ID NO 82
<211> LENGTH: 31
<212> TYPE: PRT
<213> ORGANISM: Homo sapiens
<220> FEATURE:
<221> NAME/KEY: SITE
<222> LOCATION: (21)
<223> OTHER INFORMATION: Xaa equals any of the naturally occurring
     L-amino acids
<220> FEATURE:
<221> NAME/KEY: SITE
<222> LOCATION: (31)
<223> OTHER INFORMATION: Xaa equals stop translation

<400> SEQUENCE: 82

Met Lys Thr Leu Phe Leu Gly Val Thr Leu Gly Leu Ala Leu Pro Cys
1               5                   10                  15

Pro Ser Pro Trp Xaa Arg Arg Ile Ser Gln Gly Pro Gly Thr Xaa
            20                  25                  30

<210> SEQ ID NO 83
<211> LENGTH: 374
<212> TYPE: PRT
<213> ORGANISM: Homo sapiens

<400> SEQUENCE: 83

```
Met Ser Val Pro Ala Phe Ile Asp Ile Ser Glu Glu Asp Gln Ala Ala
1               5                   10                  15

Glu Leu Arg Ala Tyr Leu Lys Ser Lys Gly Ala Glu Ile Ser Glu Glu
            20                  25                  30

Asn Ser Glu Gly Gly Leu His Val Asp Leu Ala Gln Ile Ile Glu Ala
        35                  40                  45

Cys Asp Val Cys Leu Lys Glu Asp Lys Asp Val Glu Ser Val Met
    50                  55                  60

Asn Ser Val Val Ser Leu Leu Ile Leu Gly Pro Asp Lys Gln Glu
65                  70                  75                  80

Ala Leu Ile Glu Ser Leu Cys Glu Lys Leu Val Lys Phe Arg Glu Gly
                85                  90                  95

Glu Arg Pro Ser Leu Arg Leu Gln Leu Leu Ser Asn Leu Phe His Gly
            100                 105                 110

Met Asp Lys Asn Thr Pro Val Arg Tyr Thr Val Tyr Cys Ser Leu Ile
        115                 120                 125

Lys Val Ala Ala Ser Cys Gly Ala Ile Gln Tyr Ile Pro Thr Glu Leu
130                 135                 140

Asp Gln Val Arg Lys Trp Ile Ser Asp Trp Asn Leu Thr Thr Glu Lys
145                 150                 155                 160

Lys His Thr Leu Leu Arg Leu Leu Tyr Glu Ala Leu Val Asp Cys Lys
                165                 170                 175

Lys Ser Asp Ala Ala Ser Lys Val Met Val Glu Leu Leu Gly Ser Tyr
            180                 185                 190

Thr Glu Asp Asn Ala Ser Gln Ala Arg Val Asp Ala His Arg Cys Ile
        195                 200                 205

Val Arg Ala Leu Lys Asp Pro Asn Ala Phe Leu Phe Asp His Leu Leu
    210                 215                 220

Thr Leu Lys Pro Val Lys Phe Leu Glu Gly Glu Leu Ile His Asp Leu
225                 230                 235                 240

Leu Thr Ile Phe Val Ser Ala Lys Leu Ala Ser Tyr Val Lys Phe Tyr
                245                 250                 255

Gln Asn Asn Lys Asp Phe Ile Asp Ser Leu Gly Leu Leu His Glu Gln
            260                 265                 270

Asn Met Ala Lys Met Arg Leu Leu Thr Phe Met Gly Met Ala Val Glu
        275                 280                 285

Asn Lys Glu Ile Ser Phe Asp Thr Met Gln Gln Glu Leu Gln Ile Gly
    290                 295                 300

Ala Asp Asp Val Glu Ala Phe Val Ile Asp Ala Val Arg Thr Lys Met
305                 310                 315                 320

Val Tyr Cys Lys Ile Asp Gln Thr Gln Arg Lys Val Val Val Ser His
                325                 330                 335

Ser Thr His Arg Thr Phe Gly Lys Gln Gln Trp Gln Leu Tyr Asp
            340                 345                 350

Thr Leu Asn Ala Trp Lys Gln Asn Leu Asn Lys Val Lys Asn Ser Leu
        355                 360                 365

Leu Ser Leu Ser Asp Thr
    370
```

<210> SEQ ID NO 84
<211> LENGTH: 13
<212> TYPE: PRT
<213> ORGANISM: Homo sapiens

```
<400> SEQUENCE: 84

Met Ser Val Pro Ala Phe Ile Asp Ile Ser Glu Glu Asp
1               5                   10

<210> SEQ ID NO 85
<211> LENGTH: 15
<212> TYPE: PRT
<213> ORGANISM: Homo sapiens

<400> SEQUENCE: 85

Gln Ala Ala Glu Leu Arg Ala Tyr Leu Lys Ser Lys Gly Ala Glu
1               5                   10                  15

<210> SEQ ID NO 86
<211> LENGTH: 17
<212> TYPE: PRT
<213> ORGANISM: Homo sapiens

<400> SEQUENCE: 86

Ile Ser Glu Glu Asn Ser Glu Gly Gly Leu His Val Asp Leu Ala Gln
1               5                   10                  15

Ile

<210> SEQ ID NO 87
<211> LENGTH: 18
<212> TYPE: PRT
<213> ORGANISM: Homo sapiens

<400> SEQUENCE: 87

Ile Glu Ala Cys Asp Val Cys Leu Lys Glu Asp Asp Lys Asp Val Glu
1               5                   10                  15

Ser Val

<210> SEQ ID NO 88
<211> LENGTH: 16
<212> TYPE: PRT
<213> ORGANISM: Homo sapiens

<400> SEQUENCE: 88

Val Ala Arg Pro Ser Ser Leu Phe Arg Ser Ala Trp Ser Cys Glu Trp
1               5                   10                  15

<210> SEQ ID NO 89
<211> LENGTH: 12
<212> TYPE: PRT
<213> ORGANISM: Homo sapiens

<400> SEQUENCE: 89

Leu Arg Leu Gln Leu Leu Ser Asn Leu Phe His Gly
1               5                   10

<210> SEQ ID NO 90
<211> LENGTH: 17
<212> TYPE: PRT
<213> ORGANISM: Homo sapiens

<400> SEQUENCE: 90

Lys Asp Val Glu Ser Val Met Asn Ser Val Val Ser Leu Leu Leu Ile
1               5                   10                  15

Leu

<210> SEQ ID NO 91
```

```
<211> LENGTH: 26
<212> TYPE: PRT
<213> ORGANISM: Homo sapiens

<400> SEQUENCE: 91

Asp Ala Ala Ser Lys Val Met Val Glu Leu Leu Gly Ser Tyr Thr Glu
1               5                   10                  15

Asp Asn Ala Ser Gln Ala Arg Val Asp Ala
            20                  25

<210> SEQ ID NO 92
<211> LENGTH: 10
<212> TYPE: PRT
<213> ORGANISM: Homo sapiens

<400> SEQUENCE: 92

Val Glu Ala Phe Val Ile Asp Ala Val Arg
1               5                   10

<210> SEQ ID NO 93
<211> LENGTH: 18
<212> TYPE: PRT
<213> ORGANISM: Homo sapiens

<400> SEQUENCE: 93

Lys Met Arg Leu Leu Thr Phe Met Gly Met Ala Val Glu Asn Lys Glu
1               5                   10                  15

Ile Ser

<210> SEQ ID NO 94
<211> LENGTH: 196
<212> TYPE: PRT
<213> ORGANISM: Homo sapiens

<400> SEQUENCE: 94

Met Glu Ala Val Pro Glu Gly Asp Trp Phe Cys Thr Val Cys Leu Ala
1               5                   10                  15

Gln Gln Val Glu Gly Glu Phe Thr Gln Lys Pro Gly Phe Pro Lys Arg
            20                  25                  30

Gly Gln Lys Arg Lys Ser Gly Tyr Ser Leu Asn Phe Ser Glu Gly Asp
        35                  40                  45

Gly Arg Arg Arg Arg Val Leu Leu Arg Gly Arg Glu Ser Pro Ala Ala
    50                  55                  60

Gly Pro Arg Tyr Ser Glu Glu Gly Leu Ser Pro Ser Lys Arg Arg Arg
65                  70                  75                  80

Leu Ser Met Arg Asn His His Ser Asp Leu Thr Phe Cys Glu Ile Ile
                85                  90                  95

Leu Met Glu Met Glu Ser His Asp Ala Ala Trp Pro Phe Leu Glu Pro
            100                 105                 110

Val Asn Pro Arg Leu Val Ser Gly Tyr Arg Arg Ile Ile Lys Asn Pro
        115                 120                 125

Met Asp Phe Ser Thr Met Arg Glu Arg Leu Leu Arg Gly Gly Tyr Thr
    130                 135                 140

Ser Ser Glu Glu Phe Ala Ala Asp Ala Leu Leu Val Phe Asp Asn Cys
145                 150                 155                 160

Gln Thr Phe Asn Glu Asp Asp Ser Glu Val Gly Lys Ala Gly His Ile
                165                 170                 175

Met Arg Arg Phe Phe Glu Ser Arg Trp Glu Glu Phe Tyr Gln Gly Lys
            180                 185                 190
```

-continued

Gln Ala Asn Leu
    195

<210> SEQ ID NO 95
<211> LENGTH: 20
<212> TYPE: PRT
<213> ORGANISM: Homo sapiens

<400> SEQUENCE: 95

Met Glu Ala Val Pro Glu Gly Asp Trp Phe Cys Thr Val Cys Leu Ala
1               5                   10                  15

Gln Gln Val Glu
         20

<210> SEQ ID NO 96
<211> LENGTH: 21
<212> TYPE: PRT
<213> ORGANISM: Homo sapiens

<400> SEQUENCE: 96

Gly Glu Phe Thr Gln Lys Pro Gly Phe Pro Lys Arg Gly Gln Lys Arg
1               5                   10                  15

Lys Ser Gly Tyr Ser
         20

<210> SEQ ID NO 97
<211> LENGTH: 21
<212> TYPE: PRT
<213> ORGANISM: Homo sapiens

<400> SEQUENCE: 97

Leu Asn Phe Ser Glu Gly Asp Gly Arg Arg Arg Arg Val Leu Leu Arg
1               5                   10                  15

Gly Arg Glu Ser Pro
         20

<210> SEQ ID NO 98
<211> LENGTH: 20
<212> TYPE: PRT
<213> ORGANISM: Homo sapiens

<400> SEQUENCE: 98

Ala Ala Gly Pro Arg Tyr Ser Glu Glu Gly Leu Ser Pro Ser Lys Arg
1               5                   10                  15

Arg Arg Leu Ser
         20

<210> SEQ ID NO 99
<211> LENGTH: 21
<212> TYPE: PRT
<213> ORGANISM: Homo sapiens

<400> SEQUENCE: 99

Met Arg Asn His His Ser Asp Leu Thr Phe Cys Glu Ile Ile Leu Met
1               5                   10                  15

Glu Met Glu Ser His
         20

<210> SEQ ID NO 100
<211> LENGTH: 20
<212> TYPE: PRT
<213> ORGANISM: Homo sapiens

<400> SEQUENCE: 100

Asp Ala Ala Trp Pro Phe Leu Glu Pro Val Asn Pro Arg Leu Val Ser
1               5                   10                  15

Gly Tyr Arg Arg
            20

<210> SEQ ID NO 101
<211> LENGTH: 21
<212> TYPE: PRT
<213> ORGANISM: Homo sapiens

<400> SEQUENCE: 101

Ile Ile Lys Asn Pro Met Asp Phe Ser Thr Met Arg Glu Arg Leu Leu
1               5                   10                  15

Arg Gly Gly Tyr Thr
            20

<210> SEQ ID NO 102
<211> LENGTH: 21
<212> TYPE: PRT
<213> ORGANISM: Homo sapiens

<400> SEQUENCE: 102

Ser Ser Glu Glu Phe Ala Ala Asp Ala Leu Leu Val Phe Asp Asn Cys
1               5                   10                  15

Gln Thr Phe Asn Glu
            20

<210> SEQ ID NO 103
<211> LENGTH: 17
<212> TYPE: PRT
<213> ORGANISM: Homo sapiens

<400> SEQUENCE: 103

Asp Asp Ser Glu Val Gly Lys Ala Gly His Ile Met Arg Arg Phe Phe
1               5                   10                  15

Glu

<210> SEQ ID NO 104
<211> LENGTH: 14
<212> TYPE: PRT
<213> ORGANISM: Homo sapiens

<400> SEQUENCE: 104

Ser Arg Trp Glu Glu Phe Tyr Gln Gly Lys Gln Ala Asn Leu
1               5                   10

<210> SEQ ID NO 105
<211> LENGTH: 35
<212> TYPE: PRT
<213> ORGANISM: Homo sapiens

<400> SEQUENCE: 105

Met Ser Glu Ile Tyr Leu Arg Cys Gln Asp Glu Gln Gln Tyr Ala Arg
1               5                   10                  15

Trp Met Ala Gly Cys Arg Leu Ala Ser Lys Gly Arg Thr Met Ala Asp
            20                  25                  30

Ser Ser Tyr
        35

<210> SEQ ID NO 106
<211> LENGTH: 45
<212> TYPE: PRT

<213> ORGANISM: Homo sapiens

<400> SEQUENCE: 106

Leu Val Ala Pro Arg Phe Gln Arg Lys Phe Lys Ala Lys Gln Leu Thr
1               5                   10                  15

Pro Arg Ile Leu Glu Ala His Gln Asn Val Ala Gln Leu Ser Leu Ala
            20                  25                  30

Glu Ala Gln Leu Arg Phe Ile Gln Ala Trp Gln Ser Leu
        35                  40                  45

<210> SEQ ID NO 107
<211> LENGTH: 23
<212> TYPE: PRT
<213> ORGANISM: Homo sapiens

<400> SEQUENCE: 107

Val Gly Asp Val Val Lys Thr Trp Arg Phe Ser Asn Met Arg Gln Trp
1               5                   10                  15

Asn Val Asn Trp Asp Ile Arg
            20

<210> SEQ ID NO 108
<211> LENGTH: 26
<212> TYPE: PRT
<213> ORGANISM: Homo sapiens

<400> SEQUENCE: 108

Glu Glu Ile Asp Cys Thr Glu Glu Met Met Val Phe Ala Ala Leu
1               5                   10                  15

Gln Tyr His Ile Asn Lys Leu Ser Gln Ser
            20                  25

<210> SEQ ID NO 109
<211> LENGTH: 26
<212> TYPE: PRT
<213> ORGANISM: Homo sapiens

<400> SEQUENCE: 109

Glu Glu Ile Asp Cys Thr Glu Glu Met Met Val Phe Ala Ala Leu
1               5                   10                  15

Gln Tyr His Ile Asn Lys Leu Ser Gln Ser
            20                  25

<210> SEQ ID NO 110
<211> LENGTH: 26
<212> TYPE: PRT
<213> ORGANISM: Homo sapiens

<400> SEQUENCE: 110

Lys Glu Leu Ser Phe Ala Arg Ile Lys Ala Val Glu Cys Val Glu Ser
1               5                   10                  15

Thr Gly Arg His Ile Tyr Phe Thr Leu Val
            20                  25

<210> SEQ ID NO 111
<211> LENGTH: 17
<212> TYPE: PRT
<213> ORGANISM: Homo sapiens

<400> SEQUENCE: 111

Gly Trp Asn Ala Gln Ile Thr Leu Gly Leu Val Lys Phe Lys Asn Gln
1               5                   10                  15

Gln

```
<210> SEQ ID NO 112
<211> LENGTH: 217
<212> TYPE: PRT
<213> ORGANISM: Homo sapiens
<220> FEATURE:
<221> NAME/KEY: SITE
<222> LOCATION: (82)
<223> OTHER INFORMATION: Xaa equals any of the naturally occurring
      L-amino acids
<220> FEATURE:
<221> NAME/KEY: SITE
<222> LOCATION: (83)
<223> OTHER INFORMATION: Xaa equals any of the naturally occurring
      L-amino acids
<220> FEATURE:
<221> NAME/KEY: SITE
<222> LOCATION: (123)
<223> OTHER INFORMATION: Xaa equals any of the naturally occurring
      L-amino acids
<220> FEATURE:
<221> NAME/KEY: SITE
<222> LOCATION: (194)
<223> OTHER INFORMATION: Xaa equals any of the naturally occurring
      L-amino acids

<400> SEQUENCE: 112

Met Val Thr Thr Ile Val Leu Gly Arg Arg Phe Ile Gly Ser Ile Val
1               5                   10                  15

Lys Glu Ala Ser Gln Arg Gly Lys Val Ser Leu Phe Arg Ser Ile Leu
            20                  25                  30

Leu Phe Leu Thr Arg Phe Thr Val Leu Thr Ala Thr Gly Trp Ser Leu
        35                  40                  45

Cys Arg Ser Leu Ile His Leu Phe Arg Thr Tyr Ser Phe Leu Asn Leu
    50                  55                  60

Leu Phe Leu Cys Tyr Pro Phe Gly Met Tyr Ile Pro Phe Leu Gln Leu
65                  70                  75                  80

Asn Xaa Xaa Leu Arg Lys Thr Ser Leu Phe Asn His Met Ala Ser Met
                85                  90                  95

Gly Pro Arg Glu Ala Val Ser Gly Leu Ala Lys Ser Arg Asp Tyr Leu
            100                 105                 110

Leu Thr Leu Arg Glu Thr Trp Lys Gln His Xaa Arg Gln Leu Tyr Gly
        115                 120                 125

Pro Asp Ala Met Pro Thr His Ala Cys Cys Leu Ser Pro Ser Leu Ile
    130                 135                 140

Arg Ser Glu Val Glu Phe Leu Lys Met Asp Phe Asn Trp Arg Met Lys
145                 150                 155                 160

Glu Val Leu Val Ser Ser Met Leu Ser Ala Tyr Tyr Val Ala Phe Val
                165                 170                 175

Pro Val Trp Phe Val Lys Asn Thr His Tyr Tyr Asp Lys Arg Trp Ser
            180                 185                 190

Cys Xaa Thr Leu Pro Ala Gly Val His Gln His Leu Arg Asp Pro His
        195                 200                 205

Ala Ala Pro Ala Ala Cys Gln Leu Leu
    210                 215

<210> SEQ ID NO 113
<211> LENGTH: 26
<212> TYPE: PRT
<213> ORGANISM: Homo sapiens

<400> SEQUENCE: 113
```

```
Met Val Thr Thr Ile Val Leu Gly Arg Arg Phe Ile Gly Ser Ile Val
1               5                   10                  15

Lys Glu Ala Ser Gln Arg Gly Lys Val Ser
            20                  25
```

<210> SEQ ID NO 114
<211> LENGTH: 23
<212> TYPE: PRT
<213> ORGANISM: Homo sapiens

<400> SEQUENCE: 114

```
Leu Phe Arg Ser Ile Leu Leu Phe Leu Thr Arg Phe Thr Val Leu Thr
1               5                   10                  15

Ala Thr Gly Trp Ser Leu Cys
            20
```

<210> SEQ ID NO 115
<211> LENGTH: 30
<212> TYPE: PRT
<213> ORGANISM: Homo sapiens

<400> SEQUENCE: 115

```
Arg Ser Leu Ile His Leu Phe Arg Thr Tyr Ser Phe Leu Asn Leu Leu
1               5                   10                  15

Phe Leu Cys Tyr Pro Phe Gly Met Tyr Ile Pro Phe Leu Gln
            20                  25                  30
```

<210> SEQ ID NO 116
<211> LENGTH: 30
<212> TYPE: PRT
<213> ORGANISM: Homo sapiens
<220> FEATURE:
<221> NAME/KEY: SITE
<222> LOCATION: (3)
<223> OTHER INFORMATION: Xaa equals any of the naturally occurring
      L-amino acids
<220> FEATURE:
<221> NAME/KEY: SITE
<222> LOCATION: (4)
<223> OTHER INFORMATION: Xaa equals any of the naturally occurring
      L-amino acids

<400> SEQUENCE: 116

```
Leu Asn Xaa Xaa Leu Arg Lys Thr Ser Leu Phe Asn His Met Ala Ser
1               5                   10                  15

Met Gly Pro Arg Glu Ala Val Ser Gly Leu Ala Lys Ser Arg
            20                  25                  30
```

<210> SEQ ID NO 117
<211> LENGTH: 30
<212> TYPE: PRT
<213> ORGANISM: Homo sapiens
<220> FEATURE:
<221> NAME/KEY: SITE
<222> LOCATION: (14)
<223> OTHER INFORMATION: Xaa equals any of the naturally occurring
      L-amino acids

<400> SEQUENCE: 117

```
Asp Tyr Leu Leu Thr Leu Arg Glu Thr Trp Lys Gln His Xaa Arg Gln
1               5                   10                  15

Leu Tyr Gly Pro Asp Ala Met Pro Thr His Ala Cys Cys Leu
            20                  25                  30
```

<210> SEQ ID NO 118
<211> LENGTH: 31

```
<212> TYPE: PRT
<213> ORGANISM: Homo sapiens

<400> SEQUENCE: 118

Ser Pro Ser Leu Ile Arg Ser Glu Val Glu Phe Leu Lys Met Asp Phe
1               5                   10                  15

Asn Trp Arg Met Lys Glu Val Leu Val Ser Ser Met Leu Ser Ala
            20                  25                  30

<210> SEQ ID NO 119
<211> LENGTH: 27
<212> TYPE: PRT
<213> ORGANISM: Homo sapiens
<220> FEATURE:
<221> NAME/KEY: SITE
<222> LOCATION: (24)
<223> OTHER INFORMATION: Xaa equals any of the naturally occurring
      L-amino acids

<400> SEQUENCE: 119

Tyr Tyr Val Ala Phe Val Pro Val Trp Phe Val Lys Asn Thr His Tyr
1               5                   10                  15

Tyr Asp Lys Arg Trp Ser Cys Xaa Thr Leu Pro
            20                  25

<210> SEQ ID NO 120
<211> LENGTH: 20
<212> TYPE: PRT
<213> ORGANISM: Homo sapiens

<400> SEQUENCE: 120

Ala Gly Val His Gln His Leu Arg Asp Pro His Ala Ala Pro Ala Ala
1               5                   10                  15

Cys Gln Leu Leu
            20

<210> SEQ ID NO 121
<211> LENGTH: 16
<212> TYPE: PRT
<213> ORGANISM: Homo sapiens
<220> FEATURE:
<221> NAME/KEY: SITE
<222> LOCATION: (7)
<223> OTHER INFORMATION: Xaa equals any of the naturally occurring
      L-amino acids

<400> SEQUENCE: 121

Leu Val Leu Gly Leu Ser Xaa Leu Asn Asn Ser Tyr Asn Phe Ser Phe
1               5                   10                  15

<210> SEQ ID NO 122
<211> LENGTH: 17
<212> TYPE: PRT
<213> ORGANISM: Homo sapiens

<400> SEQUENCE: 122

His Val Val Ile Gly Ser Gln Ala Glu Glu Gly Gln Tyr Ser Leu Asn
1               5                   10                  15

Phe

<210> SEQ ID NO 123
<211> LENGTH: 19
<212> TYPE: PRT
<213> ORGANISM: Homo sapiens

<400> SEQUENCE: 123
```

His Asn Cys Asn Asn Ser Val Pro Gly Lys Glu His Pro Phe Asp Ile
1               5                   10                  15

Thr Val Met

<210> SEQ ID NO 124
<211> LENGTH: 17
<212> TYPE: PRT
<213> ORGANISM: Homo sapiens

<400> SEQUENCE: 124

Phe Ile Lys Tyr Val Leu Ser Asp Lys Glu Lys Val Phe Gly Ile
1               5                   10                  15

Val

<210> SEQ ID NO 125
<211> LENGTH: 13
<212> TYPE: PRT
<213> ORGANISM: Homo sapiens

<400> SEQUENCE: 125

Ile Pro Met Gln Val Leu Ala Asn Val Ala Tyr Ile Ile
1               5                   10

<210> SEQ ID NO 126
<211> LENGTH: 13
<212> TYPE: PRT
<213> ORGANISM: Homo sapiens

<400> SEQUENCE: 126

Ile Pro Met Gln Val Leu Ala Asn Val Ala Tyr Ile Ile
1               5                   10

<210> SEQ ID NO 127
<211> LENGTH: 15
<212> TYPE: PRT
<213> ORGANISM: Homo sapiens

<400> SEQUENCE: 127

Asp Gly Lys Val Ala Val Asn Leu Ala Lys Leu Lys Leu Phe Arg
1               5                   10                  15

<210> SEQ ID NO 128
<211> LENGTH: 13
<212> TYPE: PRT
<213> ORGANISM: Homo sapiens

<400> SEQUENCE: 128

Ile Arg Glu Lys Asn Pro Asp Gly Phe Leu Ser Ala Ala
1               5                   10

<210> SEQ ID NO 129
<211> LENGTH: 9
<212> TYPE: PRT
<213> ORGANISM: Homo sapiens

<400> SEQUENCE: 129

Met Met Phe Gly Gly Tyr Glu Thr Ile
1               5

<210> SEQ ID NO 130
<211> LENGTH: 24
<212> TYPE: PRT
<213> ORGANISM: Homo sapiens -continued

```
<400> SEQUENCE: 130

Tyr Arg Asp Glu Ser Ser Glu Leu Ser Val Asp Ser Glu Val Glu
1               5                   10                  15

Phe Gln Leu Tyr Ser Gln Ile His
            20

<210> SEQ ID NO 131
<211> LENGTH: 136
<212> TYPE: PRT
<213> ORGANISM: Homo sapiens

<400> SEQUENCE: 131

Tyr Ala Gln Asp Leu Asp Asp Val Ile Arg Glu Glu Glu His Glu
1               5                   10                  15

Lys Asn Ser Gly Asn Ser Glu Ser Ser Ser Lys Pro Asn Gln Lys
            20                  25                  30

Lys Leu Ile Val Leu Ser Asp Ser Glu Val Ile Gln Leu Ser Asp Gly
        35                  40                  45

Ser Glu Val Ile Thr Leu Ser Asp Glu Asp Ser Ile Tyr Arg Cys Lys
    50                  55                  60

Gly Lys Asn Val Arg Val Gln Ala Gln Glu Asn Ala His Gly Leu Ser
65                  70                  75                  80

Ser Ser Leu Gln Ser Asn Glu Leu Val Asp Lys Lys Cys Lys Ser Asp
                85                  90                  95

Ile Glu Lys Pro Lys Ser Glu Glu Arg Ser Gly Val Ile Arg Glu Val
                100                 105                 110

Met Ile Ile Glu Val Ser Ser Glu Glu Glu Ser Thr Ile Ser
        115                 120                 125

Glu Gly Asp Asn Val Glu Ser Trp
    130                 135

<210> SEQ ID NO 132
<211> LENGTH: 37
<212> TYPE: PRT
<213> ORGANISM: Homo sapiens

<400> SEQUENCE: 132

Met Leu Leu Gly Cys Glu Val Asp Asp Lys Asp Asp Ile Leu Leu
1               5                   10                  15

Asn Leu Val Gly Cys Glu Asn Ser Val Thr Glu Gly Glu Asp Gly Ile
            20                  25                  30

Asn Trp Ser Ile Ser
        35

<210> SEQ ID NO 133
<211> LENGTH: 18
<212> TYPE: PRT
<213> ORGANISM: Homo sapiens

<400> SEQUENCE: 133

Asp Lys Asp Ile Glu Ala Gln Ile Ala Asn Asn Arg Thr Pro Gly Arg
1               5                   10                  15

Trp Thr

<210> SEQ ID NO 134
<211> LENGTH: 31
<212> TYPE: PRT
<213> ORGANISM: Homo sapiens

<400> SEQUENCE: 134
```

Gln Arg Tyr Tyr Ser Ala Asn Lys Asn Ile Ile Cys Arg Asn Cys Asp
1               5                   10                  15

Lys Arg Gly His Leu Ser Lys Asn Cys Pro Leu Pro Arg Lys Val
                20                  25                  30

<210> SEQ ID NO 135
<211> LENGTH: 179
<212> TYPE: PRT
<213> ORGANISM: Homo sapiens
<220> FEATURE:
<221> NAME/KEY: SITE
<222> LOCATION: (120)
<223> OTHER INFORMATION: Xaa equals any of the naturally occurring
      L-amino acids
<220> FEATURE:
<221> NAME/KEY: SITE
<222> LOCATION: (139)
<223> OTHER INFORMATION: Xaa equals any of the naturally occurring
      L-amino acids

<400> SEQUENCE: 135

Arg Arg Cys Phe Leu Cys Ser Arg Arg Gly His Leu Leu Tyr Ser Cys
1               5                   10                  15

Pro Ala Pro Leu Cys Glu Tyr Cys Pro Val Pro Lys Met Leu Asp His
                20                  25                  30

Ser Cys Leu Phe Arg His Ser Trp Asp Lys Gln Cys Asp Arg Cys His
        35                  40                  45

Met Leu Gly His Tyr Thr Asp Ala Cys Thr Glu Ile Trp Arg Gln Tyr
    50                  55                  60

His Leu Thr Thr Lys Pro Gly Pro Lys Lys Pro Lys Thr Pro Ser
65                  70                  75                  80

Arg Pro Ser Ala Leu Ala Tyr Cys Tyr His Cys Ala Gln Lys Gly His
                85                  90                  95

Tyr Gly His Glu Cys Pro Glu Arg Glu Val Tyr Asp Pro Ser Pro Val
            100                 105                 110

Ser Pro Phe Ile Cys Tyr Tyr Xaa Asp Lys Tyr Glu Ile Gln Glu Arg
        115                 120                 125

Glu Lys Arg Leu Lys Gln Lys Ile Lys Val Xaa Lys Lys Asn Gly Val
    130                 135                 140

Ile Pro Glu Pro Ser Lys Leu Pro Tyr Ile Lys Ala Ala Asn Glu Asn
145                 150                 155                 160

Pro His His Asp Ile Arg Lys Gly Arg Ala Ser Trp Lys Ser Asn Arg
                165                 170                 175

Trp Pro Gln

<210> SEQ ID NO 136
<211> LENGTH: 416
<212> TYPE: PRT
<213> ORGANISM: Homo sapiens

<400> SEQUENCE: 136

Met Ser Phe Pro Pro His Leu Asn Arg Pro Met Gly Ile Pro Ala
1               5                   10                  15

Leu Pro Pro Gly Ile Pro Pro Gln Phe Pro Gly Phe Pro Pro Pro
                20                  25                  30

Val Pro Pro Gly Thr Pro Met Ile Pro Val Pro Met Ser Ile Met Ala
        35                  40                  45

Pro Ala Pro Thr Val Leu Val Pro Thr Val Ser Met Val Gly Lys His
    50                  55                  60

Leu Gly Ala Arg Lys Asp His Pro Gly Leu Lys Ala Lys Glu Asn Asp
65                  70                  75                  80

Glu Asn Cys Gly Pro Thr Thr Thr Val Phe Val Gly Asn Ile Ser Glu
                85                  90                  95

Lys Ala Ser Asp Met Leu Ile Arg Gln Leu Leu Ala Lys Cys Gly Leu
            100                 105                 110

Val Leu Ser Trp Lys Arg Val Gln Gly Ala Ser Gly Lys Leu Gln Ala
        115                 120                 125

Phe Gly Phe Cys Glu Tyr Lys Glu Pro Glu Ser Thr Leu Arg Ala Leu
130                 135                 140

Arg Leu Leu His Asp Leu Gln Ile Gly Lys Lys Leu Leu Val Lys
145                 150                 155                 160

Val Asp Ala Lys Thr Lys Ala Gln Leu Asp Glu Trp Lys Ala Lys Lys
                165                 170                 175

Lys Ala Ser Asn Gly Asn Ala Arg Pro Glu Thr Val Thr Asn Asp Asp
            180                 185                 190

Glu Glu Ala Leu Asp Glu Gly Thr Lys Arg Arg Asp Gln Met Ile Lys
        195                 200                 205

Gly Ala Ile Glu Val Leu Ile Arg Glu Tyr Ser Ser Glu Leu Asn Ala
210                 215                 220

Pro Ser Gln Glu Ser Asp Ser His Pro Arg Lys Lys Lys Glu Lys
225                 230                 235                 240

Lys Glu Asp Ile Phe Arg Arg Phe Pro Val Ala Pro Leu Ile Pro Tyr
                245                 250                 255

Pro Leu Ile Thr Lys Glu Asp Ile Asn Ala Ile Glu Met Glu Glu Asp
            260                 265                 270

Lys Arg Asp Leu Ile Ser Arg Glu Ile Ser Lys Phe Arg Asp Thr His
        275                 280                 285

Lys Lys Leu Glu Glu Glu Lys Gly Lys Lys Glu Lys Glu Arg Gln Glu
290                 295                 300

Ile Glu Lys Glu Arg Arg Glu Arg Glu Arg Glu Arg Glu Arg Glu Arg
305                 310                 315                 320

Glu Arg Arg Glu Arg Glu Arg Glu Arg Glu Arg Glu Arg Glu Arg Glu
                325                 330                 335

Lys Glu Lys Glu Arg Glu Arg Glu Arg Glu Asp Arg Asp Arg Asp
            340                 345                 350

Arg Thr Lys Glu Arg Asp Arg Asp Arg Asp Glu Arg Asp Arg Asp
        355                 360                 365

Arg Asp Arg Glu Arg Ser Ser Asp Arg Asn Lys Asp Arg Ile Arg Ser
370                 375                 380

Arg Glu Lys Ser Arg Asp Arg Glu Arg Glu Arg Glu Arg Glu Arg Glu
385                 390                 395                 400

Arg Glu Arg Glu Arg Glu Arg Glu Arg Glu Arg Glu Arg Glu Arg Glu
                405                 410                 415

<210> SEQ ID NO 137
<211> LENGTH: 43
<212> TYPE: PRT
<213> ORGANISM: Homo sapiens

<400> SEQUENCE: 137

Met Ser Phe Pro Pro His Leu Asn Arg Pro Met Gly Ile Pro Ala
1               5                   10                  15

Leu Pro Pro Gly Ile Pro Pro Gln Phe Pro Gly Phe Pro Pro Pro
            20                  25                  30

Val Pro Pro Gly Thr Pro Met Ile Pro Val Pro
            35                  40

<210> SEQ ID NO 138
<211> LENGTH: 35
<212> TYPE: PRT
<213> ORGANISM: Homo sapiens

<400> SEQUENCE: 138

Met Ser Ile Met Ala Pro Ala Pro Thr Val Leu Val Pro Thr Val Ser
1               5                   10                  15

Met Val Gly Lys His Leu Gly Ala Arg Lys Asp His Pro Gly Leu Lys
            20                  25                  30

Ala Lys Glu
        35

<210> SEQ ID NO 139
<211> LENGTH: 41
<212> TYPE: PRT
<213> ORGANISM: Homo sapiens

<400> SEQUENCE: 139

Asn Asp Glu Asn Cys Gly Pro Thr Thr Thr Val Phe Val Gly Asn Ile
1               5                   10                  15

Ser Glu Lys Ala Ser Asp Met Leu Ile Arg Gln Leu Leu Ala Lys Cys
            20                  25                  30

Gly Leu Val Leu Ser Trp Lys Arg Val
        35                  40

<210> SEQ ID NO 140
<211> LENGTH: 40
<212> TYPE: PRT
<213> ORGANISM: Homo sapiens

<400> SEQUENCE: 140

Gln Gly Ala Ser Gly Lys Leu Gln Ala Phe Gly Phe Cys Glu Tyr Lys
1               5                   10                  15

Glu Pro Glu Ser Thr Leu Arg Ala Leu Arg Leu Leu His Asp Leu Gln
            20                  25                  30

Ile Gly Glu Lys Lys Leu Leu Val
        35                  40

<210> SEQ ID NO 141
<211> LENGTH: 39
<212> TYPE: PRT
<213> ORGANISM: Homo sapiens

<400> SEQUENCE: 141

Lys Val Asp Ala Lys Thr Lys Ala Gln Leu Asp Glu Trp Lys Ala Lys
1               5                   10                  15

Lys Lys Ala Ser Asn Gly Asn Ala Arg Pro Glu Thr Val Thr Asn Asp
            20                  25                  30

Asp Glu Glu Ala Leu Asp Glu
        35

<210> SEQ ID NO 142
<211> LENGTH: 40
<212> TYPE: PRT
<213> ORGANISM: Homo sapiens

<400> SEQUENCE: 142

Glu Thr Lys Arg Arg Asp Gln Met Ile Lys Gly Ala Ile Glu Val Leu

-continued

```
                1               5                  10                  15
Ile Arg Glu Tyr Ser Ser Glu Leu Asn Ala Pro Ser Gln Glu Ser Asp
                20                  25                  30

Ser His Pro Arg Lys Lys Lys
            35                  40

<210> SEQ ID NO 143
<211> LENGTH: 44
<212> TYPE: PRT
<213> ORGANISM: Homo sapiens

<400> SEQUENCE: 143

Glu Lys Lys Glu Asp Ile Phe Arg Arg Phe Pro Val Ala Pro Leu Ile
1               5                   10                  15

Pro Tyr Pro Leu Ile Thr Lys Glu Asp Ile Asn Ala Ile Glu Met Glu
                20                  25                  30

Glu Asp Lys Arg Asp Leu Ile Ser Arg Glu Ile Ser
            35                  40

<210> SEQ ID NO 144
<211> LENGTH: 41
<212> TYPE: PRT
<213> ORGANISM: Homo sapiens

<400> SEQUENCE: 144

Lys Phe Arg Asp Thr His Lys Lys Leu Glu Glu Lys Gly Lys Lys
1               5                   10                  15

Glu Lys Glu Arg Gln Glu Ile Glu Lys Glu Arg Arg Glu Arg Glu Arg
                20                  25                  30

Glu Arg Glu Arg Glu Arg Glu Arg Arg
            35                  40

<210> SEQ ID NO 145
<211> LENGTH: 93
<212> TYPE: PRT
<213> ORGANISM: Homo sapiens

<400> SEQUENCE: 145

Glu Arg Glu Arg Glu Arg Glu Arg Glu Arg Glu Arg Glu Lys Glu Lys
1               5                   10                  15

Glu Arg Glu Arg Glu Arg Glu Arg Asp Arg Asp Arg Asp Arg Thr Lys
                20                  25                  30

Glu Arg Asp Arg Asp Arg Asp Arg Glu Arg Asp Arg Asp Arg Asp Arg
            35                  40                  45

Glu Arg Ser Ser Asp Arg Asn Lys Asp Arg Ile Arg Ser Arg Glu Lys
        50                  55                  60

Ser Arg Asp Arg Glu Arg Glu Arg Glu Arg Glu Arg Glu Arg Glu Arg
65                  70                  75                  80

Glu Arg Glu Arg Glu Arg Glu Arg Glu Arg Glu Arg Glu
                85                  90

<210> SEQ ID NO 146
<211> LENGTH: 52
<212> TYPE: PRT
<213> ORGANISM: Homo sapiens

<400> SEQUENCE: 146

Arg Asp Arg Asp Arg Asp Arg Glu Arg Ser Ser Asp Arg Asn Lys Asp
1               5                   10                  15

Arg Ile Arg Ser Arg Glu Lys Ser Arg Asp Arg Glu Arg Glu Arg Glu
```

-continued

```
                20                  25                  30

Arg Glu Arg Glu Arg Glu Arg Glu Arg Glu Arg Glu Arg Glu
        35                  40                  45

Arg Glu Arg Glu
    50

<210> SEQ ID NO 147
<211> LENGTH: 22
<212> TYPE: PRT
<213> ORGANISM: Homo sapiens

<400> SEQUENCE: 147

Lys Pro Gln Met Glu Gly Arg Leu Val Gly Gly Gly Ser Phe Ser
1               5                   10                  15

Ser Arg Gly Arg His Pro
            20

<210> SEQ ID NO 148
<211> LENGTH: 25
<212> TYPE: PRT
<213> ORGANISM: Homo sapiens

<400> SEQUENCE: 148

Leu Leu Val Pro Ser Pro Ser Leu Leu Pro Ala Val Ser Ser Tyr His
1               5                   10                  15

Leu Pro Leu Gly Arg Gly Leu Ile Arg
            20                  25

<210> SEQ ID NO 149
<211> LENGTH: 23
<212> TYPE: PRT
<213> ORGANISM: Homo sapiens

<400> SEQUENCE: 149

Glu Gln Gly Ser Ala Val Arg Ser Pro Ala Phe Pro Val Arg Gln Ala
1               5                   10                  15

Trp Leu Pro Cys Ser Gly Ser
            20

<210> SEQ ID NO 150
<211> LENGTH: 151
<212> TYPE: PRT
<213> ORGANISM: Homo sapiens
<220> FEATURE:
<221> NAME/KEY: SITE
<222> LOCATION: (123)
<223> OTHER INFORMATION: Xaa equals any of the naturally occurring
      L-amino acids

<400> SEQUENCE: 150

Met Gly Leu Asn Pro Gly Leu Thr Ser Ala Leu Lys Pro Gln Met
1               5                   10                  15

Glu Gly Arg Leu Val Gly Gly Gly Ser Phe Ser Ser Arg Gly Arg
                20                  25                  30

His Pro Ala Gly Trp Val Leu Pro Gln Pro Cys Leu Leu Leu Ser Pro
        35                  40                  45

Thr Leu Ser Phe Pro Pro Ala Cys Gly Leu Leu Val Pro Ser Pro Ser
    50                  55                  60

Leu Leu Pro Ala Val Ser Ser Tyr His Leu Pro Leu Gly Arg Gly Leu
65                  70                  75                  80

Ile Arg Pro Ala Phe Lys Ile Lys Val Cys Ser Lys Leu Thr Val Trp
                85                  90                  95
```

```
Cys Ser Leu Pro Ser Pro Ser Arg Trp Arg Cys Cys His Gly Asn Ala
            100                 105                 110

Val Ala Leu Pro Ala Leu Gly Pro Trp Arg Xaa Trp Glu Gln Gly Ser
        115                 120                 125

Ala Val Arg Ser Pro Ala Phe Pro Val Arg Gln Ala Trp Leu Pro Cys
    130                 135                 140

Ser Gly Ser Leu Thr Ser Trp
145                 150

<210> SEQ ID NO 151
<211> LENGTH: 64
<212> TYPE: PRT
<213> ORGANISM: Homo sapiens

<400> SEQUENCE: 151

Asn Val Thr Lys Ile Thr Leu Glu Ser Phe Leu Ala Trp Lys Lys Arg
1               5                   10                  15

Lys Arg Gln Glu Lys Ile Asp Lys Leu Glu Gln Asp Met Glu Arg Arg
            20                  25                  30

Lys Ala Asp Phe Lys Ala Gly Lys Ala Leu Val Ile Ser Gly Arg Glu
        35                  40                  45

Val Phe Glu Phe Arg Pro Glu Leu Val Asn Asp Asp Asp Glu Glu Ala
    50                  55                  60

<210> SEQ ID NO 152
<211> LENGTH: 22
<212> TYPE: PRT
<213> ORGANISM: Homo sapiens

<400> SEQUENCE: 152

Glu Arg Arg Lys Ala Asp Phe Lys Ala Gly Lys Ala Leu Val Ile Ser
1               5                   10                  15

Gly Arg Glu Val Phe Glu
            20

<210> SEQ ID NO 153
<211> LENGTH: 89
<212> TYPE: PRT
<213> ORGANISM: Homo sapiens
<220> FEATURE:
<221> NAME/KEY: SITE
<222> LOCATION: (81)
<223> OTHER INFORMATION: Xaa equals any of the naturally occurring
      L-amino acids

<400> SEQUENCE: 153

Met Cys Asp Glu Leu Pro Gly Glu Gly Arg Trp Glu Pro Gly Gln Asp
1               5                   10                  15

Arg Lys Leu Cys Leu Ser Phe Pro Leu Gly Thr Pro Ala Arg Pro Ile
            20                  25                  30

Lys Ser Val Cys Pro Thr Leu Leu Ser Leu Val Phe Leu Ser Arg Gly
        35                  40                  45

Met Glu Gln Arg Val Arg Glu Ala Val Ala Val Ser Thr Ser Ala Pro
    50                  55                  60

Ala Pro Ser Ala Ser Glu Pro Phe Leu Ser Trp Gly Met Gly Leu Ala
65                  70                  75                  80

Xaa Phe Ser Phe Pro Phe Leu Tyr Leu
                85

<210> SEQ ID NO 154
```

-continued

```
<211> LENGTH: 95
<212> TYPE: PRT
<213> ORGANISM: Homo sapiens
<220> FEATURE:
<221> NAME/KEY: SITE
<222> LOCATION: (71)
<223> OTHER INFORMATION: Xaa equals any of the naturally occurring
      L-amino acids

<400> SEQUENCE: 154

Gly Ala Ser Leu Gly Ser Ser Ser Cys Pro Ser His Ser Trp Trp
1               5                   10                  15

Gly Gln Arg Ser Val Cys Arg Glu Thr Ala Ser Pro Leu Pro Arg Trp
                20                  25                  30

Met Leu Tyr Leu Asp Gly Leu Ala Thr Ser His Phe Leu His His Pro
            35                  40                  45

Glu Pro His Leu Leu Pro Ser Pro Gly Val Phe Thr Arg Leu Cys Cys
        50                  55                  60

His Leu Cys Pro Gly His Xaa Ser Leu Ser Gly Cys Val Met Asn Ser
65                  70                  75                  80

Gln Glu Arg Glu Asp Gly Ser Gln Gly Lys Ile Gly Ser Ser Ala
                85                  90                  95

<210> SEQ ID NO 155
<211> LENGTH: 125
<212> TYPE: PRT
<213> ORGANISM: Homo sapiens
<220> FEATURE:
<221> NAME/KEY: SITE
<222> LOCATION: (30)
<223> OTHER INFORMATION: Xaa equals any of the naturally occurring
      L-amino acids
<220> FEATURE:
<221> NAME/KEY: SITE
<222> LOCATION: (115)
<223> OTHER INFORMATION: Xaa equals any of the naturally occurring
      L-amino acids

<400> SEQUENCE: 155

Thr Ser Val Leu Ser Ser Ser Val Tyr Cys Met Gln Ala Arg Lys
1               5                   10                  15

Leu Ser Val Ser Gln Arg Tyr Arg Lys Gly Lys Glu Lys Xaa Ala Arg
                20                  25                  30

Pro Ile Pro Gln Glu Arg Lys Gly Ser Asp Ala Glu Gly Ala Gly Ala
            35                  40                  45

Glu Val Glu Thr Ala Thr Ala Ser Leu Thr Leu Cys Ser Ile Pro Leu
        50                  55                  60

Leu Lys Lys Thr Arg Leu Ser Arg Val Gly Gln Thr Leu Phe Ile Gly
65                  70                  75                  80

Leu Ala Gly Val Pro Ser Gly Lys Leu Arg Gln Ser Phe Leu Ser Cys
                85                  90                  95

Pro Gly Ser His Leu Pro Ser Pro Gly Ser Ser His Ile Pro Arg
            100                 105                 110

Gly Lys Xaa Val Leu Gly Arg Gly Gly Ser Lys Ala Gly
        115                 120                 125

<210> SEQ ID NO 156
<211> LENGTH: 125
<212> TYPE: PRT
<213> ORGANISM: Homo sapiens
<220> FEATURE:
<221> NAME/KEY: SITE
<222> LOCATION: (13)
<223> OTHER INFORMATION: Xaa equals any of the naturally occurring
```

```
        L-amino acids
<220> FEATURE:
<221> NAME/KEY: SITE
<222> LOCATION: (97)
<223> OTHER INFORMATION: Xaa equals any of the naturally occurring
      L-amino acids

<400> SEQUENCE: 156

Ala Leu Val Lys Gly Thr Gly Arg Glu Lys Arg Arg Xaa Gln Gly Pro
1               5                   10                  15

Ser Pro Lys Lys Gly Arg Ala Leu Met Gln Arg Glu Gln Glu Leu Arg
            20                  25                  30

Trp Arg Arg Pro Leu Pro Leu Ser Pro Ser Val Pro Ser Leu Cys Ser
        35                  40                  45

Arg Lys Pro Gly Leu Ala Glu Trp Asp Arg Arg Phe Leu Leu Val Trp
    50                  55                  60

Leu Ala Cys Leu Val Glu Ser Ser Gly Arg Ala Ser Tyr Leu Ala Leu
65                  70                  75                  80

Ala Pro Ile Phe Pro Leu Leu Gly Val His His Thr Ser Arg Glu Gly
                85                  90                  95

Xaa Val Ser Trp Ala Glu Val Ala Ala Lys Pro Gly Lys Asn Ser Arg
            100                 105                 110

Ala Gly Lys Gln Met Gly Leu Arg Val Met Gln Lys Met
        115                 120                 125

<210> SEQ ID NO 157
<211> LENGTH: 32
<212> TYPE: PRT
<213> ORGANISM: Homo sapiens

<400> SEQUENCE: 157

Ser Phe Pro Leu Gly Thr Pro Ala Arg Pro Ile Lys Ser Val Cys Pro
1               5                   10                  15

Thr Leu Leu Ser Leu Val Phe Leu Ser Arg Gly Met Glu Gln Arg Val
            20                  25                  30

<210> SEQ ID NO 158
<211> LENGTH: 31
<212> TYPE: PRT
<213> ORGANISM: Homo sapiens

<400> SEQUENCE: 158

Thr Ala Ser Pro Leu Pro Arg Trp Met Leu Tyr Leu Asp Gly Leu Ala
1               5                   10                  15

Thr Ser His Phe Leu His His Pro Glu Pro His Leu Leu Pro Ser
            20                  25                  30

<210> SEQ ID NO 159
<211> LENGTH: 31
<212> TYPE: PRT
<213> ORGANISM: Homo sapiens

<400> SEQUENCE: 159

Arg Lys Gly Ser Asp Ala Glu Gly Ala Gly Ala Glu Val Glu Thr Ala
1               5                   10                  15

Thr Ala Ser Leu Thr Leu Cys Ser Ile Pro Leu Leu Lys Lys Thr
            20                  25                  30

<210> SEQ ID NO 160
<211> LENGTH: 25
<212> TYPE: PRT
<213> ORGANISM: Homo sapiens
```

<400> SEQUENCE: 160

Gln Arg Glu Gln Glu Leu Arg Trp Arg Arg Pro Leu Pro Leu Ser Pro
1               5                   10                  15

Ser Val Pro Ser Leu Cys Ser Arg Lys
            20                  25

<210> SEQ ID NO 161
<211> LENGTH: 29
<212> TYPE: PRT
<213> ORGANISM: Homo sapiens
<220> FEATURE:
<221> NAME/KEY: SITE
<222> LOCATION: (13)
<223> OTHER INFORMATION: Xaa equals any of the naturally occurring
      L-amino acids

<400> SEQUENCE: 161

Pro Leu Leu Gly Val His His Thr Ser Arg Glu Gly Xaa Val Ser Trp
1               5                   10                  15

Ala Glu Val Ala Ala Lys Pro Gly Lys Asn Ser Arg Ala
            20                  25

<210> SEQ ID NO 162
<211> LENGTH: 73
<212> TYPE: PRT
<213> ORGANISM: Homo sapiens

<400> SEQUENCE: 162

Met Ser Val Leu Lys Gly Glu Arg Gln Gln Thr Leu Ala Leu Ala Val
1               5                   10                  15

Leu Ser Val Ala Lys Glu Asn Ala Arg Asp Val Cys Cys Leu Gln Gly
            20                  25                  30

Trp Gln Asp Thr Ser Cys Arg Asp Thr Ser Cys Ala Ala Leu Arg Gly
        35                  40                  45

Gly Leu Gln Thr Leu Phe Pro Ala Pro Val His Phe Arg Cys Gly Gly
    50                  55                  60

Pro Ala Glu Leu Lys Gly Arg Gly Ser
65                  70

<210> SEQ ID NO 163
<211> LENGTH: 68
<212> TYPE: PRT
<213> ORGANISM: Homo sapiens

<400> SEQUENCE: 163

Ala His Ser Phe Thr Thr Pro Glu Glu Ala Arg Gly Ala Gly Ser Met
1               5                   10                  15

Gly Cys Arg Phe Pro Phe Lys His Thr His Ser Pro His Pro Arg Arg
            20                  25                  30

Pro Glu Val Gln Gly Ala Trp Ala Gly Cys Thr Ser Ala Gly Glu Lys
        35                  40                  45

Ala Glu Pro Pro Pro Ser Arg Glu Pro Gly Ser Gln Ala Ser Arg Phe
    50                  55                  60

Pro Leu Pro Pro
65

<210> SEQ ID NO 164
<211> LENGTH: 25
<212> TYPE: PRT
<213> ORGANISM: Homo sapiens

```
<400> SEQUENCE: 164

Gly Trp Gln Asp Thr Ser Cys Arg Asp Thr Ser Cys Ala Ala Leu Arg
1               5                   10                  15

Gly Gly Leu Gln Thr Leu Phe Pro Ala
            20                  25

<210> SEQ ID NO 165
<211> LENGTH: 24
<212> TYPE: PRT
<213> ORGANISM: Homo sapiens

<400> SEQUENCE: 165

Gly Cys Arg Phe Pro Phe Lys His Thr His Ser Pro His Pro Arg Arg
1               5                   10                  15

Pro Glu Val Gln Gly Ala Trp Ala
            20

<210> SEQ ID NO 166
<211> LENGTH: 81
<212> TYPE: PRT
<213> ORGANISM: Homo sapiens

<400> SEQUENCE: 166

Pro His Gln Val Glu Gly Arg Leu Gly Thr Met Glu Thr Trp Asp Ser
1               5                   10                  15

Ser His Glu Gly Leu Leu His Cys Arg Ile Pro Leu Lys Gly Ser Trp
            20                  25                  30

Val Gln Glu Pro Ser Cys Gln Tyr Gln Trp Arg Arg Thr Arg Cys Met
        35                  40                  45

Gly Ile Pro Pro Ala Thr Ser Gly Trp Pro Cys Arg Ala Pro Ala Phe
    50                  55                  60

Leu Cys Ala Arg Ala Glu Phe Pro Ala Ser Pro Gly Gly Ser Thr Asn
65                  70                  75                  80

Phe

<210> SEQ ID NO 167
<211> LENGTH: 81
<212> TYPE: PRT
<213> ORGANISM: Homo sapiens

<400> SEQUENCE: 167

Leu Val Thr Pro Pro Ser Gly Gly Glu Thr Gly Asp His Gly Asn Met
1               5                   10                  15

Gly Gln Leu Pro Arg Arg Ala Leu Ala Leu Gln Asn Ser Thr Gln Gly
            20                  25                  30

Ile Leu Gly Pro Gly Ala Glu Leu Pro Val Ser Val Glu Lys Asp Lys
        35                  40                  45

Val His Gly Asp Pro Ala Ser Asn Ile Arg Met Ala Met Pro Gly Thr
    50                  55                  60

Arg Phe Pro Leu Cys Ser Cys Arg Ile Pro Cys Gln Pro Gly Gly Ile
65                  70                  75                  80

His

<210> SEQ ID NO 168
<211> LENGTH: 32
<212> TYPE: PRT
<213> ORGANISM: Homo sapiens

<400> SEQUENCE: 168
```

```
Glu Gly Leu Leu His Cys Arg Ile Pro Leu Lys Gly Ser Trp Val Gln
1               5                   10                  15

Glu Pro Ser Cys Gln Tyr Gln Trp Arg Arg Thr Arg Cys Met Gly Ile
            20                  25                  30
```

<210> SEQ ID NO 169
<211> LENGTH: 29
<212> TYPE: PRT
<213> ORGANISM: Homo sapiens

<400> SEQUENCE: 169

```
Gln Asn Ser Thr Gln Gly Ile Leu Gly Pro Gly Ala Glu Leu Pro Val
1               5                   10                  15

Ser Val Glu Lys Asp Lys Val His Gly Asp Pro Ala Ser
            20                  25
```

<210> SEQ ID NO 170
<211> LENGTH: 42
<212> TYPE: PRT
<213> ORGANISM: Homo sapiens

<400> SEQUENCE: 170

```
Phe Gly Thr Arg Lys Lys Tyr His Leu Cys Met Ile Pro Asn Leu Asp
1               5                   10                  15

Leu Asn Leu Asp Arg Asp Leu Val Leu Pro Asp Val Ser Tyr Gln Val
            20                  25                  30

Glu Ser Ser Glu Glu Asp Gln Ser Gln Thr
        35                  40
```

<210> SEQ ID NO 171
<211> LENGTH: 115
<212> TYPE: PRT
<213> ORGANISM: Homo sapiens
<220> FEATURE:
<221> NAME/KEY: SITE
<222> LOCATION: (88)
<223> OTHER INFORMATION: Xaa equals any of the naturally occurring
      L-amino acids

<400> SEQUENCE: 171

```
Phe Leu Leu Ser Leu Gly Ser Leu Val Met Leu Leu Gln Asp Leu Val
1               5                   10                  15

His Ser Glu Leu Asp Gly Thr Leu His Tyr Thr Val Ala Leu His Lys
            20                  25                  30

Asp Gly Ile Glu Met Ser Cys Glu Gln Ser Ile Asp Ser Pro Asp Phe
        35                  40                  45

His Leu Leu Asp Trp Lys Cys Thr Val Glu Ile His Lys Glu Lys Lys
    50                  55                  60

Gln Gln Ser Leu Ser Leu Arg Ile His Ser Leu Arg Leu Ile Leu Leu
65                  70                  75                  80

Thr Gly Phe His Leu Ile Thr Xaa Ile Trp Lys His Gln Ile Ser Ile
                85                  90                  95

Gln Ile Glu Ile Gln Ile Gly Tyr His Thr Gln Met Val Phe Phe Pro
            100                 105                 110

Arg Ala Glu
    115
```

<210> SEQ ID NO 172
<211> LENGTH: 26
<212> TYPE: PRT
<213> ORGANISM: Homo sapiens

```
<400> SEQUENCE: 172

Val His Ser Glu Leu Asp Gly Thr Leu His Tyr Thr Val Ala Leu His
1               5                   10                  15

Lys Asp Gly Ile Glu Met Ser Cys Glu Gln
            20                  25

<210> SEQ ID NO 173
<211> LENGTH: 28
<212> TYPE: PRT
<213> ORGANISM: Homo sapiens
<220> FEATURE:
<221> NAME/KEY: SITE
<222> LOCATION: (23)
<223> OTHER INFORMATION: Xaa equals any of the naturally occurring
      L-amino acids

<400> SEQUENCE: 173

Gln Ser Leu Ser Leu Arg Ile His Ser Leu Arg Leu Ile Leu Leu Thr
1               5                   10                  15

Gly Phe His Leu Ile Thr Xaa Ile Trp Lys His Gln
            20                  25

<210> SEQ ID NO 174
<211> LENGTH: 340
<212> TYPE: PRT
<213> ORGANISM: Homo sapiens

<400> SEQUENCE: 174

Met Ala Ala Ala Cys Gly Pro Gly Ala Ala Gly Thr Ala Cys Ser Ser
1               5                   10                  15

Ala Cys Ile Cys Phe Cys Asp Arg Gly Pro Cys Leu Gly Trp Asn Asp
            20                  25                  30

Pro Asp Arg Met Leu Leu Arg Asp Val Lys Ala Leu Thr Leu His Tyr
        35                  40                  45

Asp Arg Tyr Thr Thr Ser Arg Ser Trp Ile Pro Ser His Ser Pro Gln
    50                  55                  60

Leu Lys Cys Val Gly Gly Thr Ala Gly Cys Asp Ser Tyr Thr Pro Lys
65                  70                  75                  80

Val Ile Gln Cys Gln Asn Lys Gly Trp Asp Gly Tyr Asp Val Gln Trp
                85                  90                  95

Glu Cys Lys Thr Asp Leu Asp Ile Ala Tyr Lys Phe Gly Lys Thr Val
            100                 105                 110

Val Ser Cys Glu Gly Tyr Glu Ser Ser Glu Asp Gln Tyr Val Leu Arg
        115                 120                 125

Gly Ser Cys Gly Leu Glu Tyr Asn Leu Asp Tyr Thr Glu Leu Gly Leu
    130                 135                 140

Gln Lys Leu Lys Glu Ser Gly Lys Gln His Gly Phe Ala Ser Phe Ser
145                 150                 155                 160

Asp Tyr Tyr Tyr Lys Trp Ser Ala Asp Ser Cys Asn Met Ser Gly
                165                 170                 175

Leu Ile Thr Ile Val Val Leu Leu Gly Ile Ala Phe Val Val Tyr Lys
            180                 185                 190

Leu Phe Leu Ser Asp Gly Gln Tyr Ser Pro Pro Tyr Ser Glu Tyr
        195                 200                 205

Pro Pro Phe Ser His Arg Tyr Gln Arg Phe Thr Asn Ser Ala Gly Pro
    210                 215                 220

Pro Pro Pro Gly Phe Lys Ser Glu Phe Thr Gly Pro Gln Asn Thr Gly
225                 230                 235                 240
```

His Gly Ala Thr Ser Gly Phe Gly Ser Ala Phe Thr Gly Gln Gln Gly
                245                 250                 255

Tyr Glu Asn Ser Gly Pro Gly Phe Trp Thr Gly Leu Gly Thr Gly Gly
            260                 265                 270

Ile Leu Gly Tyr Leu Phe Gly Ser Asn Arg Ala Ala Thr Pro Phe Ser
        275                 280                 285

Asp Ser Trp Tyr Tyr Pro Ser Tyr Pro Pro Ser Tyr Pro Gly Thr Trp
    290                 295                 300

Asn Arg Ala Tyr Ser Pro Leu His Gly Gly Ser Gly Ser Tyr Ser Val
305                 310                 315                 320

Cys Ser Asn Ser Asp Thr Lys Thr Arg Thr Ala Ser Gly Tyr Gly Gly
                325                 330                 335

Thr Arg Arg Arg
        340

<210> SEQ ID NO 175
<211> LENGTH: 24
<212> TYPE: PRT
<213> ORGANISM: Homo sapiens

<400> SEQUENCE: 175

Ala Cys Ser Ser Ala Cys Ile Cys Phe Cys Asp Arg Gly Pro Cys Leu
1               5                   10                  15

Gly Trp Asn Asp Pro Asp Arg Met
            20

<210> SEQ ID NO 176
<211> LENGTH: 26
<212> TYPE: PRT
<213> ORGANISM: Homo sapiens

<400> SEQUENCE: 176

Thr Ala Gly Cys Asp Ser Tyr Thr Pro Lys Val Ile Gln Cys Gln Asn
1               5                   10                  15

Lys Gly Trp Asp Gly Tyr Asp Val Gln Trp
            20                  25

<210> SEQ ID NO 177
<211> LENGTH: 32
<212> TYPE: PRT
<213> ORGANISM: Homo sapiens

<400> SEQUENCE: 177

Glu Tyr Asn Leu Asp Tyr Thr Glu Leu Gly Leu Gln Lys Leu Lys Glu
1               5                   10                  15

Ser Gly Lys Gln His Gly Phe Ala Ser Phe Ser Asp Tyr Tyr Tyr Lys
            20                  25                  30

<210> SEQ ID NO 178
<211> LENGTH: 28
<212> TYPE: PRT
<213> ORGANISM: Homo sapiens

<400> SEQUENCE: 178

Tyr Lys Leu Phe Leu Ser Asp Gly Gln Tyr Ser Pro Pro Tyr Tyr Ser
1               5                   10                  15

Glu Tyr Pro Pro Phe Ser His Arg Tyr Gln Arg Phe
            20                  25

<210> SEQ ID NO 179
<211> LENGTH: 26

```
<212> TYPE: PRT
<213> ORGANISM: Homo sapiens

<400> SEQUENCE: 179

Glu Asn Ser Gly Pro Gly Phe Trp Thr Gly Leu Gly Thr Gly Gly Ile
1               5                   10                  15

Leu Gly Tyr Leu Phe Gly Ser Asn Arg Ala
            20                  25

<210> SEQ ID NO 180
<211> LENGTH: 25
<212> TYPE: PRT
<213> ORGANISM: Homo sapiens

<400> SEQUENCE: 180

Asn Arg Ala Tyr Ser Pro Leu His Gly Gly Ser Gly Ser Tyr Ser Val
1               5                   10                  15

Cys Ser Asn Ser Asp Thr Lys Thr Arg
            20                  25

<210> SEQ ID NO 181
<211> LENGTH: 124
<212> TYPE: PRT
<213> ORGANISM: Homo sapiens
<220> FEATURE:
<221> NAME/KEY: SITE
<222> LOCATION: (30)
<223> OTHER INFORMATION: Xaa equals any of the naturally occurring
      L-amino acids
<220> FEATURE:
<221> NAME/KEY: SITE
<222> LOCATION: (31)
<223> OTHER INFORMATION: Xaa equals any of the naturally occurring
      L-amino acids
<220> FEATURE:
<221> NAME/KEY: SITE
<222> LOCATION: (32)
<223> OTHER INFORMATION: Xaa equals any of the naturally occurring
      L-amino acids

<400> SEQUENCE: 181

Thr Glu Ser Gln Met Lys Cys Phe Leu Gly Asn Ser His Asp Thr Ala
1               5                   10                  15

Pro Arg His Thr Cys Ser Gly Gln Gly Leu His Gly Gly Xaa Xaa Xaa
            20                  25                  30

Thr Ala Pro Leu Arg Ala Leu Gln Gln His Ser Gln Asp Gly Lys Leu
        35                  40                  45

Cys Thr Asn Ser Leu Pro Ala Ala Arg Gly Gly Pro His Lys His Val
    50                  55                  60

Val Val Thr Val Val Tyr Ser Val Lys His Trp Lys Pro Thr Glu Arg
65                  70                  75                  80

Ser Ser Val Ser Ile Lys Lys Glu Glu Glu Thr Asp Trp Asp Met Asp
                85                  90                  95

Gln Leu Ser Lys Gln Arg Thr Thr Tyr Glu Met Lys Ser Gly Ser Ser
            100                 105                 110

Gly Val Gln Thr Glu Glu Leu Arg His Pro Ser Leu
        115                 120

<210> SEQ ID NO 182
<211> LENGTH: 77
<212> TYPE: PRT
<213> ORGANISM: Homo sapiens
<220> FEATURE:
<221> NAME/KEY: SITE
<222> LOCATION: (16)
```

```
<223> OTHER INFORMATION: Xaa equals any of the naturally occurring
      L-amino acids
<220> FEATURE:
<221> NAME/KEY: SITE
<222> LOCATION: (23)
<223> OTHER INFORMATION: Xaa equals any of the naturally occurring
      L-amino acids
<220> FEATURE:
<221> NAME/KEY: SITE
<222> LOCATION: (25)
<223> OTHER INFORMATION: Xaa equals any of the naturally occurring
      L-amino acids
<220> FEATURE:
<221> NAME/KEY: SITE
<222> LOCATION: (26)
<223> OTHER INFORMATION: Xaa equals any of the naturally occurring
      L-amino acids
<220> FEATURE:
<221> NAME/KEY: SITE
<222> LOCATION: (27)
<223> OTHER INFORMATION: Xaa equals any of the naturally occurring
      L-amino acids

<400> SEQUENCE: 182

Asn Ala Ser Trp Glu Ile His Met Thr Gln Arg His Val Ile Pro Xaa
1               5                   10                  15

Leu Ala Arg Ala Ser Met Xaa Val Xaa Xaa Xaa Gln Arg Pro Ser Glu
            20                  25                  30

Leu Cys Ser Ser Ile Arg Arg Met Ala Asn Ser Ala Gln Ile Val Phe
        35                  40                  45

Pro Leu Pro Val Gly Ala Pro Thr Asn Thr Leu Ser Ser Leu Leu Tyr
    50                  55                  60

Thr Val Leu Asn Thr Gly Asn Gln Gln Lys Glu Ala Val
65                  70                  75

<210> SEQ ID NO 183
<211> LENGTH: 30
<212> TYPE: PRT
<213> ORGANISM: Homo sapiens

<400> SEQUENCE: 183

Ala Pro Leu Arg Ala Leu Gln Gln His Ser Gln Asp Gly Lys Leu Cys
1               5                   10                  15

Thr Asn Ser Leu Pro Ala Ala Arg Gly Gly Pro His Lys His
            20                  25                  30

<210> SEQ ID NO 184
<211> LENGTH: 27
<212> TYPE: PRT
<213> ORGANISM: Homo sapiens

<400> SEQUENCE: 184

Arg Ser Ser Val Ser Ile Lys Lys Glu Glu Glu Thr Asp Trp Asp Met
1               5                   10                  15

Asp Gln Leu Ser Lys Gln Arg Thr Thr Tyr Glu
            20                  25

<210> SEQ ID NO 185
<211> LENGTH: 29
<212> TYPE: PRT
<213> ORGANISM: Homo sapiens

<400> SEQUENCE: 185

Leu Cys Ser Ser Ile Arg Arg Met Ala Asn Ser Ala Gln Ile Val Phe
1               5                   10                  15

Pro Leu Pro Val Gly Ala Pro Thr Asn Thr Leu Ser Ser
```

-continued

```
              20                  25

<210> SEQ ID NO 186
<211> LENGTH: 17
<212> TYPE: PRT
<213> ORGANISM: Homo sapiens

<400> SEQUENCE: 186

Leu Ser Ile Ile Phe Leu Ala Phe Val Ser Ile Asp Arg Cys Leu Gln
1               5                   10                  15

Leu

<210> SEQ ID NO 187
<211> LENGTH: 67
<212> TYPE: PRT
<213> ORGANISM: Homo sapiens

<400> SEQUENCE: 187

Gly Ser Cys Phe Ala Thr Trp Ala Phe Ile Gln Lys Asn Thr Asn His
1               5                   10                  15

Arg Cys Val Ser Ile Tyr Leu Ile Asn Leu Leu Thr Ala Asp Phe Leu
            20                  25                  30

Leu Thr Leu Ala Leu Pro Val Lys Ile Val Val Asp Leu Gly Val Ala
        35                  40                  45

Pro Trp Lys Leu Lys Ile Phe His Cys Gln Val Thr Ala Cys Leu Ile
    50                  55                  60

Tyr Ile Asn
65

<210> SEQ ID NO 188
<211> LENGTH: 31
<212> TYPE: PRT
<213> ORGANISM: Homo sapiens

<400> SEQUENCE: 188

Lys Asn Thr Asn His Arg Cys Val Ser Ile Tyr Leu Ile Asn Leu Leu
1               5                   10                  15

Thr Ala Asp Phe Leu Leu Thr Leu Ala Leu Pro Val Lys Ile Val
            20                  25                  30

<210> SEQ ID NO 189
<211> LENGTH: 17
<212> TYPE: PRT
<213> ORGANISM: Homo sapiens

<400> SEQUENCE: 189

Lys His Thr Val Glu Thr Arg Ser Val Ala Phe Arg Lys Gln Leu Asn
1               5                   10                  15

Arg

<210> SEQ ID NO 190
<211> LENGTH: 30
<212> TYPE: PRT
<213> ORGANISM: Homo sapiens
<220> FEATURE:
<221> NAME/KEY: SITE
<222> LOCATION: (18)
<223> OTHER INFORMATION: Xaa equals any of the naturally occurring
      L-amino acids
<220> FEATURE:
<221> NAME/KEY: SITE
<222> LOCATION: (29)
<223> OTHER INFORMATION: Xaa equals any of the naturally occurring
      L-amino acids
```

<400> SEQUENCE: 190

Pro Gln Val Leu His Leu Arg Trp Leu Pro Lys Val Leu Gly Tyr Arg
1               5                   10                  15

Ser Xaa Pro Leu Arg Leu Ala Asp Pro Ser Thr Phe Xaa Met
            20                  25                  30

<210> SEQ ID NO 191
<211> LENGTH: 131
<212> TYPE: PRT
<213> ORGANISM: Homo sapiens

<400> SEQUENCE: 191

Gln Leu Leu Gly Phe Glu Gly Asn Asp Ser Ala Gly Glu Arg Arg Trp
1               5                   10                  15

Arg Gly Ala Asn Met Gln Ile Pro Leu Leu Gln Val Ala Leu Pro Leu
            20                  25                  30

Ser Thr Glu Glu Gly Thr Gly Pro Ser Gly Pro Thr Gln Pro Ser Pro
        35                  40                  45

Gln Gly Glu Val Arg Phe Leu Arg Ser Pro Arg Met Gly Gly Gln Val
    50                  55                  60

Pro His Trp Glu Trp Arg Ser His Ser Leu Pro Trp Val Leu Thr Ser
65                  70                  75                  80

Thr Leu Ser Gly Cys Glu Gly Asp Leu Pro Gly Phe Pro His Gln Val
                85                  90                  95

Gln Leu Pro Ala Ala Glu Ser His Thr Leu Asn Thr Gly Leu Leu Arg
            100                 105                 110

Ser Asp Thr Gly Gln Phe Thr Pro Cys Leu Lys Leu Ala Phe Glu Arg
        115                 120                 125

Pro Ser Gly
    130

<210> SEQ ID NO 192
<211> LENGTH: 24
<212> TYPE: PRT
<213> ORGANISM: Homo sapiens

<400> SEQUENCE: 192

Asn Asp Ser Ala Gly Glu Arg Arg Trp Arg Gly Ala Asn Met Gln Ile
1               5                   10                  15

Pro Leu Leu Gln Val Ala Leu Pro
            20

<210> SEQ ID NO 193
<211> LENGTH: 29
<212> TYPE: PRT
<213> ORGANISM: Homo sapiens

<400> SEQUENCE: 193

Pro Ser Pro Gln Gly Glu Val Arg Phe Leu Arg Ser Pro Arg Met Gly
1               5                   10                  15

Gly Gln Val Pro His Trp Glu Trp Arg Ser His Ser Leu
            20                  25

<210> SEQ ID NO 194
<211> LENGTH: 27
<212> TYPE: PRT
<213> ORGANISM: Homo sapiens

<400> SEQUENCE: 194

```
His Gln Val Gln Leu Pro Ala Ala Glu Ser His Thr Leu Asn Thr Gly
1               5                   10                  15

Leu Leu Arg Ser Asp Thr Gly Gln Phe Thr Pro
            20                  25
```

<210> SEQ ID NO 195
<211> LENGTH: 60
<212> TYPE: PRT
<213> ORGANISM: Homo sapiens

<400> SEQUENCE: 195

```
Ala Pro Leu Glu Thr Met Gln Asn Lys Pro Arg Ala Pro Gln Lys Arg
1               5                   10                  15

Ala Leu Pro Phe Pro Glu Leu Glu Leu Arg Asp Tyr Ala Ser Val Leu
            20                  25                  30

Thr Arg Tyr Ser Leu Gly Leu Arg Asn Lys Glu Pro Ser Leu Gly His
        35                  40                  45

Arg Trp Gly Thr Gln Lys Leu Gly Arg Ser Pro Cys
    50                  55                  60
```

<210> SEQ ID NO 196
<211> LENGTH: 217
<212> TYPE: PRT
<213> ORGANISM: Homo sapiens
<220> FEATURE:
<221> NAME/KEY: SITE
<222> LOCATION: (85)
<223> OTHER INFORMATION: Xaa equals any of the naturally occurring
      L-amino acids
<220> FEATURE:
<221> NAME/KEY: SITE
<222> LOCATION: (97)
<223> OTHER INFORMATION: Xaa equals any of the naturally occurring
      L-amino acids
<220> FEATURE:
<221> NAME/KEY: SITE
<222> LOCATION: (157)
<223> OTHER INFORMATION: Xaa equals any of the naturally occurring
      L-amino acids

<400> SEQUENCE: 196

```
Met Gln Asn Lys Pro Arg Ala Pro Gln Lys Arg Ala Leu Pro Phe Pro
1               5                   10                  15

Glu Leu Glu Leu Arg Asp Tyr Ala Ser Val Leu Thr Arg Tyr Ser Leu
            20                  25                  30

Gly Leu Arg Asn Lys Glu Pro Ser Leu Gly His Arg Trp Gly Thr Gln
        35                  40                  45

Lys Leu Gly Arg Ser Pro Cys Ser Glu Gly Ser Gln Gly His Thr Thr
    50                  55                  60

Asp Ala Ala Asp Val Gln Asn His Ser Lys Glu Gln Arg Asp Ala
65                  70                  75                  80

Gly Ala Gln Arg Xaa Cys Gly Gln Gly Arg His Thr Trp Ala Tyr Arg
                85                  90                  95

Xaa Gly Ala Gln Asp Thr Ser Arg Leu Thr Gly Asp Pro Arg Gly Gly
            100                 105                 110

Glu Arg Ser Pro Pro Lys Cys Gln Ser Met Lys Gln Gln Glu Gly Ala
        115                 120                 125

Pro Ser Gly His Cys Trp Asp Gln Trp Cys His Gly Ala Ser Glu Val
    130                 135                 140

Val Trp Pro Glu Ser Arg Lys Arg Ala Gln Ile Phe Xaa Ser Pro Cys
145                 150                 155                 160

Arg Gln Ser Pro Arg Ser Ser Ala Leu Gly Ala Gly Gln Lys Leu Ala
```

165                 170                 175
Val Cys Ser Pro Asp Ile Leu Cys Cys Pro Thr Asp Thr Leu Leu Ala
            180                 185                 190

Ser His Pro His Ser Leu Leu Thr Gly Thr Gln Phe Ser Gly Gln Thr
        195                 200                 205

Gln Ala Leu Ala Pro Ser Trp Cys Ala
    210                 215

<210> SEQ ID NO 197
<211> LENGTH: 26
<212> TYPE: PRT
<213> ORGANISM: Homo sapiens

<400> SEQUENCE: 197

Ala Pro Gln Lys Arg Ala Leu Pro Phe Pro Glu Leu Glu Leu Arg Asp
1               5                   10                  15

Tyr Ala Ser Val Leu Thr Arg Tyr Ser Leu
            20                  25

<210> SEQ ID NO 198
<211> LENGTH: 27
<212> TYPE: PRT
<213> ORGANISM: Homo sapiens

<400> SEQUENCE: 198

Ala Pro Gln Lys Arg Ala Leu Pro Phe Pro Glu Leu Glu Leu Arg Asp
1               5                   10                  15

Tyr Ala Ser Val Leu Thr Arg Tyr Ser Leu Gly
            20                  25

<210> SEQ ID NO 199
<211> LENGTH: 29
<212> TYPE: PRT
<213> ORGANISM: Homo sapiens

<400> SEQUENCE: 199

Leu Gly Arg Ser Pro Cys Ser Glu Gly Ser Gln Gly His Thr Thr Asp
1               5                   10                  15

Ala Ala Asp Val Gln Asn His Ser Lys Glu Glu Gln Arg
            20                  25

<210> SEQ ID NO 200
<211> LENGTH: 25
<212> TYPE: PRT
<213> ORGANISM: Homo sapiens

<400> SEQUENCE: 200

Thr Asp Thr Leu Leu Ala Ser His Pro His Ser Leu Leu Thr Gly Thr
1               5                   10                  15

Gln Phe Ser Gly Gln Thr Gln Ala Leu
            20                  25

<210> SEQ ID NO 201
<211> LENGTH: 77
<212> TYPE: PRT
<213> ORGANISM: Homo sapiens
<220> FEATURE:
<221> NAME/KEY: SITE
<222> LOCATION: (13)
<223> OTHER INFORMATION: Xaa equals any of the naturally occurring
      L-amino acids
<220> FEATURE:
<221> NAME/KEY: SITE
<222> LOCATION: (18)

```
<223> OTHER INFORMATION: Xaa equals any of the naturally occurring
      L-amino acids
<220> FEATURE:
<221> NAME/KEY: SITE
<222> LOCATION: (39)
<223> OTHER INFORMATION: Xaa equals any of the naturally occurring
      L-amino acids

<400> SEQUENCE: 201

Ile Ala Gln Val Leu Lys Ala Glu Met Cys Leu Val Xaa Arg Pro His
1               5                   10                  15

Pro Xaa Leu Leu Asp Ser His Arg Gly Trp Ala Gly Glu Thr Leu Arg
        20                  25                  30

Gly Gln Gly Arg Gln Glu Xaa Glu Ser Asp Thr Lys Ala Gly Thr Leu
    35                  40                  45

Gln Leu Gln Arg Gln Ala Pro Leu Pro Leu Thr Gln His Ser Leu Val
50                  55                  60

Leu Pro Ile Ser Pro Gly Pro Ser Asn His Thr Gln Ser
65                  70                  75

<210> SEQ ID NO 202
<211> LENGTH: 20
<212> TYPE: PRT
<213> ORGANISM: Homo sapiens
<220> FEATURE:
<221> NAME/KEY: SITE
<222> LOCATION: (16)
<223> OTHER INFORMATION: Xaa equals any of the naturally occurring
      L-amino acids

<400> SEQUENCE: 202

Arg Gly Trp Ala Gly Glu Thr Leu Arg Gly Gln Gly Arg Gln Glu Xaa
1               5                   10                  15

Glu Ser Asp Thr
            20

<210> SEQ ID NO 203
<211> LENGTH: 20
<212> TYPE: PRT
<213> ORGANISM: Homo sapiens

<400> SEQUENCE: 203

Ala Pro Leu Pro Leu Thr Gln His Ser Leu Val Leu Pro Ile Ser Pro
1               5                   10                  15

Gly Pro Ser Asn
            20

<210> SEQ ID NO 204
<211> LENGTH: 166
<212> TYPE: PRT
<213> ORGANISM: Homo sapiens

<400> SEQUENCE: 204

Asn Arg Glu Arg Gly Gly Ala Gly Ala Thr Phe Glu Cys Asn Ile Cys
1               5                   10                  15

Leu Glu Thr Ala Arg Glu Ala Val Val Ser Val Cys Gly His Leu Tyr
            20                  25                  30

Cys Trp Pro Cys Leu His Gln Trp Leu Glu Thr Arg Pro Glu Arg Gln
        35                  40                  45

Glu Cys Pro Val Cys Lys Ala Gly Ile Ser Arg Glu Lys Val Val Pro
    50                  55                  60

Leu Tyr Gly Arg Gly Ser Gln Lys Pro Gln Asp Pro Arg Leu Lys Thr
65                  70                  75                  80
```

```
Pro Pro Arg Pro Gln Gly Gln Arg Pro Ala Pro Glu Ser Arg Gly Gly
            85                  90                  95

Phe Gln Pro Phe Gly Asp Thr Gly Gly Phe His Phe Ser Phe Gly Val
        100                 105                 110

Gly Ala Phe Pro Phe Gly Phe Phe Thr Thr Val Phe Asn Ala His Glu
    115                 120                 125

Pro Phe Arg Arg Gly Thr Gly Val Asp Leu Gly Gln Gly His Pro Ala
130                 135                 140

Ser Ser Trp Gln Asp Ser Leu Phe Leu Phe Leu Ala Ile Phe Phe Phe
145                 150                 155                 160

Phe Trp Leu Leu Ser Ile
            165

<210> SEQ ID NO 205
<211> LENGTH: 149
<212> TYPE: PRT
<213> ORGANISM: Homo sapiens

<400> SEQUENCE: 205

Asn Arg Glu Arg Gly Gly Ala Gly Ala Thr Phe Glu Cys Asn Ile Cys
1               5                   10                  15

Leu Glu Thr Ala Arg Glu Ala Val Val Ser Val Cys Gly His Leu Tyr
            20                  25                  30

Cys Trp Pro Cys Leu His Gln Trp Leu Glu Thr Arg Pro Glu Arg Gln
        35                  40                  45

Glu Cys Pro Val Cys Lys Ala Gly Ile Ser Arg Glu Lys Val Val Pro
    50                  55                  60

Leu Tyr Gly Arg Gly Ser Gln Lys Pro Gln Asp Pro Arg Leu Lys Thr
65                  70                  75                  80

Pro Pro Arg Pro Gln Gly Gln Arg Pro Ala Pro Glu Ser Arg Gly Gly
            85                  90                  95

Phe Gln Pro Phe Gly Asp Thr Gly Gly Phe His Phe Ser Phe Gly Val
        100                 105                 110

Gly Ala Phe Pro Phe Gly Phe Phe Thr Thr Val Phe Asn Ala His Glu
    115                 120                 125

Pro Phe Arg Arg Gly Thr Gly Val Asp Leu Gly Gln Gly His Pro Ala
130                 135                 140

Ser Ser Trp Gln Asp
145

<210> SEQ ID NO 206
<211> LENGTH: 41
<212> TYPE: PRT
<213> ORGANISM: Homo sapiens

<400> SEQUENCE: 206

Asn Arg Glu Arg Gly Gly Ala Gly Ala Thr Phe Glu Cys Asn Ile Cys
1               5                   10                  15

Leu Glu Thr Ala Arg Glu Ala Val Val Ser Val Cys Gly His Leu Tyr
            20                  25                  30

Cys Trp Pro Cys Leu His Gln Trp Leu
        35                  40

<210> SEQ ID NO 207
<211> LENGTH: 38
<212> TYPE: PRT
<213> ORGANISM: Homo sapiens
```

```
<400> SEQUENCE: 207

Glu Thr Arg Pro Glu Arg Gln Glu Cys Pro Val Cys Lys Ala Gly Ile
1               5                   10                  15

Ser Arg Glu Lys Val Val Pro Leu Tyr Gly Arg Gly Ser Gln Lys Pro
            20                  25                  30

Gln Asp Pro Arg Leu Lys
        35

<210> SEQ ID NO 208
<211> LENGTH: 34
<212> TYPE: PRT
<213> ORGANISM: Homo sapiens

<400> SEQUENCE: 208

Thr Pro Pro Arg Pro Gln Gly Gln Arg Pro Ala Pro Glu Ser Arg Gly
1               5                   10                  15

Gly Phe Gln Pro Phe Gly Asp Thr Gly Gly Phe His Phe Ser Phe Gly
            20                  25                  30

Val Gly

<210> SEQ ID NO 209
<211> LENGTH: 36
<212> TYPE: PRT
<213> ORGANISM: Homo sapiens

<400> SEQUENCE: 209

Ala Phe Pro Phe Gly Phe Phe Thr Thr Val Phe Asn Ala His Glu Pro
1               5                   10                  15

Phe Arg Arg Gly Thr Gly Val Asp Leu Gly Gln Gly His Pro Ala Ser
            20                  25                  30

Ser Trp Gln Asp
        35

<210> SEQ ID NO 210
<211> LENGTH: 15
<212> TYPE: PRT
<213> ORGANISM: Homo sapiens

<400> SEQUENCE: 210

Gly Leu Ser Thr Gly Pro Asp Met Ala Ser Leu Asp Leu Phe Val
1               5                   10                  15

<210> SEQ ID NO 211
<211> LENGTH: 97
<212> TYPE: PRT
<213> ORGANISM: Homo sapiens

<400> SEQUENCE: 211

Gly Arg Pro Thr Arg Pro Ser Gln Ala Thr Arg His Phe Leu Leu Gly
1               5                   10                  15

Thr Leu Phe Thr Asn Cys Leu Cys Gly Thr Phe Cys Phe Pro Cys Leu
            20                  25                  30

Gly Cys Gln Val Ala Ala Asp Met Asn Glu Cys Cys Leu Cys Gly Thr
        35                  40                  45

Ser Val Ala Met Arg Thr Leu Tyr Arg Thr Tyr Gly Ile Pro Gly
    50                  55                  60

Ser Ile Cys Asp Asp Tyr Met Ala Thr Leu Cys Cys Pro His Cys Thr
65                  70                  75                  80

Leu Cys Gln Ile Lys Arg Asp Ile Asn Arg Arg Ala Met Arg Thr
                85                  90                  95
```

Phe

<210> SEQ ID NO 212
<211> LENGTH: 146
<212> TYPE: PRT
<213> ORGANISM: Homo sapiens

<400> SEQUENCE: 212

Ile Lys Asn Leu Ile Phe Phe Met Pro Ser Val Val Leu Lys His Ile
1               5                   10                  15

His His Ile Ser Val Ala Lys Asp Gly Glu Glu Leu Lys Leu Lys Arg
            20                  25                  30

Cys Leu Leu Asn Phe Val Ala Ser Val Arg Ala Phe His His Gln Phe
        35                  40                  45

Leu Glu Ser Thr His Gly Ser Pro Ser Val Asp Ile Ser Leu Asp Leu
    50                  55                  60

Ala Lys Ser Thr Met Arg Thr Ala Lys Ser Cys His Ile Val Ile Thr
65                  70                  75                  80

Asn Arg Ser Arg Asp Ala Ile Ser Gly Pro Val Glu Ser Pro His Cys
                85                  90                  95

Asp Ala Cys Ser Thr Gln Thr Ala Phe Ile His Ile Ser Cys Asn Leu
            100                 105                 110

Thr Pro Lys Ala Arg Glu Thr Lys Cys Ala Thr Glu Thr Ile Ser Lys
        115                 120                 125

Gln Gly Ser Glu Gln Glu Met Ser Cys Gly Leu Gly Arg Thr Arg Gly
    130                 135                 140

Ser Thr
145

<210> SEQ ID NO 213
<211> LENGTH: 23
<212> TYPE: PRT
<213> ORGANISM: Homo sapiens

<400> SEQUENCE: 213

Phe Leu Leu Gly Thr Leu Phe Thr Asn Cys Leu Cys Gly Thr Phe Cys
1               5                   10                  15

Phe Pro Cys Leu Gly Cys Gln
            20

<210> SEQ ID NO 214
<211> LENGTH: 24
<212> TYPE: PRT
<213> ORGANISM: Homo sapiens

<400> SEQUENCE: 214

Ser Ile Cys Asp Asp Tyr Met Ala Thr Leu Cys Cys Pro His Cys Thr
1               5                   10                  15

Leu Cys Gln Ile Lys Arg Asp Ile
            20

<210> SEQ ID NO 215
<211> LENGTH: 30
<212> TYPE: PRT
<213> ORGANISM: Homo sapiens

<400> SEQUENCE: 215

Ser Val Val Leu Lys His Ile His Ile Ser Val Ala Lys Asp Gly
1               5                   10                  15

Glu Glu Leu Lys Leu Lys Arg Cys Leu Leu Asn Phe Val Ala
            20                  25                  30

<210> SEQ ID NO 216
<211> LENGTH: 26
<212> TYPE: PRT
<213> ORGANISM: Homo sapiens

<400> SEQUENCE: 216

Asn Phe Val Ala Ser Val Arg Ala Phe His His Gln Phe Leu Glu Ser
1               5                   10                  15

Thr His Gly Ser Pro Ser Val Asp Ile Ser
            20                  25

<210> SEQ ID NO 217
<211> LENGTH: 28
<212> TYPE: PRT
<213> ORGANISM: Homo sapiens

<400> SEQUENCE: 217

Thr Ala Phe Ile His Ile Ser Cys Asn Leu Thr Pro Lys Ala Arg Glu
1               5                   10                  15

Thr Lys Cys Ala Thr Glu Thr Ile Ser Lys Gln Gly
            20                  25

<210> SEQ ID NO 218
<211> LENGTH: 6
<212> TYPE: PRT
<213> ORGANISM: Homo sapiens

<400> SEQUENCE: 218

Met Lys Gly Glu Ile Glu
1               5

<210> SEQ ID NO 219
<211> LENGTH: 14
<212> TYPE: PRT
<213> ORGANISM: Homo sapiens

<400> SEQUENCE: 219

Glu Phe Gly Thr Ser Arg Gly Arg Gln His Arg Ala Leu Glu
1               5                   10

<210> SEQ ID NO 220
<211> LENGTH: 80
<212> TYPE: PRT
<213> ORGANISM: Homo sapiens
<220> FEATURE:
<221> NAME/KEY: SITE
<222> LOCATION: (72)
<223> OTHER INFORMATION: Xaa equals any of the naturally occurring
      L-amino acids

<400> SEQUENCE: 220

His Gln Thr Pro Gly Val Thr Gly Leu Ser Ala Val Glu Met Asp Gln
1               5                   10                  15

Ile Thr Pro Ala Leu Trp Glu Ala Leu Ala Ile Asp Thr Leu Arg Lys
            20                  25                  30

Leu Arg Ile Gly Thr Arg Arg Pro Arg Ile Arg Trp Gly Gln Glu Ala
        35                  40                  45

His Val Pro Ala Gly Ala Ala Gln Glu Gly Pro Leu His Leu Leu Leu
    50                  55                  60

Gln Arg Pro Ala Pro Trp Gly Xaa Ala Pro His Gly Lys Ala Cys Gly
65                  70                  75                  80

```
<210> SEQ ID NO 221
<211> LENGTH: 87
<212> TYPE: PRT
<213> ORGANISM: Homo sapiens
<220> FEATURE:
<221> NAME/KEY: SITE
<222> LOCATION: (39)
<223> OTHER INFORMATION: Xaa equals any of the naturally occurring
      L-amino acids

<400> SEQUENCE: 221

Gly Leu Gly Gln Gly Gly Gln Gly Leu Asp Gly Gly Arg Lys Leu Met
1               5                   10                  15

Tyr Leu Gln Glu Leu Pro Arg Arg Asp His Tyr Ile Phe Tyr Cys Lys
            20                  25                  30

Asp Gln His His Gly Gly Xaa Leu His Met Gly Lys Leu Val Gly Arg
        35                  40                  45

Asn Ser Asp Thr Asn Arg Glu Ala Leu Glu Glu Phe Lys Lys Leu Val
    50                  55                  60

Gln Arg Lys Gly Leu Ser Glu Glu Asp Ile Phe Thr Pro Leu Gln Thr
65                  70                  75                  80

Gly Ser Cys Val Pro Glu His
                85

<210> SEQ ID NO 222
<211> LENGTH: 176
<212> TYPE: PRT
<213> ORGANISM: Homo sapiens
<220> FEATURE:
<221> NAME/KEY: SITE
<222> LOCATION: (62)
<223> OTHER INFORMATION: Xaa equals any of the naturally occurring
      L-amino acids
<220> FEATURE:
<221> NAME/KEY: SITE
<222> LOCATION: (84)
<223> OTHER INFORMATION: Xaa equals any of the naturally occurring
      L-amino acids
<220> FEATURE:
<221> NAME/KEY: SITE
<222> LOCATION: (143)
<223> OTHER INFORMATION: Xaa equals any of the naturally occurring
      L-amino acids
<220> FEATURE:
<221> NAME/KEY: SITE
<222> LOCATION: (152)
<223> OTHER INFORMATION: Xaa equals any of the naturally occurring
      L-amino acids

<400> SEQUENCE: 222

Ser Gly Pro Ser Arg Leu Arg Thr Ser Leu Ser His Pro Val Ser Asp
1               5                   10                  15

Val Arg Ala Thr Ser Pro Pro Gly Arg Arg Gly Gln Pro Leu Leu Gly
            20                  25                  30

Gly Gly Gln Ser Trp Gly Pro Gly Lys Arg Ala Ala Trp Ala Leu Ser
        35                  40                  45

Thr Cys Gly Gly Trp Cys Thr Gly Val Gly Gly Gly Xaa Trp Gly
    50                  55                  60

Trp Glu Trp Gly Arg Gly Ser Gln Ala Leu Tyr Leu Pro Gly Ser Ser
65                  70                  75                  80

Val Phe Arg Xaa Arg Ile Phe Phe Trp Met His Arg Ser Ser Leu Met
            85                  90                  95

Lys Val Asn Val Ala Ser Asn Phe Pro Pro Arg Ala Val Thr Phe
        100                 105                 110
```

```
Thr Gly Asp Thr Phe Trp Ala Ser Cys Leu Arg Lys Val Leu Ser Thr
    115                 120                 125

Thr Met Ala Phe Thr Tyr Gln Val Pro Val Ile Ser Ser Ser Xaa Arg
    130                 135                 140

Val Lys Asp Arg Ala Ala Ala Xaa Pro Ser Val Thr Pro Arg Asn Arg
145                 150                 155                 160

Val Phe Ile Ser Arg Ala Leu Cys Cys Arg Pro Arg Leu Val Pro Asn
                165                 170                 175

<210> SEQ ID NO 223
<211> LENGTH: 103
<212> TYPE: PRT
<213> ORGANISM: Homo sapiens
<220> FEATURE:
<221> NAME/KEY: SITE
<222> LOCATION: (74)
<223> OTHER INFORMATION: Xaa equals any of the naturally occurring
      L-amino acids
<220> FEATURE:
<221> NAME/KEY: SITE
<222> LOCATION: (92)
<223> OTHER INFORMATION: Xaa equals any of the naturally occurring
      L-amino acids

<400> SEQUENCE: 223

Gly Leu Pro Glu Gly Arg Arg Asp Leu Val His Leu Asp Cys Gly Gln
1               5                   10                  15

Ala Cys His Thr Arg Cys Leu Met Ser Gly Pro Pro Ala Pro Gln Glu
            20                  25                  30

Gly Glu Ala Ser Pro Ser Leu Glu Val Gly Arg Ala Gly Ala Leu Ala
        35                  40                  45

Lys Gly Gln Pro Gly His Ser Leu Pro Val Glu Ala Gly Ala Leu Gly
    50                  55                  60

Leu Ala Val Gly Glu Gly Gly Gly Xaa Gly Gly Gly Ala His Arg
65                  70                  75                  80

Arg Cys Ile Cys Gln Ala Pro Pro Ser Ser Ala Xaa Gly Phe Ser Ser
                85                  90                  95

Gly Cys Thr Asp Pro Pro Ser
            100

<210> SEQ ID NO 224
<211> LENGTH: 30
<212> TYPE: PRT
<213> ORGANISM: Homo sapiens

<400> SEQUENCE: 224

Val Glu Met Asp Gln Ile Thr Pro Ala Leu Trp Glu Ala Leu Ala Ile
1               5                   10                  15

Asp Thr Leu Arg Lys Leu Arg Ile Gly Thr Arg Arg Pro Arg
            20                  25                  30

<210> SEQ ID NO 225
<211> LENGTH: 23
<212> TYPE: PRT
<213> ORGANISM: Homo sapiens

<400> SEQUENCE: 225

Arg Lys Leu Met Tyr Leu Gln Glu Leu Pro Arg Arg Asp His Tyr Ile
1               5                   10                  15

Phe Tyr Cys Lys Asp Gln His
            20
```

```
<210> SEQ ID NO 226
<211> LENGTH: 23
<212> TYPE: PRT
<213> ORGANISM: Homo sapiens

<400> SEQUENCE: 226

Glu Ala Leu Glu Glu Phe Lys Lys Leu Val Gln Arg Lys Gly Leu Ser
1               5                   10                  15

Glu Glu Asp Ile Phe Thr Pro
            20

<210> SEQ ID NO 227
<211> LENGTH: 27
<212> TYPE: PRT
<213> ORGANISM: Homo sapiens

<400> SEQUENCE: 227

Arg Ala Thr Ser Pro Pro Gly Arg Arg Gly Gln Pro Leu Leu Gly Gly
1               5                   10                  15

Gly Gln Ser Trp Gly Pro Gly Lys Arg Ala Ala
            20                  25

<210> SEQ ID NO 228
<211> LENGTH: 29
<212> TYPE: PRT
<213> ORGANISM: Homo sapiens

<400> SEQUENCE: 228

Phe Phe Trp Met His Arg Ser Ser Leu Met Lys Val Asn Val Ala Ser
1               5                   10                  15

Asn Phe Pro Pro Pro Arg Ala Val Thr Phe Thr Gly Asp
            20                  25

<210> SEQ ID NO 229
<211> LENGTH: 28
<212> TYPE: PRT
<213> ORGANISM: Homo sapiens

<400> SEQUENCE: 229

Cys Leu Met Ser Gly Pro Pro Ala Pro Gln Glu Gly Glu Ala Ser Pro
1               5                   10                  15

Ser Leu Glu Val Gly Arg Ala Gly Ala Leu Ala Lys
            20                  25
```